US012570750B2

(12) United States Patent
Sato et al.

(10) Patent No.: US 12,570,750 B2
(45) Date of Patent: Mar. 10, 2026

(54) ANTIBODIES THAT BIND ADENOSINE A2A RECEPTORS AND METHODS OF USE THEREOF TO TREAT CANCER AND NEUROLOGICAL DISEASES

(71) Applicant: Twist Bioscience Corporation, South San Francisco, CA (US)

(72) Inventors: Aaron Sato, Burlingame, CA (US); Ray Tabibiazar, Chattanooga, TN (US); Pankaj Garg, Burlingame, CA (US); Qiang Liu, Palo Alto, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 672 days.

(21) Appl. No.: 17/116,939

(22) Filed: Dec. 9, 2020

(65) Prior Publication Data

US 2021/0179724 A1 Jun. 17, 2021

Related U.S. Application Data

(60) Provisional application No. 62/945,818, filed on Dec. 9, 2019.

(51) Int. Cl.
*C07K 16/28* (2006.01)
*C12N 15/10* (2006.01)

(52) U.S. Cl.
CPC ........ *C07K 16/2869* (2013.01); *C07K 16/286* (2013.01); *C12N 15/1093* (2013.01); *C07K 2317/24* (2013.01); *C07K 2317/569* (2013.01); *C07K 2317/622* (2013.01); *C07K 2317/76* (2013.01); *C07K 2317/92* (2013.01)

(58) Field of Classification Search
CPC .............. C07K 16/2869; C07K 16/286; C07K 2317/24; C07K 2317/569; C07K 2317/622; C07K 2317/76; C07K 2317/92
See application file for complete search history.

(56) References Cited

U.S. PATENT DOCUMENTS 3,549,368 A 12/1970 Collings et al.
3,920,714 A 11/1975 Streck
4,123,661 A 10/1978 Wolf et al.
4,415,732 A 11/1983 Caruthers et al.
4,613,398 A 9/1986 Chiong et al.
4,726,877 A 2/1988 Fryd et al.
4,808,511 A 2/1989 Holmes
4,837,401 A 6/1989 Hirose et al.
4,863,557 A 9/1989 Kokaku et al.
4,981,797 A 1/1991 Jessee et al.
4,988,617 A 1/1991 Landegren et al.
5,102,797 A 4/1992 Tucker et al.
5,118,605 A 6/1992 Urdea
5,137,814 A 8/1992 Rashtchian et al.
5,143,854 A 9/1992 Pirrung et al.
5,242,794 A 9/1993 Whiteley et al.
5,242,974 A 9/1993 Holmes
5,288,514 A 2/1994 Ellman
5,299,491 A 4/1994 Kawada
5,384,261 A 1/1995 Winkler et al.
5,387,541 A 2/1995 Hodge et al.
5,395,753 A 3/1995 Prakash
5,431,720 A 7/1995 Nagai et al.
5,445,934 A 8/1995 Fodor et al.
5,449,754 A 9/1995 Nishioka
5,459,039 A 10/1995 Modrich et al.
5,474,796 A 12/1995 Brennan
5,476,930 A 12/1995 Letsinger et al.
5,487,993 A 1/1996 Herrnstadt et al.
5,494,810 A 2/1996 Barany et al.
5,501,893 A 3/1996 Laermer et al.
5,508,169 A 4/1996 Deugau et al.
5,510,270 A 4/1996 Fodor et al.
5,514,789 A 5/1996 Kempe
5,527,681 A 6/1996 Holmes
5,530,516 A 6/1996 Sheets
5,556,750 A 9/1996 Modrich et al.
5,586,211 A 12/1996 Dumitrou et al.
5,641,658 A 6/1997 Adams et al.
5,677,195 A 10/1997 Winkler et al.
5,679,522 A 10/1997 Modrich et al.
5,683,879 A 11/1997 Laney et al.
5,688,642 A 11/1997 Chrisey et al.
5,700,637 A 12/1997 Southern
5,700,642 A 12/1997 Monforte et al.
5,702,894 A 12/1997 Modrich et al.
5,707,806 A 1/1998 Shuber
5,712,124 A 1/1998 Walker
5,712,126 A 1/1998 Weissman et al.
5,739,386 A 4/1998 Holmes
5,750,672 A 5/1998 Kempe
5,780,613 A 7/1998 Letsinger et al.
5,830,643 A 11/1998 Yamamoto et al.
5,830,655 A 11/1998 Monforte et al.
(Continued)

FOREIGN PATENT DOCUMENTS

AU 3157000 A 9/2000
CA 2362939 A1 8/2000
(Continued)

OTHER PUBLICATIONS

Paul, WE (1993) Fundamental Immunology, 3rd ed. Raven Press, NY, Chap. 9, pp. 292-295.*
(Continued)

*Primary Examiner* — Robert S Landsman
(74) *Attorney, Agent, or Firm* — McNeill PLLC

(57) ABSTRACT

Provided herein are methods and compositions relating to adenosine A2A receptor libraries having nucleic acids encoding for a scaffold comprising an adenosine A2A binding domain. adenosine A2A receptor libraries described herein encode for immunoglobulins including antibodies and single domain antibodies. Libraries described herein include variegated libraries comprising nucleic acids each encoding for a predetermined variant of at least one predetermined reference nucleic acid sequence. Further described herein are protein libraries generated when the nucleic acid libraries are translated. Further described herein are cell libraries expressing variegated nucleic acid libraries described herein.

11 Claims, 62 Drawing Sheets

Specification includes a Sequence Listing.

(56) References Cited

U.S. PATENT DOCUMENTS 5,830,662 A 11/1998 Soares et al.
5,834,252 A 11/1998 Stemmer et al.
5,843,669 A 12/1998 Kaiser et al.
5,843,767 A 12/1998 Beattie
5,846,717 A 12/1998 Brow et al.
5,854,033 A 12/1998 Lizardi
5,858,754 A 1/1999 Modrich et al.
5,861,482 A 1/1999 Modrich et al.
5,863,801 A 1/1999 Southgate et al.
5,869,245 A 2/1999 Yeung
5,877,280 A 3/1999 Wetmur
5,882,496 A 3/1999 Northrup et al.
5,922,539 A 7/1999 Modrich et al.
5,922,593 A 7/1999 Livingston
5,928,907 A 7/1999 Woudenberg et al.
5,962,272 A 10/1999 Chenchik et al.
5,976,842 A 11/1999 Wurst
5,976,846 A 11/1999 Passmore et al.
5,989,872 A 11/1999 Luo et al.
5,994,069 A 11/1999 Hall et al.
6,001,567 A 12/1999 Brow et al.
6,008,031 A 12/1999 Modrich et al.
6,013,440 A 1/2000 Lipshutz et al.
6,015,674 A 1/2000 Woudenberg et al.
6,017,434 A 1/2000 Simpson et al.
6,020,481 A 2/2000 Benson et al.
6,027,898 A 2/2000 Gjerde et al.
6,028,189 A 2/2000 Blanchard
6,028,198 A 2/2000 Liu et al.
6,040,138 A 3/2000 Lockhart et al.
6,077,674 A 6/2000 Schleifer et al.
6,087,482 A 7/2000 Teng et al.
6,090,543 A 7/2000 Prudent et al.
6,090,606 A 7/2000 Kaiser et al.
6,103,474 A 8/2000 Dellinger et al.
6,107,038 A 8/2000 Choudhary et al.
6,110,682 A 8/2000 Dellinger et al.
6,114,115 A 9/2000 Wagner, Jr.
6,130,045 A 10/2000 Wurst et al.
6,132,997 A 10/2000 Shannon
6,136,568 A 10/2000 Hiatt et al.
6,171,797 B1 1/2001 Perbost
6,180,351 B1 1/2001 Cattell
6,201,112 B1 3/2001 Ach
6,218,118 B1 4/2001 Sampson et al.
6,221,653 B1 4/2001 Caren et al.
6,222,030 B1 4/2001 Dellinger et al.
6,232,072 B1 5/2001 Fisher
6,235,483 B1 5/2001 Wolber et al.
6,242,266 B1 6/2001 Schleifer et al.
6,251,588 B1 6/2001 Shannon et al.
6,251,595 B1 6/2001 Gordon et al.
6,251,685 B1 6/2001 Dorsel et al.
6,258,454 B1 7/2001 Lefkowitz et al.
6,262,490 B1 7/2001 Hsu et al.
6,274,725 B1 8/2001 Sanghvi et al.
6,284,465 B1 9/2001 Wolber
6,287,776 B1 9/2001 Hefti
6,287,824 B1 9/2001 Lizardi
6,297,017 B1 10/2001 Schmidt et al.
6,300,137 B1 10/2001 Earhart et al.
6,306,599 B1 10/2001 Perbost
6,309,822 B1 10/2001 Fodor et al.
6,309,828 B1 10/2001 Schleifer et al.
6,312,911 B1 11/2001 Bancroft et al.
6,319,674 B1 11/2001 Fulcrand et al.
6,323,043 B1 11/2001 Caren et al.
6,329,210 B1 12/2001 Schleifer
6,346,423 B1 2/2002 Schembri
6,365,355 B1 4/2002 McCutchen-Maloney
6,372,483 B2 4/2002 Schleifer et al.
6,375,903 B1 4/2002 Cerrina et al.
6,376,285 B1 4/2002 Joyner et al.
6,384,210 B1 5/2002 Blanchard
6,387,636 B1 5/2002 Perbost et al.
6,399,394 B1 6/2002 Dahm et al.
6,399,516 B1 6/2002 Ayon
6,403,314 B1 6/2002 Lange et al.
6,406,849 B1 6/2002 Dorsel et al.
6,406,851 B1 6/2002 Bass
6,408,308 B1 6/2002 Maslyn et al.
6,419,883 B1 7/2002 Blanchard
6,428,957 B1 8/2002 Delenstarr
6,440,669 B1 8/2002 Bass et al.
6,444,268 B2 9/2002 Lefkowitz et al.
6,446,642 B1 9/2002 Caren et al.
6,446,682 B1 9/2002 Viken
6,451,998 B1 9/2002 Perbost
6,458,526 B1 10/2002 Schembri et al.
6,458,535 B1 10/2002 Hall et al.
6,458,583 B1 10/2002 Bruhn et al.
6,461,812 B2 10/2002 Barth et al.
6,461,816 B1 10/2002 Wolber et al.
6,469,156 B1 10/2002 Schafer et al.
6,472,147 B1 10/2002 Janda et al.
6,492,107 B1 12/2002 Kauffman et al.
6,518,056 B2 2/2003 Schembri et al.
6,521,427 B1 2/2003 Evans
6,521,453 B1 2/2003 Crameri et al.
6,555,357 B1 4/2003 Kaiser et al.
6,558,908 B2 5/2003 Wolber et al.
6,562,611 B1 5/2003 Kaiser et al.
6,566,495 B1 5/2003 Fodor et al.
6,582,908 B2 6/2003 Fodor et al.
6,582,938 B1 6/2003 Su et al.
6,586,211 B1 7/2003 Staehler et al.
6,587,579 B1 7/2003 Bass
6,589,739 B2 7/2003 Fisher
6,599,693 B1 7/2003 Webb
6,602,472 B1 8/2003 Zimmermann et al.
6,610,978 B2 8/2003 Yin et al.
6,613,513 B1 9/2003 Parce et al.
6,613,523 B2 9/2003 Fischer
6,613,560 B1 9/2003 Tso et al.
6,613,893 B1 9/2003 Webb
6,621,076 B1 9/2003 Van et al.
6,630,581 B2 10/2003 Dellinger et al.
6,632,641 B1 10/2003 Brennan et al.
6,635,226 B1 10/2003 Tso et al.
6,642,373 B2 11/2003 Manoharan et al.
6,649,348 B2 11/2003 Bass et al.
6,660,338 B1 12/2003 Hargreaves
6,664,112 B2 12/2003 Mulligan et al.
6,670,127 B2 12/2003 Evans
6,670,461 B1 12/2003 Wengel et al.
6,673,552 B2 1/2004 Frey
6,682,702 B2 1/2004 Barth et al.
6,689,319 B1 2/2004 Fisher et al.
6,692,917 B2 2/2004 Neri et al.
6,702,256 B2 3/2004 Killeen et al.
6,706,471 B1 3/2004 Brow et al.
6,706,875 B1 3/2004 Goldberg et al.
6,709,841 B2 3/2004 Short
6,709,852 B1 3/2004 Bloom et al.
6,709,854 B2 3/2004 Donahue et al.
6,713,262 B2 3/2004 Gillibolian et al.
6,716,629 B2 4/2004 Hess et al.
6,716,634 B1 4/2004 Myerson
6,723,509 B2 4/2004 Ach
6,728,129 B2 4/2004 Lindsey et al.
6,743,585 B2 6/2004 Dellinger et al.
6,753,145 B2 6/2004 Holcomb et al.
6,768,005 B2 7/2004 Mellor et al.
6,770,748 B2 8/2004 Imanishi et al.
6,770,892 B2 8/2004 Corson et al.
6,773,676 B2 8/2004 Schembri
6,773,888 B2 8/2004 Li et al.
6,780,982 B2 8/2004 Lyamichev et al.
6,787,308 B2 9/2004 Balasubramanian et al.
6,789,965 B2 9/2004 Barth et al.
6,790,620 B2 9/2004 Bass et al.
6,794,499 B2 9/2004 Wengel et al.
6,796,634 B2 9/2004 Caren et al.
6,800,439 B1 10/2004 McGall et al.

(56) References Cited

U.S. PATENT DOCUMENTS 6,814,846 B1 11/2004 Berndt
6,815,218 B1 11/2004 Jacobson et al.
6,824,866 B1 11/2004 Glazer et al.
6,830,890 B2 12/2004 Lockhart et al.
6,833,246 B2 12/2004 Balasubramanian
6,833,450 B1 12/2004 McGall et al.
6,835,938 B2 12/2004 Ghosh et al.
6,838,888 B2 1/2005 Peck
6,841,131 B2 1/2005 Zimmermann et al.
6,845,968 B2 1/2005 Killeen et al.
6,846,454 B2 1/2005 Peck
6,846,922 B1 1/2005 Manoharan et al.
6,852,850 B2 2/2005 Myerson et al.
6,858,720 B2 2/2005 Myerson et al.
6,879,915 B2 4/2005 Cattell
6,880,576 B2 4/2005 Karp et al.
6,884,580 B2 4/2005 Caren et al.
6,887,715 B2 5/2005 Schembri
6,890,723 B2 5/2005 Perbost et al.
6,890,760 B1 5/2005 Webb
6,893,816 B1 5/2005 Beattie
6,897,023 B2 5/2005 Fu et al.
6,900,047 B2 5/2005 Bass
6,900,048 B2 5/2005 Perbost
6,911,611 B2 6/2005 Wong et al.
6,914,229 B2 7/2005 Corson et al.
6,916,113 B2 7/2005 De et al.
6,916,633 B1 7/2005 Shannon
6,919,181 B2 7/2005 Hargreaves
6,927,029 B2 8/2005 Lefkowitz et al.
6,929,951 B2 8/2005 Corson et al.
6,936,472 B2 8/2005 Earhart et al.
6,938,476 B2 9/2005 Chesk
6,939,673 B2 9/2005 Bass et al.
6,943,036 B2 9/2005 Bass
6,946,285 B2 9/2005 Bass
6,950,756 B2 9/2005 Kincaid
6,951,719 B1 10/2005 Dupret et al.
6,958,119 B2 10/2005 Yin et al.
6,960,464 B2 11/2005 Jessee et al.
6,969,449 B2 11/2005 Maher et al.
6,969,488 B2 11/2005 Bridgham et al.
6,976,384 B2 12/2005 Hobbs et al.
6,977,223 B2 12/2005 George et al.
6,987,263 B2 1/2006 Hobbs et al.
6,989,267 B2 1/2006 Kim et al.
6,991,922 B2 1/2006 Dupret et al.
7,008,037 B2 3/2006 Caren et al.
7,025,324 B1 4/2006 Slocum et al.
7,026,124 B2 4/2006 Barth et al.
7,027,930 B2 4/2006 Cattell
7,028,536 B2 4/2006 Karp et al.
7,029,854 B2 4/2006 Collins et al.
7,034,290 B2 4/2006 Lu et al.
7,041,445 B2 5/2006 Chenchik et al.
7,045,289 B2 5/2006 Allawi et al.
7,051,574 B2 5/2006 Peck
7,052,841 B2 5/2006 Delenstarr
7,062,385 B2 6/2006 White et al.
7,064,197 B1 6/2006 Rabbani et al.
7,070,932 B2 7/2006 Leproust et al.
7,075,161 B2 7/2006 Barth
7,078,167 B2 7/2006 Delenstarr et al.
7,078,505 B2 7/2006 Bass et al.
7,094,537 B2 8/2006 Leproust et al.
7,097,974 B1 8/2006 Stahler et al.
7,101,508 B2 9/2006 Thompson et al.
7,101,986 B2 9/2006 Dellinger et al.
7,105,295 B2 9/2006 Bass et al.
7,115,423 B1 10/2006 Mitchell
7,122,303 B2 10/2006 Delenstarr et al.
7,122,364 B1 10/2006 Lyamichev et al.
7,125,488 B2 10/2006 Li
7,125,523 B2 10/2006 Sillman
7,128,876 B2 10/2006 Yin et al.
7,129,075 B2 10/2006 Gerard et al.
7,135,565 B2 11/2006 Dellinger et al.
7,138,062 B2 11/2006 Yin et al.
7,141,368 B2 11/2006 Fisher et al.
7,141,807 B2 11/2006 Joyce et al.
7,147,362 B2 12/2006 Caren et al.
7,150,982 B2 12/2006 Allawi et al.
7,153,689 B2 12/2006 Tolosko et al.
7,163,660 B2 1/2007 Lehmann
7,166,258 B2 1/2007 Bass et al.
7,179,659 B2 2/2007 Stolowitz et al.
7,183,406 B2 2/2007 Belshaw et al.
7,192,710 B2 3/2007 Gellibolian et al.
7,193,077 B2 3/2007 Dellinger et al.
7,198,939 B2 4/2007 Dorsel et al.
7,202,264 B2 4/2007 Ravikumar et al.
7,202,358 B2 4/2007 Hargreaves
7,205,128 B2 4/2007 Ilsley et al.
7,205,400 B2 4/2007 Webb
7,206,439 B2 4/2007 Zhou et al.
7,208,322 B2 4/2007 Stolowitz et al.
7,217,522 B2 5/2007 Brenner
7,220,573 B2 5/2007 Shea et al.
7,221,785 B2 5/2007 Curry et al.
7,226,862 B2 6/2007 Staehler et al.
7,227,017 B2 6/2007 Mellor et al.
7,229,497 B2 6/2007 Stott et al.
7,247,337 B1 7/2007 Leproust et al.
7,247,497 B2 7/2007 Dahm et al.
7,252,938 B2 8/2007 Leproust et al.
7,269,518 B2 9/2007 Corson
7,271,258 B2 9/2007 Dellinger et al.
7,276,336 B1 10/2007 Webb et al.
7,276,378 B2 10/2007 Myerson
7,276,599 B2 10/2007 Moore et al.
7,282,183 B2 10/2007 Peck
7,282,332 B2 10/2007 Caren et al.
7,282,705 B2 10/2007 Brennen
7,291,471 B2 11/2007 Sampson et al.
7,302,348 B2 11/2007 Ghosh et al.
7,306,917 B2 12/2007 Prudent et al.
7,314,599 B2 1/2008 Roitman et al.
7,323,320 B2 1/2008 Oleinikov
7,344,831 B2 3/2008 Wolber et al.
7,348,144 B2 3/2008 Minor
7,351,379 B2 4/2008 Schleifer
7,353,116 B2 4/2008 Webb et al.
7,361,906 B2 4/2008 Ghosh et al.
7,364,896 B2 4/2008 Schembri
7,368,550 B2 5/2008 Dellinger et al.
7,371,348 B2 5/2008 Schleifer et al.
7,371,519 B2 5/2008 Wolber et al.
7,371,580 B2 5/2008 Yakhini et al.
7,372,982 B2 5/2008 Le
7,384,746 B2 6/2008 Lyamichev et al.
7,385,050 B2 6/2008 Dellinger et al.
7,390,457 B2 6/2008 Schembri
7,393,665 B2 7/2008 Brenner
7,396,676 B2 7/2008 Robotti et al.
7,399,844 B2 7/2008 Sampson et al.
7,402,279 B2 7/2008 Schembri
7,411,061 B2 8/2008 Myerson et al.
7,413,709 B2 8/2008 Roitman et al.
7,417,139 B2 8/2008 Dellinger et al.
7,422,911 B2 9/2008 Schembri
7,427,679 B2 9/2008 Dellinger et al.
7,432,048 B2 10/2008 Neri et al.
7,435,810 B2 10/2008 Myerson et al.
7,439,272 B2 10/2008 Xu
7,476,709 B2 1/2009 Moody et al.
7,482,118 B2 1/2009 Allawi et al.
7,488,607 B2 2/2009 Tom-Moy et al.
7,498,415 B2 3/2009 Shitara et al.
7,504,213 B2 3/2009 Sana et al.
7,514,369 B2 4/2009 Li et al.
7,517,979 B2 4/2009 Wolber
7,524,942 B2 4/2009 Wang et al.
7,524,950 B2 4/2009 Dellinger et al.
7,527,928 B2 5/2009 Neri et al.

(56) References Cited

U.S. PATENT DOCUMENTS 7,531,303 B2 5/2009 Dorsel et al.
7,534,561 B2 5/2009 Sana et al.
7,534,563 B2 5/2009 Hargreaves
7,537,936 B2 5/2009 Dahm et al.
7,541,145 B2 6/2009 Prudent et al.
7,544,473 B2 6/2009 Brenner
7,556,919 B2 7/2009 Chenchik et al.
7,563,600 B2 7/2009 Oleinikov
7,572,585 B2 8/2009 Wang
7,572,907 B2 8/2009 Dellinger et al.
7,572,908 B2 8/2009 Dellinger et al.
7,585,970 B2 9/2009 Dellinger et al.
7,588,889 B2 9/2009 Wolber et al.
7,595,350 B2 9/2009 Xu
7,604,941 B2 10/2009 Jacobson
7,604,996 B1 10/2009 Stuelpnagel et al.
7,608,396 B2 10/2009 Delenstarr
7,618,777 B2 11/2009 Myerson et al.
7,629,120 B2 12/2009 Bennett et al.
7,635,772 B2 12/2009 McCormac
7,648,832 B2 1/2010 Jessee et al.
7,651,762 B2 1/2010 Xu et al.
7,659,069 B2 2/2010 Belyaev et al.
7,678,542 B2 3/2010 Lyamichev et al.
7,682,809 B2 3/2010 Sampson
7,709,197 B2 5/2010 Drmanac
7,718,365 B2 5/2010 Wang
7,718,786 B2 5/2010 Dupret et al.
7,723,077 B2 5/2010 Young et al.
7,737,088 B1 6/2010 Stahler et al.
7,737,089 B2 6/2010 Guimil et al.
7,741,463 B2 6/2010 Gormley et al.
7,749,701 B2 7/2010 Leproust et al.
7,759,471 B2 7/2010 Dellinger et al.
7,776,021 B2 8/2010 Borenstein et al.
7,776,532 B2 8/2010 Gibson et al.
7,790,369 B2 9/2010 Stahler et al.
7,790,387 B2 9/2010 Dellinger et al.
7,807,356 B2 10/2010 Sampson et al.
7,807,806 B2 10/2010 Allawi et al.
7,811,753 B2 10/2010 Eshoo
7,816,079 B2 10/2010 Fischer
7,820,387 B2 10/2010 Neri et al.
7,829,314 B2 11/2010 Prudent et al.
7,855,281 B2 12/2010 Dellinger et al.
7,862,999 B2 1/2011 Zheng et al.
7,867,782 B2 1/2011 Barth
7,875,463 B2 1/2011 Adaskin et al.
7,879,541 B2 2/2011 Kincaid
7,879,580 B2 2/2011 Carr et al.
7,894,998 B2 2/2011 Kincaid
7,919,239 B2 4/2011 Wang
7,919,308 B2 4/2011 Schleifer
7,927,797 B2 4/2011 Nobile et al.
7,927,838 B2 4/2011 Shannon
7,932,025 B2 4/2011 Carr et al.
7,932,070 B2 4/2011 Hogrefe et al.
7,935,800 B2 5/2011 Allawi et al.
7,939,645 B2 5/2011 Borns
7,943,046 B2 5/2011 Martosella et al.
7,943,358 B2 5/2011 Hogrefe et al.
7,960,157 B2 6/2011 Borns
7,977,119 B2 7/2011 Kronick et al.
7,979,215 B2 7/2011 Sampas
7,998,437 B2 8/2011 Berndt et al.
7,999,087 B2 8/2011 Dellinger et al.
8,021,842 B2 9/2011 Brenner
8,021,844 B2 9/2011 Wang
8,034,917 B2 10/2011 Yamada
8,036,835 B2 10/2011 Sampas et al.
8,048,664 B2 11/2011 Guan et al.
8,053,191 B2 11/2011 Blake
8,058,001 B2 11/2011 Crameri et al.
8,058,004 B2 11/2011 Oleinikov
8,058,055 B2 11/2011 Barrett et al.
8,063,184 B2 11/2011 Allawi et al.
8,067,556 B2 11/2011 Hogrefe et al.
8,073,626 B2 12/2011 Troup et al.
8,076,064 B2 12/2011 Wang
8,076,152 B2 12/2011 Robotti
8,097,711 B2 1/2012 Timar et al.
8,137,936 B2 3/2012 Macevicz
8,148,068 B2 4/2012 Brenner
8,154,729 B2 4/2012 Baldo et al.
8,168,385 B2 5/2012 Brenner
8,168,388 B2 5/2012 Gormley et al.
8,173,368 B2 5/2012 Staehler et al.
8,182,991 B1 5/2012 Kaiser et al.
8,194,244 B2 6/2012 Wang et al.
8,198,071 B2 6/2012 Goshoo et al.
8,202,983 B2 6/2012 Dellinger et al.
8,202,985 B2 6/2012 Dellinger et al.
8,206,952 B2 6/2012 Carr et al.
8,213,015 B2 7/2012 Kraiczek et al.
8,242,258 B2 8/2012 Dellinger et al.
8,247,221 B2 8/2012 Fawcett et al.
8,263,335 B2 9/2012 Carr et al.
8,268,605 B2 9/2012 Sorge et al.
8,283,148 B2 10/2012 Sorge et al.
8,288,093 B2 10/2012 Hall et al.
8,298,767 B2 10/2012 Brenner et al.
8,304,273 B2 11/2012 Stellacci et al.
8,309,307 B2 11/2012 Barrett et al.
8,309,706 B2 11/2012 Dellinger et al.
8,309,710 B2 11/2012 Sierzchala et al.
8,314,220 B2 11/2012 Mullinax et al.
8,318,433 B2 11/2012 Brenner
8,318,479 B2 11/2012 Domansky et al.
8,357,489 B2 1/2013 Chua et al.
8,357,490 B2 1/2013 Froehlich et al.
8,367,016 B2 2/2013 Quan et al.
8,367,335 B2 2/2013 Staehler et al.
8,380,441 B2 2/2013 Webb et al.
8,383,338 B2 2/2013 Kitzman et al.
8,415,138 B2 4/2013 Leproust
8,435,736 B2 5/2013 Gibson et al.
8,445,205 B2 5/2013 Brenner
8,445,206 B2 5/2013 Bergmann et al.
8,470,996 B2 6/2013 Brenner
8,476,018 B2 7/2013 Brenner
8,476,598 B1 7/2013 Pralle et al.
8,481,292 B2 7/2013 Casbon et al.
8,481,309 B2 7/2013 Zhang et al.
8,491,561 B2 7/2013 Borenstein et al.
8,497,069 B2 7/2013 Hutchison et al.
8,500,979 B2 8/2013 Elibol et al.
8,501,454 B2 8/2013 Liu et al.
8,507,226 B2 8/2013 Carr et al.
8,507,239 B2 8/2013 Lubys et al.
8,507,272 B2 8/2013 Zhang et al.
8,530,197 B2 9/2013 Li et al.
8,552,174 B2 10/2013 Dellinger et al.
8,563,478 B2 10/2013 Gormley et al.
8,569,046 B2 10/2013 Love et al.
8,577,621 B2 11/2013 Troup et al.
8,586,310 B2 11/2013 Mitra et al.
8,614,092 B2 12/2013 Zhang et al.
8,642,755 B2 2/2014 Sierzchala et al.
8,664,164 B2 3/2014 Ericsson et al.
8,669,053 B2 3/2014 Stuelpnagel et al.
8,679,756 B1 3/2014 Brenner et al.
8,685,642 B2 4/2014 Sampas
8,685,676 B2 4/2014 Hogrefe et al.
8,685,678 B2 4/2014 Casbon et al.
8,715,933 B2 5/2014 Oliver
8,715,967 B2 5/2014 Casbon et al.
8,716,467 B2 5/2014 Jacobson
8,722,368 B2 5/2014 Casbon et al.
8,722,585 B2 5/2014 Wang
8,728,766 B2 5/2014 Casbon et al.
8,741,606 B2 6/2014 Casbon et al.
8,808,896 B2 8/2014 Choo et al.
8,808,986 B2 8/2014 Jacobson et al.
8,815,600 B2 8/2014 Liu et al.

(56) References Cited

U.S. PATENT DOCUMENTS 8,889,851 B2 11/2014 Leproust et al.
8,932,994 B2 1/2015 Gormley et al.
8,962,532 B2 2/2015 Shapiro et al.
8,968,999 B2 3/2015 Gibson et al.
8,980,563 B2 3/2015 Zheng et al.
9,018,365 B2 4/2015 Brenner
9,023,601 B2 5/2015 Oleinikov
9,051,666 B2 6/2015 Oleinikov
9,073,962 B2 7/2015 Fracchia et al.
9,074,204 B2 7/2015 Anderson et al.
9,085,797 B2 7/2015 Gebeyehu et al.
9,133,510 B2 9/2015 Andersen et al.
9,139,874 B2 9/2015 Myers et al.
9,150,853 B2 10/2015 Hudson et al.
9,187,777 B2 11/2015 Jacobson et al.
9,194,001 B2 11/2015 Brenner
9,216,414 B2 12/2015 Chu
9,217,144 B2 12/2015 Jacobson et al.
9,279,149 B2 3/2016 Efcavitch et al.
9,286,439 B2 3/2016 Shapiro et al.
9,295,965 B2 3/2016 Jacobson et al.
9,315,861 B2 4/2016 Hendricks et al.
9,328,378 B2 5/2016 Earnshaw et al.
9,347,091 B2 5/2016 Bergmann et al.
9,375,748 B2 6/2016 Harumoto et al.
9,376,677 B2 6/2016 Mir
9,376,678 B2 6/2016 Gormley et al.
9,384,320 B2 7/2016 Church
9,384,920 B1 7/2016 Bakulich
9,388,407 B2 7/2016 Jacobson
9,394,333 B2 7/2016 Wada et al.
9,403,141 B2 8/2016 Banyai et al.
9,409,139 B2 8/2016 Banyai et al.
9,410,149 B2 8/2016 Brenner et al.
9,410,173 B2 8/2016 Betts et al.
9,416,411 B2 8/2016 Stuelpnagel et al.
9,422,600 B2 8/2016 Ramu et al.
9,487,824 B2 11/2016 Kutyavin
9,499,848 B2 11/2016 Carr et al.
9,523,122 B2 12/2016 Zheng et al.
9,528,148 B2 12/2016 Zheng et al.
9,534,251 B2 1/2017 Young et al.
9,555,388 B2 1/2017 Banyai et al.
9,568,839 B2 2/2017 Stahler et al.
9,580,746 B2 2/2017 Leproust et al.
9,670,529 B2 6/2017 Osborne et al.
9,670,536 B2 6/2017 Casbon et al.
9,677,067 B2 6/2017 Toro et al.
9,695,211 B2 7/2017 Wada et al.
9,718,060 B2 8/2017 Venter et al.
9,745,573 B2 8/2017 Stuelpnagel et al.
9,745,619 B2 8/2017 Rabbani et al.
9,765,387 B2 9/2017 Rabbani et al.
9,771,576 B2 9/2017 Gibson et al.
9,833,761 B2 12/2017 Banyai et al.
9,834,774 B2 12/2017 Carstens
9,839,894 B2 12/2017 Banyai et al.
9,879,283 B2 1/2018 Ravinder et al.
9,889,423 B2 2/2018 Banyai et al.
9,895,673 B2 2/2018 Peck et al.
9,925,510 B2 3/2018 Jacobson et al.
9,932,576 B2 4/2018 Raymond et al.
9,981,239 B2 5/2018 Banyai et al.
10,053,688 B2 8/2018 Cox
10,272,410 B2 4/2019 Banyai et al.
10,384,188 B2 8/2019 Banyai et al.
10,384,189 B2 8/2019 Peck
10,417,457 B2 9/2019 Peck
10,583,415 B2 3/2020 Banyai et al.
10,618,024 B2 4/2020 Banyai et al.
10,632,445 B2 4/2020 Banyai et al.
10,639,609 B2 5/2020 Banyai et al.
10,669,304 B2 6/2020 Indermuhle et al.
10,744,477 B2 8/2020 Banyai et al.
10,754,994 B2 8/2020 Peck
10,773,232 B2 9/2020 Banyai et al.
10,844,373 B2 11/2020 Cox et al.
10,894,242 B2 1/2021 Eugene et al.
10,894,959 B2 1/2021 Cox et al.
10,969,965 B2 4/2021 Malina et al.
2001/0018512 A1 8/2001 Blanchard
2001/0039014 A1 11/2001 Bass et al.
2001/0055761 A1 12/2001 Kanemoto et al.
2002/0012930 A1 1/2002 Rothberg et al.
2002/0025561 A1 2/2002 Hodgson
2002/0076716 A1 6/2002 Sabanayagam et al.
2002/0081582 A1 6/2002 Gao et al.
2002/0094533 A1 7/2002 Hess et al.
2002/0095073 A1 7/2002 Jacobs et al.
2002/0119459 A1 8/2002 Griffiths
2002/0132308 A1 9/2002 Liu et al.
2002/0155439 A1 10/2002 Rodriguez et al.
2002/0160536 A1 10/2002 Regnier et al.
2002/0164824 A1 11/2002 Xiao et al.
2003/0008411 A1 1/2003 Van et al.
2003/0022207 A1 1/2003 Balasubramanian et al.
2003/0022240 A1 1/2003 Luo et al.
2003/0022317 A1 1/2003 Jack et al.
2003/0044781 A1 3/2003 Korlach et al.
2003/0058629 A1 3/2003 Hirai et al.
2003/0064398 A1 4/2003 Barnes
2003/0068633 A1 4/2003 Belshaw et al.
2003/0082719 A1 5/2003 Schumacher et al.
2003/0100102 A1 5/2003 Rothberg et al.
2003/0108903 A1 6/2003 Wang et al.
2003/0120035 A1 6/2003 Gao et al.
2003/0130827 A1 7/2003 Bentzien et al.
2003/0138782 A1 7/2003 Evans
2003/0143605 A1 7/2003 Lok et al.
2003/0148291 A1 8/2003 Robotti
2003/0148344 A1 8/2003 Rothberg et al.
2003/0170238 A1 9/2003 Gruenberg et al.
2003/0171325 A1 9/2003 Gascoyne et al.
2003/0186226 A1 10/2003 Brennan et al.
2003/0228602 A1 12/2003 Parker et al.
2003/0228620 A1 12/2003 Du
2004/0009498 A1 1/2004 Short
2004/0043509 A1 3/2004 Stahler et al.
2004/0053362 A1 3/2004 De et al.
2004/0086892 A1 5/2004 Crothers et al.
2004/0087008 A1 5/2004 Schembri
2004/0106130 A1 6/2004 Besemer et al.
2004/0106728 A1 6/2004 McGall et al.
2004/0110133 A1 6/2004 Xu et al.
2004/0175710 A1 9/2004 Haushalter
2004/0175734 A1 9/2004 Stahler et al.
2004/0191810 A1 9/2004 Yamamoto
2004/0213795 A1 10/2004 Collins et al.
2004/0219663 A1 11/2004 Page et al.
2004/0236027 A1 11/2004 Maeji et al.
2004/0248161 A1 12/2004 Rothberg et al.
2004/0259146 A1 12/2004 Friend et al.
2005/0022895 A1 2/2005 Barth et al.
2005/0049402 A1 3/2005 Babcook et al.
2005/0049796 A1 3/2005 Webb et al.
2005/0053968 A1 3/2005 Bharadwaj et al.
2005/0079510 A1 4/2005 Berka et al.
2005/0100932 A1 5/2005 Lapidus et al.
2005/0112608 A1 5/2005 Grossman et al.
2005/0112636 A1 5/2005 Hurt et al.
2005/0112679 A1 5/2005 Myerson et al.
2005/0124022 A1 6/2005 Srinivasan et al.
2005/0137805 A1 6/2005 Lewin et al.
2005/0208513 A1 9/2005 Agbo et al.
2005/0214778 A1 9/2005 Peck et al.
2005/0227235 A1 10/2005 Carr et al.
2005/0255477 A1 11/2005 Carr et al.
2005/0266045 A1 12/2005 Canham et al.
2005/0277125 A1 12/2005 Benn et al.
2005/0282158 A1 12/2005 Landegren
2006/0003381 A1 1/2006 Gilmore et al.
2006/0003958 A1 1/2006 Melville et al.
2006/0012784 A1 1/2006 Ulmer
2006/0012793 A1 1/2006 Harris

(56) References Cited

U.S. PATENT DOCUMENTS

| | | | |
|---|---|---|---|
| 2006/0019084 | A1 | 1/2006 | Pearson |
| 2006/0024678 | A1 | 2/2006 | Buzby |
| 2006/0024711 | A1 | 2/2006 | Lapidus et al. |
| 2006/0024721 | A1 | 2/2006 | Pedersen |
| 2006/0076482 | A1 | 4/2006 | Hobbs et al. |
| 2006/0078909 | A1 | 4/2006 | Srinivasan et al. |
| 2006/0078927 | A1 | 4/2006 | Peck et al. |
| 2006/0078937 | A1 | 4/2006 | Korlach et al. |
| 2006/0127920 | A1 | 6/2006 | Church et al. |
| 2006/0134638 | A1 | 6/2006 | Mulligan et al. |
| 2006/0160138 | A1 | 7/2006 | Church |
| 2006/0171855 | A1 | 8/2006 | Yin et al. |
| 2006/0202330 | A1 | 9/2006 | Reinhardt et al. |
| 2006/0203236 | A1 | 9/2006 | Ji et al. |
| 2006/0203237 | A1 | 9/2006 | Ji et al. |
| 2006/0207923 | A1 | 9/2006 | Li |
| 2006/0219637 | A1 | 10/2006 | Killeen et al. |
| 2007/0031857 | A1 | 2/2007 | Makarov et al. |
| 2007/0031877 | A1 | 2/2007 | Stahler et al. |
| 2007/0043516 | A1 | 2/2007 | Gustafsson et al. |
| 2007/0054127 | A1 | 3/2007 | Hergenrother et al. |
| 2007/0059692 | A1 | 3/2007 | Gao et al. |
| 2007/0087349 | A1 | 4/2007 | Staehler et al. |
| 2007/0099208 | A1 | 5/2007 | Drmanac et al. |
| 2007/0122817 | A1 | 5/2007 | Church et al. |
| 2007/0141557 | A1 | 6/2007 | Raab et al. |
| 2007/0196854 | A1 | 8/2007 | Stahler et al. |
| 2007/0207482 | A1 | 9/2007 | Church et al. |
| 2007/0207487 | A1 | 9/2007 | Emig et al. |
| 2007/0231800 | A1 | 10/2007 | Roberts et al. |
| 2007/0238104 | A1 | 10/2007 | Barrett et al. |
| 2007/0238106 | A1 | 10/2007 | Barrett et al. |
| 2007/0238108 | A1 | 10/2007 | Barrett et al. |
| 2007/0259344 | A1 | 11/2007 | Leproust et al. |
| 2007/0259345 | A1 | 11/2007 | Sampas |
| 2007/0259346 | A1 | 11/2007 | Gordon et al. |
| 2007/0259347 | A1 | 11/2007 | Gordon et al. |
| 2007/0269870 | A1 | 11/2007 | Church et al. |
| 2008/0085511 | A1 | 4/2008 | Peck et al. |
| 2008/0085514 | A1 | 4/2008 | Peck et al. |
| 2008/0087545 | A1 | 4/2008 | Jensen et al. |
| 2008/0161200 | A1 | 7/2008 | Yu et al. |
| 2008/0182296 | A1 | 7/2008 | Chanda et al. |
| 2008/0214412 | A1 | 9/2008 | Stahler et al. |
| 2008/0227160 | A1 | 9/2008 | Kool |
| 2008/0233616 | A1 | 9/2008 | Liss |
| 2008/0287320 | A1 | 11/2008 | Baynes et al. |
| 2008/0300842 | A1 | 12/2008 | Govindarajan et al. |
| 2008/0308884 | A1 | 12/2008 | Kalvesten |
| 2008/0311628 | A1 | 12/2008 | Shoemaker |
| 2009/0036664 | A1 | 2/2009 | Peter |
| 2009/0053704 | A1 | 2/2009 | Novoradovskaya et al. |
| 2009/0062129 | A1 | 3/2009 | McKernan et al. |
| 2009/0074771 | A1 | 3/2009 | Koenig et al. |
| 2009/0087840 | A1 | 4/2009 | Baynes et al. |
| 2009/0088679 | A1 | 4/2009 | Wood et al. |
| 2009/0105094 | A1 | 4/2009 | Heiner et al. |
| 2009/0170802 | A1 | 7/2009 | Stahler et al. |
| 2009/0176280 | A1 | 7/2009 | Hutchison, III et al. |
| 2009/0181861 | A1 | 7/2009 | Li et al. |
| 2009/0194483 | A1 | 8/2009 | Robotti et al. |
| 2009/0230044 | A1 | 9/2009 | Bek |
| 2009/0238722 | A1 | 9/2009 | Mora-Fillat et al. |
| 2009/0239759 | A1 | 9/2009 | Balch |
| 2009/0246788 | A1 | 10/2009 | Albert et al. |
| 2009/0263802 | A1 | 10/2009 | Drmanac |
| 2009/0285825 | A1 | 11/2009 | Kini et al. |
| 2009/0324546 | A1 | 12/2009 | Notka et al. |
| 2010/0004143 | A1 | 1/2010 | Shibahara |
| 2010/0008851 | A1 | 1/2010 | Nicolaides et al. |
| 2010/0009872 | A1 | 1/2010 | Eid et al. |
| 2010/0047805 | A1 | 2/2010 | Wang |
| 2010/0051967 | A1 | 3/2010 | Bradley et al. |
| 2010/0069250 | A1 | 3/2010 | White, III et al. |
| 2010/0090341 | A1 | 4/2010 | Wan et al. |
| 2010/0099103 | A1 | 4/2010 | Hsieh et al. |
| 2010/0111768 | A1 | 5/2010 | Banerjee et al. |
| 2010/0160463 | A1 | 6/2010 | Wang et al. |
| 2010/0167950 | A1 | 7/2010 | Juang et al. |
| 2010/0173364 | A1 | 7/2010 | Evans, Jr. et al. |
| 2010/0216648 | A1 | 8/2010 | Staehler et al. |
| 2010/0256017 | A1 | 10/2010 | Larman et al. |
| 2010/0258487 | A1 | 10/2010 | Zelechonok et al. |
| 2010/0272711 | A1 | 10/2010 | Feldman et al. |
| 2010/0286290 | A1 | 11/2010 | Lohmann et al. |
| 2010/0292102 | A1 | 11/2010 | Nouri |
| 2010/0300882 | A1 | 12/2010 | Zhang et al. |
| 2011/0009607 | A1 | 1/2011 | Komiyama et al. |
| 2011/0082055 | A1 | 4/2011 | Fox et al. |
| 2011/0114244 | A1 | 5/2011 | Yoo et al. |
| 2011/0114549 | A1 | 5/2011 | Yin et al. |
| 2011/0124049 | A1 | 5/2011 | Li et al. |
| 2011/0124055 | A1 | 5/2011 | Carr et al. |
| 2011/0126929 | A1 | 6/2011 | Velasquez-Garcia et al. |
| 2011/0171651 | A1 | 7/2011 | Richmond |
| 2011/0172127 | A1 | 7/2011 | Jacobson et al. |
| 2011/0201057 | A1 | 8/2011 | Carr et al. |
| 2011/0217738 | A1 | 9/2011 | Jacobson |
| 2011/0230653 | A1 | 9/2011 | Novoradovskaya et al. |
| 2011/0254107 | A1 | 10/2011 | Bulovic et al. |
| 2011/0287435 | A1 | 11/2011 | Grunenwald et al. |
| 2012/0003713 | A1 | 1/2012 | Hansen et al. |
| 2012/0021932 | A1 | 1/2012 | Mershin et al. |
| 2012/0027786 | A1 | 2/2012 | Gupta et al. |
| 2012/0028843 | A1 | 2/2012 | Ramu et al. |
| 2012/0032366 | A1 | 2/2012 | Ivniski et al. |
| 2012/0046175 | A1 | 2/2012 | Rodesch et al. |
| 2012/0050411 | A1 | 3/2012 | Mabritto et al. |
| 2012/0094847 | A1 | 4/2012 | Warthmann et al. |
| 2012/0128548 | A1 | 5/2012 | West et al. |
| 2012/0129704 | A1 | 5/2012 | Gunderson et al. |
| 2012/0149602 | A1 | 6/2012 | Friend et al. |
| 2012/0164127 | A1 | 6/2012 | Short et al. |
| 2012/0164633 | A1 | 6/2012 | Laffler |
| 2012/0164691 | A1 | 6/2012 | Eshoo et al. |
| 2012/0184724 | A1 | 7/2012 | Sierzchala et al. |
| 2012/0220497 | A1 | 8/2012 | Jacobson et al. |
| 2012/0231968 | A1 | 9/2012 | Bruhn et al. |
| 2012/0238737 | A1 | 9/2012 | Dellinger et al. |
| 2012/0258487 | A1 | 10/2012 | Chang et al. |
| 2012/0264653 | A1 | 10/2012 | Carr et al. |
| 2012/0270750 | A1 | 10/2012 | Oleinikov |
| 2012/0270754 | A1 | 10/2012 | Blake |
| 2012/0283140 | A1 | 11/2012 | Chu |
| 2012/0288476 | A1 | 11/2012 | Hartmann et al. |
| 2012/0289691 | A1 | 11/2012 | Dellinger et al. |
| 2012/0315670 | A1 | 12/2012 | Jacobson et al. |
| 2012/0322681 | A1 | 12/2012 | Kung et al. |
| 2013/0005585 | A1 | 1/2013 | Anderson et al. |
| 2013/0005612 | A1 | 1/2013 | Carr et al. |
| 2013/0017642 | A1 | 1/2013 | Milgrew et al. |
| 2013/0017977 | A1 | 1/2013 | Oleinikov |
| 2013/0017978 | A1 | 1/2013 | Kavanagh et al. |
| 2013/0035261 | A1 | 2/2013 | Sierzchala et al. |
| 2013/0040836 | A1 | 2/2013 | Himmler et al. |
| 2013/0045483 | A1 | 2/2013 | Treusch et al. |
| 2013/0053252 | A1 | 2/2013 | Xie et al. |
| 2013/0059296 | A1 | 3/2013 | Jacobson et al. |
| 2013/0059761 | A1 | 3/2013 | Jacobson et al. |
| 2013/0065017 | A1 | 3/2013 | Sieber |
| 2013/0109595 | A1 | 5/2013 | Routenberg |
| 2013/0109596 | A1 | 5/2013 | Peterson et al. |
| 2013/0123129 | A1 | 5/2013 | Zeiner et al. |
| 2013/0130321 | A1 | 5/2013 | Staehler et al. |
| 2013/0137161 | A1 | 5/2013 | Zhang et al. |
| 2013/0137173 | A1 | 5/2013 | Zhang et al. |
| 2013/0137174 | A1 | 5/2013 | Zhang et al. |
| 2013/0137861 | A1 | 5/2013 | Leproust et al. |
| 2013/0164308 | A1 | 6/2013 | Foletti et al. |
| 2013/0165328 | A1 | 6/2013 | Previte et al. |
| 2013/0196864 | A1 | 8/2013 | Govindarajan et al. |
| 2013/0225421 | A1 | 8/2013 | Li et al. |
| 2013/0244884 | A1 | 9/2013 | Jacobson et al. |
| 2013/0252849 | A1 | 9/2013 | Hudson et al. |

(56) References Cited

U.S. PATENT DOCUMENTS

2013/0261027 A1 10/2013 Li et al.
2013/0281308 A1 10/2013 Kung et al.
2013/0289246 A1 10/2013 Crowe et al.
2013/0296192 A1 11/2013 Jacobson et al.
2013/0296194 A1 11/2013 Jacobson et al.
2013/0298265 A1 11/2013 Cunnac et al.
2013/0309725 A1 11/2013 Jacobson et al.
2013/0323725 A1 12/2013 Peter et al.
2013/0330778 A1 12/2013 Zeiner et al.
2014/0011226 A1 1/2014 Bernick et al.
2014/0018441 A1 1/2014 Fracchia et al.
2014/0031240 A1 1/2014 Behlke et al.
2014/0038240 A1 2/2014 Temme et al.
2014/0106394 A1 4/2014 Ko et al.
2014/0141982 A1 5/2014 Jacobson et al.
2014/0170665 A1 6/2014 Hiddessen et al.
2014/0178992 A1 6/2014 Nakashima et al.
2014/0221250 A1 8/2014 Vasquez et al.
2014/0274729 A1 9/2014 Kurn et al.
2014/0274741 A1 9/2014 Hunter et al.
2014/0303000 A1 10/2014 Armour et al.
2014/0309119 A1 10/2014 Jacobson et al.
2014/0309142 A1 10/2014 Tian
2014/0322236 A1 10/2014 Chambers et al.
2015/0010953 A1 1/2015 Lindstrom et al.
2015/0012723 A1 1/2015 Park et al.
2015/0031089 A1 1/2015 Lindstrom
2015/0038373 A1 2/2015 Banyai et al.
2015/0056609 A1 2/2015 Daum et al.
2015/0057625 A1 2/2015 Coulthard
2015/0065357 A1 3/2015 Fox
2015/0065393 A1 3/2015 Jacobson
2015/0099870 A1 4/2015 Bennett et al.
2015/0120265 A1 4/2015 Amirav-Drory et al.
2015/0159152 A1 6/2015 Allen et al.
2015/0183853 A1 7/2015 Sharma et al.
2015/0191524 A1 7/2015 Smith et al.
2015/0191719 A1 7/2015 Hudson et al.
2015/0196917 A1 7/2015 Kay et al.
2015/0203839 A1 7/2015 Jacobson et al.
2015/0211047 A1 7/2015 Borns
2015/0225782 A1 8/2015 Walder et al.
2015/0240232 A1 8/2015 Zamore et al.
2015/0240280 A1 8/2015 Gibson et al.
2015/0261664 A1 9/2015 Goldman et al.
2015/0269313 A1 9/2015 Church
2015/0293102 A1 10/2015 Shim
2015/0307875 A1 10/2015 Happe et al.
2015/0321191 A1 11/2015 Kendall et al.
2015/0322504 A1 11/2015 Lao et al.
2015/0344927 A1 12/2015 Sampson et al.
2015/0353921 A9 12/2015 Tian
2015/0353994 A1 12/2015 Myers et al.
2015/0361420 A1 12/2015 Hudson et al.
2015/0361422 A1 12/2015 Sampson et al.
2015/0361423 A1 12/2015 Sampson et al.
2015/0368349 A1 12/2015 Gonzalez et al.
2015/0368687 A1 12/2015 Saaem et al.
2015/0376602 A1 12/2015 Jacobson et al.
2016/0001247 A1 1/2016 Oleinikov
2016/0002621 A1 1/2016 Nelson et al.
2016/0002622 A1 1/2016 Nelson et al.
2016/0010045 A1 1/2016 Cohen et al.
2016/0017394 A1 1/2016 Liang et al.
2016/0017425 A1 1/2016 Ruvolo et al.
2016/0019341 A1 1/2016 Harris et al.
2016/0024138 A1 1/2016 Gebeyehu et al.
2016/0024576 A1 1/2016 Chee
2016/0026753 A1 1/2016 Krishnaswami et al.
2016/0026758 A1 1/2016 Jabara et al.
2016/0032396 A1 2/2016 Diehn et al.
2016/0046973 A1 2/2016 Efcavitch et al.
2016/0046974 A1 2/2016 Efcavitch et al.
2016/0082472 A1 3/2016 Perego et al.
2016/0089651 A1 3/2016 Banyai
2016/0090422 A1 3/2016 Reif et al.
2016/0090592 A1 3/2016 Banyai et al.
2016/0096160 A1 4/2016 Banyai et al.
2016/0097051 A1 4/2016 Jacobson et al.
2016/0102322 A1 4/2016 Ravinder et al.
2016/0108466 A1 4/2016 Nazarenko et al.
2016/0122755 A1 5/2016 Hall et al.
2016/0122800 A1 5/2016 Bernick et al.
2016/0152972 A1 6/2016 Stapleton et al.
2016/0168611 A1 6/2016 Efcavitch et al.
2016/0184788 A1 6/2016 Hall et al.
2016/0200759 A1 7/2016 Srivastava et al.
2016/0215283 A1 7/2016 Braman et al.
2016/0229884 A1 8/2016 Indermuhle et al.
2016/0230175 A1 8/2016 Carstens
2016/0230221 A1 8/2016 Bergmann et al.
2016/0251651 A1 9/2016 Banyai et al.
2016/0256846 A1 9/2016 Smith et al.
2016/0264958 A1 9/2016 Toro et al.
2016/0289758 A1 10/2016 Akeson et al.
2016/0289839 A1 10/2016 Harumoto et al.
2016/0303535 A1 10/2016 Banyai et al.
2016/0304862 A1 10/2016 Igawa et al.
2016/0304946 A1 10/2016 Betts et al.
2016/0310426 A1 10/2016 Wu
2016/0310927 A1 10/2016 Banyai et al.
2016/0318016 A1 11/2016 Hou et al.
2016/0333340 A1 11/2016 Wu
2016/0339409 A1 11/2016 Banyai et al.
2016/0340672 A1 11/2016 Banyai et al.
2016/0348098 A1 12/2016 Stuelpnagel et al.
2016/0354752 A1 12/2016 Banyai et al.
2016/0355880 A1 12/2016 Gormley et al.
2017/0017436 A1 1/2017 Church
2017/0066844 A1 3/2017 Glanville
2017/0067099 A1 3/2017 Zheng et al.
2017/0073664 A1 3/2017 McCafferty et al.
2017/0073731 A1 3/2017 Zheng et al.
2017/0081716 A1 3/2017 Peck
2017/0088887 A1 3/2017 Makarov et al.
2017/0095785 A1 4/2017 Banyai et al.
2017/0096706 A1 4/2017 Behlke et al.
2017/0114404 A1 4/2017 Behlke et al.
2017/0141793 A1 5/2017 Strauss et al.
2017/0147748 A1 5/2017 Staehler et al.
2017/0151546 A1 6/2017 Peck et al.
2017/0159044 A1 6/2017 Toro et al.
2017/0175110 A1 6/2017 Jacobson et al.
2017/0218537 A1 8/2017 Olivares
2017/0233764 A1 8/2017 Young et al.
2017/0247473 A1 8/2017 Short
2017/0249345 A1 8/2017 Malik et al.
2017/0253644 A1 9/2017 Steyaert et al.
2017/0315140 A1 11/2017 Ruf et al.
2017/0320061 A1 11/2017 Venter et al.
2017/0355984 A1 12/2017 Evans et al.
2017/0357752 A1 12/2017 Diggans
2017/0362589 A1 12/2017 Banyai et al.
2018/0051278 A1 2/2018 Cox et al.
2018/0051280 A1 2/2018 Gibson et al.
2018/0068060 A1 3/2018 Ceze et al.
2018/0104664 A1 4/2018 Fernandez
2018/0126355 A1 5/2018 Peck et al.
2018/0142289 A1 5/2018 Zeitoun et al.
2018/0171509 A1 6/2018 Cox
2018/0253563 A1 9/2018 Peck et al.
2018/0264428 A1 9/2018 Banyai et al.
2018/0282721 A1 10/2018 Cox et al.
2018/0291445 A1 10/2018 Betts et al.
2018/0312834 A1 11/2018 Cox et al.
2018/0326388 A1 11/2018 Banyai et al.
2018/0334712 A1 11/2018 Singer et al.
2018/0346585 A1 12/2018 Zhang et al.
2018/0355351 A1 12/2018 Nugent et al.
2019/0060345 A1 2/2019 Harrison et al.
2019/0083596 A1 3/2019 Orentas et al.
2019/0135926 A1 5/2019 Glanville
2019/0240636 A1 8/2019 Peck et al.
2019/0244109 A1 8/2019 Bramlett et al.

(56) References Cited

U.S. PATENT DOCUMENTS

| | | | |
|---|---|---|---|
| 2019/0330335 | A1 | 10/2019 | Schwabe et al. |
| 2019/0352635 | A1 | 11/2019 | Toro et al. |
| 2019/0366293 | A1 | 12/2019 | Banyai et al. |
| 2019/0382481 | A1 | 12/2019 | Diem et al. |
| 2020/0017907 | A1 | 1/2020 | Zeitoun et al. |
| 2020/0102390 | A1 | 4/2020 | Beers et al. |
| 2020/0102611 | A1 | 4/2020 | Zeitoun et al. |
| 2020/0156037 | A1 | 5/2020 | Banyai et al. |
| 2020/0181667 | A1 | 6/2020 | Wu et al. |
| 2020/0222875 | A1 | 7/2020 | Peck et al. |
| 2020/0283760 | A1 | 9/2020 | Nugent et al. |
| 2020/0299322 | A1 | 9/2020 | Indermuhle et al. |
| 2020/0299684 | A1 | 9/2020 | Toro et al. |
| 2020/0308575 | A1 | 10/2020 | Sato |
| 2020/0325235 | A1 | 10/2020 | Tabibiazar et al. |
| 2020/0342143 | A1 | 10/2020 | Peck |
| 2021/0002710 | A1 | 1/2021 | Gantt et al. |
| 2021/0040476 | A1 | 2/2021 | Cox et al. |
| 2021/0179724 | A1 | 6/2021 | Sato et al. |
| 2022/0259319 | A1 | 8/2022 | Sato et al. |

FOREIGN PATENT DOCUMENTS

| | | | |
|---|---|---|---|
| CN | 1771336 | A | 5/2006 |
| CN | 102159726 | A | 8/2011 |
| CN | 103907117 | A | 7/2014 |
| CN | 104520864 | A | 4/2015 |
| CN | 104562213 | A | 4/2015 |
| CN | 104734848 | A | 6/2015 |
| CN | 105637097 | A | 6/2016 |
| DE | 10260805 | A1 | 7/2004 |
| EP | 0090789 | A1 | 10/1983 |
| EP | 0126621 | B1 | 8/1990 |
| EP | 0753057 | A1 | 1/1997 |
| EP | 1314783 | A1 | 5/2003 |
| EP | 1363125 | A2 | 11/2003 |
| EP | 1546387 | A2 | 6/2005 |
| EP | 1153127 | B1 | 7/2006 |
| EP | 1728860 | A1 | 12/2006 |
| EP | 1072010 | B1 | 4/2010 |
| EP | 2175021 | A2 | 4/2010 |
| EP | 2330216 | A1 | 6/2011 |
| EP | 1343802 | B1 | 5/2012 |
| EP | 2504449 | A1 | 10/2012 |
| EP | 2751729 | A1 | 7/2014 |
| EP | 2872629 | A1 | 5/2015 |
| EP | 2928500 | A1 | 10/2015 |
| EP | 2971034 | A1 | 1/2016 |
| EP | 3030682 | A2 | 6/2016 |
| EP | 3044228 | A4 | 4/2017 |
| EP | 2994509 | B1 | 6/2017 |
| EP | 3204518 | A1 | 8/2017 |
| JP | 2001518086 | A | 10/2001 |
| JP | 2002511276 | A | 4/2002 |
| JP | 2002536977 | A | 11/2002 |
| JP | 2002538790 | A | 11/2002 |
| JP | 2006503586 | A | 2/2006 |
| JP | 2006238724 | A | 9/2006 |
| JP | 2008505642 | A | 2/2008 |
| JP | 2008097189 | A | 4/2008 |
| JP | 2008523786 | A | 7/2008 |
| JP | 2008214343 | A | 9/2008 |
| JP | 2009294195 | A | 12/2009 |
| JP | 2011097869 | A | 5/2011 |
| JP | 2013183660 | A | 9/2013 |
| JP | 2016527313 | A | 9/2016 |
| WO | WO-9015070 | A1 | 12/1990 |
| WO | WO-9210092 | A1 | 6/1992 |
| WO | WO-9210588 | A1 | 6/1992 |
| WO | WO-9309668 | A1 | 5/1993 |
| WO | WO-9320242 | A1 | 10/1993 |
| WO | WO-9525116 | A1 | 9/1995 |
| WO | WO-9526397 | A1 | 10/1995 |
| WO | WO-9615861 | A1 | 5/1996 |
| WO | WO-9710365 | A1 | 3/1997 |
| WO | WO-9822541 | A2 | 5/1998 |
| WO | WO-9841531 | A2 | 9/1998 |
| WO | WO-9942813 | A1 | 8/1999 |
| WO | WO-9953101 | A1 | 10/1999 |
| WO | WO-0013017 | A2 | 3/2000 |
| WO | WO-0018957 | A1 | 4/2000 |
| WO | WO-0042559 | A1 | 7/2000 |
| WO | WO-0042560 | A2 | 7/2000 |
| WO | WO-0042561 | A2 | 7/2000 |
| WO | WO-0049142 | A1 | 8/2000 |
| WO | WO-0053617 | A1 | 9/2000 |
| WO | WO-0156216 | A2 | 8/2001 |
| WO | WO-0210443 | A1 | 2/2002 |
| WO | WO-0156216 | A3 | 3/2002 |
| WO | WO-0220537 | A2 | 3/2002 |
| WO | WO-0224597 | A2 | 3/2002 |
| WO | WO-0227638 | A1 | 4/2002 |
| WO | WO-02072791 | A2 | 9/2002 |
| WO | WO-03040410 | A1 | 5/2003 |
| WO | WO-03046223 | A1 | 6/2003 |
| WO | WO-03054232 | A2 | 7/2003 |
| WO | WO-03060084 | A2 | 7/2003 |
| WO | WO-03064026 | A1 | 8/2003 |
| WO | WO-03064027 | A2 | 8/2003 |
| WO | WO-03064699 | A2 | 8/2003 |
| WO | WO-03065038 | A2 | 8/2003 |
| WO | WO-03066212 | A2 | 8/2003 |
| WO | WO-03089605 | A2 | 10/2003 |
| WO | WO-03093504 | A1 | 11/2003 |
| WO | WO-03100012 | A2 | 12/2003 |
| WO | WO-2004024886 | A2 | 3/2004 |
| WO | WO-2004029220 | A2 | 4/2004 |
| WO | WO-2004029586 | A1 | 4/2004 |
| WO | WO-2004031351 | A2 | 4/2004 |
| WO | WO-2004031399 | A2 | 4/2004 |
| WO | WO-2004059556 | A2 | 7/2004 |
| WO | WO-03060084 | A3 | 8/2004 |
| WO | WO-2005014850 | A2 | 2/2005 |
| WO | WO-2005051970 | A2 | 6/2005 |
| WO | WO-2005059096 | A2 | 6/2005 |
| WO | WO-2005059097 | A2 | 6/2005 |
| WO | WO-2005093092 | A2 | 10/2005 |
| WO | WO-2006023144 | | 3/2006 |
| WO | WO-2006044956 | A1 | 4/2006 |
| WO | WO-2006076679 | A1 | 7/2006 |
| WO | WO-2006116476 | A1 | 11/2006 |
| WO | WO-2007109221 | A2 | 9/2007 |
| WO | WO-2007118214 | A2 | 10/2007 |
| WO | WO-2007120627 | A2 | 10/2007 |
| WO | WO-2007137242 | A2 | 11/2007 |
| WO | WO-2008003116 | A2 | 1/2008 |
| WO | WO-2008006078 | A2 | 1/2008 |
| WO | WO-2008027558 | A2 | 3/2008 |
| WO | WO-2008045380 | | 4/2008 |
| WO | WO-2008054543 | A2 | 5/2008 |
| WO | WO-2008063134 | A1 | 5/2008 |
| WO | WO-2008063135 | A1 | 5/2008 |
| WO | WO-2008068280 | A1 | 6/2008 |
| WO | WO-2008103474 | A1 | 8/2008 |
| WO | WO-2008109176 | A2 | 9/2008 |
| WO | WO-2010001251 | A2 | 1/2010 |
| WO | WO-2010025310 | A2 | 3/2010 |
| WO | WO-2010025566 | A1 | 3/2010 |
| WO | WO-2010027512 | A2 | 3/2010 |
| WO | WO-2010089412 | A1 | 8/2010 |
| WO | WO-2010141249 | A2 | 12/2010 |
| WO | WO-2010141433 | A2 | 12/2010 |
| WO | WO-2011020529 | A2 | 2/2011 |
| WO | WO-2010141433 | A3 | 4/2011 |
| WO | WO-2011053957 | A2 | 5/2011 |
| WO | WO-2011056644 | A2 | 5/2011 |
| WO | WO-2011056872 | A2 | 5/2011 |
| WO | WO-2011066185 | A1 | 6/2011 |
| WO | WO-2011066186 | A1 | 6/2011 |
| WO | WO-2011085075 | A2 | 7/2011 |
| WO | WO-2011103468 | A2 | 8/2011 |
| WO | WO-2011109031 | A1 | 9/2011 |
| WO | WO-2011143556 | A1 | 11/2011 |
| WO | WO-2011150168 | A1 | 12/2011 |

(56) References Cited

FOREIGN PATENT DOCUMENTS

| | | | |
|---|---|---|---|
| WO | WO-2011161413 | A2 | 12/2011 |
| WO | WO-2012013913 | A1 | 2/2012 |
| WO | WO-2012061832 | A1 | 5/2012 |
| WO | WO-2012078312 | A2 | 6/2012 |
| WO | WO-2012149171 | A1 | 11/2012 |
| WO | WO-2012154201 | A1 | 11/2012 |
| WO | WO-2013030827 | A1 | 3/2013 |
| WO | WO-2013032850 | A2 | 3/2013 |
| WO | WO-2013036668 | A1 | 3/2013 |
| WO | WO-2013101896 | A1 | 7/2013 |
| WO | WO-2013154770 | A1 | 10/2013 |
| WO | WO-2013177220 | A1 | 11/2013 |
| WO | WO-2014004393 | A1 | 1/2014 |
| WO | WO-2014008447 | A1 | 1/2014 |
| WO | WO-2014035693 | A2 | 3/2014 |
| WO | WO-2014088693 | A1 | 6/2014 |
| WO | WO-2014089160 | A1 | 6/2014 |
| WO | WO-2014093330 | A1 | 6/2014 |
| WO | WO-2014093694 | A1 | 6/2014 |
| WO | WO-2014151117 | A1 | 9/2014 |
| WO | WO-2014151696 | A1 | 9/2014 |
| WO | WO-2014160004 | A1 | 10/2014 |
| WO | WO-2014160059 | A1 | 10/2014 |
| WO | WO-2014206304 | A1 | 12/2014 |
| WO | WO-2015017527 | A2 | 2/2015 |
| WO | WO-2015021080 | A2 | 2/2015 |
| WO | WO-2015021280 | A1 | 2/2015 |
| WO | WO-2015031689 | A1 | 3/2015 |
| WO | WO-2015040075 | A1 | 3/2015 |
| WO | WO-2015054292 | A1 | 4/2015 |
| WO | WO-2015066174 | A1 | 5/2015 |
| WO | 2015081440 | A1 | 6/2015 |
| WO | WO-2015081114 | A2 | 6/2015 |
| WO | WO-2015081142 | A1 | 6/2015 |
| WO | WO-2015090879 | A1 | 6/2015 |
| WO | WO-2015095404 | A2 | 6/2015 |
| WO | WO-2015120403 | A1 | 8/2015 |
| WO | WO-2015136072 | A1 | 9/2015 |
| WO | WO-2015175832 | A1 | 11/2015 |
| WO | WO-2016007604 | A1 | 1/2016 |
| WO | WO-2016011080 | A2 | 1/2016 |
| WO | WO-2016022557 | A1 | 2/2016 |
| WO | WO-2016053883 | A1 | 4/2016 |
| WO | WO-2016055956 | A1 | 4/2016 |
| WO | WO-2016065056 | A1 | 4/2016 |
| WO | WO-2016126882 | A1 | 8/2016 |
| WO | WO-2016126987 | A1 | 8/2016 |
| WO | WO-2016130868 | A2 | 8/2016 |
| WO | WO-2016161244 | A2 | 10/2016 |
| WO | WO-2016162127 | A1 | 10/2016 |
| WO | WO-2016164779 | A1 | 10/2016 |
| WO | WO-2016172377 | A1 | 10/2016 |
| WO | WO-2016173719 | A1 | 11/2016 |
| WO | WO-2016183100 | A1 | 11/2016 |
| WO | WO-2017049231 | A1 | 3/2017 |
| WO | WO-2017053450 | A1 | 3/2017 |
| WO | WO-2017059399 | A1 | 4/2017 |
| WO | 2017112917 | A1 | 6/2017 |
| WO | WO-2017095958 | A1 | 6/2017 |
| WO | WO-2017100441 | A1 | 6/2017 |
| WO | WO-2017118761 | A1 | 7/2017 |
| WO | WO-2017158103 | A1 | 9/2017 |
| WO | WO-2017214574 | A1 | 12/2017 |
| WO | WO-2018026920 | A1 | 2/2018 |
| WO | WO-2018038772 | A1 | 3/2018 |
| WO | WO-2018057526 | A2 | 3/2018 |
| WO | WO-2018094263 | A1 | 5/2018 |
| WO | 2018119246 | A1 | 6/2018 |
| WO | WO-2018112426 | A1 | 6/2018 |
| WO | WO-2018156792 | A1 | 8/2018 |
| WO | 2018170559 | A1 | 9/2018 |
| WO | WO-2018170164 | A1 | 9/2018 |
| WO | WO-2018170169 | A1 | 9/2018 |
| WO | WO-2018200380 | A1 | 11/2018 |
| WO | 2018231864 | A1 | 12/2018 |
| WO | WO-2018231872 | A1 | 12/2018 |
| WO | WO-2019014781 | A1 | 1/2019 |
| WO | WO-2019051501 | A1 | 3/2019 |
| WO | WO-2019079769 | A1 | 4/2019 |
| WO | 2019090347 | A1 | 5/2019 |
| WO | WO-2019084500 | A1 | 5/2019 |
| WO | WO-2019136175 | A1 | 7/2019 |
| WO | 2019224711 | A2 | 11/2019 |
| WO | WO-2019222706 | A1 | 11/2019 |
| WO | WO-2020139871 | A1 | 7/2020 |
| WO | WO-2020176362 | A1 | 9/2020 |
| WO | WO-2020176678 | A1 | 9/2020 |
| WO | WO-2020176680 | A1 | 9/2020 |
| WO | WO-2020257612 | A1 | 12/2020 |
| WO | 2021061829 | A1 | 4/2021 |
| WO | 2021061842 | A1 | 4/2021 |
| WO | 2021119193 | A2 | 6/2021 |
| WO | 2021222315 | A2 | 11/2021 |
| WO | 2021222316 | A2 | 11/2021 |
| WO | 2022010934 | A2 | 1/2022 |
| WO | 2022046797 | A1 | 3/2022 |
| WO | 2022046944 | A2 | 3/2022 |
| WO | 2022047076 | A1 | 3/2022 |
| WO | 2022076326 | A1 | 4/2022 |
| WO | 2022086866 | A1 | 4/2022 |
| WO | 2022087293 | A1 | 4/2022 |
| WO | 2022093811 | A1 | 5/2022 |
| WO | 2022098662 | A2 | 5/2022 |
| WO | 2022159620 | A1 | 7/2022 |
| WO | 2022178137 | A1 | 8/2022 |
| WO | 2022204301 | A1 | 9/2022 |
| WO | 2022204309 | A1 | 9/2022 |
| WO | 2022204316 | A2 | 9/2022 |
| WO | 2022217004 | A1 | 10/2022 |
| WO | 2022235579 | A1 | 11/2022 |
| WO | 2022235584 | A1 | 11/2022 |
| WO | 2022271884 | A2 | 12/2022 |
| WO | 2023023183 | A2 | 2/2023 |
| WO | 2023023190 | A2 | 2/2023 |
| WO | 2023023285 | A2 | 2/2023 |
| WO | 2023069367 | A1 | 4/2023 |
| WO | 2023076419 | A2 | 5/2023 |
| WO | 2023076420 | A2 | 5/2023 |
| WO | 2023076687 | A1 | 5/2023 |
| WO | 2023091609 | A2 | 5/2023 |
| WO | 2023091614 | A2 | 5/2023 |
| WO | 2023102034 | A2 | 6/2023 |
| WO | 2023114432 | A2 | 6/2023 |
| WO | 2023130123 | A2 | 7/2023 |
| WO | 2023154533 | A2 | 8/2023 |
| WO | 2023172520 | A2 | 9/2023 |
| WO | 2023191858 | A2 | 10/2023 |
| WO | 2023192635 | A2 | 10/2023 |
| WO | 2023196499 | A1 | 10/2023 |
| WO | 2023205345 | A2 | 10/2023 |

OTHER PUBLICATIONS

Rudikoff, S et al. (1982) Proc. Natl. Acad. Sci. USA, 79:1979-1983 (doi: 10.1073/pnas.79.6.1979).*

Colman, PM (1994) Research in Immunology, Elsevier, NY, 145(1):33-36.*

Bendig M. M. (1995) Methods: A Companion to Methods in Enzymology, 8:83-93.*

MacCallum et al. (Oct. 11, 1996) J. Mol. Biol., 262(5):732-745. (doi: 10.1006/jmbi.1996.0548).*

Casset et al (2003) Biochemical and Biophysical Research Communications, 307:198-205. (doi:10.1016/S0006-291X(03)01131-8).*

Chen et al. (1995) EMBO J., 14(12):2784-2794. (doi: 10.1002/j.1460-2075.1995.tb07278.x).*

Abudayyeh et al.: C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf 17 pages.

Acevedo-Rocha et al.: Directed evolution of stereoselective enzymes based on genetic selection as opposed to screening systems. J. Biotechnol. 191:3-10 (2014).

(56) References Cited

OTHER PUBLICATIONS

Adessi et al.: Solid phase DNA amplification: characterisation of primer attachment and amplification mechanisms. Nucleic Acids Res. 28(20):E87, 2000.
Alberts et al.: Molecular Biology of the Cell. 4th edition. New York: Garland Science; 2002. The Generation of Antibody Diversity. https://www.ncbi.nlm.nih.gov/books/NBK26860/.
Alexeyev et al.: Gene synthesis, bacterial expression and purification of the Rickettsia prowazekii ATP/ADP translocase, Biochimica et Biophysics Acta, 1419:299-306, 1999.
Al-Housseiny et al.: Control of interfacial instabilities using flow geometry Nature Physics, 8:747-750, 2012.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Amblard et al.: A magnetic manipulator for studying local rheology and micromechanical properties of biological systems, Rev. Sci. Instrum., 67(3):18-827, 1996.
Andoni and Indyk. Near-Optimal Hashing Algorithms for Approximate Nearest Neighbor in High Dimensions, Communications of the ACM, 51(1):117-122, 2008.
Arand et al.: Structure of Rhodococcus erythropolis limonene-1,2-epoxide hydrolase reveals a novel active site. EMBO J. 22:2583-2592 (2003).
Arkles et al.: The Role of Polarity in the Structure of Silanes Employed in Surface Modification. Silanes and Other Coupling Agents. 5:51-64, 2009.
Arkles. Hydrophobicity, Hydrophilicity Reprinted with permission from the Oct. 2006 issue of Paint & Coatings Industry magazine, Retrieved on Mar. 19, 2016, 10 pages.
Assembly manual for the POSaM: The ISB Piezoelectric Oligonucleotide Synthesizer and Microarrayer, The Institute for Systems Biology, May 28, 2004 (50 pages).
Assi et al.: Massive-parallel adhesion and reactivity-measurements using simple and inexpensive magnetic tweezers. J. Appl. Phys. 92(9):5584-5586 (2002).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Au et al.: Gene synthesis by a LCR-based approach: high level production of Leptin-L54 using synthetic gene in *Escherichia coli*. Biochemical and Biophysical Research Communications 248:200-203 (1998).
Baedeker et al.: Overexpression of a designed 2.2kb gene of eukaryotic phenylalanine ammonialyase in *Escherichia coli*•. FEBS Letters, 457:57-60, 1999.
Barbee et al.: Magnetic Assembly of High-Density DNA Arrays for Genomic Analyses. Anal Chem. 80(6):2149-2154, 2008.
Barton et al.: A desk electrohydrodynamic jet printing system. Mechatronics, 20:611-616, 2010.
Beaucage et al.: Advances in the synthesis of oligonucleotides by the phosphoramidite approach. Tetrahedron. 48:2223-2311, 1992.
Beaucage et al.: Deoxynucleoside phosphoramidites—A new class of key intermediates for deoxypolynucleotide synthesis. Tetrahedron Lett. 22(20):1859-1862, 1981.
Beaucage et al.: The Chemical synthesis of DNA/RNA Chapter 2 in: Encyclopedia of Cell Biology, 1:36-53, 2016.
Beaulieu et al.: PCR candidate region mismatch scanning adaptation to quantitative, high-throughput genotyping, Nucleic Acids Research, 29(5):1114-1124, 2001.
Beigelman et al.: Base-modified phosphoramidite analogs of pyrimidine ribonucleosides for RNA structure-activity studies. Methods Enzymol. 317:39-65, 2000.
Bethge et al.: Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%2001igonucleotides%20%2864-108%29.pdf.
Binkowski et al.: Correcting errors in synthetic DNA through consensus shuffling. Nucleic Acids Research, 33(6):e55, 8 pages, 2005.
Biswas et al.: Identification and characterization of a thermostable MutS homolog from Thennus aquaticus, The Journal of Biological Chemistry, 271(9):5040-5048, 1996.
Biswas et al.: Interaction of MutS protein with the major and minor grooves of a heteroduplex DNA, The Journal of Biological Chemistry, 272(20):13355-13364, 1997.
Bjornson et al.: Differential and simultaneous adenosine Di- and Triphosphate binding by MutS, The Journal of Biological Chemistry, 278(20):18557-18562, 2003.
Blanchard et al.: High-Density Oligonucleotide Arrays, Biosensors & Bioelectronics, 11(6/7):687-690, 1996.
Blanchard: Genetic Engineering, Principles and Methods, vol. 20, Ed. J. Sedlow, New York: Plenum Press, p. 111-124, 1979.
Blawat et al.: Forward error correction for DNA data storage. Procedia Computer Science, 80:1011-1022, 2016.
Bonini and Mondino. Adoptive T-cell therapy for cancer: The era of engineered T cells. European Journal of Immunology, 45:2457-2469, 2015.
Bornholt et al.: A DNA-Based Archival Storage System, in International Conference on Architectural Support for Programming Languages and Operating Systems (ASPLOS), Apr. 2-6, 2016, Atlanta, GA, 2016, 637-649.
Borovkov et al.: High-quality gene assembly directly from unpurified mixtures of microassay-synthesized oligonucleotides. Nucleic Acid Research, 38(19):e180, 10 pages, 2010.
Brunet: Aims and methods of biosteganography. Journal of Biotechnology, 226:56-64, 2016.
Buermans et al.: Next Generation sequencing technology: Advances and applications, Biochimica et Biophysica Acta (BBA)—Molecular Basis of Disease, 1842:1931-1941, 2014.
Butler et al.: In situ synthesis of oligonucleotide arrays by using surface tension. J Am Chem Soc. 123(37):8887-94, 2001.
Calvert. Lithographically patterned self-assembled films. In: Organic Thin Films and Surfaces: Directions for the Nineties, vol. 20, p. 109, ed. by Abraham Ulman, San Diego: Academic Press, 1995.
Cardelli. Two-Domain DNA Strand Displacement, Electron. Proc. Theor. Comput. Sci., 26:47-61, 2010.
Carlson. Time for New DNA Synthesis and Sequencing Cost Curves, 2014. [Online]. Available: http://www.synthesis.cc/synthesis/2014/02/time_for_new_cost_curves_2014. 10 pages.
Carr et al.: Protein-mediated error correction for de novo DNA synthesis. Nucleic Acids Res. 32(20):e162, 9 pages, 2004.
Carter and Friedman. DNA synthesis and Biosecurity: Lessons learned and options for the future. J. Craig Venter Institute, La Jolla, CA, 28 pages, Oct. 2015.
Caruthers. Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science 230(4723):281-285 (1985).
Caruthers. The Chemical Synthesis of DNA/RNA: Our Gift to Science. J. Biol. Chem., 288(2):1420-1427, 2013.
Casmiro et al.: PCR-based gene synthesis and protein NMR spectroscopy, Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello et al.: Chemical synthesis of poliovirus cDNA: generation of infectious virus in the absence of natural template. Science. 297(5583):1016-8, 2000.
Chalmers et al.: Scaling up the ligase chain reaction-based approach to gene synthesis. Biotechniques. 30(2):249-52, 2001.
Chan et al.: Natural and engineered nicking endonucleases—from cleavage mechanism to engineering of strand-specificity. Nucleic Acids Res. 39(1):1-18, 2011.
Chen et al.: Chemical modification of gene silencing oligonucleotides for drug discovery and development. Drug Discov Today. 10(8):587-93 2005.

(56) References Cited

OTHER PUBLICATIONS

Chen et al.: Programmable chemical controllers made from DNA, Nat. Nanotechnol., 8(10):755-762, 2013.
Cheng et al.: High throughput parallel synthesis of oligonucleotides with 1536 channel synthesizer. Nucleic Acids Res. 30(18):e93, 2002.
Chervin et al.: Design of T-cell receptor libraries with diverse binding properties to examine adoptive T-cell responses. Gene Therapy. 20(6):634-644 (2012).
Chilamakuri et al.: Performance comparison of four exome capture systems for deep sequencing. BMC Genomics 15(1):449 (2014).
Cho et al.: Capillary passive valve in microfluidic systems. NSTI-Nanotech. 2004; 1:263-266.
Chrisey et al.: Fabrication of patterned DNA surfaces Nucleic Acids Research, 24(15):3040-3047 (1996).
Chung et al.: One-step preparation of competent *Escherichia coli*: Transformation and storage of bacterial cells in the same solution. Proc Natl Acad Sci U S A. Apr. 1989;86(7):2172-2175.
Church et al.: Next-generation digital information storage in DNA. Science, 337:6102, 1628-1629, 2012.
Cleary et al.: Production of complex nucleic acid libraries using highly parallel in situ oligonucleotide synthesis. Nat Methods 1(3):241-248 (2004).
Cohen et al.: Human population: The next half century. Science, 302:1172-1175, 2003.
Crick. On protein synthesis. Symp Soc Exp Biol12:138-163, 1958.
Cruse et al.: Atlas of Immunology, Third Edition. Boca Raton:CRC Press (pp. 282-283) (2010).
Cui et al.: Information Security Technology Based on DNA Computing. International Workshop on Anti-Counterfeiting, Security and Identification (ASID); IEEE Xplore 4 pages (2007).
Cutler et al.: High-throughput variation detection and genotyping using microarrays, Genome Research, vol. 11, 1913-19 (2001).
Dahl et al.: Circle-to-circle amplification for precise and sensitive DNA analysis. Proc Natl Acad Sci U S A. Mar. 30, 2004;101(13):4548-53. Epub Mar. 15, 2004.
De Mesmaeker et al.: Backbone modifications in oligonucleotides and peptide nucleic acid systems. Curr Opin Struct Biol. Jun. 1995;5(3):343-55.
De Silva et al.: New Trends of Digital Data Storage in DNA. BioMed Res Int. 2016:8072463 (2016).
Deamer et al.: Characterization of nucleic acids by nanopore analysis, Ace. Cham. Res., vol. 35, No. 10, 817-825 (2002).
Deaven. The Human Genome Project: Recombinant clones for mapping and sequencing DNA. Los Alamos Science, 20:218-249, 1992.
Deng et al.: Targeted bisulfite sequencing reveals changes in DNA methylation associated with nuclear reprogramming Nature Biotechnology, 27:352-360 (2009).
Dietrich et al.: Gene assembly based on blunt-ended double-stranded DNA-modules, Biotechnology Techniques, vol. 12, No. 1, 49-54 (Jan. 1998).
Dillon et al.: Exome sequencing has higher diagnostic yield compared to simulated disease-specific panels in children with suspected monogenic disorders. Eur J Hum Genet 26(5):644-651 (2018).
Dormitzer et al.: Synthetic generation of influenza vaccine viruses for rapid response to pandemics. Sci Translational Medicine, 5(185):185ra68, 14 pages, 2013.
Doudna et al.: Genome editing. The new frontier of genome engineering with CRISPR-Cas9. Science 346(6213):1258096-1-1258096-9, 2014.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Dower et al.: High efficiency transformation of *E.coli* by high voltage electroporation. Nucleic Acids Res. 16(13):6127-45 (1988).
Dressman et al.: Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al.: Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill. The Genome Sequencer FLXTM System-Longer reads, more applications, straight forward bioinformatics and more complete data sets Journal of Biotechnology, 136:3-10, 2008.
Duffy et al.: Rapid Prototyping of Microfluidic Systems in Poly(dimethylsiloxane). Anal Chem. Dec. 1, 1998;70(23):4974-84. doi: 10.1021/ac980656z.
Duggan et al.: Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie et al.: Guanine modification during chemical DNA synthesis. Nucleic Acids Res. Oct. 26, 1987;15(20):8333-49.
Eisen. A phylogenomic study of the MutS family of proteins, Nucleic Acids Research, vol. 26, No. 18, 4291-4300 (1998).
Ellis et al.: DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer et al.: Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al.: The Genome sequence of taurine cattle: A window of ruminant biology and evolution. Science, 324:522-528, 2009.
Elsner et al.: 172 nm excimer VUV-triggered photodegradation and micropatterning of aminosilane films, Thin Solid Films, 517:6772-6776 (2009).
Engler et al.: A one pot, one step, precision cloning method with high throughput capability. PLoS One. 2008;3(11):e3647. doi: 10.1371/journal.pone.0003647. Epub Nov. 5, 2008.
Engler et al.: Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski. DNA fountain enables a robust and efficient storage architecture. Science, 355(6328):950-054, 2017.
Eroshenko et al.: Gene Assembly from Chip-Synthesized Oligonucleotides; Current Protocols in Chemical biology 4: 1-17 (2012).
Evans et al.: DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy et al.: Self-sustained sequence replication (3SR): an isothermal transcription-based amplification system alternative to PCR. PCR Methods Appl. Aug. 1991;1(1):25-33.
Fedoryak et al.: Brominated hydroxyquinoline as a photolabile protecting group with sensitivity to multiphoton excitation, Org. Lett., vol. 4, No. 2 , 3419-3422 (2002).
Ferretti et al.: Total synthesis of a gene for bovine rhodopsin. PNAS, 83:599-603 (1986).
Finger et al.: The wonders of Flap Endonucleases: Structure, function, mechanism and regulation. Subcell Biochem., 62:301-326, 2012.
Fodor et al.: Light-directed, spatially addressable parallel chemical synthesis. Science. 251(4995):767-773 (1991).
Fogg et al.: Structural basis for uracil recognition by archaeal family B DNA polymerases. Nature Structural Biology, 9(12):922-927, 2002.
Foldesi et al.: The synthesis of deuterionucleosides. Nucleosides Nucleotides Nucleic Acids. Oct.-Dec. 2000;19(10-12):1615-56.
Frandsen et al.: Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.

(56) References Cited

OTHER PUBLICATIONS

Frandsen. The User Friendly technology. User cloning. Oct. 7, 2010, 2 pages. http://www.rasmusfrandsen.dk/user_cloning.htm.
Fullwood et al.: Next-generation DNA sequencing of paired-end tags [PET] for transcriptome and genome analysis Genome Research, 19:521-532, 2009.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:S2 figure (2017).
Galneder et al.: Microelectrophoresis of a bilayer-coated silica bead in an optical trap: application to enzymology. Biophysical Journal, vol. 80, No. 5, 2298-2309 (May 2001).
Gao et al.: A flexible light-directed DNA chip synthesis gated by deprotection using solution photogenerated acids. Nucleic Acids Res. Nov. 15, 2001;29(22):4744-50.
Gao et al.: A method for the generation of combinatorial antibody libraries using pIX phage display. PNAS 99(20):12612-12616 (2002).
Gao et al.: Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj et al.: Graphene as a subnanometre trans-electrode membrane. Nature. Sep. 9, 2010;467(7312):190-3. doi: 10.1038/nature09379.
Garbow et al.: Optical tweezing electrophoresis of isolated, highly charged colloidal spheres, Colloids and Surfaces A: Physiochem. Eng. Aspects, vol. 195, 227-241 (2001).
Geetha et al.: Survey on Security Mechanisms for Public Cloud Data. 2016 International Conference on Emerging Trends in Engineering, Technology and Science (ICETETS). 8 pages (2016).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores et al.: User fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson et al.: Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gibson et al.: Creation of a Bacterial Cell Controlled by a Chemically Synthesized Genome. Science 329(5989):52-56 (2010).
Goldfeder et al.: Medical implications of technical accuracy in genome sequencing. Genome Med 8(1):24 (2016).
Goldman et al.: Towards practical, high-capacity, low-maintenance information storage in synthesized DNA, Nature, 494(7435):77-80, 2013.
Goodwin et al.: immunoglobulin heavy chain variable region, partial [*Homo sapiens*]. Genbank entry (online). National Institute of Biotechnology Information. (2018) https://www.ncbi.nim.nih.gov/protein/AXA12486.1.
Gosse et al.: Magnetic tweezers: micromanipulation and force measurement at the molecular level, Biophysical Journal, vol. 8, 3314-3329 (Jun. 2002).
Grass et al.: Robust chemical preservation of digital information on DNA in silica with error-correcting codes, Angew. Chemie—Int. Ed., 54(8):2552-2555, 2015.
Greagg et al.: A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al.: Depletion of abundant sequences by hybridization (DASH): using Cas9 to remove unwanted high-abundance species in sequencing libraries and molecular counting applications. Genome Biology, 17:41, 13 pages, 2016.
Haber et al.: Magnetic tweezers for DNA micromanipulation, Rev. Sci. Instrum., vol. 71, No. 12, 4561-4570 (Dec. 2000).
Han et al.: Linking T-cell receptor sequence to functional phenotype at the single-cell level. Nat Biotechnol 32(7):684-692 (2014).
Hanahan and Cold Spring Harbor Laboratory. Studies on transformation of *Escherichia coli* with plasmids J. Mol. Biol. 166:557-580 (1983).
Hanahan et al.: Plasmid transformation of *Escherichia coli* and other bacteria. Methods Enzymol, vol. 204, p. 63-113 (1991).
Harada et al.: Unexpected substrate specificity of T4 DNA ligase revealed by in vitro selection. Nucleic Acids Res. May 25, 1993;21(10):2287-91.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Heckers et al.: Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al.: DNAWorks: an automated method for designing oligonucleotides for PCR-based gene synthesis, Nucleic Acids Research, vol. 30, No. 10, e43, 7 pages (2002).
Hopcroft et al.: What is the Young's Modulus of Silicon?. Journal of Microelectromechanical Systems. 19(2):229-238 (2010).
Hosu et al.: Magnetic tweezers for intracellular applications•, Rev. Sci. Instrum., vol. 74, No. 9, 4158-4163 (Sep. 2003).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Huang et al.: Three-dimensional cellular deformation analysis with a two-photon magnetic manipulator workstation, Biophysical Journal, vol. 82, No. 4, 2211•2223 (Apr. 2002).
Hughes et al.: Expression profiling using microarrays fabricated by an ink-jet oligonucleotide synthesizer Nat Biotech 4:342-347 (2001).
Hughes et al.: Principles of early drug discovery. Br J Pharmacol 162(2):1239-1249, 2011.
Hutchison et al.: Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
Jackson et al.: Recognition of DNA base mismatches by a rhodium intercalator, J. Am. Chem. Soc., vol. 19, 12986•12987 (1997).
Jacobs et al. DNA glycosylases: In DNA repair and beyond. Chromosoma 121:1-20 (2012)—http://www.ncbi.nlm.nih.gov/pmc/articles/PMC3260424/.
Jacobus et al.: Optimal cloning of PCR fragments by homologous recombination in *Escherichia soli*. PLoS One 10(3):e0119221 (2015).
Jager et al.: Simultaneous Humoral and Cellular: Immune Response against Cancer—Testis Antigen NY-ES0-1: Definition of Human Histocompatibility Leukocyte Antigen (HLA)-A2—binding Peptide Epitopes. J. Exp. Med. 187(2):265-270 (1998).
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).

(56) References Cited

OTHER PUBLICATIONS

Jang et al.: Characterization of T cell repertoire of blood, tumor, and ascites in ovarian cancer patients using next generation sequencing. Oncoimmunology, 4(11):e1030561:1-10 (2015).
Jinek et al.: A Programmable dual-RNA-guided DNA endonuclease in adaptive bacterial immunity. Science, 337:816-821, 2012.
Jo et al.: Engineering therapeutic antibodies targeting G-protein-coupled receptors; Experimental & Molecular Medicine; 48; 9 pages (2016).
Karagiannis and El-Osta. RNA interference and potential therapeutic applications of short interfering RNAs Cancer Gene Therapy, 12:787-795, 2005.
Ke et al.: Influence of neighboring base pairs on the stability of single base bulges and base pairs in a DNA fragment, Biochemistry, Vo. 34, 4593-4600 (1995).
Kelley et al.: Single-base mismatch detection based on charge transduction through DNA, Nucleic Acids Research, vol. 27, No. 24, 4830-4837 (1999).
Kim et al.: Chimeric restriction endonuclease, Proc. Natl. Acad. Sci. USA, vol. 91, 883-887 (Feb. 1994).
Kim et al.: High-resolution patterns of quantum dots formed by electrohydrodynamic jet printing for light-emitting diodes. Nano Letters, 15:969-973, 2015.
Kim et al.: Site-specific cleavage of DNA-RNA hybrids by zinc finger/Fok I cleavage domain fusions Gene, vol. 203, 43-49 (1997).
Kim. The interaction between Z-ONA and the Zab domain of double-stranded RNA adenosine deaminase characterized using fusion nucleases, The Journal of Biological Chemistry, vol. 274, No. 27, 19081-19086 (1999).
Kinde et al.: Detection and quantification of rare mutations with massively parallel sequencing. Proc Natl Acad Sci U S A. Jun. 7, 2011;108(23):9530-5. Epub May 17, 2011.
Kodumal et al.: Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al.: Genome-wide recessive genetic screening in mammalian cells with a lentiviral CRISPR-guide RNA library. Nature Biotechnology, 32:267-273, 2014 (with three pages of supplemental Online Methods).
Kong et al.: Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp et al.: Chemical amplification: continuous-flow PCR on a chip, Science, vol. 280, 1046-1048 (May 15, 1998).
Kosuri and Church. Large-scale de novo DNA synthesis: technologies and applications, Nature Methods, 11:499-507, 2014. Available at: http://www.nature.com/nmeth/journal/v11/n5/full/nmeth.2918.html.
Kosuri et al.: A scalable gene synthesis platform using high-fidelity DNA microchips Nat.Biotechnol. 28(12):1295-1299 (2010).
Kosuri et al.: A scalable gene synthesis by selective amplification of DNA pools from high-fidelity microchips. Nature Biotechnology. 2010; 28:1295-1299.
Krayden, Inc.: A Guide to Silane Solutions. Silane coupling agents. 7 pages. Published on May 31, 2005 at: http://krayden.com/pdf/xia_silane_chemistry.pdf.
Lagally et al.: Single-Molecule DNA Amplification and Analysis in an Integrated Microfluidic Device. Analytical Chemistry. 2001;73(3): 565-570.
Lahue et al.: DNA mismatch correction in a defined system, Science, vol. 425; No. 4914, 160-164 (Jul. 14, 1989).
Lambrinakos et al.: Reactivity of potassium permanganate and tetraethylammonium chloride with mismatched bases and a simple mutation detection protocol. Nucleic Acids Research, vol. 27, No. 8, 1866-1874 (1999).
Landegren et al.: A ligase-mediated gene detection technique. Science. Aug. 26, 1988;241(4869):1077-80.
Lang et al.: An automated two-dimensional optical force clamp for single molecule studies, Biophysical Journal, vol. 83, 491•501 (Jul. 2002).
Lashkari et al.: An automated multiplex oligonucleotide synthesizer: development of high-throughput, low-cost DNA synthesis. Proc Natl Acad Sci U S A. Aug. 15, 1995;92(17):7912-5.
Lausted et al.: POSaM: a fast, flexible, open-source, inkjet oligonucleotide synthesizer and microarrayer, Genome Biology, 5:R58, 17 pages, 2004. available at https://www.ncbi.nlm.nih.gov/pmc/articles/PMC507883/.
Leamon et al.: A massively parallel PicoTiterPlate based platform for discrete picoliter-scale polymerase chain reactions. Electrophoresis. Nov. 2003;24(21):3769-77.
Lee et al.: A microfluidic oligonucleotide synthesizer. Nucleic Acids Research 2010 vol. 38(8):2514-2521. DOI: 10.1093/nar/gkq092.
Lee et al.: Microelectromagnets for the control of magnetic nanoparticles, Appl. Phys. Lett., vol. 79, No. 20, 3308-3310 (Nov. 12, 2001).
Lee: Covalent End-Immobilization of Oligonucleotides onto Solid Surfaces; Thesis, Massachusetts Institute of Technology, Aug. 2001 (315 pages).
Leproust et al.: Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust et al.: Synthesis of high-quality libraries of long (150mer) oligonucleotides by a novel depurination controlled process. Nucleic Acids Research. 2010; 38(8):2522-2540.
Lesnikowski et al.: Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene et al.: Zero-mode waveguides for single-molecule analysis at high concentrations. Science. Jan. 31, 2003;299(5607):682-6.
Lewontin and Harti. Population genetics in forensic DNA typing. Science, 254:1745-1750, 1991.
Li et al.: Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Li et al.: Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Light source unit for printable patterning VUV-Aligner / Ushio Inc., Link here: https://www.ushio.co.jp/en/products/1005.html, published Apr. 25, 2016, printed from the internet on Aug. 2, 2016, 3 pages.
Limbachiya et al.: Natural data storage: A review on sending information from now to then via Nature. ACM Journal on Emerging Technologies in Computing Systems, V(N):Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz et al.: High density synthetic oligonucleotide arrays, Nature Genetics Supplement, vol. 21, 20-24 (Jan. 1999).
Lishanski et al.: Mutation detection by mismatch binding protein, MutS, in amplified DNA: application to the cystic fibrosis gene, Proc. Natl. Acad. Sci. USA, vol. 91, 2674-2678 (Mar. 1994).
Liu et al.: Comparison of Next-Generation Sequencing Systems. J Biomed Biotechnol 2012: 251364 (2012).
Liu et al.: Enhanced Signals and Fast Nucleic Acid Hybridization by Microfluidic Chaotic Mixing. Angew. Chem. Int. Ed. 2006; 45:3618-3623.
Liu et al.: Rational design of CXCR4 specific antibodies with elongated CDRs. JACS, 136:10557-10560, 2014.
Lizardi et al.: Mutation detection and single-molecule counting using isothermal rolling-circle amplification. Nat Genet. Jul. 1998;19(3):225-32.

(56) References Cited

OTHER PUBLICATIONS

Li et al.: Functional domains in Fok I restriction endonuclease, Proc. Natl. Acad. Sci. USA, 89:4275-4279, 1992.
Lu et al.: Methyl-directed repair of DNA base-pair mismatches in vitro, Proc. Natl. Acad. Sci. USA, 80:4639-4643, 1983.
Lund et al.: A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma et al.: DNA synthesis, assembly and application in synthetic biology. Current Opinion in Chemical Biology. 16:260-267, 2012.
Ma et al.: Versatile surface functionalization of cyclic olefin copolymer (COC) with sputtered SiO2 thin film for potential BioMEMS applications. Journal of Materials Chemistry, 11 pages, 2009.
Mahato et al.: Modulation of gene expression by antisense and antigene oligodeoxynucleotides and small interfering RNA Expert Opin. Drug Delivery, 2(1):3-28, 2005.
Malecek et al.: Engineering improved T cell receptors using an alanine-scan guided T cell display selection system. Journal of Immunological Methods. Elsevier Science Publishers. 392(1):1-11 (2013).
Margulies et al.: Genome sequencing in open microfabricated high-density picolitre reactors. Nature. 437(7057):376-80, 2005.
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Matteucci et al.: Synthesis of deoxyoligonucleotides on a polymer support. J. Am. Chem. Soc. 103(11):3185-3191, 1981.
Matzas et al.: Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24: 245-248, 1983.
McGall et al.: Light-directed synthesis of high-density oligonucleotide arrays using semiconductor photoresists. Proc Natl Acad Sci U S A. 93(24):13555-60, 1996.
McGall et al.: The Efficiency of Light-Directed Synthesis of DNA Arrays on Glass Substrates. J. Am. Chem. Soc. 119(22):5081-5090, 1997.
Mei et al.: Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland. Knowledge-based simulation of genetic regulation in bacteriophage lambda. Nucl. Acids Research, 12(1):1-16, 1984.
Meynert et al.: Quantifying single nucleotide variant detection sensitivity in exome sequencing. BMC Bioinformatics 14:195 (2013).
Meynert et al.: Variant detection sensitivity and biases in whole genome and exome sequencing. BMC Bioinformatics 15:247 (2014).
Milo and Phillips. Numbers here reflect the number of protein coding genes and excludes tRNA and non-coding RNA. Cell Biology by the Numbers, p. 286, 2015.
Mitra et al.: In situ localized amplification and contact replication of many individual DNA molecules. Nucleic Acids Res. 27(24):e34, 1999.
Morin et al.: Profiling the HeLa S3 transcriptome using randomly primed cDNA and massively parallel short-read sequencing. Biotechniques, 45:81-94, 2008.
Morris and Stauss. Optimizing T-cell receptor gene therapy for hematologic malignancies. Blood, 127(26):3305-3311, 2016.
Muller et al.: Protection and labelling of thymidine by a fluorescent photolabile group, Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani et al.: Recognition of a single guanine bulge by 2-Acylamino-1,8-naphthyridine, J. Am. Chem. Soc., vol. 122, 2172-2177 (2000).
Neiman M.S.: Negentropy principle in information processing systems. Radiotekhnika, 1966, No. 11, p. 2-9.
Neiman M.S.: On the bases of the theory of information retrieval. Radiotekhnika, 1967, No. 5, p. 2-10.
Neiman M.S.: On the molecular memory systems and the directed mutations. Radiotekhnika, 1965, No. 6, pp. 1-8.
Neiman M.S.: On the relationships between the reliability, performance and degree of microminiaturization at the molecular-atomic level. Radiotekhnika, 1965, No. 1, pp. 1-9.
Neiman M.S.: Some fundamental issues of microminiaturization. Radiotekhnika, 1964, No. 1, pp. 3-12.
Nishikura. A short primer on RNAi: RNA-directed RNA polymerase acts as a key catalyst Cell, 107:415-418, 2001.
Nour-Eldin et al.: User Cloning and User Fusion: The Ideal Cloning Techniques for Small and Big Laboratories. Plant Secondary Metabolism Engineering. Methods in Molecular Biology vol. 643, 2010, pp. 185-200.
Novartis Institutes for Biomedical Research. Immunoglobulin Heavy Chain [*Homo sapiens*]. National Center for Biotechnology Information. Genbank Entry. pp. 1-2 (2018) https://www.ncbi.nlm.nih.gov/nuccore/MH975524.1ttps://https://www.ncbi.nlm.nih.gov/nuccore/MH975524.1.
Novartis Institutes for Biomedical Research. Immunoglobulin Lambda Chain [*Homo sapiens*]. National Center for Biotechnology Information. Genbank Entry. pp. 1-2 (2018) https://www.ncbi.nlm.nih.gov/nuccore/MH975524.1.
Ochman et al.: Genetic applications of an inverse polymerase chain reaction. Genetics. Nov. 1988;120(3):621-3.
O'Driscoll et al.: Synthetic DNA: The next generation of big data storage. Bioengineered. 4(3):123-125 (2013).
Organick et al.: Random access in large-scale DNA data storage. Nature Biotechnology, Advance Online Publication, 8 pages, 2018.
Organick et al.: Scaling up DNA data storage and random access retrieval, bioRxiv, preprint first posted online Mar. 7, 2017, 14 pages.
Pan et al.: An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
Paul et al.: Acid binding and detritylation during oligonucleotide synthesis. Nucleic Acids Research. 15. pp. 3048-3052 (1996).
PCT/IL2012/000326 International Preliminary Report on Patentability dated Dec. 5, 2013.
PCT/IL2012/000326 International Search Report dated Jan. 29, 2013.
PCT/US2014/049834 International Preliminary Report on Patentability dated Feb. 18, 2016.
PCT/US2014/049834 International Search Report and Written Opinion dated Mar. 19, 2015.
PCT/US2014/049834, Invitation to Pay Additional Fees and, where applicable, protest fee, dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.

(56) References Cited

OTHER PUBLICATIONS

PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Preliminary Report on Patentability dated Feb. 26, 2019.
PCT/US2017/026232 International Search Report and Written Opinion dated Aug. 28, 2017.
PCT/US2017/036868 International Search Report and Written Opinion dated Aug. 11, 2017.
PCT/US2017/045105 International Preliminary Report on Patentability dated Feb. 5, 2019.
PCT/US2017/045105 International Search Report and Written Opinion dated Oct. 20, 2017.
PCT/US2017/052305 International Preliminary Report on Patentability dated Apr. 30, 2019.
PCT/US2017/052305 International Search Report and Written Opinion dated Feb. 2, 2018.
PCT/US2017/062391 International Preliminary Report on Patentability dated May 21, 2019.
PCT/US2017/062391 International Search Report and Written Opinion dated Mar. 28, 2018.
PCT/US2017/066847 International Search Report and Written Opinion dated May 4, 2018.
PCT/US2018/019268 International Preliminary Report on Patentability dated Aug. 27, 2019.
PCT/US2018/022487 International Search Report and Written Opinion dated Aug. 1, 2018.
PCT/US2018/022493 International Search Report and Written Opinion dated Aug. 1, 2018.
PCT/US2018/037152 International Preliminary Report on Patentability dated Dec. 17, 2019.
PCT/US2018/037152 International Search Report and Written Opinion dated Aug. 28, 2018.
PCT/US2018/037161 International Preliminary Report on Patentability dated Dec. 17, 2019.
PCT/US2018/037161 International Search Report and Written Opinion dated Oct. 22, 2018.
PCT/US2018/037161 Invitation to Pay Additional Fees dated Aug. 27, 2018.
PCT/US2018/050511 International Preliminary Report on Patentability dated Mar. 17, 2020.
PCT/US2018/050511 International Search Report and Written Opinion dated Jan. 11, 2019.
PCT/US2018/056783 International Preliminary Report on Patentability dated Apr. 30, 2020.
PCT/US2018/056783 International Search Report and Written Opinion of the International Searching Authority dated Dec. 20, 2018.
PCT/US2018/057857 International Preliminary Report on Patentability dated Apr. 28, 2020.
PCT/US2018/057857 International Search Report and Written Opinion dated Mar. 18, 2019.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
PCT/US2019/012218 International Preliminary Report on Patentability dated Jul. 16, 2020.
PCT/US2019/012218 International Search Report and Written Opinion dated Mar. 21, 2019.
PCT/US2019/032992 International Search Report and Written Opinion dated Oct. 28, 2019.
PCT/US2019/032992 International Preliminary Report on Patentability dated Nov. 24, 2020.
PCT/US2019/032992 Invitation to Pay Additional Fees dated Sep. 6, 2019.
PCT/US2019/068435 International Search Report and Written Opinion dated Apr. 23, 2020.
PCT/US2020/019371 International Search Report and Written Opinion dated Jun. 25, 2020.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Search Report and Written Opinion dated Jul. 29, 2020.
PCT/US2020/019988 Invitation to Pay Additional Fees dated Jun. 8, 2020.
PCT/US2020/038679 International Search Report and Written Opinion dated Oct. 28, 2020.
PCT/US2020/052306 Invitation to Pay Additional Fees dated Dec. 18, 2020.
PCT/US2020/052291 Invitation to Pay Additional Fees dated Dec. 31, 2020.
Pease et al.: Light-generated oligonucleotide arrays for rapid DNA sequence analysis. Proc Natl Acad Sci U S A. May 24, 1994;91(11):5022-6.
Peisajovich et al.: BBF RFC 28: A method for combinatorial multi-part assembly based on the type-lis restriction enzyme aarl. Sep. 16, 2009, 7 pages.
Pellois et al.: Individually addressable parallel peptide synthesis on microchips, Nature Biotechnology, vol. 20 , 922-926 (Sep. 2002).
Petersen et al.: LNA: a versatile tool for therapeutics and genomics. Trends Biotechnol. Feb. 2003;21(2):74-81.
Pierce and Wangh. Linear-after-the-exponential polymerase chain reaction and allied technologies Real-time detection strategies for rapid, reliable diagnosis from single cells Methods Mol. Med. 132:65-85 (2007) (Abstract only).
Pierce et al.: Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al.: Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al.: Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages. available at: http://www.nature.com/scitable/topicpage/discovery-of-dna-structure-and-function-watson-397.

(56) References Cited

OTHER PUBLICATIONS

Prodromou et al.: Recursive PCR: a novel technique for total gene synthesis. Protein Eng. Dec. 1992;5(8):827-9.
PubChem Data Sheet Acetonitrile. Printed from website https://pubchem.ncbi.nlm.nig.gov/ pp. 1-124 (2020).
PubChem Data Sheet Dichloromethane. Printed from website https://pubchem.ncbi.nlm.nih.gov/compound/Dichloromethane (2020).
PubChem Data Sheet Methylene Chloride. Printed from website https://pubchem.ncbi.nlm.nih.gov/ pp. 1-140 (2020).
Puigbo. Optimizer: a web server for optimizing the codon usage of DNA sequences. Nucleic Acid Research, 35(14):126-131, 2007.
Qian and Winfree. Scaling up digital circuit computation with DNA strand displacement cascades. Science, 332(6034):196-1201, 2011.
Qian et al.: Neural network computation with DNA strand displacement cascades, Nature, 475(7356):368-372, 2011.
Quan et al.: Parallel on-chip gene synthesis and application to optimization of protein expression, Nature Biotechnology, 29(5):449-452, 2011.
Rafalski and Morgante. Corn and humans: recombination and linkage disequilibrium in two genomes of similar size. Trends in Genetics, 20(2):103-111, 2004.
Raje and Murma. A Review of electrohydrodynamic-inkjet printing technology. International Journal of Emerging Technology and Advanced Engineering, 4(5):174-183, 2014.
Rajpal et al.: A general method for greatly improving the affinity of antibodies by using combinatorial libraries. Proc. Natl. Acad. Sci. 102(24):8466-8471 (2005).
Rastegari et al.: XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond et al.: Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—a Tradition of Premium Quality and Scientific Support. FAQS and Ordering Guide. Roche Applied Science. Accessed Jan. 12, 2015, 37 pages.
Rogozin et al.: Origin and evolution of spliceosomal introns. Biology Direct, 7:11, 2012.
Ruminy et al.: Long-range identification of hepatocyte nuclear factor-3 (FoxA) high and low-affinity binding Sites with a chimeric nuclease, J. Mol. Bioi., vol. 310, 523-535 (2001).
Saaem et al.: In situ synthesis of DNA microarray on functionalized cyclic olefin copolymer substrate ACS Applied Materials & Interfaces, 2(2):491-497, 2010.
Saboulard et al.: High-throughput site-directed mutagenesis using oligonucleotides synthesized on DNA chips. Biotechniques. Sep. 2005;39(3):363-8.
Sacconi et al.: Three-dimensional magneto-optic trap for micro-object manipulation, Optics Letters, vol. 26, No. 17, 1359-1361 (Sep. 1, 2001).
Saiki et al.: Analysis of enzymatically amplified beta-globin and HLA-DQ alpha DNA with allele-specific oligonucleotide probes. Nature 324:163-166 (1986).
Sandhu et al.: Dual asymmetric PCR: one-step construction of synthetic genes. Biotechniques. Jan. 1992;12(1):14-6.
Sargolzaei et al.: Extent of linkage disequilibrium in Holstein cattle in North America. J.Dairy Science, 91:2106-2117, 2007.
Schaller et al.: Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Shipman et al.: Molecular recordings by directed CRISPR spacer acquisition. Science. 353(6298):1-16 (2016).
Schmalzing et al.: Microchip electrophoresis: a method for high-speed SNP detection. Nucleic Acids Res 28(9):E43 (2000).
Schmitt et al.: New strategies in engineering T-cell receptor gene-modified T cells to more effectively target malignancies. Clinical Cancer Research, 21(23):5191-5197, 2015.
Seelig et al.: Enzyme-Free Nucleic Acid Logic Circuits, Science 314(5805):1585-1588, 2006.
Sharan et al.: Recombineering: a homologous recombination-based method of genetic engineering. Nat Profile 4(2):1-37 (originally pp. 206-223) (2009).
Sharpe and Mount. Genetically modified T cells in cancer therapy: opportunities and challenges. Disease Models and Mechanisms, 8:337-350, 2015.
Sierzchala et al.: Solid-phase oligodeoxynucleotide synthesis : a two-step cycle using peroxy anion deprotection, J. Am. Chem. Soc., vol. 125, No. 44, 13427-13441 (2003).
Simonyan and Zisserman. Very Deep Convolutional Networks for Large-Scale Image Recognition, Published as a conference paper at Int. Conf. Learn. Represent., pp. 1-14, 2015.
Singh-Gasson et al.: Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith et al.: Direct mechanical measurements of the elasticity of single DNA molecules using magnetic beads, Science, vol. 258, 1122-1126 (Nov. 13, 1992).
Smith et al.: Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith et al.: Generation of cohesive ends on PCR products by UDG-mediated excision of dU, and application for cloning into restriction digest-linearized vectors. PCR Methods Appl. May 1993;2(4):328-32.
Smith et al.: Mutation detection with MutH, MutL, and MutS mismatch repair proteins, Proc. Natl. Acad. Sci. USA, vol. 93, 4374-4379 (Apr. 1996).
Smith et al.: Removal of Polymerase-Produced mutant sequences from PCR products, Proc. Natl. Acad. Sci. USA, vol. 94, 6847-6850 (Jun. 1997).
Solomon et al.: Genomics at Agilent: Driving Value in DNA Sequencing.https://www.agilent.com/labs/features/2010_genomics.html, 8 pages (Aug. 5, 2010).
Soni et al.: Progress toward ultrafast DNA sequencing using solid-state nanopores. Clin Chem. Nov. 2007;53(11):1996-2001. Epub Sep. 21, 2007.
Southern et al.: Analyzing and comparing nucleic acid sequences by hybridization to arrays of oligonucleotides: evaluation using experimental models. Genomics. Aug. 1992;13(4):1008-17.
Sproat et al.: An efficient method for the isolation and purification of oligoribonucleotides. Nucleosides & Nucleotides. 1995; 14(1 &2):255-273.
Srivannavit et al.: Design and fabrication of microwell array chips for a solution-based, photogenerated acid-catalyzed parallel oligonucleotide DNA synthesis. Sensors and Actuators A, 116:150-160, 2004.
Srivastava et al.: RNA synthesis: phosphoramidites for RNA synthesis in the reverse direction. Highly efficient synthesis and application to convenient introduction of ligands, chromophores and modifications of synthetic RNA at the 3'-end, Nucleic Acids Symposium Series, 52(1):103-104, 2008.
Steel. The Flow-Thru Chip a Three-dimensional biochip platform. In: Schena, Microarray Biochip Technology, Chapter 5, Natick, MA: Eaton Publishing, 2000, 33 pages.
Stemmer et al.: Single-step assembly of a gene and entire plasmid from large numbers of oligodeoxyribonucleotides. Gene. Oct. 16, 1995;164(1):49-53.

(56) References Cited

OTHER PUBLICATIONS

Stryer. DNA Probes and genes can be synthesized by automated solid-phase methods. Biochemistry, 3rd edition, New York: W.H. Freeman and Company, 1988; 123-125.
Stutz et al.: Novel fluoride-labile nucleobase-protecting groups for the synthesis of 3'(2')-O-amino-acylated RNA sequences. Helv. Chim. Acta. 2000; 83(9):2477-2503.
Sullivan et al.: Library construction and evaluation for site saturation mutagenesis. Enzyme Microb. Technol. 53:70-77 (2013).
Sun et al.: Structure-Guided Triple-Code Saturation Mutagenesis: Efficient Tuning of the Stereoselectivity of an Epoxide Hydrolase. ACS Catal. 6:1590-1597 (2016).
Takahashi. Cell-free cloning using multiply-primed rolling circle amplification with modified RNA primers. Biotechniques. Jul. 2009;47(1):609-15. doi: 10.2144/000113155.
Tanase et al.: Magnetic trapping of multicomponent nanowires, The Johns Hopkins University, Baltimore, Maryland, p. 1-3 (Jun. 25, 2001).
Taylor et al.: Impact of surface chemistry and blocking strategies on DNA microarrays. Nucleic Acids Research, 31(16):e87, 19 pages, 2003.
The SLIC. Gibson, CPEC and SLiCE assembly methods (and GeneArt Seamless, In-Fusion Cloning). 5 pages, available online Sep. 2, 2010.
Tian et al.: Accurate multiplex gene synthesis from programmable DNA microchips. Nature. Dec. 23, 2004;432(7020):1050-4.
Tsai et al.: Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
U.S. Appl. No. 14/241,874 Final Office Action dated Jan. 28, 2019.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action dated Apr. 9, 2015.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and dated Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Aug. 19, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Final Office Action dated Jul. 9, 2020.
U.S. Appl. No. 15/151,316 Final Office Action dated Feb. 21, 2019.
U.S. Appl. No. 15/151,316 Office Action dated Jun. 7, 2018.
U.S. Appl. No. 15/151,316 Office Action dated Oct. 4, 2019.
U.S. Appl. No. 15/154,879 Notice of Allowance dated Feb. 1, 2017.
U.S. Appl. No. 15/156,134 Final Office Action dated Jan. 3, 2020.
U.S. Appl. No. 15/156,134 Office Action dated Apr. 4, 2019.
U.S. Appl. No. 15/156,134 Office Action dated Nov. 25, 2020.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Final Office Action dated Oct. 3, 2019.
U.S. Appl. No. 15/268,422 Office Action dated Mar. 1, 2019.
U.S. Appl. No. 15/268,422 Restriction Requirement dated Oct. 4, 2018.
U.S. Appl. No. 15/272,004 Office Action dated Jun. 12, 2020.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jun. 26, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/619,322 Final Office Action dated Mar. 30, 2020.
U.S. Appl. No. 15/619,322 Office Action dated Aug. 14, 2019.
U.S. Appl. No. 15/619,322 Office Action dated Nov. 4, 2020.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Office Action dated May 19, 2020.
U.S. Appl. No. 15/816,995 Office Action dated Sep. 20, 2019.
U.S. Appl. No. 15/816,995 Restriction Requirement dated Apr. 4, 2019.
U.S. Appl. No. 15/835,342 Final Office Action dated Sep. 8, 2020.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Final Office Action dated Jun. 15, 2020.
U.S. Appl. No. 15/921,479 Office Action dated Nov. 12, 2019.
U.S. Appl. No. 15/921,479 Restriction Requirement dated May 24, 2019.
U.S. Appl. No. 15/921,537 Office Action dated Apr. 1, 2020.
U.S. Appl. No. 15/960,319 Office Action dated Aug. 16, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/006,581 Office Action dated Sep. 25, 2019.
U.S. Appl. No. 16/031,784 Office Action dated May 12, 2020.
U.S. Appl. No. 16/039,256 Office Action dated Aug. 20, 2020.

(56) References Cited

OTHER PUBLICATIONS

U.S. Appl. No. 16/039,256 Restriction Requirement dated May 18, 2020.
U.S. Appl. No. 16/128,372 Office Action dated Oct. 8, 2020.
U.S. Appl. No. 16/128,372 Restriction Requirement dated May 18, 2020.
U.S. Appl. No. 16/165,952 Office Action dated Mar. 12, 2020.
U.S. Appl. No. 16/239,453 Office Action dated May 11, 2020.
U.S. Appl. No. 16/239,453 Office Action dated Nov. 7, 2019.
U.S. Appl. No. 16/384,678 Final Office Action dated Oct. 15, 2020.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Final Office Action dated Apr. 15, 2020.
U.S. Appl. No. 16/530,717 Office Action dated Sep. 6, 2019.
U.S. Appl. No. 16/535,777 Final Office Action dated Oct. 20, 2020.
U.S. Appl. No. 16/535,777 Office Action dated Jan. 23, 2020.
U.S. Appl. No. 16/535,779 First Action Interview dated Feb. 10, 2020.
Unger et al.: Monolithic microfabricated valves and pumps by multilayer soft lithography. Science. Apr. 7, 2000;288(5463):113-6.
Vaijayanthi et al.: Recent advances in oligonucleotide synthesis and their applications. Indian J Biochem Biophys. Dec. 2003;40(6):377-91.
Van Den Brulle et al.: A novel solid phase technology for high-throughput gene synthesis. Biotechniques. 2008; 45(3):340-343.
Van der Velde: Thesis. Finding the Strength of Glass. Delft University of Technology. 1-16 (2015).
Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Van Tassell et al.: SNP discovery and allele frequency estimation by deep sequencing of reduced representation libraries. Nature Methods, 5:247-252, 2008.
Vargeese et al.: Efficient activation of nucleoside phosphoramidites with 4,5-dicyanoimidazole during oligonucleotide synthesis. Nucleic Acids Res. Feb. 15, 1998;26(4):1046-50.
Verma et al.: Modified oligonucleotides: synthesis and strategy for users. Annu Rev Biochem 67:99-134 (1998).
Vincent et al.: Helicase-dependent isothermal DNA amplification. EMBO Rep. Aug. 2004;5(8):795-800.
Visscher et al.: Construction of multiple-beam optical traps with nanometer-resolution position sensing, IEEE Journal of Selected Topics in Quantum Electronics, vol. 2, No. 4, 1066-1076 (Dec. 1996).
Voldmans et al.: Holding forces of single-particle dielectrophoretic traps. Biophysical Journal, vol. 80, No. 1, 531-541 (Jan. 2001).
Vos et al.: AFLP: A new technique for DNA fingerprinting. Nucleic Acids Res. Nov. 11, 1995;23(21):4407-14.
Wagner et al.: Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.
Wah et al.: Structure of Fok I has implications for DNA cleavage, Proc. Natl. Acad. Sci. USA, vol. 95, 10564-10569 (Sep. 1998).
Wah et al.: Structure of the multimodular endonuclease Fok I bound to DNA, Nature, vol. 388, 97-100 ( Jul. 1997).
Walker et al.: Strand displacement amplification—an isothermal, in vitro DNA amplification technique. Nucleic Acids Res. Apr. 11, 1992;20(7):1691-6.
Wan et al.: Deep Learning for Content-Based Image Retrieval: A comprehensive study. in Proceedings of the 22nd ACM International Conference on Multimedia—Nov. 3-7, 2014, Orlando, FL, p. 157-166, 2014.
Warr et al.: Exome Sequencing: current and future perspectives. G3: (Bethesda) 5(8):1543-1550 (2015).
Weber et al.: A modular cloning system for standardized assembly of multigene constructs. PLoS One. Feb. 18, 2011;6(2):e16765. doi: 10.1371/journal.pone.0016765.
Welz et al.: 5-(Benzylmercapto)-1H-tetrazole as activator for 2'-O-TBDMS phosphoramidite building blocks in RNA synthesis. Tetrahedron Lett. 2002; 43(5):795-797.
Westin et al.: Anchored multiplex amplification on a microelectronic chip array Nature Biotechnology, 18:199-202 (2000) (abstract only).
Whitehouse et al.: Analysis of the mismatch and insertion/deletion binding properties of Thermus thermophilus, HB8, MutS, Biochemical and Biophysical Research Communications, vol. 233, 834-837 (1997).
Wiedenheft et al.: RNA-guided genetic silencing systems in bacteria and archaea. Nature 482:331-338 (2012).
Wijshoff. Structure and fluid-dynamics in Piezo inkjet printheads. Thesis. Venio, The Netherlands, published 2008, p. 1-185.
Wirtz. Direct measurement of the transport properties of a single DNA molecule, Physical Review Letters, vol. 75, No. 12, 2436-2439 (Sep. 18, 1995).
Withers-Martinez et al.: PCR-based gene synthesis as an efficient approach for expression of the A+ T-rich malaria genome, Protein Engineering, vol. 12, No. 12, 1113-1120 (1999).
Wood et al.: Human DNA repair genes, Science, vol. 291, 1284-1289 (Feb. 16, 2001).
Wosnick et al.: Rapid construction of large synthetic genes: total chemical synthesis of two different versions of the bovine prochymosin gene. Gene. 1987;60(1):115-27.
Wright and Church. An open-source oligomicroarray standard for human and mouse. Nature Biotechnology, 20:1082-1083, 2002.
Wu et al.: An improvement of the on-line electrophoretic concentration method for capillary electrophoresis of proteins an experimental factors affecting he concentration effect, Analytical Sciences, vol. 16, 329-331 (Mar. 2000).
Wu et al.: RNA-mediated gene assembly from DNA arrays. Angew Chem Int Ed Engl. May 7, 2012;51(19):4628-32. doi: 10.1002/anie.201109058.
Wu et al.: Sequence-Specific Capture of Protein-DNA Complexes for Mass Spectrometric Protein Identification PLoS ONE. Oct. 20, 2011, vol. 6, No. 10.
Wu et al.: Specificity of the nick-closing activity of bacteriophage T4 DNA ligase. Gene. 1989;76(2):245-54.
Xiong et al.: A simple, rapid, high-fidelity and cost-effective PCR-based two-step DNA synthesis method for long gene sequences. Nucleic Acids Res. 2004, 32(12):e98.
Xiong et al.: Chemical gene synthesis: Strategies, softwares, error corrections, and applications. FEMS Microbiol. Rev., 32:522-540, 2008.
Xiong et al.: Non-polymerase-cycling-assembly-based chemical gene synthesis: Strategies, methods, and progress. Biotechnology Advances. 26(2):121-134, 2008.
Xu et al.: Design of 240,000 orthogonal 25mer DNA barcode probes. PNAS, 106(7):2289-2294, 2009.
Xu et al.: Coordination between the Polymerase and 5'-Nuclease Components of DNA Polymerase I of *Escherichia coli*. The Journal of Biological Chemistry. 275(27):20949-20955 (2000).
Yang et al.: Purification, cloning, and characterization of the CEL I nuclease, Biochemistry, 39(13):3533-35, 2000.
Yazdi et al.: A Rewritable, Random-Access DNA-Based Storage System, Scientific Reports, 5, Article No. 14138, 27 pages, 2015.
Yazdi et al.: DNA-Based Storage: Trends and Methods. IEEE Transactions on Molecular, Biological and Multi-Scale Communications. IEEE. 1(3):230-248 (2016).
Yehezkel et al.: De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil et al.: Detection of 81 of 81 known mouse Beta-Globin promoter mutations with T4 Endonuclease VII• The EMC Method. Genomics, 32:431-435, 1996.
Young et al.: Two-step total gene synthesis method. Nucleic Acids Res. 32(7):e59, 2004.

(56) References Cited

OTHER PUBLICATIONS

Zhang and Seelig. Dynamic DNA nanotechnology using strand-displacement reactions, Nat. Chem., 3(2):103-113, 2011.
Zheleznaya et al.: Nicking endonucleases. Biochemistry (Mosc). 74(13):1457-66, 2009.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al.: Nucleic acid memory. Nature Materials, 15:366, 2016.
Zhou et al.: Establishment and application of a loop-mediated isothermal amplification (LAMP) system for detection of cry1Ac transgenic sugarcane Scientific Reports May 9, 2014, vol. 4, No. 4912.
Zhou et al.: Microfluidic PicoArray synthesis of oligodeoxynucleotides and simultaneous assembling of multiple DNA sequences Nucleic Acids Research, 32(18):5409-5417, 2004.
Bai. A Novel Human scFv Library with Non-Combinatorial Synthetic CDR Diversity. PLoS One. 10(10):1-18 (2015).
MLAB 2321 Molecular Diagnostics for Clinical Laboratory Science. Mar. 6, 2015.
Nucleic acid thermodynamics. Wikipedia. Feb. 4, 2021.
PCT/US2020/052291 International Search Report and Written Opinion dated Mar. 10, 2021.
PCT/US2020/052306 International Search Report and Written Opinion dated Mar. 2, 2021.
Ponsel. High Affinity, Developability and Functional Size: The Holy Grail of Combinatorial Antibody Library Generation. Molecules. 16:3675-3700 (2011).
U.S. Appl. No. 16/535,777 Office Action dated Feb. 8, 2021.
U.S. Appl. No. 16/798,275 Office Action dated Feb. 10, 2021.
Almagro, J., et al., "Humanization of Antibodies," Frontiers in Bioscience, vol. 13, pp. 1619-1633 (2008).
Chen, C., et al., "Enhancement and destruction of antibody function by somatic mutation: unequal occurrence is controlled by V gene combinatorial associations," The EMBO Journal, vol. 14, No. 12, pp. 2784-2794 (1995).
Edwards, B., et al., "The Remarkable Flexibility of the Human Antibody Repertoire; Isolation of Over One Thousand Different Antibodies to a Single Protein, BLyS," Journal of Molecular Biology, vol. 334, pp. 103-118 (2003).
International Search Report & Written Opinion of International Application No. PCT/US2022/013184, dated Jun. 15, 2022, by Examiner T. Matos (18 pages).
International Search Report and Written Opinion of International Application No. PCT/US2020/064106, dated Jun. 3, 2021, by Examiner H. Kim (20 pages).
Koenig et al., "Mutational landscape of antibody variable domains reveals a switch modulating the interdomain conformational dynamics and antigen binding," PNAS, 2017, 114(4)E486-495 (10 pages).
Kussie, P., et al., "A single engineered amino acid substitution changes antibody fine specificity," The Journal of Immunology, vol. 152, No. 1, pp. 146-152; (1994).
Supplementary Partial Search Report of European Application No. EP20897702, dated Dec. 6, 2023, by Examiner R. Chapman (5 pages).
File History for U.S. Appl. No. 17/580,547, filed Jan. 20, 2022, available on PAIR.
Extended European Search Report of European Application No. 20897702.5, dated Apr. 11, 2024, by Examiner Rob Chapman (7 pages).
Extended European Search Report of European Application No. 22743191.3, dated Dec. 12, 2024, by Examiner G. Brouns (10 pages).
Koshiba et al., Patterns of A2A extracellular adenosine receptor expression in different functional subsets of human peripheral T Cells. Flow cytometry studies with anti-A2A receptor monoclonal antibodies,' Molecular Pharmacology, American Society for Pharmacology and Experimental Therapeutics, vol. 55, No. 3, Feb. 28, 1999, pp. 614-624.
Leone et al., "A2ar antagonists: Next generation checkpoint for cancer immunotherapy," Computational and Structural Biotechnology Journal, vol. 13, Jan. 1, 2015, pp. 265-272.
Y. By et al., "Production of an agonist-like monoclonal antibody to the human A2a receptor of adenosine for clinical use," Molecular Immunology 46 (2009) pp. 400-405 (7 pages).

* cited by examiner

| Clone | ELISA | Library | ProA (mg/ml) | $K_D$ (nM) |
|---|---|---|---|---|
| TB31-1 | 5.7 | VHH hShuffle | 0.29 | 12 |
| TB31-6 | 9.6 | VHH hShuffle | 0.29 | 14 |
| TB31-26 | 5.1 | VHH hShuffle | 0.31 | 19 |
| TB30-30 | 8.0 | VHH Shuffle | 0.11 | 23 |
| TB31-32 | 8.0 | VHH hShuffle | 0.25 | 27 |
| TB29-10 | 5.0 | VHH Ratio | 0.19 | 32 |
| TB29-7 | 7.3 | VHH Ratio | 0.28 | 41 |
| TB30-43 | 13.5 | VHH Shuffle | 0.18 | 44 |
| TB31-8 | 12.7 | VHH hShuffle | 0.29 | 45 |
| TB31-56 | 11.7 | VHH hShuffle | 0.26 | 46 |
| TB30-52 | 4.2 | VHH Shuffle | 0.22 | 49 |
| TB31-47 | 8.8 | VHH hShuffle | 0.23 | 53 |
| TB30-15 | 9.3 | VHH Shuffle | 0.26 | 55 |
| TB30-54 | 5.5 | VHH Shuffle | 0.30 | 58 |
| TB30-49 | 10.3 | VHH Shuffle | 0.26 | 62 |
| TB29-22 | 3.4 | VHH Ratio | 0.27 | 65 |
| TB29-30 | 9.2 | VHH Ratio | 0.28 | 65 |
| TB31-35 | 5.7 | VHH hShuffle | 0.24 | 66 |
| TB29-1 | 10.4 | VHH Ratio | 0.09 | 68 |
| TB29-6 | 6.8 | VHH Ratio | 0.29 | 69 |
| TB31-34 | 6.0 | VHH hShuffle | 0.32 | 70 |
| TB29-12 | 6.2 | VHH Ratio | 0.23 | 70 |
| TB30-1 | 5.4 | VHH Shuffle | 0.39 | 71 |
| TB29-33 | 3.9 | VHH Ratio | 0.15 | 74 |
| TB30-20 | 4.6 | VHH Shuffle | 0.19 | 74 |
| TB31-20 | 6.6 | VHH hShuffle | 0.37 | 74 |
| TB31-24 | 3.1 | VHH hShuffle | 0.15 | 75 |
| TB30-14 | 9.9 | VHH Shuffle | 0.19 | 75 |
| TB30-53 | 7.6 | VHH Shuffle | 0.24 | 78 |
| TB31-39 | 9.9 | VHH hShuffle | 0.32 | 78 |
| TB29-18 | 10.9 | VHH Ratio | 0.19 | 78 |
| TB30-9 | 8.0 | VHH Shuffle | 0.40 | 79 |
| TB29-34 | 8.6 | VHH Ratio | 0.21 | 80 |
| TB29-27 | 8.6 | VHH Ratio | 0.18 | 82 |
| TB29-20 | 5.9 | VHH Ratio | 0.26 | 83 |
| TB30-55 | 6.0 | VHH Shuffle | 0.41 | 85 |
| TB30-39 | 6.1 | VHH Shuffle | 0.07 | 88 |
| TB31-15 | 6.2 | VHH hShuffle | 0.32 | 88 |
| TB29-21 | 4.3 | VHH Ratio | 0.23 | 88 |
| TB29-37 | 5.3 | VHH Ratio | 0.26 | 89 |
| TB29-40 | 6.6 | VHH Ratio | 0.31 | 90 |
| TB31-30 | 3.2 | VHH hShuffle | 0.33 | 93 |
| TB31-10 | 12.3 | VHH hShuffle | 0.31 | 94 |
| TB29-3 | 13.6 | VHH Ratio | 0.11 | 94 |
| TB30-57 | 5.2 | VHH Shuffle | 0.24 | 95 |
| TB29-31 | 4.4 | VHH Ratio | 0.18 | 96 |
| TB31-27 | 8.1 | VHH hShuffle | 0.31 | 96 |
| TB31-33 | 6.0 | VHH hShuffle | 0.32 | 96 |
| TB30-40 | 7.1 | VHH Shuffle | 0.21 | 99 |
| TB31-18 | 4.1 | VHH hShuffle | 0.36 | 99 |
| TB30-5 | 9.3 | VHH Shuffle | 0.05 | 100 |

*FIG. 12*

FIG. 15D
Kv2-28
1.4 x $10^{4}$
2.7 x $10^{17}$
Hv3-23
1.9 x $10^{13}$
Kv2-28
1.4 x $10^{4}$
5.7 x $10^{16}$
Hv1-69
4.1 x $10^{12}$
Lv1-51
5.2 x $10^{3}$
9.9 x $10^{15}$
Hv3-23
1.9 x $10^{13}$
Lv1-51
2.1 x $10^{16}$
Hv1-69
4.1 x $10^{12}$

| Sample Name | Subset Name | Count | Median : RL1-H |
|---|---|---|---|
| Well_H12.fcs | A0s Singlets | 980 | 7502 |
| Well_H12.fcs | Parent Singlets | 6639 | 220 |

MAB9497

RL1-H :: APC (RL1-H)

Normalized To Mode

| | |
|---|---|
| A2A – 17 | SC-29_001 |
| A2A – 31 | SC-29_002 |
| A2A – 35 | SC-29_004 |
| A2A – 52 | ZM 241385 |
| A2A – 72 | MAB9497 |
| A2A – 73 | |
| A2A – 74 | |

| | | |
|---|---|---|
| SC-30-7 | A2A – 60 | SC-29-3 |
| SC-31-20 | A2A – 19 | SC-29-7 |
| A2A – 80 | A2A – 27 | SC-30-12 |
| A2A – 53 | A2A – 56 | SC-31-14 |
| A2A – 26 | A2A – 48 | SC-31-19 |
| A2A – 58 | MAB9497 | SC-31-21 |
| A2A – 59 | ZM 241385 | A2A – 18 |

SEQUENCE LISTING

<160> NUMBER OF SEQ ID NOS: 743

<210> SEQ ID NO 1
<211> LENGTH: 412
<212> TYPE: PRT
<213> ORGANISM: Unknown
<220> FEATURE:
<223> OTHER INFORMATION: Description of Unknown:
Adenosine A2A sequence

<400> SEQUENCE: 1

Met Pro Ile Met Gly Ser Ser Val Tyr Ile Thr Val Glu Leu Ala Ile
1 5 10 15

Ala Val Leu Ala Ile Leu Gly Asn Val Leu Val Cys Trp Ala Val Trp
20 25 30

Leu Asn Ser Asn Leu Gln Asn Val Thr Asn Tyr Phe Val Val Ser Leu
35 40 45

Ala Ala Ala Asp Ile Ala Val Gly Val Leu Ala Ile Pro Phe Ala Ile
50 55 60

Thr Ile Ser Thr Gly Phe Cys Ala Ala Cys His Gly Cys Leu Phe Ile
65 70 75 80

Ala Cys Phe Val Leu Val Leu Thr Gln Ser Ser Ile Phe Ser Leu Leu
85 90 95

-continued

```
Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
    370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410
```

```
<210> SEQ ID NO 2
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 2

agacaatcaa ccatttgggg tggacagcct tgacctctag acttcggcat tttttttttt     60

tt                                                                    62
```

<210> SEQ ID NO 3
<211> LENGTH: 112
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 3
cgggatcctt atcgtcatcg tcgtacagat cccgacccat ttgctgtcca ccagtcatgc 60
tagccatacc atgatgatga tgatgatgag aaccccgcat tttttttttt tt 112

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4
atgcggggtt ctcatcatc 19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
cgggatcctt atcgtcatcg 20

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Gly Gly Ser Ile Ser Ser Ser Asn
1 5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Gly Tyr Thr Phe Thr Gly Tyr
1 5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Gly Tyr Thr Phe Thr Gly Tyr
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Gly Phe Thr Phe Ser Asp Tyr
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Gly Phe Thr Phe Ser Ser Tyr
1 5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Gly Phe Thr Phe Ser Asn Tyr
1 5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gly Phe Thr Phe Ser Ser Tyr
1 5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gly Tyr Ser Ile Thr Ser Gly Tyr
1 5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Tyr Ser Ile Thr Ser Gly Tyr
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Tyr Ser Ile Thr Ser Gly Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Phe Thr Phe Ser Asp Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Thr Phe Asn Asp Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Thr Phe Ser Asp Phe
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Asp Tyr
1 5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gly Phe Thr Phe Ser Thr Tyr
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Gly Phe Thr Phe Asn Asn Tyr
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Gly Phe Asn Ile Gly Asn Thr
1 5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gly Phe Ser Phe Ser Gly Tyr
1 5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Phe Thr Phe Ser Gly Tyr
1 5

<210> SEQ ID NO 25
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 25

Gly Phe Ala Phe Ser Asn Tyr
1 5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gly Gly Ser Ile Ser Ser Gly Gly Tyr
1 5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Gly Tyr Thr Phe Thr Glu Tyr
1 5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Gly Phe Thr Phe Ser Thr Tyr
1 5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Gly Phe Asn Ile Gly Asn Thr
1 5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Gly Phe Thr Phe Gly Asn Tyr
1 5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Gly Phe Thr Phe Ser Thr Tyr
1 5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gly Phe Thr Phe Ser Ser Tyr
1 5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Gly Phe Thr Phe Ser Ser Gln
1 5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Gly Tyr Ser Phe Thr Gly Tyr
1 5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Gly Tyr Arg Leu Thr Gly Tyr
1 5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Gly Tyr Leu Phe Thr Asp Tyr
1 5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gly Phe Thr Phe Ile Asp Tyr
1 5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gly Phe Pro Phe Ser Ser Tyr
1 5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Gly Phe Asn Phe Asn Thr Tyr
1 5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Gly Phe Thr Phe Ser Thr Tyr
1 5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Gly Phe Asn Ile Gly Asn Thr
1 5

<210> SEQ ID NO 42
<211> LENGTH: 7

<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Gly Tyr Thr Phe Thr Ser Tyr
1 5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Gly Phe Ser Leu Thr Ser Tyr
1 5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gly Phe Thr Phe Ser Asn Tyr
1 5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Gly Phe Asn Phe Arg Ser Tyr
1 5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gly Phe Ser Leu Ser Ile Tyr
1 5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Gly Tyr Thr Phe Thr Ser Tyr 1 5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Gly Phe Thr Phe Ser Ser Tyr
1 5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Gly Phe Thr Phe Ser Ala Tyr
1 5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Gly Tyr Ser Phe Thr Gly Tyr
1 5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Gly Gly Tyr Ile Ser Ser Ser Asn
1 5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Gly Thr Phe Thr Asp Tyr
1 5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Gly Tyr Thr Phe Thr Ser Ser
1 5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Tyr Thr Phe Asn Asp Asp
1 5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Gly Tyr Ser Phe Thr Gly Tyr
1 5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Gly Tyr Thr Phe Asn Asp Tyr
1 5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Gly Tyr Thr Phe Asn Asp Tyr
1 5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Gly Phe Asn Ile Ile Asp Asp
1 5

<210> SEQ ID NO 59

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gly Tyr Thr Phe Thr Asp Tyr
1 5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Gly Tyr Glu Phe Ser Ser Ser
1 5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Phe Thr Phe Ser Ser Tyr
1 5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Gly Phe Ile Phe Ser Asp Phe
1 5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gly Phe Asn Ile Lys Asp Tyr
1 5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Gly Tyr Thr Phe Thr Asp Tyr
1 5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Gly Tyr Thr Phe Thr Glu Tyr
1 5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Gly Phe Thr Phe Ser Thr Tyr
1 5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Gly Tyr Thr Phe Thr Asn Tyr
1 5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gly Phe Thr Phe Ser Asp His
1 5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Gly Phe Thr Phe Asp Asp Tyr
1 5

<210> SEQ ID NO 70
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 70

Gly Ser Ala Phe Ser Ala Ser
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Thr Phe Ser Ser Tyr
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly His Thr Ile Thr Ser Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Thr Phe Ser Gly Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gly Tyr Ile Ser Ser Ser Asn
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Asn Ile Lys Asp Tyr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Gly Gly Ser Ile Ser Ser Ser Asn
1 5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Gly Phe Thr Ile Ser Thr Tyr
1 5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Gly Phe Thr Val Ser Thr Tyr
1 5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Gly Phe Thr Phe Thr Thr Tyr
1 5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Gly Gly Ser Ile Ser Ser Ser Asn
1 5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Gly Phe Thr Phe Ser Ser Tyr
1 5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gly Gly Ser Ile Ser Ser Ser Asn
1 5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gly Phe Thr Phe Ser Ala Tyr
1 5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Gly Phe Thr Phe Asp Asp Tyr
1 5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Gly Phe Thr Ile Ser Thr Tyr
1 5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Gly Gly Ser Ile Ser Ser Ser Asn
1 5

<210> SEQ ID NO 87
<211> LENGTH: 8
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 87

Gly Tyr Ser Ile Thr Ser Gly Tyr
1 5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Gly Tyr Ala Phe Ser Ser Tyr
1 5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Gly Tyr Thr Phe Thr Glu Tyr
1 5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Gly Phe Ser Leu Thr Ala Tyr
1 5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Gly Tyr Ser Ile Thr Ser Asp
1 5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Gly Phe Asn Ile Lys Asn Thr
1 5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Gly Phe Thr Phe Arg Thr Tyr
1 5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Gly Phe Thr Phe Asn Asn Tyr
1 5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Tyr Pro Ser Gly Asn
1 5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Asn Pro Asn Ser Gly Gly
1 5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Asn Pro Asn Ser Gly Gly
1 5

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Ser Ser Ser Gly Ser Thr
1 5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Ser Ser Ser Ser Ser Tyr
1 5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Ser Ser Ser Ser Ser Tyr
1 5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Ser Gly Ser Gly Gly Ser
1 5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Ser Tyr Asp Gly Ser
1 5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Arg Tyr Asp Gly Ser
1 5

<210> SEQ ID NO 104
<211> LENGTH: 5
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 104

Ser Tyr Asp Gly Ser
1 5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Asn Tyr Asp Gly Ser Ser
1 5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Asn Tyr Asp Gly Ser Ser
1 5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Ser Ser Gly Ser Ser Thr
1 5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Ser Ser Gly Ser Gly Thr
1 5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Ser Gly Ser Gly Gly Ser
1 5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Ser Gly Ser Gly Gly Asp
1 5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Asn Pro Asn Tyr Gly Thr
1 5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Ser Gly Ser Gly Gly Ser
1 5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Ser Gly Ser Gly Ala Ser
1 5

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Tyr Pro Lys Ser Gly Ser
1 5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Asn Pro Asn Ser Gly Asn
1 5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

His Pro Ser Ser Gly Ser
1 5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Ser Gly Ser Gly Gly Ser
1 5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Asn Pro Asn Tyr Gly Thr
1 5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Asp Pro Ala Asn Gly Asp
1 5

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Ser Gly Ser Ala Gly Ser
1 5

<210> SEQ ID NO 121
<211> LENGTH: 6

<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Ser Gly Ser Gly Gly Ser
1 5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Ser Gly Ser Gly Val Ser
1 5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Tyr Pro Gly Ser Gly Asn
1 5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Asp Pro Ala Ser Gly Asp
1 5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Tyr Pro Gly Thr Gly
1 5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Asn Pro Asn Tyr Gly Thr 1 5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Ser Gly Ser Gly Gly Arg
1 5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Tyr Pro Gly Asn Ser Asp
1 5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Ser Gly Ser Gly Gly Ser
1 5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Asn Pro Asn Tyr Gly Thr
1 5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Asn His Asp Gly Ser Asn
1 5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Asp Pro Glu Thr Asp Asp
1 5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Asn Pro Asn Asn Gly Gly
1 5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Ser Gly Gly Gly Gly Ser
1 5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Ser Pro Gly Ser Gly Ser
1 5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Ser Ser Gly Gly Asp Ser
1 5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Ser Asp Gly Gly Ser Tyr
1 5

<210> SEQ ID NO 138

<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Gly Thr Ala Gly Asp
1 5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Leu Pro Gly Ser Gly Gly
1 5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Glu Gln Asp Gly Ser Glu
1 5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Leu Pro Gly Ser Gly Gly
1 5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Tyr Pro Arg Asp Gly Ser
1 5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Asn Pro Asn Asn Gly Ala
1 5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Tyr Pro Lys Asp Gly Ser
1 5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Asn Pro Asn Asn Gly Ala
1 5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Asn Pro Asn Asn Gly Gly
1 5

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Thr Asp Thr Gly Glu Pro
1 5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Asp Pro Ala Asn Gly Asp
1 5

<210> SEQ ID NO 149
<211> LENGTH: 6
<212> TYPE: PRT
<213> ORGANISM: Artificial Sequence
<220> FEATURE:

-continued

<223> OTHER INFORMATION: Description of Artificial Sequence: Synthetic
peptide

<400> SEQUENCE: 149

Tyr Pro Gly Thr Gly Asn
1 5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Asp Pro Gly Thr Gly Gly
1 5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Asp Pro Glu Asp Gly
1 5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Asn Pro Asn Asn Gly Gly
1 5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Asn Ile Asn Asn Gly Gly
1 5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Asn Phe Asp Gly Ser Ser
1 5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Tyr Pro Gly Asp Thr Asp
1 5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Asn Pro Asn Asn Gly Gly
1 5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Asn Pro Asn Ser Gly Ile
1 5

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Asn Thr Asn Thr Gly Asn
1 5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Asp Pro Asp Asn Gly Asp
1 5

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Tyr Pro Lys Asp Gly Ser
1 5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Leu Pro Gly Ser Gly Thr
1 5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Asp Pro Ser Asp Ser Phe
1 5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 163

Lys Thr Lys Thr Asp Gly Gly Thr
1 5

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 164

Ser Asp Gly Gly Ser
1 5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 165

Tyr His Ser Gly Ser
1 5

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 166

Gly Thr Ala Gly Asp
1 5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Gly Thr Ala Gly Asp
1 5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Gly Thr Ala Gly Asp
1 5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Tyr His Ser Gly Asn
1 5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 170

Gly Thr Ala Gly Asp
1 5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

Tyr His Ser Gly Asn
1 5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Gly Thr Ala Gly Asp
1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Thr Trp Asn Gly Asp Arg
1               5

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Gly Thr Ala Gly Asp
1               5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Tyr His Ser Gly Ser
1               5

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 176

Ser Tyr Gly Gly Ser
1               5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

Tyr Pro Gly Asp Gly Asp
1 5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Ser Gly Gly Gly Ser Tyr
1 5

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Trp Thr Gly Gly Gly
1 5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Asn Tyr Ser Gly Ser
1 5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Asp Pro Ala Asn Gly Asn
1 5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 182

Ser Ala Glu Gly Ser Asn
1 5

<210> SEQ ID NO 183
<211> LENGTH: 6
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 183

Ser Tyr Gly Gly Ser Asp
1               5

<210> SEQ ID NO 184
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp Glu Gly Tyr
1

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Gly Pro Phe Asp Tyr
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Val Tyr Ser Tyr Gly Phe Asp Tyr
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Asn Trp Ala Phe Asp Leu
1               5

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Thr Trp Tyr Ser Ser Ser Pro Phe Asp Tyr
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Asp Ser Gly Ser Tyr Tyr Asp Trp Phe Asp Pro
1 5 10

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Tyr Ser Asn Tyr Phe Asp Tyr
1 5

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Val His His Tyr Tyr Gly Ser Ser Tyr Phe Asp Tyr
1 5 10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Val His His Tyr Tyr Gly Ser Ser Tyr Phe Asp Tyr
1 5 10

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Asp Pro Tyr Tyr Tyr Gly Ser Ser Tyr Phe Asp Tyr
1 5 10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Glu Tyr Tyr Tyr Gly Ser Ser Ser Phe Ala Tyr
1 5 10

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Glu Tyr Tyr Tyr Gly Ser Ser Ser Phe Ala Tyr
1 5 10

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Arg Glu Phe Ala Tyr
1 5

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Pro Asn Tyr His Gly Ser Ser Pro Phe Ala Tyr
1 5 10

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Ala Arg Gly Lys Trp Arg Trp Arg Leu Gly Arg Arg Tyr Asp Tyr
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Ala Arg Gly Tyr Trp Arg Trp Arg Leu Leu Arg Arg Tyr Asp Tyr
1 5 10 15

<210> SEQ ID NO 200
<211> LENGTH: 9

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 200

Asp Tyr Gly Ser Ser Ser Phe Asp Tyr
1 5

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Ala Arg Gly Tyr Pro Arg Trp Arg Leu Gly Arg Arg Tyr Asp Tyr
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Ala Arg Gly Tyr Lys Arg Trp Arg Leu Gly Arg Arg Tyr Asp Tyr
1 5 10 15

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Leu Tyr Gly Tyr Asp Leu His Trp Tyr Phe Asp Val
1 5 10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 204

Asp Glu Val Ala Ala Ala Gly Leu Phe Asp Tyr
1 5 10

<210> SEQ ID NO 205
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 205

His Glu Val Glu Tyr Tyr Gly Pro Ser Ser Ser Trp Phe Ala Tyr 1 5 10 15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Ala Arg Gly Lys Trp Arg Trp Arg Leu Gly Arg Arg Tyr Asp Tyr
1 5 10 15

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Asp Tyr Gly Ser Ser Ser Phe Asp Tyr
1 5

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Glu Gly Asp Asn Ser Asn Tyr Tyr Ala Met Asp Tyr
1 5 10

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Ala Arg Gly His Trp Arg Trp Arg Leu Gly Arg Arg Tyr Asp Tyr
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Ala Arg Gly Tyr Trp Arg Trp Arg Leu Trp Arg Arg Tyr Asp Tyr
1 5 10 15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Ala Arg Gly Arg Trp Arg Trp Arg Leu Gly Arg Arg Tyr Asp Tyr
1 5 10 15

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

Glu Asp Asp Tyr Gly Trp Tyr Phe Gly Val
1 5 10

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

His Glu Asp Pro Ile Tyr Tyr Gly Asn Tyr Val Phe Ala Tyr
1 5 10

<210> SEQ ID NO 214
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

Leu Tyr Tyr Gly Ser Ser Trp Glu Arg Tyr Phe Asp Val
1 5 10

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Gln Gly Ser Asn Tyr Gly Gly Tyr Phe Asp Val
1 5 10

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

Ala Arg Gly Tyr Trp Arg Trp Arg Leu Gly Arg Arg Ala Asp Tyr
1 5 10 15

<210> SEQ ID NO 217

<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Val Ile Tyr Tyr Tyr Gly Ser Ser Asp Tyr Thr Leu Asp Tyr
1 5 10

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Ala Arg Gly Lys Trp Arg Trp Arg Leu Gly Arg Arg Tyr Asp Tyr
1 5 10 15

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Asp Tyr Gly Ser Ser Ser Phe Asp Tyr
1 5

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Ser Met Ile Thr Arg Phe Ala Tyr
1 5

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Tyr Tyr Tyr Gly Ser Ser Ala Phe Ala Tyr
1 5 10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

-continued

Ala Tyr Tyr Ser Asn Tyr Gly Val Met Tyr Phe
1 5 10

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Ala Arg Gly Gly Trp Arg Trp Arg Leu Gly Arg Arg Tyr Asp Tyr
1 5 10 15

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Pro Tyr Tyr Tyr Gly Ser Ser Arg Tyr Tyr Ala Met Asp Tyr
1 5 10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Asp Tyr Tyr Gly Ser Ser Trp His Phe Asp Val
1 5 10

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

Tyr Ile Trp Tyr Tyr Gly Ser Ser Trp Ser Trp Tyr Phe Asp Ala
1 5 10 15

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Gly Tyr Asn Trp Ile Phe Asp Leu
1 5

<210> SEQ ID NO 228
<211> LENGTH: 8
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 228

Gly Asn Tyr Asp Ala Met Asp Tyr
1 5

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 229

Gly Glu Tyr Ser Arg Leu Trp Tyr Phe Asp Leu
1 5 10

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 230

Pro Tyr Asp Tyr Asp Phe Asp Tyr
1 5

<210> SEQ ID NO 231
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 231

Thr Val Val Ala Asp Trp Tyr Phe Asp Val
1 5 10

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Lys Gly Asp Gly Gly Ser Tyr Ala Ala Met Asp Tyr
1 5 10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Thr Val Val Ala Asp Trp Tyr Phe Asp Val
1 5 10

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asn Tyr Gly Ser Ser Tyr Tyr Ala Leu Asp Tyr
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Gly Ser Asn Tyr Gly Gly Tyr Phe Asp Val
1               5                   10

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Asp Tyr Ile Tyr Ala Met Asp Tyr
1               5

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Asp Tyr Gly Ser Ser Tyr Ala Met Asp Tyr
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Tyr Tyr Tyr Gly Ser Ser Ala Phe Ala Tyr
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ile Tyr Tyr Asp Tyr Ser Ala Met Asp Tyr
1 5 10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 240

Asp Tyr Tyr Gly Ser Ser Tyr Leu Asp Tyr
1 5 10

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 241

Asp Tyr Tyr Gly Ser Phe His Arg Arg Trp Tyr Phe Asp Val
1 5 10

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 242

Asp Tyr His Gly Ser Ser Phe Tyr Trp Tyr Phe Asp Val
1 5 10

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 243

Tyr Tyr Asp Ser Ser Tyr Tyr Ala Met Asp Tyr
1 5 10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 244

Gly Ile Ala Val Ala Gly Thr Phe Asp Tyr
1 5 10

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 245

His Ala Leu Leu Trp Tyr Tyr Tyr Ala Met Asp Tyr
1 5 10

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 246

Val Ser Tyr Ser Gly Ser Leu His Tyr
1 5

<210> SEQ ID NO 247
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 247

Ser Asn Trp Asn Tyr Phe Asp Tyr
1 5

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Pro Arg Asp Ser Gly Pro Ser Phe Ala Ser
1 5 10

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Ser Arg Gly Tyr Tyr Tyr Gly Ser Ser Tyr Gly Tyr Tyr Asp Val
1 5 10 15

<210> SEQ ID NO 250
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

Asn Trp Gly Phe Ala Tyr
1 5

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

Asp Tyr Gly Ser Ser Tyr Glu Phe Thr Tyr
1 5 10

<210> SEQ ID NO 252
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 252

Gly Tyr Ser Gly Ser Val Asp Tyr
1 5

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Asp Ala Thr Gly Thr Phe Ala Tyr
1 5

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Glu Val Val Ser Gly Met Ile Gly Thr Val Phe Asp Tyr
1 5 10

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Gly Tyr Asn Trp Ile Phe Asp Tyr
1 5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Gly Tyr Asn Trp Ile Phe Asp Phe
1 5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Gly Tyr Asn Trp Ile Phe Asp Phe
1 5

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Glu Val Val Ser Gly Met Ile Gly Thr Ile Phe Asp Tyr
1 5 10

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Gly Tyr Asn Trp Ile Phe Asp Phe
1 5

<210> SEQ ID NO 260
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Glu Val Val Ser Gly Met Ile Gly Thr Ile Phe Asp Tyr
1 5 10

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Gly Tyr Asn Trp Val Phe Asp Leu
1 5

<210> SEQ ID NO 262
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 262

Asp Gly Leu Thr Gly Ile Phe Asp Tyr
1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 263

Gly Tyr Asn Trp Ile Phe Asp Tyr
1               5

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 264

Glu Val Val Ser Gly Leu Tyr Gly Thr Ile Phe Asp Tyr
1               5                   10

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 265

Asp Tyr Asp Tyr Phe Asp Tyr
1               5

<210> SEQ ID NO 266
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 266

Gly Ala Tyr
1

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 267

Pro Asn Tyr Ser Gly Ser Ser Pro Phe Ala Tyr
1               5                   10

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Ser Arg Gly Tyr Tyr Tyr Gly Ser Ser Tyr Gly Tyr Phe Asp Val
1 5 10 15

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Lys Leu Asp Trp Asp Gly Tyr Phe Asp Val
1 5 10

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Gly Ser Pro Tyr Gly Tyr Asp Gly His Tyr Val Met Asp Tyr
1 5 10

<210> SEQ ID NO 271
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 271

Asp Gly Arg Gly Ser Leu Pro Arg Pro Lys Gly Gly Phe Ile Gly Ala
1 5 10 15

Leu Ser Phe His Trp Pro Phe Gly Arg Trp Leu Gly Gly Ser Tyr Gly
20 25 30

Thr Tyr Asp Ser Ser Glu Asp Ser Gly Gly Ala Phe Asp Ile
35 40 45

<210> SEQ ID NO 272
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 272

Asp Gly Arg Gly Ser Leu Pro Arg Pro Lys Gly Gly Phe Ile Gly Asp
1 5 10 15

Leu Ser Phe His Trp Pro Phe Gly Arg Trp Leu Gly Lys Ser Tyr Gly
20 25 30

Thr Tyr Asp Ser Ser Glu Asp Ser Gly Gly Ala Phe Asp Ile
35 40 45

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Arg Ser Ser Gln Ser Leu Val Tyr Ser Asp Gly Asn Thr Tyr Leu Asn
1 5 10 15

<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Lys Ala Ser Gln Asp Ile Asp Asp Asp Met Asn
1 5 10

<210> SEQ ID NO 275
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Lys Ser Ser Gln Ser Val Leu Tyr Ser Ser Asn Asn Lys Asn Tyr Leu
1 5 10 15

Ala

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Arg Ala Ser Gln Ser Val Ser Ser Asn Leu Ala
1 5 10

<210> SEQ ID NO 277
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Lys Ala Ser Gln Asp Ile Asp Asp Asp Met Asn
1 5 10

<210> SEQ ID NO 278
<211> LENGTH: 11

<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Arg Ala Ser Gln Gly Ile Ser Ser Trp Leu Ala
1 5 10

<210> SEQ ID NO 279
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Lys Ala Ser Gln Asp Val Asp Asp Asp Met Asn
1 5 10

<210> SEQ ID NO 280
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Lys Ala Ser Gln Asn Val Gly Thr Asn Val Ala
1 5 10

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

Lys Ala Ser Gln Asn Val Gly Ser Ser Val Ala
1 5 10

<210> SEQ ID NO 282
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 282

Arg Ala Ser Gln Ser Ile Ser Asp Tyr Leu His
1 5 10

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 283

Lys Ala Ser Arg Asn Val Gly Thr Asn Val Ala 1 5 10

<210> SEQ ID NO 284
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 284

Arg Ala Ser Gln Ser Ile Ser Asp Tyr Leu His
1 5 10

<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 285

Lys Ala Ser Gln Asn Val Gly Thr Asn Val Ala
1 5 10

<210> SEQ ID NO 286
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 286

Arg Ala Ser Gln Ser Ile Ser Asn Tyr Leu His
1 5 10

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 287

Arg Ala Ser Gln Ser Ile Gly Arg Tyr Leu Asn
1 5 10

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Arg Ala Ser Gln Ser Ile Gly Thr Tyr Leu Asn
1 5 10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

Lys Ala Ser Gln Ser Val Arg Asn Asp Val Val
1 5 10

<210> SEQ ID NO 290
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

Arg Ala Ser Gln Ser Val Thr Thr Tyr Leu Asn
1 5 10

<210> SEQ ID NO 291
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 291

Arg Ala Ser Gln Ser Ile Ser Asp Tyr Leu Asn
1 5 10

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 292

Lys Ala Ser His Ser Val Asp Tyr Asp Gly Asp Asn Tyr Met Asn
1 5 10 15

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 293

Lys Ser Ser Gln Ser Val Leu Tyr Ser Ser Asn Asn Lys Asn Tyr Phe
1 5 10 15

Ala

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Arg Ala Ser Gln Asp Ile Gly Arg Ser Leu Ser
1 5 10

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Arg Ala Ser Gln Ser Ile Gly Arg Tyr Leu Asn
1 5 10

<210> SEQ ID NO 296
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Lys Ala Ser Gln Ser Val Arg Asn Asp Val Val
1 5 10

<210> SEQ ID NO 297
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Lys Ala Ser Gln Ser Val Asp Tyr Asp Gly Asp Ser Tyr Met Asn
1 5 10 15

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Arg Ala Ser Gln Thr Ile Ser Arg Tyr Leu Asn
1 5 10

<210> SEQ ID NO 299
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

Arg Ala Ser Gln Ser Ile Gly Ser Tyr Leu Asn
1 5 10

<210> SEQ ID NO 300
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Arg Ala Ser Arg Ser Ile Ser Ser Tyr Leu Asn
1 5 10

<210> SEQ ID NO 301
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 301

Lys Val Ser Gln Asp Val Arg Thr Ala Val Ala
1 5 10

<210> SEQ ID NO 302
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Gly Gly Gly Asn Asp Ile Gly Ser Ser Met Tyr
1 5 10

<210> SEQ ID NO 303
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 303

Arg Ala Ser Gln Ser Ile Ser Asp Tyr Leu Asn
1 5 10

<210> SEQ ID NO 304
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Gly Gly Gly Asn Asp Ile Gly Ser Ser Met Tyr
1 5 10

<210> SEQ ID NO 305
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Arg Ala Ser Glu Ser Val Asp Ser Phe Gly Asn Asn Phe Met Asn
1 5 10 15

<210> SEQ ID NO 306
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 306

Arg Ala Ser Ser Ser Val Thr Tyr Ile His
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Ala Ser Gln Ser Ile Gly Arg Tyr Leu Asn
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Lys Ala Ser Gln Ser Val Arg Asn Asp Val Val
1               5                   10

<210> SEQ ID NO 309
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Lys Ala Ser His Ser Val Asp Tyr Asp Gly Asp Asn Tyr Met Asn
1               5                   10                  15

<210> SEQ ID NO 310
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Arg Ala Ser Glu Ser Val Asn Ser Tyr Gly Asn Ser Phe Met His
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Arg Ser Ser Lys Ser Leu Leu His Ser Ser Gly Asn Ala Tyr Val Tyr
1               5                   10                  15

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Arg Ala Ser Gln Ser Ile Gly Thr Tyr Leu Asn
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Ala Ser Ser Arg Val Ser Ser Ser Tyr Leu Tyr
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Ala Ser Gln Ser Ile Gly Thr Ile Ile His
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Arg Ala Ser Glu Asn Ile Tyr Val Pro Leu Asn
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Arg Ala Ser Gln Ser Val Ser Ser Ser Tyr Leu Ala
1               5                   10

<210> SEQ ID NO 317
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Lys Ser Ser Gln Ser Leu Leu Tyr Ser Gly Glu Lys Thr Tyr Pro Tyr
1 5 10 15

<210> SEQ ID NO 318
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gln Ser Ser Gln Asp Ile Phe Asn Tyr Leu Glu
1 5 10

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 319

Arg Ser Thr Arg Asn Ile Leu Ser Asn Met Pro
1 5 10

<210> SEQ ID NO 320
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Arg Ala Ser Gln Asp Ile Ser Asn Asn Leu His
1 5 10

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Ser Ala Ser Gln Ser Met Ser Asn Asn Leu His
1 5 10

<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Arg Ala Ser Gln Asp Ile Ser Asn Asn Leu His
1 5 10

<210> SEQ ID NO 323
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Ser Ala Ser Ser Ser Leu Ser Tyr Met His
1 5 10

<210> SEQ ID NO 324
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Ser Ala Ser Ser Ser Val Ser Tyr Met Asn
1 5 10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Lys Ala Ser Gln Asn Met Gly Ser Asn Val Ala
1 5 10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 326

Lys Ala Ser Gln Asn Gly Gly Thr Asn Val Asp
1 5 10

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

Arg Ala Ser Glu Asn Ile Tyr Val Pro Leu Asn
1 5 10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Lys Ala Ser Gln Asn Met Gly Ser Asn Val Ala 1 5 10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Lys Ala Ser Gln Asn Gly Gly Thr Asn Val Asp
1 5 10

<210> SEQ ID NO 330
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Lys Ala Ser Gln Gly Val Asp Thr Asn Val Ala
1 5 10

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Lys Ala Ser Gln Asp Val Gly Thr Ala Ile Thr
1 5 10

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Lys Ala Ser Gln Asp Val Gly Thr Ser Val Ala
1 5 10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 333

Arg Ala Ser Gln Val Ile Asp Asp Asp Ile Asn
1 5 10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 334

Arg Ala Ser Gln Glu Ile Ser Gly Tyr Leu Thr
1 5 10

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 335

Arg Ala Ser Gln Ser Ile Ser Arg Tyr Leu Asn
1 5 10

<210> SEQ ID NO 336
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 336

Arg Ala Ser Gln Gly Ile Ser Ser Trp Leu Asp
1 5 10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 337

Lys Ala Ser Gln Asn Met Gly Ser Asn Val Ala
1 5 10

<210> SEQ ID NO 338
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 338

Arg Ala Ser Gln Gly Ile Leu Gly Tyr Leu Asn
1 5 10

<210> SEQ ID NO 339
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 339

Arg Ala Ser Glu Ser Val Asp Asn Tyr Gly Ile Ser Phe Met Ser
1 5 10 15

<210> SEQ ID NO 340

<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Lys Ser Ser Gln Ser Leu Leu Tyr Ser Gly Glu Lys Thr Tyr Pro Tyr
1 5 10 15

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 341

Arg Ala Ser Gln Gly Leu Arg His Asp Leu Gly
1 5 10

<210> SEQ ID NO 342
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 342

His Ala Ser Glu Ser Val Ser Val Ala Gly Thr Ser Leu Leu His
1 5 10 15

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 343

Arg Val Ser Gln Gly Ile Ser Asn Tyr Leu Asn
1 5 10

<210> SEQ ID NO 344
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

Arg Ala Ser Gln Ser Val Ser Ser Asn Leu Ala
1 5 10

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Arg Ala Ser Gln Ser Val Ser Ser Asn Leu Ala
1 5 10

<210> SEQ ID NO 346
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Arg Ala Ser Gln Ser Val Ser Ser Ser Tyr Leu Ala
1 5 10

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Arg Ala Ser Gln Ser Ile Ser Ser Tyr Leu Asn
1 5 10

<210> SEQ ID NO 348
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Arg Ala Ser Gln Ser Val Ser Ser Asn Leu Ala
1 5 10

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Arg Ala Ser Gln Arg Ile Ser Ser Tyr Leu Asn
1 5 10

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Arg Ala Ile Gln Ser Val Ser Ser Ser Tyr Leu Ala
1 5 10

<210> SEQ ID NO 351
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 351

Arg Ala Ser Gln Ser Val Ser Ser Tyr Leu Ala
1               5                   10


<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ala Ser Gln Ser Val Ser Ser Asn Leu Ala
1               5                   10


<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Arg Ala Ser Gln Ser Ile Ser Ser Tyr Leu Asn
1               5                   10


<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Lys Ala Ser Gln Ser Val Ser Asn Asp Val Ala
1               5                   10


<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Lys Ala Ser Gln Asn Val Gly Thr Asn Val Ala
1               5                   10


<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ser Ala Ser Ser Ser Val Ser Tyr Met Tyr
1               5                   10
```

<210> SEQ ID NO 357
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 357

Arg Ala Ser Gln Ser Ile Ser Asp Tyr Leu His
1 5 10

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 358

His Ala Ser Gln Asn Ile Asn Val Trp Leu Asn
1 5 10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Lys Ala Ser Gln Asn Val Gly Ser Asn Val Ala
1 5 10

<210> SEQ ID NO 360
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Ser Gly Ile Ser Ser Asn Ile Gly Asn Asn Tyr Val Ser
1 5 10

<210> SEQ ID NO 361
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Ser Gly Ser Ser Ser Asn Ile Gly Asn His Tyr Val Ser
1 5 10

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Lys Val Ser Asn Arg Asp Ser
1 5

<210> SEQ ID NO 363
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Glu Ala Thr Thr Leu Val Pro
1 5

<210> SEQ ID NO 364
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 364

Trp Ala Ser Thr Arg Glu Ser
1 5

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 365

Gly Ala Ser Thr Arg Ala Thr
1 5

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 366

Glu Ala Thr Thr Leu Val Pro
1 5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 367

Ala Ala Ser Ser Leu Gln Ser
1 5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 368

Glu Ala Thr Thr Leu Val Pro
1 5

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 369

Ser Ala Ser Tyr Arg Tyr Ser
1 5

<210> SEQ ID NO 370
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 370

Ser Thr Ser Tyr Arg Tyr Ser
1 5

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 371

Tyr Ala Ser Gln Ser Ile Ser
1 5

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 372

Ser Ala Ser Tyr Arg Tyr Ser
1 5

<210> SEQ ID NO 373
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 373

Tyr Ala Ser Gln Ser Ile Ser
1 5

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Ser Ala Ser Tyr Arg Tyr Ser
1 5

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 375

Tyr Ala Ser Gln Ser Ile Ser
1 5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 376

Ala Ala Ser Ser Leu His Ser
1 5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 377

Gly Ala Ser Thr Leu His Ser
1 5

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 378

Arg Gly Asn Thr Leu Arg Pro
1 5

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 379

Ser Ala Ser Ser Leu Gln Ser
1 5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 380

Thr Ala Ser Thr Leu Gln Ser
1 5

<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 381

Trp Ala Ser Thr Arg Leu Thr
1 5

<210> SEQ ID NO 382
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 382

Asp Ala Pro Asn Arg Ala Thr
1 5

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 383

Asp Ala Ser Arg Phe Ile Ser
1 5

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 384

Ala Ala Ser Ser Leu His Ser
1 5

<210> SEQ ID NO 385
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 385

Arg Gly Asn Thr Leu Arg Pro
1 5

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 386

Arg Ala Asn Arg Leu Val Asp
1 5

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 387

Ser Ala Ser Thr Leu Gln Ser
1 5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 388

Gly Ala Ser Asn Leu Gln Ser
1 5

<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 389

Ala Ala Ser Ser Leu Pro Ser
1 5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 390

Asp Thr Ser Tyr Leu Ala Ser
1 5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 391

Trp Met Ser Asn Leu Ala Ser
1 5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 392

Gly Ala Ser Pro Arg Glu Ser
1 5

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 393

Asp Ala Ser Arg Phe Ile Ser
1 5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 394

His Thr Ser Arg Leu Asn Ser
1 5

<210> SEQ ID NO 395
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 395

Ala Val Ser Arg Leu Asp Ser
1 5

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Ala Ala Ser Ser Leu His Ser
1 5

<210> SEQ ID NO 397
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

Arg Gly Asn Thr Leu Arg Pro
1 5

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 398

Asp Ala Ser Arg Phe Ile Ser
1 5

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 399

Asp Ala Ser Arg Phe Ile Ser
1 5

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 400

Tyr Thr Ser Lys Pro Asn Ser
1 5

<210> SEQ ID NO 401
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 401

Ala Ala Ser Ser Leu Glu Ser
1 5

<210> SEQ ID NO 402
<211> LENGTH: 7

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 402

Ala Thr Tyr Ser Leu Asp Tyr
1 5

<210> SEQ ID NO 403
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 403

Asp Thr Ser Tyr Leu Ala Ser
1 5

<210> SEQ ID NO 404
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 404

Asp Ala Ser Arg Phe Ile Ser
1 5

<210> SEQ ID NO 405
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 405

Gly Ala Ser Ser Arg Ala Thr
1 5

<210> SEQ ID NO 406
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 406

Trp Ala Ser Thr Arg Leu Thr
1 5

<210> SEQ ID NO 407
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 407

Thr Ala Ser Asn Leu Asp Thr 1 5

<210> SEQ ID NO 408
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 408

Asn Ala Asn Thr Leu Ala Glu
1 5

<210> SEQ ID NO 409
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 409

Glu Ile Ser Gly Trp Leu Ser
1 5

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 410

Leu Ala Ser Asn Leu Gly Tyr
1 5

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Trp Ala Ser Thr Arg Leu Thr
1 5

<210> SEQ ID NO 412
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Gly Ala Ser Pro Arg Glu Ser
1 5

<210> SEQ ID NO 413
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

Glu Ile Ser Gly Trp Leu Ser
1 5

<210> SEQ ID NO 414
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 414

Ser Ala Ser His Arg Ser Ser
1 5

<210> SEQ ID NO 415
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 415

Glu Ile Ser Gly Trp Leu Ser
1 5

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Leu Ala Ser Tyr Arg Phe Thr
1 5

<210> SEQ ID NO 417
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Ala Ala Thr Arg Leu Ala Asp
1 5

<210> SEQ ID NO 418
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Val Ala Ser Asn Gln Gly Thr
1 5

<210> SEQ ID NO 419

<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 419

Ser Ser Ser Ile Ser
1 5

<210> SEQ ID NO 420
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 420

Ser Ala Ser Lys Arg Asn Thr
1 5

<210> SEQ ID NO 421
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 421

Pro Ala Ser Tyr Arg Ser Ser
1 5

<210> SEQ ID NO 422
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 422

Leu Gly Ser Asn Arg Ala Pro
1 5

<210> SEQ ID NO 423
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 423

Ser Ala Ser His Arg Ser Ser
1 5

<210> SEQ ID NO 424
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Lys Ala Ser Ser Leu Glu Arg
1 5

<210> SEQ ID NO 425
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

Thr Pro Phe Ser Leu Gln Ser
1 5

<210> SEQ ID NO 426
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 426

Glu Ala Ser Thr Arg Phe Ser
1 5

<210> SEQ ID NO 427
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

Ser Thr Ser Asn Leu Leu Leu
1 5

<210> SEQ ID NO 428
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

Asp Ala Ser Arg Phe Ile Ser
1 5

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 429

Glu Ala Ser Asn Arg Tyr Thr
1 5

<210> SEQ ID NO 430
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 430

Trp Ala Ser Asn Arg Glu Ser
1               5

<210> SEQ ID NO 431
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Ala Ala Ser Asn Arg Glu Ser
1               5

<210> SEQ ID NO 432
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Ala Ser Ser Leu Gln Ser
1               5

<210> SEQ ID NO 433
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Gly Ala Ser Ser Arg Ala Thr
1               5

<210> SEQ ID NO 434
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gly Ala Ser Ser Arg Ala Thr
1               5

<210> SEQ ID NO 435
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Gly Ala Ser Ser Arg Ala Thr
1               5

<210> SEQ ID NO 436
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 436

Ala Ala Ser Ser Leu Gln Ser
1 5

<210> SEQ ID NO 437
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 437

Asp Ala Ser Asn Arg Ala Thr
1 5

<210> SEQ ID NO 438
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 438

Ala Ala Ser Ser Leu Gln Ser
1 5

<210> SEQ ID NO 439
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 439

Gly Ala Ser Ser Arg Ala Thr
1 5

<210> SEQ ID NO 440
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 440

Gly Ala Ser Ser Arg Ala Thr
1 5

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 441

Gly Ala Ser Thr Arg Ala Thr
1 5

<210> SEQ ID NO 442
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Ala Ala Ser Ser Leu Gln Ser
1 5

<210> SEQ ID NO 443
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 443

Tyr Ala Ser Asn Arg Tyr Thr
1 5

<210> SEQ ID NO 444
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 444

Ser Ala Ser Tyr Arg Tyr Ser
1 5

<210> SEQ ID NO 445
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 445

Asp Thr Ser Asn Leu Ala Ser
1 5

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 446

Tyr Ala Ser Gln Ser Ile Ser
1 5

<210> SEQ ID NO 447
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Lys Ala Ser Asn Leu His Thr
1               5

<210> SEQ ID NO 448
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Ser Ala Ser Tyr Arg Tyr Ser
1               5

<210> SEQ ID NO 449
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Asp Asn Asn Lys Arg Ala Ser Gly
1               5

<210> SEQ ID NO 450
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Asp Asn Thr Lys Arg Pro Ser Gly
1               5

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Met Gln Gly Thr His Trp Pro Arg Thr
1               5

<210> SEQ ID NO 452
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Leu Gln His Asp Asn Phe Pro Met Tyr Thr
1               5                   10

<210> SEQ ID NO 453
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 453

Gln Gln Tyr Tyr Ser Thr Pro Tyr Thr
1 5

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 454

Gln Gln Tyr Tyr Ser Thr Pro Leu Thr
1 5

<210> SEQ ID NO 455
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 455

Leu Gln His Asp Asn Phe Pro Trp Thr
1 5

<210> SEQ ID NO 456
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 456

Gln Gln Thr Asn Ser Phe Pro Arg Thr
1 5

<210> SEQ ID NO 457
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 457

Leu Gln His Asp Asn Phe Pro Trp Thr
1 5

<210> SEQ ID NO 458
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 458

Gln Arg Phe Asn Asn Tyr Pro Leu Thr
1               5

<210> SEQ ID NO 459
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Gln Gln Tyr Asn Ser Tyr Pro Leu Thr
1               5

<210> SEQ ID NO 460
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Gln Asn Gly His Ser Phe Pro Leu Thr
1               5

<210> SEQ ID NO 461
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Gln Gln Tyr Asn Ser Tyr Pro Leu Thr
1               5

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Gln Asn Gly His Ser Phe Pro His Thr
1               5

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Gln Gln Tyr Asn Ile Tyr Pro Leu Thr
1               5

<210> SEQ ID NO 464
<211> LENGTH: 9
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 464

Gln Asn Gly His Ser Phe Pro Leu Thr
1 5

<210> SEQ ID NO 465
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 465

Gln Gln Ser Tyr Val Thr Pro Trp Thr
1 5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 466

Gln Gln Ser Tyr Ser Ala Pro Trp Thr
1 5

<210> SEQ ID NO 467
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 467

Gln Gln Tyr Tyr Gly Ile Pro Leu Thr
1 5

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 468

Gln Gln Thr Tyr Ala Thr Pro Trp Thr
1 5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Glu Gln Ser Tyr Ser Thr Pro Trp Thr
1 5

<210> SEQ ID NO 470
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 470

Leu Gln His Ile Glu Tyr Pro Phe Thr
1 5

<210> SEQ ID NO 471
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 471

Gln Gln Gly Tyr Thr Thr Pro Tyr Thr
1 5

<210> SEQ ID NO 472
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 472

Gln Trp Ser Asn Ser Trp Pro Tyr Thr
1 5

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 473

Gln Gln Ser Tyr Val Thr Pro Trp Thr
1 5

<210> SEQ ID NO 474
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 474

Gln Gln Tyr Tyr Gly Ile Pro Leu Thr
1 5

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 475

Gln Asn Gly His Ser Phe Pro Leu Thr
1               5

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Gln Gln Ser Tyr Ser Thr Pro His Thr
1               5

<210> SEQ ID NO 477
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Gln Gln Gly Tyr Ser Ala Pro Arg Thr
1               5

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gln Gln Ser Tyr Ser Thr Pro Arg Thr
1               5

<210> SEQ ID NO 479
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Gln Gln Ser Tyr Ser Trp Ser Leu Thr
1               5

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Gln Gln Tyr Ser Thr Tyr Pro Phe Ala
1               5

<210> SEQ ID NO 481
<211> LENGTH: 9

<212> TYPE: PRT
<213> ORGANISM: Artificial Sequence
<220> FEATURE:
<223> OTHER INFORMATION: Description of Artificial Sequence: Synthetic peptide

<400> SEQUENCE: 481

Gln Gln Asp Asn Ile Trp Pro Tyr Thr
1 5

<210> SEQ ID NO 482
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 482

Gln Gln Ser Asn Glu Asp Pro Pro Phe Thr
1 5 10

<210> SEQ ID NO 483
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 483

Gln Gln Asn Asn Glu Val Pro Arg Thr
1 5

<210> SEQ ID NO 484
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 484

His Gln Ser Asn Glu Asp Pro Tyr Thr
1 5

<210> SEQ ID NO 485
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 485

Gln Gln Ser Tyr Val Thr Pro Trp Thr
1 5

<210> SEQ ID NO 486
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 486

Gln Gln Tyr Tyr Gly Ile Pro Leu Thr 1 5

<210> SEQ ID NO 487
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 487

Leu Arg Tyr Ala Ser Tyr Arg Thr
1 5

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 488

Leu Gln Tyr Gly Glu Ser Pro Leu Thr
1 5

<210> SEQ ID NO 489
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 489

Gln His His Tyr Gly Ile Pro Leu Thr
1 5

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 490

Gln Gln Thr Tyr Asn Thr Pro Trp Thr
1 5

<210> SEQ ID NO 491
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 491

Leu Gln His Gly Glu Arg Pro Leu Thr
1 5

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 492

Gln Gln Gly Asn Thr Arg Pro Trp Thr
1 5

<210> SEQ ID NO 493
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 493

Gln Gln Tyr Asn Ser Phe Pro Leu Tyr Thr
1 5 10

<210> SEQ ID NO 494
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 494

Gln Gln Tyr Gly Ser Ser Pro Ile Thr
1 5

<210> SEQ ID NO 495
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 495

Gln Gln Ser Asn Glu Asp Ser Trp Thr
1 5

<210> SEQ ID NO 496
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 496

Gln Gln Gly Tyr Ser Thr Pro Pro Glu Ile Thr
1 5 10

<210> SEQ ID NO 497
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 497

Leu Gln His Trp Asn Tyr Pro Tyr Met
1 5

<210> SEQ ID NO 498

<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 498

Gln Gln Ser Asn Ser Trp Ser Leu Leu Thr
1 5 10

<210> SEQ ID NO 499
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 499

Arg Gln Asn Gly His Ser Phe Pro Leu Thr
1 5 10

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 500

Gln Gln Trp Ser Asp Tyr Pro Phe Thr
1 5

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 501

Arg Gln Met Ser Ser Tyr Pro Pro Thr
1 5

<210> SEQ ID NO 502
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 502

Leu Arg Tyr Ala Ser Tyr Arg Thr
1 5

<210> SEQ ID NO 503
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 503

Gln Gln Trp Asn Tyr Pro Arg Ile Thr
1 5

<210> SEQ ID NO 504
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 504

Gln His Tyr Tyr Ser Trp Pro Pro Thr
1 5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 505

Gln Gln Ile Asn Gly Trp Pro Tyr Thr
1 5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 506

Arg Gln His Tyr Ser Ser Pro Pro Thr
1 5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 507

Gln Gln Tyr Tyr Thr Tyr Pro Leu Thr
1 5

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 508

Ala Gln Asn Arg Glu Leu Pro Phe Thr
1 5

<210> SEQ ID NO 509
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 509

Leu His His Tyr Gly Thr Pro Tyr Thr
1               5

<210> SEQ ID NO 510
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gln Gln Gly Ser Ser Asn Pro Leu Thr
1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

His Gln Ser Tyr Thr Thr Pro His Thr
1               5

<210> SEQ ID NO 512
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Gln Gln Trp Asp Asn Asn Pro Tyr Thr
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Leu Gln Pro Asn Ser Tyr Pro Trp Thr
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Gln His Tyr Asp Asp Leu Pro Leu Thr
1               5

<210> SEQ ID NO 515
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 515

Gln Gln Tyr Ser Ser Tyr Pro Leu Arg
1 5

<210> SEQ ID NO 516
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 516

Arg Gln Leu Ser Ser Asn Pro Leu Thr
1 5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 517

Gln Gln Ile Asn Ser Trp Pro Leu Thr
1 5

<210> SEQ ID NO 518
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 518

Gln Gln Trp Ser Ser Tyr Pro Pro Ile Ala
1 5 10

<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 519

Gln Lys Tyr Ser Ser Thr Pro Tyr Thr
1 5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 520

Gln His Trp Ser Ser Phe Pro Leu Thr
1               5

<210> SEQ ID NO 521
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Gln Gln Ser Tyr Ser Thr Pro Leu Thr
1               5

<210> SEQ ID NO 522
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Gln Gln Tyr Gly Ser Ser Pro Pro Thr
1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Gln Gln Tyr Gly Ser Ser Pro Leu Thr
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Gln Gln Tyr Tyr Ser Thr Pro Leu Thr
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gln Gln Ala Asn Ser Phe Pro Ile Thr
1               5

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 526

Gln Gln Tyr Gly Ser Ser Pro Leu Thr
1 5

<210> SEQ ID NO 527
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 527

Gln Gln Ser Tyr Ser Thr Pro Leu Thr
1 5

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 528

Gln Gln Tyr Gly Ser Ser Pro Leu Thr
1 5

<210> SEQ ID NO 529
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 529

Gln Gln Tyr Gly Asn Ser Tyr Thr
1 5

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 530

Gln Gln Tyr Gly Ser Ser Pro Pro Thr
1 5

<210> SEQ ID NO 531
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 531

Gln Gln Ser Tyr Ser Thr Pro Ile Thr
1 5

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 532

Gln Gln Asp Tyr Arg Ser Pro Leu Thr
1 5

<210> SEQ ID NO 533
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 533

Gln Gln Tyr Asn Ser Tyr Pro Leu Thr
1 5

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 534

Gln Gln Trp Asn Ser Asn Pro Leu Thr
1 5

<210> SEQ ID NO 535
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 535

Gln Asn Gly His Ser Phe Pro Leu Thr
1 5

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 536

Gln Gln Gly Gln Ser Tyr Pro Leu Thr
1 5

<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 537

Gln Gln Tyr Asn Ser Tyr Pro Leu Thr
1 5

<210> SEQ ID NO 538
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 538

Gly Thr Trp Asp Thr Ser Leu Ser Ala Gly Val
1 5 10

<210> SEQ ID NO 539
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 539

Gly Thr Trp Asp Ala Ser Leu Ser Thr Trp Val
1 5 10

<210> SEQ ID NO 540
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 540

Gln Val Gln Leu Gln Glu Ser Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr Pro Ser Gly Asn Thr Tyr Tyr Asn Pro Ser Leu
50 55 60

Lys Ser Arg Val Thr Ile Ser Val Asp Lys Ser Lys Asn Gln Phe Ser
65 70 75 80

Leu Lys Leu Asn Ser Val Thr Ala Ala Asp Thr Ala Val Tyr Tyr Cys
85 90 95

Ala Arg Asp Glu Gly Tyr Trp Gly Gln Gly Thr Leu Val Thr Val Ser
100 105 110

Ser

<210> SEQ ID NO 541
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 541

Glu Val Gln Leu Leu Glu Ser Gly Ala Glu Val Lys Lys Pro Gly Ala 1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Pro Phe Asp Tyr Trp Gly Gln Gly Thr Met Val Thr
100 105 110

Val Ser Ser
115

<210> SEQ ID NO 542
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 542

Glu Val Gln Leu Leu Glu Ser Gly Ala Glu Val Lys Lys Pro Gly Ala
1 5 10 15

Ser Val Lys Ala Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Val Tyr Ser Tyr Gly Phe Asp Tyr Trp Gly Gln Gly Thr Leu
100 105 110

Val Thr Val Ser Ser
115

<210> SEQ ID NO 543
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 543

Ala Gly Gln Leu Gln Glu Ser Gly Gly Gly Leu Val Lys Pro Gly Gly
1 5 10 15

Ser Leu Arg Pro Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val

```
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Ala Phe Asp Leu Trp Gly Gln Gly Thr Leu Val
            100                 105                 110

Thr Val Ser Ser
        115


<210> SEQ ID NO 544
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Gly Gly Ala Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Thr Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu His
65                  70                  75                  80

Leu Gln Met Asn Ser Leu Arg Asp Glu Asp Thr Ala Val Tyr Tyr Cys
                85                  90                  95

Ala Arg Thr Trp Tyr Ser Ser Ser Pro Phe Asp Tyr Trp Gly Gln Gly
            100                 105                 110

Thr Leu Val Thr Val Ser Ser
        115


<210> SEQ ID NO 545
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 545

Glu Val Gln Leu Leu Glu Ser Gly Gly Gly Leu Val Lys Pro Gly Gly
1               5                   10                  15

Ser Pro Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Asn Gly Arg Phe Thr Ile Ser Arg Asp Tyr Ala Lys Asn Ser Leu Tyr
65                  70                  75                  80

Leu Gln Met Asn Ser Leu Arg Ala Glu Asp Thr Ala Val Cys Tyr Cys
                85                  90                  95

Ala Arg Asp Ser Gly Ser Tyr Tyr Asp Trp Phe Asp Pro Trp Gly Gln
```

```
            100                 105                 110

Gly Thr Leu Val Thr Val Ser Ser
        115                 120


<210> SEQ ID NO 546
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Arg Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Asn Tyr Phe Asp Tyr Trp Gly Gln Gly Thr Leu Val
            100                 105                 110

Thr Val Ser Ser
        115


<210> SEQ ID NO 547
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Glu Val Gln Leu Gln Gln Pro Gly Pro Gly Leu Val Lys Pro Ser Leu
1               5                   10                  15

Ser Leu Ser His Thr Cys Ser Val Thr Gly Tyr Ser Ile Thr Ser Gly
            20                  25                  30

Tyr Tyr Trp Asn Trp Ile Arg Gln Phe Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Thr Ser Ile Thr Arg Asp Thr Ser Lys Asn Gln Phe Phe
65                  70                  75                  80

Leu Lys Leu Ser Ser Val Thr Thr Asp Asp Thr Ala Thr Tyr Tyr Cys
                85                  90                  95

Ala Arg Val His His Tyr Tyr Gly Ser Ser Tyr Phe Asp Tyr Trp Gly
            100                 105                 110

Gln Gly Thr Thr Leu Thr Val Ser Ser
        115                 120


<210> SEQ ID NO 548
<211> LENGTH: 121
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 548

Glu Val Gln Leu Gln Gln Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Lys Lys Leu Glu Trp
35 40 45

Met Gly Tyr Ile Arg Tyr Asp Gly Ser Asn Asn Tyr Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Asp Asp Thr Ala Thr Tyr Tyr Cys
85 90 95

Ala Arg Val His His Tyr Tyr Gly Ser Ser Tyr Phe Asp Tyr Trp Gly
100 105 110

Gln Gly Thr Thr Leu Thr Val Ser Ser
115 120

<210> SEQ ID NO 549
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 549

Glu Val Gln Leu Gln Gln Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Tyr Asp Gly Ser Asn Asn Tyr Asn Pro Ser Leu
50 55 60

Lys Asn Arg Ile Ser Ile Thr Arg Asp Thr Ser Lys Asn Gln Phe Phe
65 70 75 80

Leu Lys Leu Asn Ser Val Thr Thr Glu Asp Thr Ala Thr Tyr Tyr Cys
85 90 95

Ala Arg Asp Pro Tyr Tyr Tyr Gly Ser Ser Tyr Phe Asp Tyr Trp Gly
100 105 110

Gln Gly Thr Thr Leu Thr Val Ser Ser
115 120

<210> SEQ ID NO 550
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 550

Glu Val Lys Leu Val Glu Ser Glu Gly Gly Leu Val Gln Pro Gly Ser
1 5 10 15

```
Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Thr Ile Ser Arg Asp Asn Ala Lys Asn Ile Leu Tyr
65                  70                  75                  80

Leu Gln Met Ser Ser Leu Lys Ser Glu Asp Ile Ala Thr Tyr Tyr Cys
                85                  90                  95

Ala Arg Glu Tyr Tyr Tyr Gly Ser Ser Ser Phe Ala Tyr Trp Gly Gln
            100                 105                 110

Gly Thr Thr Leu Thr Val Ser Ser
        115                 120
```

<210> SEQ ID NO 551
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 551

```
Glu Val Asn Pro Val Glu Ser Glu Gly Gly Leu Val Gln Pro Gly Ser
1               5                   10                  15

Ser Met Lys Leu Ser Cys Thr Ala Ser Gly Phe Thr Phe Asn Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Ser Thr Tyr Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Glu Tyr Tyr Tyr Gly Ser Ser Ser Phe Ala Tyr Trp Gly Gln
            100                 105                 110

Gly Thr Leu Val Thr Val Ser Ala
        115                 120
```

<210> SEQ ID NO 552
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 552

```
Gly Gly Glu Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60
```

```
Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Glu Phe Ala Tyr Trp Gly Gln Gly Thr Leu Val Thr Val
            100                 105                 110

Ser Ala


<210> SEQ ID NO 553
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Glu Val Lys Leu Glu Glu Ser Gly Gly Gly Leu Val Lys Pro Gly Gly
1               5                   10                  15

Ser Leu Lys Leu Ser Cys Ala Val Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Gly Thr Ile Tyr Tyr Glu Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Gly Thr Ala Ile Tyr Tyr Cys
                85                  90                  95

Ala Arg Pro Asn Tyr His Gly Ser Ser Pro Phe Ala Tyr Trp Gly Gln
            100                 105                 110

Gly Thr Leu Val Thr Val Ser Ala
        115                 120


<210> SEQ ID NO 554
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Gly Lys Trp Arg Trp Arg Leu Gly Arg Arg Tyr Asp
            100                 105                 110
```

Tyr Trp Gly Gln Gly Thr Leu Val Thr Val Ser Ser
115 120

<210> SEQ ID NO 555
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 555

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Asn Asn Tyr
20 25 30

Ala Met Asn Trp Val Arg Gln Ala Pro Gly Lys Gly Leu Glu Trp Val
35 40 45

Ser Ser Ile Ser Gly Ser Gly Gly Asp Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Ala Arg Gly Tyr Trp Arg Trp Arg Leu Leu Arg Arg Tyr Asp
100 105 110

Tyr Trp Gly Gln Gly Thr Leu Val Thr Val Ser Ser
115 120

<210> SEQ ID NO 556
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 556

Glu Val Gln Leu Val Glu Ser Gly Gly Gly Leu Val Lys Pro Gly Gly
1 5 10 15

Ser Leu Arg Leu Ser Cys Ala Ala Ser Gly Phe Asn Ile Gly Asn Thr
20 25 30

Tyr Met His Trp Phe Arg Gln Ala Pro Gly Lys Gly Leu Glu Trp Val
35 40 45

Gly Val Ile Asn Pro Asn Tyr Gly Thr Thr Arg Tyr Asn Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Tyr Gly Ser Ser Ser Phe Asp Tyr Trp Gly Gln Gly Thr
100 105 110

Leu Val Thr Val Ser Ser
115

<210> SEQ ID NO 557
<211> LENGTH: 124
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 557

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Gly Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Gly Tyr Pro Arg Trp Arg Leu Gly Arg Arg Tyr Asp
            100                 105                 110

Tyr Trp Gly Gln Gly Thr Leu Val Thr Val Ser Ser
        115                 120

<210> SEQ ID NO 558
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 558

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Gly Tyr Lys Arg Trp Arg Leu Gly Arg Arg Tyr Asp
            100                 105                 110

Tyr Trp Gly Gln Gly Thr Leu Val Thr Val Ser Ser
        115                 120

<210> SEQ ID NO 559
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 559

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Asn Tyr

```
            20                  25                  30

Trp Met Asn Trp Val Arg Gln Ala Pro Gly Lys Gly Leu Glu Trp Val
        35                  40                  45

Gly Trp Phe Tyr Pro Lys Ser Gly Ser Ile Lys Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Leu Tyr Gly Tyr Asp Leu His Trp Tyr Phe Asp Val Trp Gly
            100                 105                 110

Gln Gly Thr Leu Val Thr Val Ser Ser
        115                 120


<210> SEQ ID NO 560
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 560

Gln Val Gln Leu Val Gln Ser Gly Ala Glu Val Lys Lys Pro Gly Ala
1               5                   10                  15

Ser Val Lys Val Ser Cys Lys Ala Ser Gly Gly Ser Ile Ser Ser Gly
            20                  25                  30

Gly Tyr Tyr Trp Asn Trp Val Arg Gln Ala Thr Gly Gln Gly Leu Glu
        35                  40                  45

Trp Met Gly Trp Met Asn Pro Asn Ser Gly Asn Arg Gly Ser Ala Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Asp Glu Val Ala Ala Ala Gly Leu Phe Asp Tyr Trp
            100                 105                 110

Gly Gln Gly Thr Leu Val Thr Val Ser Ser
        115                 120


<210> SEQ ID NO 561
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 561

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Glu Tyr
            20                  25                  30

Ile Thr His Trp Val Arg Gln Ala Pro Gly Lys Gly Leu Glu Trp Val
        35                  40                  45

Gly Met Ile His Pro Ser Ser Gly Ser Ile Ser Tyr Asn Asp Ser Val
    50                  55                  60

Lys Gly Arg Phe Thr Ile Ser Arg Asp Asn Ser Lys Asn Thr Leu Tyr
```

```
65                  70                  75                  80

Leu Gln Met Asn Ser Leu Arg Ala Glu Asp Thr Ala Val Tyr Tyr Cys
                85                  90                  95

Ala Arg His Glu Val Glu Tyr Tyr Gly Pro Ser Ser Ser Trp Phe Ala
            100                 105                 110

Tyr Trp Gly Gln Gly Thr Leu Val Thr Val Ser Ser
        115                 120


<210> SEQ ID NO 562
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 562

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Gly Lys Trp Arg Trp Arg Leu Gly Arg Arg Tyr Asp
            100                 105                 110

Tyr Trp Gly Gln Gly Thr Leu Val Thr Val Ser Ser
        115                 120


<210> SEQ ID NO 563
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 563

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Ile Gly Asn Thr
            20                  25                  30

Tyr Met His Trp Phe Arg Gln Ala Pro Gly Lys Gly Leu Glu Trp Val
        35                  40                  45

Gly Val Ile Asn Pro Asn Tyr Gly Thr Thr Arg Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Ser Ser Ser Phe Asp Tyr Trp Gly Gln Gly Thr
            100                 105                 110

Leu Val Thr Val Ser Ser
```

115

<210> SEQ ID NO 564
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 564

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Gly Asn Tyr
20 25 30

Trp Met Asn Trp Val Arg Gln Ala Pro Gly Lys Gly Leu Glu Trp Val
35 40 45

Gly Arg Ile Asp Pro Ala Asn Gly Asp Thr Lys Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Glu Gly Asp Asn Ser Asn Tyr Tyr Ala Met Asp Tyr Trp Gly
100 105 110

Gln Gly Thr Leu Val Thr Val Ser Ser
115 120

<210> SEQ ID NO 565
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 565

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Gly Trp Val Arg Gln Ala Pro Gly Lys Gly Leu Glu Trp Val
35 40 45

Ser Gly Ile Ser Gly Ser Ala Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Ala Arg Gly His Trp Arg Trp Arg Leu Gly Arg Arg Tyr Asp
100 105 110

Tyr Trp Gly Gln Gly Thr Leu Val Thr Val Ser Ser
115 120

<210> SEQ ID NO 566
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 566

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ala Met Ala Trp Val Arg Gln Ala Pro Gly Lys Gly Leu Glu Trp Val
35 40 45

Ser Ala Ile Ser Gly Ser Gly Gly Ser Thr Tyr Phe Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Ala Arg Gly Tyr Trp Arg Trp Arg Leu Trp Arg Arg Tyr Asp
100 105 110

Tyr Trp Gly Gln Gly Thr Leu Val Thr Val Ser Ser
115 120

<210> SEQ ID NO 567
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 567

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Gln
20 25 30

Ala Met Ser Trp Val Arg Gln Ala Pro Gly Lys Gly Leu Glu Trp Val
35 40 45

Ser Ser Ile Ser Gly Ser Gly Val Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Ala Arg Gly Arg Trp Arg Trp Arg Leu Gly Arg Arg Tyr Asp
100 105 110

Tyr Trp Gly Gln Gly Thr Leu Val Thr Val Ser Ser
115 120

<210> SEQ ID NO 568
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 568

Glu Val Gln Leu Val Glu Ser Gly Gly Gly Leu Val Lys Pro Gly Gly
1 5 10 15

Ser Leu Arg Leu Ser Cys Ala Ala Ser Gly Tyr Ser Phe Thr Gly Tyr
20 25 30

Asp Ile Ser Trp Val Arg Gln Ala Pro Gly Lys Gly Leu Glu Trp Val
35 40 45

Ala Arg Ile Tyr Pro Gly Ser Gly Asn Thr Tyr Tyr Asp Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Glu Asp Asp Tyr Gly Trp Tyr Phe Gly Val Trp Gly Gln Gly
100 105 110

Thr Leu Val Thr Val Ser Ser
115

<210> SEQ ID NO 569
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 569

Glu Val Gln Leu Val Glu Ser Gly Gly Gly Leu Val Lys Pro Gly Gly
1 5 10 15

Ser Leu Arg Leu Ser Cys Ala Ala Ser Gly Tyr Arg Leu Thr Gly Tyr
20 25 30

Trp Ile Glu Trp Val Arg Gln Ala Pro Gly Lys Gly Leu Glu Trp Val
35 40 45

Gly Arg Ile Asp Pro Ala Ser Gly Asp Thr Thr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Glu Asp Pro Ile Tyr Tyr Gly Asn Tyr Val Phe Ala Tyr
100 105 110

Trp Gly Gln Gly Thr Leu Val Thr Val Ser Ser
115 120

<210> SEQ ID NO 570
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 570

Glu Val Gln Leu Val Glu Ser Gly Gly Gly Leu Val Lys Pro Gly Gly
1 5 10 15

Ser Leu Arg Leu Ser Cys Ala Ala Ser Gly Tyr Leu Phe Thr Asp Tyr
20 25 30

Asn Met Asn Trp Val Arg Gln Ala Pro Gly Lys Gly Leu Glu Trp Val
35 40 45

Gly Trp Ile Tyr Pro Gly Thr Gly Asn Thr Tyr Asn Asp Ser Val Lys
50 55 60

Gly Arg Phe Thr Ile Ser Arg Asp Asn Ser Lys Asn Thr Leu Tyr Leu
65 70 75 80

```
Gln Met Asn Ser Leu Arg Ala Glu Asp Thr Ala Val Tyr Tyr Cys Thr
                85                  90                  95

Ala Leu Tyr Tyr Gly Ser Ser Trp Glu Arg Tyr Phe Asp Val Trp Gly
            100                 105                 110

Gln Gly Thr Leu Val Thr Val Ser Ser
        115                 120


<210> SEQ ID NO 571
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 571

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ile Asp Tyr
            20                  25                  30

Gly Met His Trp Val Arg Gln Ala Pro Gly Lys Gly Leu Glu Trp Val
        35                  40                  45

Gly Val Ile Asn Pro Asn Tyr Gly Thr Thr Arg Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Ser Asn Tyr Gly Gly Tyr Phe Asp Val Trp Gly Gln
            100                 105                 110

Gly Thr Leu Val Thr Val Ser Ser
        115                 120


<210> SEQ ID NO 572
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Ser Tyr
            20                  25                  30

Ala Met Thr Trp Val Arg Gln Ala Pro Gly Lys Gly Leu Glu Trp Val
        35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Gly Tyr Trp Arg Trp Arg Leu Gly Arg Arg Ala Asp
            100                 105                 110

Tyr Trp Gly Gln Gly Thr Leu Val Thr Val Ser Ser
        115                 120
```

<210> SEQ ID NO 573
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 573

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Phe Asn Thr Tyr
            20                  25                  30

Ala Met Asn Trp Val Arg Gln Ala Pro Gly Lys Gly Leu Glu Trp Val
        35                  40                  45

Gly Val Ile Tyr Pro Gly Asn Ser Asp Thr Thr Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Gly Val Ile Tyr Tyr Tyr Gly Ser Ser Asp Tyr Thr Leu Asp Tyr
            100                 105                 110

Trp Gly Gln Gly Thr Leu Val Thr Val Ser Ser
        115                 120
```

<210> SEQ ID NO 574
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 574

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Arg Gly Lys Trp Arg Trp Arg Leu Gly Arg Arg Tyr Asp
            100                 105                 110

Tyr Trp Gly Gln Gly Thr Leu Val Thr Val Ser Ser
        115                 120
```

<210> SEQ ID NO 575
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 575

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Ile Gly Asn Thr
            20                  25                  30

Tyr Met His Trp Phe Arg Gln Ala Pro Gly Lys Gly Leu Glu Trp Val
        35                  40                  45

Gly Val Ile Asn Pro Asn Tyr Gly Thr Thr Arg Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Ser Ser Ser Phe Asp Tyr Trp Gly Gln Gly Thr
            100                 105                 110

Leu Val Thr Val Ser Ser
        115

<210> SEQ ID NO 576
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Ser Tyr
            20                  25                  30

Trp Val His Trp Val Arg Gln Ala Pro Gly Lys Gly Leu Glu Trp Val
        35                  40                  45

Ala Asn Ile Asn His Asp Gly Ser Asn Thr Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Met Ile Thr Arg Phe Ala Tyr Trp Gly Gln Gly Thr Leu
            100                 105                 110

Val Thr Val Ser Ser
        115

<210> SEQ ID NO 577
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Thr Ser Tyr
            20                  25                  30

```
Asn Ile Asp Trp Val Arg Gln Ala Pro Gly Lys Gly Leu Glu Trp Val
        35                  40                  45

Gly Gly Val Asp Pro Glu Thr Asp Asp Thr Ala Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Tyr Tyr Tyr Gly Ser Ser Ala Phe Ala Tyr Trp Gly Gln Gly
            100                 105                 110

Thr Leu Val Thr Val Ser Ser
        115


<210> SEQ ID NO 578
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 578

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Gly Asp Ile Asn Pro Asn Asn Gly Gly Thr Thr Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Ala Tyr Tyr Ser Asn Tyr Gly Val Met Tyr Phe Trp Gly Gln
            100                 105                 110

Gly Thr Leu Val Thr Val Ser Ser
        115                 120


<210> SEQ ID NO 579
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Asn Phe Arg Ser Tyr
            20                  25                  30

Ala Met Ser Trp Val Arg Gln Ala Pro Gly Lys Gly Leu Glu Trp Val
        35                  40                  45

Ser Val Ile Ser Gly Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ala Ala Arg Gly Gly Trp Arg Trp Arg Leu Gly Arg Arg Tyr Asp
            100                 105                 110

Tyr Trp Gly Gln Gly Thr Leu Val Thr Val Ser Ser
        115                 120


<210> SEQ ID NO 580
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ile Tyr
            20                  25                  30

Gly Ile Ser Trp Val Arg Gln Ala Pro Gly Lys Gly Leu Glu Trp Val
        35                  40                  45

Gly Asp Ile Ser Pro Gly Ser Gly Ser Thr Asn Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Pro Tyr Tyr Tyr Gly Ser Ser Arg Tyr Tyr Ala Met Asp Tyr
            100                 105                 110

Trp Gly Gln Gly Thr Leu Val Thr Val Ser Ser
        115                 120


<210> SEQ ID NO 581
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 581

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Ser Tyr
            20                  25                  30

Asn Ile Asn Trp Val Arg Gln Ala Pro Gly Lys Gly Leu Glu Trp Val
        35                  40                  45

Ala Thr Ile Ser Ser Gly Gly Asp Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Glu Arg Asp Tyr Tyr Gly Ser Ser Trp His Phe Asp Val Trp Gly Gln
            100                 105                 110

Gly Thr Leu Val Thr Val Ser Ser
        115                 120
```

<210> SEQ ID NO 582
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 582

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Tyr Trp Val Arg Gln Ala Pro Gly Lys Gly Leu Glu Trp Val
        35                  40                  45

Ala Ser Ile Ser Asp Gly Gly Ser Tyr Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ile Trp Tyr Tyr Gly Ser Ser Trp Ser Trp Tyr Phe Asp
            100                 105                 110

Ala Trp Gly Gln Gly Thr Leu Val Thr Val Ser Ser
        115                 120
```

<210> SEQ ID NO 583
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 583

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ala Tyr
            20                  25                  30

Asp Ile Tyr Trp Val Arg Gln Pro Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Ile Ile Ser Arg Glu Ser Ala Lys Asn Ser Val Tyr Leu
65                  70                  75                  80

Gln Met Asn Ser Leu Arg Ala Gly Asp Thr Ala Val Tyr Tyr Cys Ala
                85                  90                  95

Val Gly Tyr Asn Trp Ile Phe Asp Leu Trp Gly Gln Gly Thr Leu Val
            100                 105                 110

Thr Val Ser Ser
        115
```

<210> SEQ ID NO 584
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 584

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Ser Phe Thr Gly Tyr
            20                  25                  30

Asp Ile Ser Trp Phe Arg Gln Ala Pro Gly Lys Gly Leu Glu Trp Val
        35                  40                  45

Gly Glu Ile Leu Pro Gly Ser Gly Gly Thr Asn Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Ser Gly Asn Tyr Asp Ala Met Asp Tyr Trp Gly Gln Gly Thr Leu
            100                 105                 110

Val Thr Val Ser Ser
        115

<210> SEQ ID NO 585
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 585

Gln Val Gln Leu Val Gln Ser Gly Ala Glu Val Lys Lys Pro Gly Ala
1               5                   10                  15

Ser Val Lys Val Ser Cys Lys Ala Ser Gly Gly Tyr Ile Ser Ser Ser
            20                  25                  30

Asn Trp Trp Ser Trp Val Arg Gln Ala Thr Gly Gln Gly Leu Glu Trp
        35                  40                  45

Met Ala Asn Ile Glu Gln Asp Gly Ser Glu Lys Asn Tyr Val Gln Lys
    50                  55                  60

Phe Gln Gly Arg Val Thr Met Thr Arg Asp Thr Ser Thr Ser Thr Val
65                  70                  75                  80

Tyr Met Glu Leu Ser Ser Leu Arg Ser Glu Asp Thr Ala Val Tyr Tyr
                85                  90                  95

Cys Ala Arg Gly Glu Tyr Ser Arg Leu Trp Tyr Phe Asp Leu Trp Gly
            100                 105                 110

Gln Gly Thr Leu Val Thr Val Ser Ser
        115                 120

<210> SEQ ID NO 586
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 586

Glu Val Gln Leu Val Glu Ser Gly Gly Gly Leu Val Lys Pro Gly Gly
1               5                   10                  15

Ser Leu Arg Leu Ser Cys Ala Ala Ser Gly Thr Phe Thr Asp Tyr Tyr
            20                  25                  30

Met Lys Trp Val Arg Gln Ala Pro Gly Lys Gly Leu Glu Trp Val Gly

```
        35                  40                  45

Glu Ile Leu Pro Gly Ser Gly Gly Thr Asn Tyr Asn Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Pro Tyr Asp Tyr Asp Phe Asp Tyr Trp Gly Gln Gly Thr Leu Val
            100                 105                 110

Thr Val Ser Ser
        115


<210> SEQ ID NO 587
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 587

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Ser Ser
            20                  25                  30

Trp Met His Trp Ala Arg Gln Ala Pro Gly Lys Gly Leu Glu Trp Val
        35                  40                  45

Gly Trp Leu Tyr Pro Arg Asp Gly Ser Thr Glu Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Thr Thr Val Val Ala Asp Trp Tyr Phe Asp Val Trp Gly Gln Gly
            100                 105                 110

Thr Leu Val Thr Val Ser Ser
        115


<210> SEQ ID NO 588
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 588

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Asn Asp Asp
            20                  25                  30

Tyr Thr Asn Trp Val Arg Gln Ala Pro Gly Lys Gly Leu Glu Trp Val
        35                  40                  45

Gly Asn Ile Asn Pro Asn Asn Gly Ala Met Ile Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Lys Gly Asp Gly Gly Ser Tyr Ala Ala Met Asp Tyr Trp Gly
            100                 105                 110

Gln Gly Thr Leu Val Thr Val Ser Ser
        115                 120
```

<210> SEQ ID NO 589
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 589

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Ser Phe Thr Gly Tyr
            20                  25                  30

Asp Ile Ser Trp Val Arg Gln Ala Pro Gly Lys Gly Leu Glu Trp Val
        35                  40                  45

Gly Trp Ile Tyr Pro Lys Asp Gly Ser Thr Lys Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ile Thr Thr Val Val Ala Asp Trp Tyr Phe Asp Val Trp Gly Gln Gly
            100                 105                 110

Thr Leu Val Thr Val Ser Ser
        115
```

<210> SEQ ID NO 590
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 590

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Asn Asp Tyr
            20                  25                  30

Tyr Ile Asn Trp Val Arg Gln Ala Pro Gly Lys Gly Leu Glu Trp Val
        35                  40                  45

Gly Asp Ile Asn Pro Asn Asn Gly Ala Asn Ile Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Gly Ser Ser Tyr Tyr Ala Leu Asp Tyr Trp Gly Gln
            100                 105                 110

Gly Thr Leu Val Thr Val Ser Ser
        115                 120
```

-continued

<210> SEQ ID NO 591
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 591

Glu Val Gln Leu Val Glu Ser Gly Gly Gly Leu Val Lys Pro Gly Gly
1 5 10 15

Ser Leu Arg Leu Ser Cys Ala Ala Ser Gly Tyr Thr Phe Asn Asp Tyr
20 25 30

Tyr Ile Asn Trp Val Arg Gln Ala Pro Gly Lys Gly Leu Glu Trp Val
35 40 45

Gly Asp Ile Asn Pro Asn Asn Gly Gly Thr Thr Tyr Asn Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Gly Ser Asn Tyr Gly Gly Tyr Phe Asp Val Trp Gly Gln
100 105 110

Gly Thr Leu Val Thr Val Ser Ser
115 120

<210> SEQ ID NO 592
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 592

Glu Val Gln Leu Val Glu Ser Gly Gly Gly Leu Val Lys Pro Gly Gly
1 5 10 15

Ser Leu Arg Leu Ser Cys Ala Ala Ser Gly Phe Asn Ile Ile Asp Asp
20 25 30

Tyr Met His Trp Val Arg Gln Ala Pro Gly Lys Gly Leu Glu Trp Val
35 40 45

Gly Met Ile Thr Asp Thr Gly Glu Pro Thr Asp Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Val
85 90 95

Tyr Asp Tyr Ile Tyr Ala Met Asp Tyr Trp Gly Gln Gly Thr Leu Val
100 105 110

Thr Val Ser Ser
115

<210> SEQ ID NO 593
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 593

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Tyr
            20                  25                  30

Asp Met Tyr Trp Val Arg Gln Ala Pro Gly Lys Gly Leu Glu Trp Val
        35                  40                  45

Gly Arg Ile Asp Pro Ala Asn Gly Asp Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Gly Ser Ser Tyr Ala Met Asp Tyr Trp Gly Gln
            100                 105                 110

Gly Thr Leu Val Thr Val Ser Ser
        115                 120


<210> SEQ ID NO 594
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 594

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Glu Phe Ser Ser Ser
            20                  25                  30

Trp Met Asn Trp Val Arg Gln Ala Pro Gly Lys Gly Leu Glu Trp Val
        35                  40                  45

Gly Trp Ile Tyr Pro Gly Thr Gly Asn Thr Asn Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Tyr Tyr Tyr Gly Ser Ser Ala Phe Ala Tyr Trp Gly Gln Gly
            100                 105                 110

Thr Leu Val Thr Val Ser Ser
        115


<210> SEQ ID NO 595
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Leu Pro Trp Val Arg Gln Ala Pro Gly Lys Gly Leu Glu Trp Val
        35                  40                  45
```

Gly Ala Ile Asp Pro Gly Thr Gly Gly Thr Ala Ser Asn Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ile Tyr Tyr Asp Tyr Ser Ala Met Asp Tyr Trp Gly Gln Gly
100 105 110

Thr Leu Val Thr Val Ser Ser
115

<210> SEQ ID NO 596
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 596

Glu Val Gln Leu Val Glu Ser Gly Gly Gly Leu Val Lys Pro Gly Gly
1 5 10 15

Ser Leu Arg Leu Ser Cys Ala Ala Ser Gly Phe Ile Phe Ser Asp Phe
20 25 30

Tyr Met Ala Trp Val Arg Gln Ala Pro Gly Lys Gly Leu Glu Trp Val
35 40 45

Gly Arg Ile Asp Pro Glu Asp Gly Asp Glu His Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp Tyr Tyr Gly Ser Ser Tyr Leu Asp Tyr Trp Gly Gln Gly Thr
100 105 110

Leu Val Thr Val Ser Ser
115

<210> SEQ ID NO 597
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 597

Glu Val Gln Leu Val Glu Ser Gly Gly Gly Leu Val Lys Pro Gly Gly
1 5 10 15

Ser Leu Arg Leu Ser Cys Ala Ala Ser Gly Phe Asn Ile Lys Asp Tyr
20 25 30

Tyr Met His Trp Val Arg Gln Ala Pro Gly Lys Gly Leu Glu Trp Val
35 40 45

Gly Asp Ile Asn Pro Asn Asn Gly Gly Thr Thr Tyr Asn Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Arg Asp Tyr Tyr Gly Ser Phe His Arg Arg Trp Tyr Phe Asp Val
            100                 105                 110

Trp Gly Gln Gly Thr Leu Val Thr Val Ser Ser
        115                 120


<210> SEQ ID NO 598
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 598

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Asp Tyr
            20                  25                  30

Asn Ile Asp Trp Val Arg Gln Ala Pro Gly Lys Gly Leu Glu Trp Val
        35                  40                  45

Gly Asp Ile Asn Ile Asn Asn Gly Gly Thr Thr Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr His Gly Ser Ser Phe Tyr Trp Tyr Phe Asp Val Trp
            100                 105                 110

Gly Gln Gly Thr Leu Val Thr Val Ser Ser
        115                 120


<210> SEQ ID NO 599
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 599

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Glu Tyr
            20                  25                  30

Ile Thr His Trp Val Arg Gln Ala Pro Gly Lys Gly Leu Glu Trp Val
        35                  40                  45

Ala Asn Ile Asn Phe Asp Gly Ser Ser Thr Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Ser Ser Tyr Tyr Ala Met Asp Tyr Trp Gly Gln
            100                 105                 110

Gly Thr Leu Val Thr Val Ser Ser
        115                 120


<210> SEQ ID NO 600
```

<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 600

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Phe Ser Thr Tyr
20 25 30

Ile Met Ser Trp Val Arg Gln Ala Thr Gly Gln Gly Leu Glu Trp Met
35 40 45

Gly Ile Ile Tyr Pro Gly Asp Thr Asp Thr Arg Tyr Ser Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Ile Ala Val Ala Gly Thr Phe Asp Tyr Trp Gly Gln Gly
100 105 110

Thr Leu Val Thr Val Ser Ser
115

<210> SEQ ID NO 601
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 601

Glu Val Gln Leu Val Glu Ser Gly Gly Gly Leu Val Lys Pro Gly Gly
1 5 10 15

Ser Leu Arg Leu Ser Cys Ala Ala Ser Gly Tyr Thr Phe Thr Asn Tyr
20 25 30

Leu Ile Glu Trp Val Arg Gln Ala Pro Gly Lys Gly Leu Glu Trp Val
35 40 45

Gly Asp Ile Asn Pro Asn Asn Gly Gly Thr Tyr Tyr Asn Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Val Arg His Ala Leu Leu Trp Tyr Tyr Tyr Ala Met Asp Tyr Trp Gly
100 105 110

Gln Gly Thr Leu Val Thr Val Ser Ser
115 120

<210> SEQ ID NO 602
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 602

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Phe Ser Asp His
20 25 30

Tyr Met Thr Trp Val Arg Gln Ala Thr Gly Gln Gly Leu Glu Trp Met
35 40 45

Gly Trp Met Asn Pro Asn Ser Gly Ile Thr Gly Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Val Ser Tyr Ser Gly Ser Leu His Tyr Trp Gly Gln Gly Thr
100 105 110

Leu Val Thr Val Ser Ser
115

<210> SEQ ID NO 603
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 603

Gln Val Gln Leu Val Gln Ser Gly Ala Glu Val Lys Lys Pro Gly Ala
1 5 10 15

Ser Val Lys Val Ser Cys Lys Ala Ser Gly Phe Thr Phe Asp Asp Tyr
20 25 30

Ala Met His Trp Val Arg Gln Ala Thr Gly Gln Gly Leu Glu Trp Met
35 40 45

Gly Val Ile Asn Thr Asn Thr Gly Asn Pro Thr Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Ser Asn Trp Asn Tyr Phe Asp Tyr Trp Gly Gln Gly Thr Leu
100 105 110

Val Thr Val Ser Ser
115

<210> SEQ ID NO 604
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 604

Glu Val Gln Leu Val Glu Ser Gly Gly Gly Leu Val Lys Pro Gly Gly
1 5 10 15

Ser Leu Arg Leu Ser Cys Ala Ala Ser Gly Ser Ala Phe Ser Ala Ser
20 25 30

Trp Met Asn Leu Val Arg Gln Ala Pro Gly Lys Gly Leu Glu Trp Val
35 40 45

```
Gly Trp Val Asp Pro Asp Asn Gly Asp Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Lys Pro Arg Asp Ser Gly Pro Ser Phe Ala Ser Trp Gly Gln Gly
            100                 105                 110

Thr Leu Val Thr Val Ser Ser
        115
```

<210> SEQ ID NO 605
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 605

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Met Tyr Trp Val Arg Gln Ala Pro Gly Lys Gly Leu Glu Trp Val
        35                  40                  45

Gly Trp Ile Tyr Pro Lys Asp Gly Ser Thr Lys Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Arg Gly Tyr Tyr Tyr Gly Ser Ser Tyr Gly Tyr Tyr Asp
            100                 105                 110

Val Trp Gly Gln Gly Thr Leu Val Thr Val Ser Ser
        115                 120
```

<210> SEQ ID NO 606
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 606

```
Glu Val Gln Leu Val Glu Ser Gly Gly Gly Leu Val Lys Pro Gly Gly
1               5                   10                  15

Ser Leu Arg Leu Ser Cys Ala Ala Ser Gly His Thr Ile Thr Ser Tyr
            20                  25                  30

Gly Ile Asn Trp Val Arg Gln Ala Pro Gly Lys Gly Leu Glu Trp Val
        35                  40                  45

Gly Glu Ile Leu Pro Gly Ser Gly Thr Ser Asp Tyr Asn Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

Ala Thr Asn Trp Gly Phe Ala Tyr Trp Gly Gln Gly Thr Leu Val Thr
100 105 110

Val Ser Ser
115

<210> SEQ ID NO 607
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 607

Glu Val Gln Leu Val Glu Ser Gly Gly Gly Leu Val Lys Pro Gly Gly
1 5 10 15

Ser Leu Arg Leu Ser Cys Ala Ala Ser Gly Tyr Thr Phe Ser Gly Tyr
20 25 30

Thr Met His Trp Val Arg Gln Ala Pro Gly Lys Gly Leu Glu Trp Val
35 40 45

Gly Glu Ile Asp Pro Ser Asp Ser Phe Ala Asn Tyr Asn Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Tyr Gly Ser Ser Tyr Glu Phe Thr Tyr Trp Gly Gln Gly
100 105 110

Thr Leu Val Thr Val Ser Ser
115

<210> SEQ ID NO 608
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 608

Gln Val Gln Leu Val Gln Ser Gly Ala Glu Val Lys Lys Pro Gly Ala
1 5 10 15

Ser Val Lys Val Ser Cys Lys Ala Ser Gly Gly Tyr Ile Ser Ser Ser
20 25 30

Asn Trp Trp Ser Trp Val Arg Gln Ala Thr Gly Gln Gly Leu Glu Trp
35 40 45

Met Gly Arg Ile Lys Thr Lys Thr Asp Gly Gly Thr Ile Asp Tyr Ala
50 55 60

Gln Lys Phe Gln Gly Arg Val Thr Met Thr Arg Asp Thr Ser Thr Ser
65 70 75 80

Thr Val Tyr Met Glu Leu Ser Ser Leu Arg Ser Glu Asp Thr Ala Val
85 90 95

Tyr Tyr Cys Ala Lys Gly Tyr Ser Gly Ser Val Asp Tyr Trp Gly Gln
100 105 110

Gly Thr Leu Val Thr Val Ser Ser
115 120

<210> SEQ ID NO 609
<211> LENGTH: 116

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 609

Glu Val Gln Leu Val Glu Ser Gly Gly Gly Leu Val Lys Pro Gly Gly
1               5                   10                  15

Ser Leu Arg Leu Ser Cys Ala Ala Ser Gly Ser Asn Ile Lys Asp Tyr
            20                  25                  30

Tyr Ile His Trp Val Arg Gln Ala Pro Gly Lys Gly Leu Glu Trp Val
        35                  40                  45

Ala Thr Ile Ser Asp Gly Gly Ser Tyr Ile Phe Asp Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ala Thr Gly Thr Phe Ala Tyr Trp Gly Gln Gly Thr Leu Val
            100                 105                 110

Thr Val Ser Ser
        115

<210> SEQ ID NO 610
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 610

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Arg Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Pro Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Val Ser Gly Met Ile Gly Thr Val Phe Asp Tyr Trp
            100                 105                 110

Gly Gln Gly Thr Leu Val Thr Val Ser Ser
        115                 120

<210> SEQ ID NO 611
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 611

Gln Val Gln Leu Val Gln Ser Gly Gly Gly Leu Val Gln Pro Gly Gly

```
1               5                   10                  15

Ser Leu Arg Leu Ser Cys Ala Val Ser Gly Phe Thr Ile Ser Thr Tyr
            20                  25                  30

Asp Ile Tyr Trp Val Arg Gln Ala Thr Gly Lys Gly Leu Glu Trp Val
        35                  40                  45

Ser Ala Ile Gly Thr Ala Gly Asp Thr Tyr Tyr Pro Asp Ser Val Arg
    50                  55                  60

Gly Arg Phe Thr Ile Ser Arg Glu Asp Ala Arg Asn Ser Leu Tyr Leu
65                  70                  75                  80

Gln Met Asn Ser Leu Arg Thr Gly Asp Thr Ala Val Tyr Tyr Cys Ala
                85                  90                  95

Thr Gly Tyr Asn Trp Ile Phe Asp Tyr Trp Gly Gln Gly Thr Leu Val
            100                 105                 110

Thr Val Ser Ser
        115


<210> SEQ ID NO 612
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 612

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Val Ser Thr Tyr
            20                  25                  30

Asp Ile Tyr Trp Val Arg Gln Thr Thr Gly Lys Gly Leu Glu Leu Val
        35                  40                  45

Ser Ala Ile Gly Thr Ala Gly Asp Thr Tyr Tyr Pro Asp Ser Val Lys
    50                  55                  60

Gly Arg Phe Thr Ile Ser Arg Glu Asn Ala Arg Asn Ser Leu Tyr Leu
65                  70                  75                  80

Gln Met Asn Ser Leu Arg Ala Gly Asp Thr Ala Val Tyr Tyr Cys Ala
                85                  90                  95

Val Gly Tyr Asn Trp Ile Phe Asp Phe Trp Gly Gln Gly Thr Leu Val
            100                 105                 110

Thr Val Ser Ser
        115


<210> SEQ ID NO 613
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 613

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Thr Tyr
            20                  25                  30

Asp Met Tyr Trp Val Arg Gln Thr Thr Gly Lys Gly Leu Glu Trp Val
        35                  40                  45

Ser Ala Ile Gly Thr Ala Gly Asp Thr Tyr Tyr Pro Asp Ser Val Lys
```

50                  55                  60

Gly Arg Phe Thr Ile Ser Arg Glu Ser Ala Lys Asn Ser Leu Tyr Leu
65                  70                  75                  80

Gln Met Asn Ser Leu Arg Ala Gly Asp Thr Ala Val Tyr Tyr Cys Thr
                85                  90                  95

Val Gly Tyr Asn Trp Ile Phe Asp Phe Trp Gly His Gly Thr Leu Val
            100                 105                 110

Thr Val Ser Ser
        115

<210> SEQ ID NO 614
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 614

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Met Ser Val Asp Lys Ser Lys Asn Gln Phe Ser
65                  70                  75                  80

Leu Asn Leu His Ser Val Thr Ala Ala Asp Thr Ala Val Tyr Tyr Cys
                85                  90                  95

Ala Arg Glu Val Val Ser Gly Met Ile Gly Thr Ile Phe Asp Tyr Trp
            100                 105                 110

Gly Gln Gly Thr Leu Val Thr Val Ser Ser
        115                 120

<210> SEQ ID NO 615
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 615

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Tyr Trp Val Arg Gln Pro Thr Gly Lys Gly Leu Glu Trp Val
        35                  40                  45

Ser Ala Ile Gly Thr Ala Gly Asp Thr Tyr Tyr Ser Gly Ser Val Lys
    50                  55                  60

Gly Arg Phe Thr Ile Ser Arg Glu Ser Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Val Gly Tyr Asn Trp Ile Phe Asp Phe Trp Gly Gln Gly Thr Leu Val

```
            100                 105                 110

Thr Val Ser Ser
        115


<210> SEQ ID NO 616
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 616

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Thr Asn Tyr Asn Pro Ser Leu
    50                  55                  60

Lys Ser Arg Val Thr Met Ser Val Asp Lys Ser Lys Asn Gln Phe Ser
65                  70                  75                  80

Leu Asn Leu His Ser Val Thr Ala Ala Asp Thr Ala Val Tyr Tyr Cys
                85                  90                  95

Ala Arg Glu Val Val Ser Gly Met Ile Gly Thr Ile Phe Asp Tyr Trp
            100                 105                 110

Gly Gln Gly Thr Leu Val Thr Val Ser Ser
        115                 120


<210> SEQ ID NO 617
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 617

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asp Ile Tyr Trp Val Arg Gln Pro Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Ile Ile Ser Arg Glu Ser Ala Lys Asn Ser Val Tyr Leu
65                  70                  75                  80

Gln Met Asn Ser Leu Arg Ala Gly Asp Thr Ala Val Tyr Tyr Cys Ala
                85                  90                  95

Val Gly Tyr Asn Trp Val Phe Asp Leu Trp Gly Gln Gly Thr Leu Val
            100                 105                 110

Thr Val Ser Ser
        115


<210> SEQ ID NO 618
<211> LENGTH: 118
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 618

```
Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Val Pro Gly Lys Gly Leu Glu Trp Val
        35                  40                  45

Ser Gly Ile Thr Trp Asn Gly Asp Arg Ser Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Arg Asp Gly Leu Thr Gly Ile Phe Asp Tyr Trp Gly Gln Gly Thr
            100                 105                 110

Leu Val Thr Val Ser Ser
        115
```

<210> SEQ ID NO 619
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 619

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Ile Ser Thr Tyr
            20                  25                  30

Asp Ile Tyr Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Ser Gly Tyr Asn Trp Ile Phe Asp Tyr Trp Gly Gln Gly Thr Leu Val
            100                 105                 110

Thr Val Ser Ser
        115
```

<210> SEQ ID NO 620
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 620

```
Gln Val Gln Leu Gln Glu Ser Gly Pro Gly Leu Val Lys Pro Ser Gly
1               5                   10                  15
```

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Gly Ser Val Thr Ala Ala Asp Thr Ala Val Tyr Tyr Cys
85 90 95

Ala Arg Glu Val Val Ser Gly Leu Tyr Gly Thr Ile Phe Asp Tyr Trp
100 105 110

Gly Gln Gly Thr Leu Val Thr Val Ser Ser
115 120

<210> SEQ ID NO 621
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 621

Glu Val Gln Leu Gln Gln Ser Gly Pro Gly Leu Val Lys Pro Ser Gln
1 5 10 15

Ser Leu Ser Leu Thr Cys Ser Val Thr Gly Tyr Ser Ile Thr Ser Gly
20 25 30

Tyr Tyr Trp Asn Trp Ile Arg Gln Phe Pro Gly Asn Lys Leu Glu Trp
35 40 45

Met Gly Tyr Ile Ser Tyr Gly Gly Ser Asn Asp Tyr Asn Pro Ser Leu
50 55 60

Lys Asn Arg Ile Ser Ile Thr Arg Asp Ser Ser Lys Asn Gln Phe Phe
65 70 75 80

Leu Lys Leu Asn Ser Val Thr Thr Glu Asp Thr Ala Thr Tyr Tyr Cys
85 90 95

Ala Arg Asp Tyr Asp Tyr Phe Asp Tyr Trp Gly Gln Gly Thr Thr Leu
100 105 110

Thr Val Ser Ser
115

<210> SEQ ID NO 622
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 622

Glu Val Gln Arg Val Gln Ser Gly Ala Glu Leu Val Lys Pro Gly Ala
1 5 10 15

Ser Val Lys Ile Ser Cys Lys Ala Ser Gly Tyr Ala Phe Ser Ser Tyr
20 25 30

Trp Met Asn Trp Val Lys Gln Arg Pro Gly Lys Gly Leu Glu Trp Ile
35 40 45

Gly Gln Ile Tyr Pro Gly Asp Gly Asp Thr Asn Tyr Asn Gly Lys Phe
50 55 60

```
Glu Gly Lys Ala Thr Leu Thr Ala Asp Lys Ser Ser Ser Thr Ala Tyr
65                  70                  75                  80

Met Gln Leu Thr Ser Leu Thr Ser Asp Asp Ser Ala Val Tyr Tyr Cys
                85                  90                  95

Ala Arg Gly Ala Tyr Trp Gly Gln Gly Thr Thr Leu Thr Val Ser Ser
            100                 105                 110


<210> SEQ ID NO 623
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Glu Tyr
            20                  25                  30

Ile Thr His Trp Val Arg Gln Ala Pro Gly Lys Gly Leu Glu Trp Val
        35                  40                  45

Ala Thr Ile Ser Gly Gly Gly Ser Tyr Thr Asn Phe Pro Asp Ser Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Asn Tyr Ser Gly Ser Ser Pro Phe Ala Tyr Trp Gly Gln
            100                 105                 110

Gly Thr Leu Val Thr Val Ser Ala
        115                 120


<210> SEQ ID NO 624
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 624

Glu Val Gln Leu Gln Gln Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Ala Ile Ser Trp Val Arg Gln Pro Pro Gly Lys Gly Leu Glu Trp Leu
        35                  40                  45

Gly Val Ile Trp Thr Gly Gly Gly Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Ser Arg Gly Tyr Tyr Tyr Gly Ser Ser Tyr Gly Tyr Phe Asp Val
            100                 105                 110

Trp Gly Thr Gly Thr Thr Val Thr Val Ser Ser
        115                 120
```

<210> SEQ ID NO 625
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 625

Glu Val Gln Leu Gln Glu Ser Gly Pro Gly Leu Ala Lys Pro Ser Gln
1 5 10 15

Thr Leu Pro Leu Thr Cys Ser Val Ile Gly Tyr Ser Ile Thr Ser Asp
20 25 30

Tyr Trp Asn Trp Ile Arg Lys Phe Pro Gly Asn Lys Leu Glu Tyr Met
35 40 45

Gly Tyr Ile Asn Tyr Ser Gly Ser Thr Tyr Tyr Asn Pro Ser Leu Lys
50 55 60

Ser Arg Ile Ser Ile Thr Arg Asp Thr Ser Lys Asn Gln Tyr Tyr Leu
65 70 75 80

Gln Leu Asn Ser Val Thr Thr Glu Asp Thr Ala Thr Tyr Tyr Cys Thr
85 90 95

Arg Lys Leu Asp Trp Asp Gly Tyr Phe Asp Val Trp Gly Thr Gly Thr
100 105 110

Thr Val Thr Val Ser Ser
115

<210> SEQ ID NO 626
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 626

Glu Val Gln Leu Gln Gln Ser Glu Ala Glu Leu Val Arg Pro Gly Ala
1 5 10 15

Pro Val Lys Leu Ser Cys Thr Ala Ser Gly Phe Asn Ile Lys Asn Thr
20 25 30

Tyr Met His Trp Val Lys Gln Arg Pro Glu Gln Gly Leu Glu Trp Ile
35 40 45

Gly Arg Ile Asp Pro Ala Asn Gly Asn Thr Lys Tyr Ala Pro Lys Phe
50 55 60

Gln Gly Lys Ala Thr Ile Thr Ala Asp Thr Ser Ser Asn Thr Ala Tyr
65 70 75 80

Leu Gln Leu Ser Ser Leu Ala Ser Glu Asp Ser Ala Val Tyr Phe Cys
85 90 95

Ala Arg Gly Ser Pro Tyr Gly Tyr Asp Gly His Tyr Val Met Asp Tyr
100 105 110

Trp Gly Gln Gly Thr Ser Val Thr Val Ser Ser
115 120

<210> SEQ ID NO 627
<211> LENGTH: 155
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 627

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Arg Thr Tyr
20 25 30

Gly Met His Trp Val Arg Gln Ala Pro Gly Lys Gly Leu Glu Trp Val
35 40 45

Ala Val Ile Ser Ala Glu Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Arg Gly Ser Leu Pro Arg Pro Lys Gly Gly Phe Ile
100 105 110

Gly Ala Leu Ser Phe His Trp Pro Phe Gly Arg Trp Leu Gly Gly Ser
115 120 125

Tyr Gly Thr Tyr Asp Ser Ser Glu Asp Ser Gly Gly Ala Phe Asp Ile
130 135 140

Trp Gly Gln Gly Thr Leu Val Thr Val Ser Ser
145 150 155

<210> SEQ ID NO 628
<211> LENGTH: 155
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 628

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Asn Asn Tyr
20 25 30

Gly Met His Trp Val Arg Gln Ala Pro Gly Lys Gly Leu Glu Trp Val
35 40 45

Ala Val Ile Ser Tyr Gly Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Gly Arg Gly Ser Leu Pro Arg Pro Lys Gly Gly Phe Ile
100 105 110

Gly Asp Leu Ser Phe His Trp Pro Phe Gly Arg Trp Leu Gly Lys Ser
115 120 125

Tyr Gly Thr Tyr Asp Ser Ser Glu Asp Ser Gly Gly Ala Phe Asp Ile
130 135 140

Trp Gly Gln Gly Thr Leu Val Thr Val Ser Ser
145 150 155

<210> SEQ ID NO 629
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 629

Glu Leu Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Val Asp Ile Lys
            100                 105                 110

<210> SEQ ID NO 630
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 630

Glu Leu Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Met
                85                  90                  95

Tyr Thr Phe Gly Gln Gly Thr Lys Leu Glu Ile Lys
            100                 105

<210> SEQ ID NO 631
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 631

Glu Leu Val Leu Thr Gln Ser Pro Asp Ser Leu Ala Val Ser Leu Gly
1               5                   10                  15

Glu Arg Ala Thr Phe Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Ser Thr Pro Tyr Thr Phe Gly Gln Gly Thr Lys Val Asp Ile
100 105 110

Lys

<210> SEQ ID NO 632
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 632

Glu Leu Thr Leu Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ala
65 70 75 80

Glu Asp Val Ala Val Tyr Tyr Cys Gln Gln Tyr Tyr Ser Thr Pro Leu
85 90 95

Thr Phe Gly Gly Gly Thr Lys Val Glu Ile Lys
100 105

<210> SEQ ID NO 633
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 633

Glu Leu Thr Leu Thr Gln Ser Pro Ala Phe Met Ser Ala Thr Pro Gly
1 5 10 15

Asp Lys Val Asn Ile Ser Cys Lys Ala Ser Gln Asp Ile Asp Asp Asp
20 25 30

Met Asn Trp Tyr Gln Gln Lys Pro Gly Glu Ala Ala Ile Phe Ile Ile
35 40 45

Gln Glu Ala Thr Thr Leu Val Pro Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Asn Phe Pro Trp
85 90 95

Thr Phe Gly Gln Gly Thr Lys Val Asp Thr Lys
100 105

<210> SEQ ID NO 634
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 634

Glu Leu Gln Met Thr Gln Ser Pro Ser Ser Val Ser Ala Ser Val Gly
1 5 10 15

Asp Lys Val Thr Ile Thr Cys Arg Ala Ser Gln Gly Ile Ser Ser Trp
20 25 30

Leu Ala Trp Tyr Gln Gln Lys Pro Gly Lys Gly Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Pro Thr Ile Ser Ser Leu Gln Pro
65 70 75 80

Glu Asp Phe Ala Thr Tyr Tyr Cys Gln Gln Thr Asn Ser Phe Pro Arg
85 90 95

Thr Leu Gly Gln Gly Thr Lys Leu Glu Ile Lys
100 105

<210> SEQ ID NO 635
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 635

Glu Leu Thr Leu Thr Gln Ser Pro Ala Phe Met Ser Ala Thr Pro Gly
1 5 10 15

Asp Lys Val Asn Ile Ser Cys Lys Ala Ser Gln Asp Val Asp Asp Asp
20 25 30

Met Asn Trp Tyr Gln Gln Lys Pro Gly Glu Ala Ala Ile Phe Ile Ile
35 40 45

Gln Glu Ala Thr Thr Leu Val Pro Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Asn Phe Pro Trp
85 90 95

Thr Phe Gly Gln Gly Thr Arg Leu Glu Ile Lys
100 105

<210> SEQ ID NO 636
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 636

Asp Ile Val Met Thr Gln Ala Gln Lys Phe Met Ser Thr Ser Val Gly
1 5 10 15

Asp Arg Val Ser Val Thr Cys Lys Ala Ser Gln Asn Val Gly Thr Asn
20 25 30

```
Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Val Thr Asn Val Gln Ser
65                  70                  75                  80

Glu Asp Leu Ala Glu Tyr Phe Cys Gln Arg Phe Asn Asn Tyr Pro Leu
                85                  90                  95

Thr Phe Gly Ala Gly Thr Lys Leu Glu Ile Lys
            100                 105


<210> SEQ ID NO 637
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 637

Asp Ile Val Met Thr Gln Ser Gln Lys Phe Met Ser Thr Ser Val Gly
1               5                   10                  15

Asp Arg Val Ser Ala Thr Cys Lys Ala Ser Gln Asn Val Gly Ser Ser
            20                  25                  30

Val Ala Trp Phe Gln Gln Lys Pro Gly Gln Ser Pro Lys Ala Leu Ile
        35                  40                  45

Tyr Ser Thr Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys
            100                 105


<210> SEQ ID NO 638
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 638

Asp Ile Val Met Thr Gln Ala Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Ile Lys
            100                 105
```

<210> SEQ ID NO 639
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 639

Asp Ile Val Met Thr Gln Ser Gln Lys Phe Met Ser Thr Ser Val Gly
1 5 10 15

Asp Arg Val Ser Val Thr Cys Lys Ala Ser Arg Asn Val Gly Thr Asn
20 25 30

Val Ala Trp Tyr Gln Gln Lys Leu Gly Gln Ser Pro Lys Thr Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro Leu
85 90 95

Thr Phe Gly Ala Gly Thr Lys Leu Glu Ile Lys
100 105

<210> SEQ ID NO 640
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 640

Asp Ile Gln Met Thr Gln Thr Pro Ala Thr Leu Ser Val Thr Pro Gly
1 5 10 15

Asp Arg Val Ser Leu Ser Cys Arg Ala Ser Gln Ser Ile Ser Asp Tyr
20 25 30

Leu His Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Gly Ser Asp Phe Thr Leu Ser Ile Asn Ser Val Glu Pro
65 70 75 80

Glu Asp Val Gly Val Tyr Tyr Cys Gln Asn Gly His Ser Phe Pro His
85 90 95

Thr Leu Gly Ser Gly Thr Lys Leu Glu Ile Lys
100 105

<210> SEQ ID NO 641
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 641

Asp Ile Gln Met Ile Gln Ser Gln Lys Phe Met Ser Thr Ser Val Gly
1 5 10 15

-continued

```
Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Gly Asn Val Gln Ser
65                  70                  75                  80

Glu Asp Leu Val Glu Tyr Phe Cys Gln Gln Tyr Asn Ile Tyr Pro Leu
                85                  90                  95

Thr Phe Gly Ala Gly Thr Lys Leu Glu Leu Lys
            100                 105


<210> SEQ ID NO 642
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 642

Asp Ile Val Met Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Gly Gly Thr Lys Leu Glu Leu Lys
            100                 105


<210> SEQ ID NO 643
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 643

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Val Thr Pro Trp
                85                  90                  95
```

Thr Phe Gly Gly Gly Thr Lys Leu Glu Ile Lys
100 105

<210> SEQ ID NO 644
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 644

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Gly Thr Tyr
20 25 30

Leu Asn Trp Tyr Gln Gln Lys Pro Gly Lys Ala Pro Lys Leu Leu Ile
35 40 45

Tyr Gly Ala Ser Thr Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ala Pro Trp
85 90 95

Thr Phe Gly Gly Gly Thr Lys Val Glu Ile Lys
100 105

<210> SEQ ID NO 645
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 645

Asp Ile Gln Met Thr Gln Ser Pro Ser Ser Leu Ser Ala Ser Val Gly
1 5 10 15

Asp Arg Val Thr Ile Thr Cys Lys Ala Ser Gln Ser Val Arg Asn Asp
20 25 30

Val Val Trp Tyr Gln Gln Lys Pro Gly Lys Ala Pro Lys Leu Leu Ile
35 40 45

Tyr Arg Gly Asn Thr Leu Arg Pro Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Gly Ile Pro Leu
85 90 95

Thr Phe Gly Gln Gly Thr Lys Leu Glu Ile Lys
100 105

<210> SEQ ID NO 646
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 646

Asp Ile Gln Met Thr Gln Ser Pro Ser Ser Leu Ser Ala Ser Val Gly

-continued

```
1               5                   10                  15

Asp Arg Val Thr Ile Thr Cys Arg Ala Ser Gln Ser Val Thr Thr Tyr
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ala Thr Pro Trp
                85                  90                  95

Thr Phe Gly Gly Gly Thr Lys Val Glu Ile Lys
            100                 105


<210> SEQ ID NO 647
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 647

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu Asn Trp Tyr Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Glu Gln Ser Tyr Ser Thr Pro Trp
                85                  90                  95

Thr Phe Gly Gly Gly Thr Lys Leu Glu Ile Lys
            100                 105


<210> SEQ ID NO 648
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Asp Ile Gln Met Thr Gln Ser Pro Ser Ser Leu Ser Ala Ser Val Gly
1               5                   10                  15

Asp Arg Val Thr Ile Thr Cys Lys Ala Ser His Ser Val Asp Tyr Asp
            20                  25                  30

Gly Asp Asn Tyr Met Asn Trp Tyr Gln Gln Lys Pro Gly Lys Ala Pro
        35                  40                  45

Lys Leu Leu Ile Tyr Trp Ala Ser Thr Arg Leu Thr Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Leu Gln His Ile
```

```
                85                  90                  95

Glu Tyr Pro Phe Thr Phe Gly Gln Gly Thr Lys Leu Glu Ile Lys
            100                 105                 110


<210> SEQ ID NO 649
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 649

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
            20                  25                  30

Ser Asn Asn Lys Asn Tyr Phe Ala Trp Tyr Gln Gln Lys Pro Gly Lys
        35                  40                  45

Ala Pro Lys Leu Leu Ile Tyr Asp Ala Pro Asn Arg Ala Thr Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Gly Tyr Thr Thr Pro Tyr Thr Phe Gly Gly Gly Thr Lys Val Glu Ile
            100                 105                 110

Lys


<210> SEQ ID NO 650
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 650

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Arg Ser
            20                  25                  30

Leu Ser Trp Tyr Gln Gln Lys Pro Gly Lys Ala Pro Lys Leu Leu Ile
        35                  40                  45

Tyr Asp Ala Ser Arg Phe Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Trp Ser Asn Ser Trp Pro Tyr
                85                  90                  95

Thr Phe Gly Gln Gly Thr Lys Leu Glu Ile Lys
            100                 105


<210> SEQ ID NO 651
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 651

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Val Thr Pro Trp
                85                  90                  95

Thr Phe Gly Gly Gly Thr Lys Leu Glu Ile Lys
            100                 105

<210> SEQ ID NO 652
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 652

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Arg Asn Asp
            20                  25                  30

Val Val Trp Tyr Gln Gln Lys Pro Gly Lys Ala Pro Lys Leu Leu Ile
        35                  40                  45

Tyr Arg Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Ile Pro Leu
                85                  90                  95

Thr Phe Gly Gln Gly Thr Lys Leu Glu Ile Lys
            100                 105

<210> SEQ ID NO 653
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 653

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Arg Ala Asn Arg Leu Val Asp Gly Val Pro Ser
    50                  55                  60

```
Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Asn Gly His
                85                  90                  95

Ser Phe Pro Leu Thr Phe Gly Gln Gly Thr Lys Leu Glu Ile Lys
            100                 105                 110


<210> SEQ ID NO 654
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 654

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Arg Tyr
            20                  25                  30

Leu Asn Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro His
                85                  90                  95

Thr Phe Gly Gly Gly Thr Lys Val Glu Ile Lys
            100                 105


<210> SEQ ID NO 655
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 655

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Ala Pro Arg
                85                  90                  95

Thr Phe Gly Gly Gly Thr Lys Leu Glu Ile Lys
            100                 105


<210> SEQ ID NO 656
<211> LENGTH: 107
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 656

Asp Ile Gln Met Thr Gln Ser Pro Ser Ser Leu Ser Ala Ser Val Gly
1 5 10 15

Asp Arg Val Thr Ile Thr Cys Arg Ala Ser Arg Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Pro Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Arg
85 90 95

Thr Phe Gly Gly Gly Thr Lys Leu Glu Ile Lys
100 105

<210> SEQ ID NO 657
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 657

Asp Ile Gln Met Thr Gln Ser Pro Ser Ser Leu Ser Ala Ser Val Gly
1 5 10 15

Asp Arg Val Thr Ile Thr Cys Lys Val Ser Gln Asp Val Arg Thr Ala
20 25 30

Val Ala Trp Tyr Gln Gln Lys Pro Gly Lys Ala Pro Lys Leu Leu Ile
35 40 45

Tyr Asp Thr Ser Tyr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Trp Ser Leu
85 90 95

Thr Phe Gly Gln Gly Thr Lys Leu Glu Ile Lys
100 105

<210> SEQ ID NO 658
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 658

Asp Ile Gln Met Thr Gln Ser Pro Ser Ser Leu Ser Ala Ser Val Gly
1 5 10 15

Asp Arg Val Thr Ile Thr Cys Gly Gly Gly Asn Asp Ile Gly Ser Ser
20 25 30

Met Tyr Trp Tyr Gln Gln Lys Pro Gly Lys Ala Pro Lys Leu Leu Ile
35 40 45

Tyr Trp Met Ser Asn Leu Ala Ser Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Phe
                85                  90                  95

Ala Leu Gly Gln Gly Thr Lys Leu Glu Ile Lys
            100                 105


<210> SEQ ID NO 659
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 659

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu Asn Trp Tyr Gln Gln Lys Pro Gly Lys Ala Pro Lys Leu Leu Ile
        35                  40                  45

Tyr Gly Ala Ser Pro Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Asn Ile Trp Pro Tyr
                85                  90                  95

Thr Phe Gly Gln Gly Thr Lys Leu Glu Ile Lys
            100                 105


<210> SEQ ID NO 660
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 660

Asp Ile Gln Met Thr Gln Ser Pro Ser Ser Leu Ser Ala Ser Val Gly
1               5                   10                  15

Asp Arg Val Thr Ile Thr Cys Gly Gly Gly Asn Asp Ile Gly Ser Ser
            20                  25                  30

Met Tyr Trp Tyr Gln Gln Lys Pro Gly Lys Ala Pro Lys Leu Leu Ile
        35                  40                  45

Tyr Asp Ala Ser Arg Phe Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Glu Asp Pro Pro
                85                  90                  95

Phe Thr Phe Gly Gln Gly Thr Lys Leu Glu Ile Lys
            100                 105


<210> SEQ ID NO 661
<211> LENGTH: 111
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 661

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Phe
            20                  25                  30

Gly Asn Asn Phe Met Asn Trp Tyr Gln Gln Lys Pro Gly Lys Ala Pro
        35                  40                  45

Lys Leu Leu Ile Tyr His Thr Ser Arg Leu Asn Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Val Pro Arg Thr Phe Gly Gln Gly Thr Lys Leu Glu Ile Lys
            100                 105                 110
```

<210> SEQ ID NO 662
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 662

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Thr Tyr Ile
            20                  25                  30

His Trp Tyr Gln Gln Lys Pro Gly Lys Ala Pro Lys Leu Leu Ile Tyr
        35                  40                  45

Ala Val Ser Arg Leu Asp Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Ser Asn Glu Asp Pro Tyr Thr
                85                  90                  95

Phe Gly Gln Gly Thr Lys Leu Glu Ile Lys
            100                 105
```

<210> SEQ ID NO 663
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 663

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Val Thr Pro Trp
                85                  90                  95

Thr Phe Gly Gly Gly Thr Lys Val Glu Ile Lys
            100                 105


<210> SEQ ID NO 664
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 664

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Arg Asn Asp
            20                  25                  30

Val Val Trp Tyr Gln Gln Lys Pro Gly Lys Ala Pro Lys Leu Leu Ile
        35                  40                  45

Tyr Arg Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Gly Ile Pro Leu
                85                  90                  95

Thr Phe Gly Gln Gly Thr Lys Leu Glu Ile Lys
            100                 105


<210> SEQ ID NO 665
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 665

Asp Ile Gln Met Thr Gln Ser Pro Ser Ser Leu Ser Ala Ser Val Gly
1               5                   10                  15

Asp Arg Val Thr Ile Thr Cys Lys Ala Ser His Ser Val Asp Tyr Asp
            20                  25                  30

Gly Asp Asn Tyr Met Asn Trp Tyr Gln Gln Lys Pro Gly Lys Ala Pro
        35                  40                  45

Lys Leu Leu Ile Tyr Asp Ala Ser Arg Phe Ile Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Leu Arg Tyr Ala
                85                  90                  95

Ser Tyr Arg Thr Phe Gly Gln Gly Thr Lys Leu Glu Ile Lys
            100                 105                 110


<210> SEQ ID NO 666
```

<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 666

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asn Ser Tyr
20 25 30

Gly Asn Ser Phe Met His Trp Tyr Gln Gln Lys Pro Gly Lys Ala Pro
35 40 45

Lys Leu Leu Ile Tyr Asp Ala Ser Arg Phe Ile Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Leu Gln Tyr Gly
85 90 95

Glu Ser Pro Leu Thr Phe Gly Gln Gly Thr Lys Leu Glu Ile Lys
100 105 110

<210> SEQ ID NO 667
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 667

Asp Ile Gln Met Thr Gln Ser Pro Ser Ser Leu Ser Ala Ser Val Gly
1 5 10 15

Asp Arg Val Thr Ile Thr Cys Arg Ser Ser Lys Ser Leu Leu His Ser
20 25 30

Ser Gly Asn Ala Tyr Val Tyr Trp Tyr Gln Gln Lys Pro Gly Lys Ala
35 40 45

Pro Lys Leu Leu Ile Tyr Tyr Thr Ser Lys Pro Asn Ser Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Gln His His
85 90 95

Tyr Gly Ile Pro Leu Thr Phe Gly Gln Gly Thr Lys Leu Glu Ile Lys
100 105 110

<210> SEQ ID NO 668
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 668

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Gly Thr Tyr
20 25 30

```
Leu Asn Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Asn Thr Pro Trp
                85                  90                  95

Thr Phe Gly Gly Gly Thr Lys Val Glu Ile Lys
            100                 105


<210> SEQ ID NO 669
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 669

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Arg Val Ser Ser Ser
            20                  25                  30

Tyr Leu Tyr Trp Tyr Gln Gln Lys Pro Gly Lys Ala Pro Lys Leu Leu
        35                  40                  45

Ile Tyr Ala Thr Tyr Ser Leu Asp Tyr Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gln His Gly Glu Arg Pro
                85                  90                  95

Leu Thr Phe Gly Gln Gly Thr Lys Leu Glu Ile Lys
            100                 105


<210> SEQ ID NO 670
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 670

Asp Ile Gln Met Thr Gln Ser Pro Ser Ser Leu Ser Ala Ser Val Gly
1               5                   10                  15

Asp Arg Val Thr Ile Thr Cys Gly Ala Ser Gln Ser Ile Gly Thr Ile
            20                  25                  30

Ile His Trp Tyr Gln Gln Lys Pro Gly Lys Ala Pro Lys Leu Leu Ile
        35                  40                  45

Tyr Asp Thr Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Arg Pro Trp
                85                  90                  95

Thr Phe Gly Gln Gly Thr Lys Leu Glu Ile Lys
            100                 105
```

<210> SEQ ID NO 671
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 671

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Val Pro
            20                  25                  30

Leu Asn Trp Tyr Gln Gln Lys Pro Gly Lys Ala Pro Lys Leu Leu Ile
        35                  40                  45

Tyr Asp Ala Ser Arg Phe Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Leu
                85                  90                  95

Tyr Thr Phe Gly Gln Gly Thr Lys Leu Glu Ile Lys
            100                 105
```

<210> SEQ ID NO 672
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 672

```
Glu Leu Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Lys Val Asp Ile Lys
            100                 105
```

<210> SEQ ID NO 673
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 673

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
```

```
            20                  25                  30

Gly Glu Lys Thr Tyr Pro Tyr Trp Tyr Gln Gln Lys Pro Gly Lys Ala
        35                  40                  45

Pro Lys Leu Leu Ile Tyr Trp Ala Ser Thr Arg Leu Thr Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Ser
                85                  90                  95

Asn Glu Asp Ser Trp Thr Phe Gly Gln Gly Thr Lys Leu Glu Ile Lys
            100                 105                 110


<210> SEQ ID NO 674
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 674

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Asp Ile Phe Asn Tyr
            20                  25                  30

Leu Glu Trp Tyr Gln Gln Lys Pro Gly Lys Ala Pro Lys Leu Leu Ile
        35                  40                  45

Tyr Thr Ala Ser Asn Leu Asp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Thr Pro Pro
                85                  90                  95

Glu Ile Thr Phe Gly Gly Gly Thr Lys Val Glu Ile Lys
            100                 105


<210> SEQ ID NO 675
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Asp Ile Gln Met Thr Gln Ser Pro Ser Ser Leu Ser Ala Ser Val Gly
1               5                   10                  15

Asp Arg Val Thr Ile Thr Cys Arg Ser Thr Arg Asn Ile Leu Ser Asn
            20                  25                  30

Met Pro Trp Tyr Gln Gln Lys Pro Gly Lys Ala Pro Lys Leu Leu Ile
        35                  40                  45

Tyr Asn Ala Asn Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Trp Asn Tyr Pro Tyr
                85                  90                  95

Met Phe Gly Gln Gly Thr Lys Leu Glu Ile Lys
```

100 105

<210> SEQ ID NO 676
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 676

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asn Asn
20 25 30

Leu His Trp Tyr Gln Gln Lys Pro Gly Lys Ala Pro Lys Leu Leu Ile
35 40 45

Tyr Glu Ile Ser Gly Trp Leu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asn Ser Trp Ser Leu
85 90 95

Leu Thr Phe Gly Gln Gly Thr Lys Leu Glu Ile Lys
100 105

<210> SEQ ID NO 677
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 677

Asp Ile Gln Met Thr Gln Ser Pro Ser Ser Leu Ser Ala Ser Val Gly
1 5 10 15

Asp Arg Val Thr Ile Thr Cys Ser Ala Ser Gln Ser Met Ser Asn Asn
20 25 30

Leu His Trp Tyr Gln Gln Lys Pro Gly Lys Ala Pro Lys Leu Leu Ile
35 40 45

Tyr Leu Ala Ser Asn Leu Gly Tyr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Arg Gln Asn Gly His Ser Phe Pro
85 90 95

Leu Thr Phe Gly Gln Gly Thr Lys Leu Glu Ile Lys
100 105

<210> SEQ ID NO 678
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 678

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Asp Ile Ser Asn Asn
            20                  25                  30

Leu His Trp Tyr Gln Gln Lys Pro Gly Lys Ala Pro Lys Leu Leu Ile
        35                  40                  45

Tyr Trp Ala Ser Thr Arg Leu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Asp Tyr Pro Phe
                85                  90                  95

Thr Phe Gly Gln Gly Thr Lys Leu Glu Ile Lys
            100                 105


<210> SEQ ID NO 679
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 679

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Leu Ser Tyr Met
            20                  25                  30

His Trp Tyr Gln Gln Lys Pro Gly Lys Ala Pro Lys Leu Leu Ile Tyr
        35                  40                  45

Gly Ala Ser Pro Arg Glu Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Arg Gln Met Ser Ser Tyr Pro Pro Thr
                85                  90                  95

Phe Gly Gln Gly Thr Lys Leu Glu Ile Lys
            100                 105


<210> SEQ ID NO 680
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 680

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Leu Leu Ile Tyr
        35                  40                  45

Glu Ile Ser Gly Trp Leu Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Leu Arg Tyr Ala Ser Tyr Arg Thr Phe
                85                  90                  95
```

Gly Gln Gly Thr Lys Leu Glu Ile Lys
100 105

<210> SEQ ID NO 681
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 681

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Met Gly Ser Asn
20 25 30

Val Ala Trp Tyr Gln Gln Lys Pro Gly Lys Ala Pro Lys Leu Leu Ile
35 40 45

Tyr Ser Ala Ser His Arg Ser Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Trp Asn Tyr Pro Arg Ile
85 90 95

Thr Phe Gly Gln Gly Thr Lys Leu Glu Ile Lys
100 105

<210> SEQ ID NO 682
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 682

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Gly Gly Thr Asn
20 25 30

Val Asp Trp Tyr Gln Gln Lys Pro Gly Lys Ala Pro Lys Leu Leu Ile
35 40 45

Tyr Glu Ile Ser Gly Trp Leu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Tyr Tyr Ser Trp Pro Pro
85 90 95

Thr Phe Gly Gln Gly Thr Lys Leu Glu Ile Lys
100 105

<210> SEQ ID NO 683
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 683

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asn Ile Tyr Val Pro
20 25 30

Leu Asn Trp Tyr Gln Gln Lys Pro Gly Lys Ala Pro Lys Leu Leu Ile
35 40 45

Tyr Leu Ala Ser Tyr Arg Phe Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ile Asn Gly Trp Pro Tyr
85 90 95

Thr Phe Gly Gln Gly Thr Lys Leu Glu Ile Lys
100 105

<210> SEQ ID NO 684
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 684

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Met Gly Ser Asn
20 25 30

Val Ala Trp Tyr Gln Gln Lys Pro Gly Lys Ala Pro Lys Leu Leu Ile
35 40 45

Tyr Ala Ala Thr Arg Leu Ala Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Arg Gln His Tyr Ser Ser Pro Pro
85 90 95

Thr Phe Gly Gln Gly Thr Lys Leu Glu Ile Lys
100 105

<210> SEQ ID NO 685
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 685

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Gly Gly Thr Asn
20 25 30

Val Asp Trp Tyr Gln Gln Lys Pro Gly Lys Ala Pro Lys Leu Leu Ile
35 40 45

Tyr Val Ala Ser Asn Gln Gly Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Tyr Tyr Thr Tyr Pro Leu
                85                  90                  95

Thr Phe Gly Gln Gly Thr Lys Leu Glu Ile Lys
            100                 105


<210> SEQ ID NO 686
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 686

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Asp Thr Asn
            20                  25                  30

Val Ala Trp Tyr Gln Gln Lys Pro Gly Lys Ala Pro Lys Leu Leu Ile
        35                  40                  45

Tyr Ser Ser Ser Ile Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Ala Gln Asn Arg Glu Leu Pro Phe Thr Phe
                85                  90                  95

Gly Gln Gly Thr Lys Leu Glu Ile Lys
            100                 105


<210> SEQ ID NO 687
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 687

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Ile Thr Trp Tyr Gln Gln Lys Pro Gly Lys Ala Pro Lys Leu Leu Ile
        35                  40                  45

Tyr Ser Ala Ser Lys Arg Asn Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu His His Tyr Gly Thr Pro Tyr
                85                  90                  95

Thr Phe Gly Gln Gly Thr Lys Leu Glu Ile Lys
            100                 105


<210> SEQ ID NO 688
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 688

Asp Ile Gln Met Thr Gln Ser Pro Ser Ser Leu Ser Thr Ser Val Gly
1 5 10 15

Asp Arg Val Thr Ile Thr Cys Lys Ala Ser Gln Asp Val Gly Thr Ser
20 25 30

Val Ala Trp Tyr Gln Gln Lys Pro Gly Lys Ala Pro Lys Leu Leu Ile
35 40 45

Tyr Pro Ala Ser Tyr Arg Ser Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Ser Ser Asn Pro Leu
85 90 95

Thr Phe Gly Gln Gly Thr Lys Leu Glu Ile Lys
100 105

<210> SEQ ID NO 689
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 689

Asp Ile Gln Met Thr Gln Ser Pro Ser Ser Leu Ser Ala Ser Val Gly
1 5 10 15

Asp Arg Val Thr Ile Thr Cys Arg Ala Ser Gln Val Ile Asp Asp Asp
20 25 30

Ile Asn Trp Tyr Gln Gln Lys Pro Gly Lys Ala Pro Lys Leu Leu Ile
35 40 45

Tyr Leu Gly Ser Asn Arg Ala Pro Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Ser Tyr Thr Thr Pro His
85 90 95

Thr Phe Gly Gly Gly Thr Lys Val Glu Ile Lys
100 105

<210> SEQ ID NO 690
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 690

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Ser Gly Tyr
20 25 30

Leu Thr Trp Tyr Gln Gln Lys Pro Gly Lys Ala Pro Lys Leu Leu Ile
35 40 45

Tyr Ser Ala Ser His Arg Ser Ser Gly Val Pro Ser Arg Phe Ser Gly
50 55 60

Ser Gly Ser Gly Thr Asp Phe Thr Leu Thr Ile Ser Ser Leu Gln Pro 65 70 75 80

Glu Asp Phe Ala Thr Tyr Tyr Cys Gln Gln Trp Asp Asn Asn Pro Tyr
85 90 95

Thr Phe Gly Gln Gly Thr Lys Leu Glu Ile Lys
100 105

<210> SEQ ID NO 691
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 691

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Arg Tyr
20 25 30

Leu Asn Trp Tyr Gln Gln Lys Pro Gly Lys Ala Pro Lys Leu Leu Ile
35 40 45

Tyr Lys Ala Ser Ser Leu Glu Arg Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Pro Asn Ser Tyr Pro Trp
85 90 95

Thr Phe Gly Gly Gly Thr Lys Val Glu Ile Lys
100 105

<210> SEQ ID NO 692
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 692

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Asp Trp Tyr Gln Gln Lys Pro Gly Lys Ala Pro Lys Leu Leu Ile
35 40 45

Tyr Thr Pro Phe Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln His Tyr Asp Asp Leu Pro Leu
85 90 95

Thr Phe Gly Gly Gly Thr Lys Val Glu Ile Lys
100 105

<210> SEQ ID NO 693
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 693

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asn Met Gly Ser Asn
20 25 30

Val Ala Trp Tyr Gln Gln Lys Pro Gly Lys Ala Pro Lys Leu Leu Ile
35 40 45

Tyr Glu Ala Ser Thr Arg Phe Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Ser Tyr Pro Leu
85 90 95

Arg Phe Gly Gln Gly Thr Lys Leu Glu Ile Lys
100 105

<210> SEQ ID NO 694
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 694

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Leu Gly Tyr
20 25 30

Leu Asn Trp Tyr Gln Gln Lys Pro Gly Lys Ala Pro Lys Leu Leu Ile
35 40 45

Tyr Ser Thr Ser Asn Leu Leu Leu Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Arg Gln Leu Ser Ser Asn Pro Leu
85 90 95

Thr Phe Gly Gln Gly Thr Lys Leu Glu Ile Lys
100 105

<210> SEQ ID NO 695
<211> LENGTH: 111
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 695

Asp Ile Gln Met Thr Gln Ser Pro Ser Ser Leu Ser Ala Ser Val Gly
1 5 10 15

Asp Arg Val Thr Ile Thr Cys Arg Ala Ser Glu Ser Val Asp Asn Tyr
20 25 30

Gly Ile Ser Phe Met Ser Trp Tyr Gln Gln Lys Pro Gly Lys Ala Pro
35 40 45

Lys Leu Leu Ile Tyr Asp Ala Ser Arg Phe Ile Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln Gln Ile Asn
85 90 95

Ser Trp Pro Leu Thr Phe Gly Gln Gly Thr Lys Leu Glu Ile Lys
100 105 110

<210> SEQ ID NO 696
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 696

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Tyr Ser
20 25 30

Gly Glu Lys Thr Tyr Pro Tyr Trp Tyr Gln Gln Lys Pro Gly Lys Ala
35 40 45

Pro Lys Leu Leu Ile Tyr Glu Ala Ser Asn Arg Tyr Thr Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Gln Gln Trp
85 90 95

Ser Ser Tyr Pro Pro Ile Ala Phe Gly Gln Gly Thr Lys Leu Glu Ile
100 105 110

Lys

<210> SEQ ID NO 697
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 697

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Leu Arg His Asp
20 25 30

Leu Gly Trp Tyr Gln Gln Lys Pro Gly Lys Ala Pro Lys Leu Leu Ile
35 40 45

Tyr Trp Ala Ser Asn Arg Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Lys Tyr Ser Ser Thr Pro Tyr
85 90 95

Thr Phe Gly Gly Gly Thr Lys Val Glu Ile Lys
100 105

<210> SEQ ID NO 698
<211> LENGTH: 111

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 698

Asp Ile Gln Met Thr Gln Ser Pro Ser Ser Leu Ser Ala Ser Val Gly
1 5 10 15

Asp Arg Val Thr Ile Thr Cys His Ala Ser Glu Ser Val Ser Val Ala
20 25 30

Gly Thr Ser Leu Leu His Trp Tyr Gln Gln Lys Pro Gly Lys Ala Pro
35 40 45

Lys Leu Leu Ile Tyr Ala Ala Ser Asn Arg Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln His Trp Ser
85 90 95

Ser Phe Pro Leu Thr Phe Gly Gln Gly Thr Lys Leu Glu Ile Lys
100 105 110

<210> SEQ ID NO 699
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 699

Glu Leu Gln Met Thr Gln Ser Pro Ser Ser Leu Ser Ala Ser Val Gly
1 5 10 15

Asp Arg Val Thr Ile Thr Cys Arg Val Ser Gln Gly Ile Ser Asn Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gly Gly Thr Lys Val Glu Ile Lys
100 105

<210> SEQ ID NO 700
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 700

Glu Leu Thr Leu Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile

```
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105


<210> SEQ ID NO 701
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Glu Leu Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Pro Gly Thr Lys Val Asp Ile Lys
            100                 105


<210> SEQ ID NO 702
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Glu Leu Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Ala Glu Asp Val Ala Val Tyr Tyr Cys Gln Gln Tyr Tyr Ser Thr Pro
                85                  90                  95

Leu Thr Phe Gly Gly Gly Thr Lys Val Glu Ile Lys
            100                 105
```

<210> SEQ ID NO 703
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 703

Glu Leu Val Met Thr Gln Phe Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Ile
85 90 95

Thr Phe Gly Gln Gly Thr Arg Leu Glu Ile Lys
100 105

<210> SEQ ID NO 704
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 704

Glu Leu Val Met Thr Gln Ser Pro Ala Thr Leu Ser Val Ser Leu Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Arg Leu Gly Pro
65 70 75 80

Glu Asp Phe Ala Val Tyr Tyr Cys Gln Gln Tyr Gly Ser Ser Pro Leu
85 90 95

Thr Phe Gly Gly Gly Thr Lys Val Glu Ile Lys
100 105

<210> SEQ ID NO 705
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 705

Glu Leu Val Met Thr Gln Ser Pro Ser Ser Leu Ser Ala Ser Val Gly
1 5 10 15

Asp Arg Val Thr Ile Thr Cys Arg Ala Ser Gln Arg Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Arg Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gly Gly Thr Lys Leu Glu Thr Lys
100 105

<210> SEQ ID NO 706
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 706

Glu Leu Thr Leu Thr Gln Ser Pro Ala Thr Leu Ser Leu Ser Pro Gly
1 5 10 15

Glu Arg Ala Thr Leu Ser Cys Arg Ala Ile Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Leu Thr Phe Gly Gly Gly Thr Arg Leu Glu Ile Lys
100 105

<210> SEQ ID NO 707
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 707

Glu Leu Thr Leu Thr Gln Ser Pro Ala Thr Leu Ser Val Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Gly Ala Ser Ser Arg Ala Thr Gly Ile Pro Asp Arg Phe Ser Gly
50 55 60

Ser Gly Ser Gly Thr Asp Phe Thr Leu Thr Ile Ser Arg Leu Glu Pro
65 70 75 80

Glu Asp Phe Ala Val Tyr Tyr Cys Gln Gln Tyr Gly Asn Ser Tyr Thr
85 90 95

Phe Gly Gln Gly Thr Lys Val Asp Ile Lys
100 105

<210> SEQ ID NO 708
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 708

Glu Leu Thr Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Thr Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Gly Ser Ser Pro Pro
85 90 95

Thr Phe Gly Gln Gly Thr Arg Leu Glu Ile Lys
100 105

<210> SEQ ID NO 709
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 709

Glu Leu Val Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Ile
85 90 95

Thr Phe Gly Gly Gly Thr Lys Leu Glu Ile Lys
100 105

<210> SEQ ID NO 710
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 710

Asp Ile Val Ile Thr Gln Ala Pro Lys Phe Leu Leu Val Ser Ala Gly
1 5 10 15

-continued

Asp Arg Val Thr Ile Thr Cys Lys Ala Ser Gln Ser Val Ser Asn Asp
20 25 30

Val Ala Trp Tyr Gln Gln Lys Pro Gly Gln Ser Pro Lys Leu Leu Ile
35 40 45

Tyr Tyr Ala Ser Asn Arg Tyr Thr Gly Val Pro Asp Arg Phe Ser Gly
50 55 60

Ser Gly Tyr Gly Thr Asp Phe Thr Phe Thr Ile Ser Thr Val Gln Ala
65 70 75 80

Glu Asp Leu Ala Val Tyr Phe Cys Gln Gln Asp Tyr Arg Ser Pro Leu
85 90 95

Thr Phe Gly Ala Gly Thr Lys Leu Glu Leu Lys
100 105

<210> SEQ ID NO 711
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 711

Asp Ile Gln Met Lys Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Gly Asp Leu Ala Glu Tyr Phe Cys Gln Gln Tyr Asn Ser Tyr Pro Leu
85 90 95

Thr Phe Gly Ala Gly Thr Lys Leu Glu Ile Lys
100 105

<210> SEQ ID NO 712
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 712

Asp Ile Val Met Thr Gln Ala Pro Ala Ile Met Ser Ala Ser Pro Gly
1 5 10 15

Glu Lys Val Thr Met Thr Cys Ser Ala Ser Ser Ser Val Ser Tyr Met
20 25 30

Tyr Trp Tyr Gln Gln Lys Pro Gly Ser Ser Pro Arg Phe Leu Ile Tyr
35 40 45

Asp Thr Ser Asn Leu Ala Ser Gly Val Pro Val Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys Gln Gln Trp Asn Ser Asn Pro Leu Thr
85 90 95

```
Phe Ser Ala Gly Thr Lys Leu Glu Ile Lys
            100                 105


<210> SEQ ID NO 713
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 713

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
            100                 105


<210> SEQ ID NO 714
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

Asp Ile Lys Ile Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Asn Arg Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Ile Lys
            100                 105


<210> SEQ ID NO 715
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Asp Ile Gln Met Asn Gln Ser Gln Lys Phe Met Ser Thr Ser Val Gly
```

-continued

```
1               5                   10                  15

Asp Arg Val Ser Val Thr Cys Lys Ala Ser Gln Asn Val Gly Ser Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Pro Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys
            100                 105


<210> SEQ ID NO 716
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 716

Gln Ser Val Leu Thr Gln Pro Pro Ser Val Ser Ala Ala Pro Gly Gln
1               5                   10                  15

Lys Val Thr Ile Ser Cys Ser Gly Ile Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Ala Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Leu
                85                  90                  95

Ser Ala Gly Val Phe Gly Gly Gly Thr Lys Leu Thr Val Leu
            100                 105                 110


<210> SEQ ID NO 717
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 717

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn His
            20                  25                  30

Tyr Val Ser Trp Tyr Gln Gln Leu Pro Gly Thr Ala Pro Lys Leu Leu
        35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ala Ser Leu
```

85                  90                  95

Ser Thr Trp Val Phe Gly Gly Gly Thr Lys Leu Thr Val Leu
            100                 105                 110

<210> SEQ ID NO 718
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 718

Gly Gly Gly Gly Ser Gly Gly Gly Gly Ser Gly Gly Gly Gly Ser
1               5                   10                  15

<210> SEQ ID NO 719
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 719
acagaattca ttaaagagga gaaattaacc 30

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 720
tgaaccgcct ccaccgctag 20

<210> SEQ ID NO 721
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (15)..(19)
<223> OTHER INFORMATION: Any amino acid

<400> SEQUENCE: 721

Cys Ala Arg Asp Leu Arg Glu Leu Glu Cys Glu Glu Trp Thr Xaa Xaa
1               5                   10                  15

Xaa Xaa Xaa Ser Arg Gly Pro Cys Val Asp Pro Arg Gly Val Ala Gly
            20                  25                  30

Ser Phe Asp Val Trp
        35

<210> SEQ ID NO 722
<211> LENGTH: 26
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES -continued

```
<222> LOCATION: (10)..(14)
<223> OTHER INFORMATION: Any amino acid

<400> SEQUENCE: 722

Cys Ala Arg Asp Met Tyr Tyr Asp Phe Xaa Xaa Xaa Xaa Xaa Glu Val
1               5                   10                  15

Val Pro Ala Asp Asp Ala Phe Asp Ile Trp
            20                  25


<210> SEQ ID NO 723
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(21)
<223> OTHER INFORMATION: Any amino acid

<400> SEQUENCE: 723

Cys Ala Arg Asp Gly Arg Gly Ser Leu Pro Arg Pro Lys Gly Gly Pro
1               5                   10                  15

Xaa Xaa Xaa Xaa Xaa Tyr Asp Ser Ser Glu Asp Ser Gly Gly Ala Phe
            20                  25                  30

Asp Ile Trp
        35


<210> SEQ ID NO 724
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(13)
<223> OTHER INFORMATION: Any amino acid

<400> SEQUENCE: 724

Cys Ala Arg Ala Asn Gln His Phe Xaa Xaa Xaa Xaa Xaa Gly Tyr His
1               5                   10                  15

Tyr Tyr Gly Met Asp Val Trp
            20


<210> SEQ ID NO 725
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(13)
<223> OTHER INFORMATION: Any amino acid

<400> SEQUENCE: 725

Cys Ala Lys His Met Ser Met Gln Xaa Xaa Xaa Xaa Xaa Arg Ala Asp
1               5                   10                  15

Leu Val Gly Asp Ala Phe Asp Val Trp
            20                  25


<210> SEQ ID NO 726
```

<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (6)..(6)
<223> OTHER INFORMATION: S, D or N
<220> FEATURE:
<221> NAME/KEY: MOD_RES
<222> LOCATION: (8)..(8)
<223> OTHER INFORMATION: Y, A, G or W
<220> FEATURE:
<221> NAME/KEY: MOD_RES
<222> LOCATION: (10)..(10)
<223> OTHER INFORMATION: S, H or G

<400> SEQUENCE: 726

Gly Phe Thr Phe Ser Xaa Tyr Xaa Met Xaa Trp
1 5 10

<210> SEQ ID NO 727
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: S or A
<220> FEATURE:
<221> NAME/KEY: MOD_RES
<222> LOCATION: (4)..(4)
<223> OTHER INFORMATION: Y or V
<220> FEATURE:
<221> NAME/KEY: MOD_RES
<222> LOCATION: (7)..(7)
<223> OTHER INFORMATION: Y or P
<220> FEATURE:
<221> NAME/KEY: MOD_RES
<222> LOCATION: (8)..(8)
<223> OTHER INFORMATION: N, S or D
<220> FEATURE:
<221> NAME/KEY: MOD_RES
<222> LOCATION: (10)..(10)
<223> OTHER INFORMATION: G or S
<220> FEATURE:
<221> NAME/KEY: MOD_RES
<222> LOCATION: (11)..(11)
<223> OTHER INFORMATION: I, N or E
<220> FEATURE:
<221> NAME/KEY: MOD_RES
<222> LOCATION: (12)..(12)
<223> OTHER INFORMATION: T or K
<220> FEATURE:
<221> NAME/KEY: MOD_RES
<222> LOCATION: (15)..(15)
<223> OTHER INFORMATION: P or A

<400> SEQUENCE: 727

Trp Val Xaa Xaa Ile Ser Xaa Xaa Gly Xaa Xaa Xaa Tyr Tyr Xaa Asp
1 5 10 15

<210> SEQ ID NO 728
<211> LENGTH: 25
<212> TYPE: PRT
<213> ORGANISM: Artificial Sequence
<220> FEATURE:
<223> OTHER INFORMATION: Description of Artificial Sequence: Synthetic
peptide
<220> FEATURE:

<221> NAME/KEY: MOD_RES
<222> LOCATION: (4)..(4)
<223> OTHER INFORMATION: G or D
<220> FEATURE:
<221> NAME/KEY: MOD_RES
<222> LOCATION: (5)..(5)
<223> OTHER INFORMATION: R or E
<220> FEATURE:
<221> NAME/KEY: MOD_RES
<222> LOCATION: (6)..(6)
<223> OTHER INFORMATION: G, L or D
<220> FEATURE:
<221> NAME/KEY: MOD_RES
<222> LOCATION: (7)..(7)
<223> OTHER INFORMATION: Y, N or H
<220> FEATURE:
<221> NAME/KEY: MOD_RES
<222> LOCATION: (8)..(8)
<223> OTHER INFORMATION: Y or R
<220> FEATURE:
<221> NAME/KEY: MOD_RES
<222> LOCATION: (9)..(9)
<223> OTHER INFORMATION: Y or G
<220> FEATURE:
<221> NAME/KEY: MOD_RES
<222> LOCATION: (10)..(10)
<223> OTHER INFORMATION: S, D or I
<220> FEATURE:
<221> NAME/KEY: MOD_RES
<222> LOCATION: (11)..(11)
<223> OTHER INFORMATION: G, S, R or F
<220> FEATURE:
<221> NAME/KEY: MOD_RES
<222> LOCATION: (12)..(12)
<223> OTHER INFORMATION: S, W, Y, T or L
<220> FEATURE:
<221> NAME/KEY: MOD_RES
<222> LOCATION: (13)..(13)
<223> OTHER INFORMATION: R, G, T or Y
<220> FEATURE:
<221> NAME/KEY: MOD_RES
<222> LOCATION: (14)..(14)
<223> OTHER INFORMATION: Y, H, Q or F
<220> FEATURE:
<221> NAME/KEY: MOD_RES
<222> LOCATION: (15)..(15)
<223> OTHER INFORMATION: R, Y, D or N
<220> FEATURE:
<221> NAME/KEY: MOD_RES
<222> LOCATION: (16)..(16)
<223> OTHER INFORMATION: G, H, Y or F
<220> FEATURE:
<221> NAME/KEY: MOD_RES
<222> LOCATION: (17)..(17)
<223> OTHER INFORMATION: Y, G or H
<220> FEATURE:
<221> NAME/KEY: MOD_RES
<222> LOCATION: (18)..(18)
<223> OTHER INFORMATION: K, Y or F
<220> FEATURE:
<221> NAME/KEY: MOD_RES
<222> LOCATION: (19)..(19)
<223> OTHER INFORMATION: Y, G or H
<220> FEATURE:
<221> NAME/KEY: MOD_RES
<222> LOCATION: (20)..(20)
<223> OTHER INFORMATION: R, Y, G or F
<220> FEATURE:
<221> NAME/KEY: MOD_RES
<222> LOCATION: (21)..(21)
<223> OTHER INFORMATION: G or P

<400> SEQUENCE: 728

```
Cys Ala Arg Xaa Xaa Xaa Xaa Xaa Xaa Xaa Xaa Xaa Xaa Xaa Xaa Xaa
1               5                   10                  15

Xaa Xaa Xaa Xaa Xaa Met Asp Val Trp
            20                  25
```

<210> SEQ ID NO 729
<211> LENGTH: 23
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (5)..(5)
<223> OTHER INFORMATION: P, K, I or R
<220> FEATURE:
<221> NAME/KEY: MOD_RES
<222> LOCATION: (6)..(6)
<223> OTHER INFORMATION: V, S, D or R
<220> FEATURE:
<221> NAME/KEY: MOD_RES
<222> LOCATION: (7)..(7)
<223> OTHER INFORMATION: V, H, Y or G
<220> FEATURE:
<221> NAME/KEY: MOD_RES
<222> LOCATION: (8)..(8)
<223> OTHER INFORMATION: L, Y, R or W
<220> FEATURE:
<221> NAME/KEY: MOD_RES
<222> LOCATION: (9)..(9)
<223> OTHER INFORMATION: V, D, Y or F
<220> FEATURE:
<221> NAME/KEY: MOD_RES
<222> LOCATION: (10)..(10)
<223> OTHER INFORMATION: G, I, S or D
<220> FEATURE:
<221> NAME/KEY: MOD_RES
<222> LOCATION: (11)..(11)
<223> OTHER INFORMATION: V, L, R or F
<220> FEATURE:
<221> NAME/KEY: MOD_RES
<222> LOCATION: (12)..(12)
<223> OTHER INFORMATION: W, T, Y or S
<220> FEATURE:
<221> NAME/KEY: MOD_RES
<222> LOCATION: (13)..(13)
<223> OTHER INFORMATION: T, G or R
<220> FEATURE:
<221> NAME/KEY: MOD_RES
<222> LOCATION: (14)..(14)
<223> OTHER INFORMATION: Q, H, Y or N
<220> FEATURE:
<221> NAME/KEY: MOD_RES
<222> LOCATION: (15)..(15)
<223> OTHER INFORMATION: R, D, N or Y
<220> FEATURE:
<221> NAME/KEY: MOD_RES
<222> LOCATION: (16)..(16)
<223> OTHER INFORMATION: Y, G or H
<220> FEATURE:
<221> NAME/KEY: MOD_RES
<222> LOCATION: (17)..(17)
<223> OTHER INFORMATION: Y or A
<220> FEATURE:
<221> NAME/KEY: MOD_RES
<222> LOCATION: (18)..(18)
<223> OTHER INFORMATION: Y or R
<220> FEATURE:
<221> NAME/KEY: MOD_RES
<222> LOCATION: (19)..(19)
<223> OTHER INFORMATION: G or T
<220> FEATURE:
<221> NAME/KEY: MOD_RES
<222> LOCATION: (20)..(20)
<223> OTHER INFORMATION: M, L or F
<220> FEATURE:
<221> NAME/KEY: MOD_RES
<222> LOCATION: (22)..(22)
<223> OTHER INFORMATION: V or Y

<400> SEQUENCE: 729

Cys Ala Arg Glu Xaa Xaa Xaa Xaa Xaa Xaa Xaa Xaa Xaa Xaa Xaa Xaa
1 5 10 15

Xaa Xaa Xaa Xaa Asp Xaa Trp
20

<210> SEQ ID NO 730
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: G or D
<220> FEATURE:
<221> NAME/KEY: MOD_RES
<222> LOCATION: (5)..(5)
<223> OTHER INFORMATION: P, K, D, T or R
<220> FEATURE:
<221> NAME/KEY: MOD_RES
<222> LOCATION: (6)..(6)
<223> OTHER INFORMATION: D, S, Q or R
<220> FEATURE:
<221> NAME/KEY: MOD_RES
<222> LOCATION: (7)..(7)
<223> OTHER INFORMATION: G, R, D or S
<220> FEATURE:
<221> NAME/KEY: MOD_RES
<222> LOCATION: (8)..(8)
<223> OTHER INFORMATION: Y, R, W or N
<220> FEATURE:
<221> NAME/KEY: MOD_RES
<222> LOCATION: (9)..(9)
<223> OTHER INFORMATION: T, Y, G or L
<220> FEATURE:
<221> NAME/KEY: MOD_RES
<222> LOCATION: (10)..(10)
<223> OTHER INFORMATION: S, G, D, I or P
<220> FEATURE:
<221> NAME/KEY: MOD_RES
<222> LOCATION: (11)..(11)
<223> OTHER INFORMATION: F, Y, R, W or L
<220> FEATURE:
<221> NAME/KEY: MOD_RES
<222> LOCATION: (12)..(12)
<223> OTHER INFORMATION: Y, L, H, T or W
<220> FEATURE:
<221> NAME/KEY: MOD_RES
<222> LOCATION: (13)..(13)
<223> OTHER INFORMATION: G, R or T
<220> FEATURE:
<221> NAME/KEY: MOD_RES
<222> LOCATION: (14)..(14)
<223> OTHER INFORMATION: Y, H, F or Q
<220> FEATURE:
<221> NAME/KEY: MOD_RES
<222> LOCATION: (15)..(15)
<223> OTHER INFORMATION: P, Y, N or G

<400> SEQUENCE: 730

Cys Ala Arg Xaa Xaa Xaa Xaa Xaa Xaa Xaa Xaa Xaa Xaa Xaa Xaa Phe
1 5 10 15

Asp Tyr Trp

<210> SEQ ID NO 731
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: G, D, H or I
<220> FEATURE:
<221> NAME/KEY: MOD_RES
<222> LOCATION: (5)..(5)
<223> OTHER INFORMATION: R, L or D
<220> FEATURE:
<221> NAME/KEY: MOD_RES
<222> LOCATION: (6)..(6)
<223> OTHER INFORMATION: R, D, T or H
<220> FEATURE:
<221> NAME/KEY: MOD_RES
<222> LOCATION: (7)..(7)
<223> OTHER INFORMATION: G, D, Y or N
<220> FEATURE:
<221> NAME/KEY: MOD_RES
<222> LOCATION: (8)..(8)
<223> OTHER INFORMATION: Y, W, G or N
<220> FEATURE:
<221> NAME/KEY: MOD_RES
<222> LOCATION: (9)..(9)
<223> OTHER INFORMATION: F, Y or D
<220> FEATURE:
<221> NAME/KEY: MOD_RES
<222> LOCATION: (10)..(10)
<223> OTHER INFORMATION: G, P or A

<400> SEQUENCE: 731

Cys Ala Arg Xaa Xaa Xaa Xaa Xaa Xaa Xaa Phe Asp Tyr Trp
1               5                   10

<210> SEQ ID NO 732
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (6)..(6)
<223> OTHER INFORMATION: S, D or N
<220> FEATURE:
<221> NAME/KEY: MOD_RES
<222> LOCATION: (8)..(8)
<223> OTHER INFORMATION: A, Y or W
<220> FEATURE:
<221> NAME/KEY: MOD_RES
<222> LOCATION: (10)..(10)
<223> OTHER INFORMATION: S, H or N

<400> SEQUENCE: 732

Gly Gly Thr Phe Ser Xaa Tyr Xaa Met Xaa Trp
1               5                   10

<210> SEQ ID NO 733
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: V, R or T
<220> FEATURE:
<221> NAME/KEY: MOD_RES
<222> LOCATION: (6)..(6)
<223> OTHER INFORMATION: N or R
<220> FEATURE:
<221> NAME/KEY: MOD_RES
<222> LOCATION: (8)..(8)

<223> OTHER INFORMATION: G, Y or N
<220> FEATURE:
<221> NAME/KEY: MOD_RES
<222> LOCATION: (9)..(9)
<223> OTHER INFORMATION: N or D
<220> FEATURE:
<221> NAME/KEY: MOD_RES
<222> LOCATION: (11)..(11)
<223> OTHER INFORMATION: E or Y
<220> FEATURE:
<221> NAME/KEY: MOD_RES
<222> LOCATION: (13)..(13)
<223> OTHER INFORMATION: K, Y or H
<220> FEATURE:
<221> NAME/KEY: MOD_RES
<222> LOCATION: (15)..(15)
<223> OTHER INFORMATION: A or N
<220> FEATURE:
<221> NAME/KEY: MOD_RES
<222> LOCATION: (16)..(16)
<223> OTHER INFORMATION: D or Q

<400> SEQUENCE: 733

Trp Ile Gly Xaa Ile Xaa Pro Xaa Xaa Gly Xaa Thr Xaa Tyr Xaa Xaa
1 5 10 15

<210> SEQ ID NO 734
<211> LENGTH: 22
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (4)..(4)
<223> OTHER INFORMATION: P, G or H
<220> FEATURE:
<221> NAME/KEY: MOD_RES
<222> LOCATION: (5)..(5)
<223> OTHER INFORMATION: S, F or G
<220> FEATURE:
<221> NAME/KEY: MOD_RES
<222> LOCATION: (6)..(6)
<223> OTHER INFORMATION: E, R or A
<220> FEATURE:
<221> NAME/KEY: MOD_RES
<222> LOCATION: (7)..(7)
<223> OTHER INFORMATION: R, Y or P
<220> FEATURE:
<221> NAME/KEY: MOD_RES
<222> LOCATION: (8)..(8)
<223> OTHER INFORMATION: S, Y or M
<220> FEATURE:
<221> NAME/KEY: MOD_RES
<222> LOCATION: (9)..(9)
<223> OTHER INFORMATION: H, D, S or Y
<220> FEATURE:
<221> NAME/KEY: MOD_RES
<222> LOCATION: (10)..(10)
<223> OTHER INFORMATION: Y, G, T or V
<220> FEATURE:
<221> NAME/KEY: MOD_RES
<222> LOCATION: (11)..(11)
<223> OTHER INFORMATION: Y, S or E
<220> FEATURE:
<221> NAME/KEY: MOD_RES
<222> LOCATION: (12)..(12)
<223> OTHER INFORMATION: A, Y or I
<220> FEATURE:
<221> NAME/KEY: MOD_RES
<222> LOCATION: (13)..(13)
<223> OTHER INFORMATION: T, F or Y
<220> FEATURE:
<221> NAME/KEY: MOD_RES
<222> LOCATION: (14)..(14)
<223> OTHER INFORMATION: S or Y
<220> FEATURE:
<221> NAME/KEY: MOD_RES
<222> LOCATION: (15)..(15)
<223> OTHER INFORMATION: A, F or H
<220> FEATURE:
<221> NAME/KEY: MOD_RES
<222> LOCATION: (16)..(16)
<223> OTHER INFORMATION: P, Y or G
<220> FEATURE:
<221> NAME/KEY: MOD_RES
<222> LOCATION: (17)..(17)
<223> OTHER INFORMATION: Y, G or F
<220> FEATURE:
<221> NAME/KEY: MOD_RES
<222> LOCATION: (18)..(18)
<223> OTHER INFORMATION: Q, A or Y
<220> FEATURE:
<221> NAME/KEY: MOD_RES
<222> LOCATION: (19)..(19)
<223> OTHER INFORMATION: F or M
<220> FEATURE:
<221> NAME/KEY: MOD_RES
<222> LOCATION: (20)..(20)
<223> OTHER INFORMATION: D or A

<400> SEQUENCE: 734

Cys Ala Arg Xaa Xaa Xaa Xaa Xaa Xaa Xaa Xaa Xaa Xaa Xaa Xaa Xaa
1               5                   10                  15

Xaa Xaa Xaa Xaa Tyr Trp
            20

<210> SEQ ID NO 735
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D, S, L or H
<220> FEATURE:
<221> NAME/KEY: MOD_RES
<222> LOCATION: (5)..(5)
<223> OTHER INFORMATION: S, F, E, P or T
<220> FEATURE:
<221> NAME/KEY: MOD_RES
<222> LOCATION: (6)..(6)
<223> OTHER INFORMATION: S, G, F or I
<220> FEATURE:
<221> NAME/KEY: MOD_RES
<222> LOCATION: (7)..(7)
<223> OTHER INFORMATION: D, S, G, Y or R
<220> FEATURE:
<221> NAME/KEY: MOD_RES
<222> LOCATION: (8)..(8)
<223> OTHER INFORMATION: Y, N, S or F
<220> FEATURE:
<221> NAME/KEY: MOD_RES
<222> LOCATION: (9)..(9)
<223> OTHER INFORMATION: Y, D, G or T
<220> FEATURE:
<221> NAME/KEY: MOD_RES
<222> LOCATION: (10)..(10)
<223> OTHER INFORMATION: G, V, N, D or Y
<220> FEATURE:
<221> NAME/KEY: MOD_RES
<222> LOCATION: (11)..(11)
<223> OTHER INFORMATION: Y, F, S or G
<220> FEATURE:
<221> NAME/KEY: MOD_RES
<222> LOCATION: (12)..(12)
<223> OTHER INFORMATION: A, Y, N, Q or S
<220> FEATURE:
<221> NAME/KEY: MOD_RES
<222> LOCATION: (13)..(13)
<223> OTHER INFORMATION: G, Y, T or F
<220> FEATURE:
<221> NAME/KEY: MOD_RES
<222> LOCATION: (14)..(14)
<223> OTHER INFORMATION: A, W, G or Y
<220> FEATURE:
<221> NAME/KEY: MOD_RES
<222> LOCATION: (16)..(16)
<223> OTHER INFORMATION: A or D

<400> SEQUENCE: 735

Cys Ala Arg Xaa Xaa Xaa Xaa Xaa Xaa Xaa Xaa Xaa Xaa Xaa Phe Xaa
1 5 10 15

Tyr Trp

<210> SEQ ID NO 736
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: S, H, D or L
<220> FEATURE:
<221> NAME/KEY: MOD_RES
<222> LOCATION: (5)..(5)
<223> OTHER INFORMATION: Y, L, G or E
<220> FEATURE:
<221> NAME/KEY: MOD_RES
<222> LOCATION: (6)..(6)
<223> OTHER INFORMATION: Y, G, S or L
<220> FEATURE:
<221> NAME/KEY: MOD_RES
<222> LOCATION: (7)..(7)
<223> OTHER INFORMATION: D, S, K, P or W
<220> FEATURE:
<221> NAME/KEY: MOD_RES
<222> LOCATION: (8)..(8)
<223> OTHER INFORMATION: S, Y, N or H
<220> FEATURE:
<221> NAME/KEY: MOD_RES
<222> LOCATION: (9)..(9)
<223> OTHER INFORMATION: F, D, Y, T or N
<220> FEATURE:
<221> NAME/KEY: MOD_RES
<222> LOCATION: (10)..(10)
<223> OTHER INFORMATION: Y, V, G, N or D
<220> FEATURE:
<221> NAME/KEY: MOD_RES
<222> LOCATION: (11)..(11)
<223> OTHER INFORMATION: Y, T, F, L or G
<220> FEATURE:
<221> NAME/KEY: MOD_RES
<222> LOCATION: (12)..(12)
<223> OTHER INFORMATION: Y, A, N, S or H
<220> FEATURE:
<221> NAME/KEY: MOD_RES
<222> LOCATION: (13)..(13)
<223> OTHER INFORMATION: A or Y

<400> SEQUENCE: 736

Cys Ala Arg Xaa Xaa Xaa Xaa Xaa Xaa Xaa Xaa Xaa Xaa Met Asp Tyr
1 5 10 15

Trp

<210> SEQ ID NO 737
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: R, G, D or F
<220> FEATURE:
<221> NAME/KEY: MOD_RES
<222> LOCATION: (5)..(5)
<223> OTHER INFORMATION: G, D, R or Y
<220> FEATURE:
<221> NAME/KEY: MOD_RES
<222> LOCATION: (6)..(6)
<223> OTHER INFORMATION: G, Y, S, H or N
<220> FEATURE:
<221> NAME/KEY: MOD_RES
<222> LOCATION: (7)..(7)
<223> OTHER INFORMATION: G, Y, S, L or W
<220> FEATURE:
<221> NAME/KEY: MOD_RES
<222> LOCATION: (8)..(8)
<223> OTHER INFORMATION: R, G, F, A or Y
<220> FEATURE:
<221> NAME/KEY: MOD_RES
<222> LOCATION: (9)..(9)
<223> OTHER INFORMATION: R, A, F, Y or D
<220> FEATURE:
<221> NAME/KEY: MOD_RES
<222> LOCATION: (10)..(10)
<223> OTHER INFORMATION: Y, S, W, K or A
<220> FEATURE:
<221> NAME/KEY: MOD_RES
<222> LOCATION: (11)..(11)
<223> OTHER INFORMATION: F or L
<220> FEATURE:
<221> NAME/KEY: MOD_RES
<222> LOCATION: (12)..(12)
<223> OTHER INFORMATION: D, A or V

<400> SEQUENCE: 737

```
Cys Ala Arg Xaa Xaa Xaa Xaa Xaa Xaa Xaa Xaa Xaa Tyr Trp
1               5                   10
```

<210> SEQ ID NO 738
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (9)..(9)
<223> OTHER INFORMATION: H or N
<220> FEATURE:
<221> NAME/KEY: MOD_RES
<222> LOCATION: (11)..(11)
<223> OTHER INFORMATION: N or D
<220> FEATURE:
<221> NAME/KEY: MOD_RES
<222> LOCATION: (13)..(13)
<223> OTHER INFORMATION: N or K
<220> FEATURE:
<221> NAME/KEY: MOD_RES
<222> LOCATION: (17)..(17)
<223> OTHER INFORMATION: A, H or E

<400> SEQUENCE: 738

```
Cys Arg Ser Ser Gln Ser Leu Val Xaa Ser Xaa Gly Xaa Thr Tyr Leu
1               5                   10                  15

Xaa Trp
```

<210> SEQ ID NO 739

<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: A or V
<220> FEATURE:
<221> NAME/KEY: MOD_RES
<222> LOCATION: (7)..(7)
<223> OTHER INFORMATION: A or F

<400> SEQUENCE: 739

Tyr Lys Xaa Ser Asn Arg Xaa Ser Gly
1 5

<210> SEQ ID NO 740
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Q or F
<220> FEATURE:
<221> NAME/KEY: MOD_RES
<222> LOCATION: (4)..(4)
<223> OTHER INFORMATION: G or S
<220> FEATURE:
<221> NAME/KEY: MOD_RES
<222> LOCATION: (5)..(5)
<223> OTHER INFORMATION: S or Y
<220> FEATURE:
<221> NAME/KEY: MOD_RES
<222> LOCATION: (6)..(6)
<223> OTHER INFORMATION: H, S or E
<220> FEATURE:
<221> NAME/KEY: MOD_RES
<222> LOCATION: (7)..(7)
<223> OTHER INFORMATION: Y, V or T
<220> FEATURE:
<221> NAME/KEY: MOD_RES
<222> LOCATION: (9)..(9)
<223> OTHER INFORMATION: L or F

<400> SEQUENCE: 740

Cys Xaa Gln Xaa Xaa Xaa Xaa Pro Xaa Thr Phe
1 5 10

<210> SEQ ID NO 741
<211> LENGTH: 15
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (11)..(11)
<223> OTHER INFORMATION: N or H

<400> SEQUENCE: 741

Cys Ser Gly Ser Ser Ser Asn Ile Gly Ser Xaa Tyr Val Ser Trp
1 5 10 15

<210> SEQ ID NO 742
<211> LENGTH: 9

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Tyr Arg Asn Asn Gln Arg Pro Ser Gly
1               5


<210> SEQ ID NO 743
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A or G
<220> FEATURE:
<221> NAME/KEY: MOD_RES
<222> LOCATION: (3)..(3)
<223> OTHER INFORMATION: T, S or V
<220> FEATURE:
<221> NAME/KEY: MOD_RES
<222> LOCATION: (4)..(4)
<223> OTHER INFORMATION: W, T or R
<220> FEATURE:
<221> NAME/KEY: MOD_RES
<222> LOCATION: (6)..(6)
<223> OTHER INFORMATION: S or G
<220> FEATURE:
<221> NAME/KEY: MOD_RES
<222> LOCATION: (7)..(7)
<223> OTHER INFORMATION: T, R, S or Q
<220> FEATURE:
<221> NAME/KEY: MOD_RES
<222> LOCATION: (8)..(8)
<223> OTHER INFORMATION: S, L or W
<220> FEATURE:
<221> NAME/KEY: MOD_RES
<222> LOCATION: (9)..(9)
<223> OTHER INFORMATION: R or S
<220> FEATURE:
<221> NAME/KEY: MOD_RES
<222> LOCATION: (10)..(10)
<223> OTHER INFORMATION: S, A or Q

<400> SEQUENCE: 743

Cys Xaa Xaa Xaa Asp Xaa Xaa Xaa Xaa Xaa Val Val Phe
1               5                   10
```

ANTIBODIES THAT BIND ADENOSINE A2A RECEPTORS AND METHODS OF USE THEREOF TO TREAT CANCER AND NEUROLOGICAL DISEASES

CROSS-REFERENCE

This application claims the benefit of U.S. Provisional Patent Application No. 62/945,818 filed on Dec. 9, 2019, which is incorporated by reference in its entirety.

SEQUENCE LISTING

The instant application contains a Sequence Listing which has been submitted electronically in ASCII format and is hereby incorporated by reference in its entirety. Said ASCII copy, created on Feb. 1, 2021, is named 44854-802_201_SL.txt and is 343,260 bytes in size.

BACKGROUND

G protein-coupled receptors (GPCRs) such as adenosine receptors are implicated in a wide variety of diseases. Raising antibodies to GPCRs has been difficult due to problems in obtaining suitable antigen because GPCRs are often expressed at low levels in cells and are very unstable when purified. Thus, there is a need for improved agents for therapeutic intervention which target GPCRs.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF SUMMARY

Provided herein are methods for generating a nucleic acid library encoding for an adenosine A2A receptor antibody or antibody fragment thereof comprising: (a) providing predetermined sequences encoding for: i. a first plurality of polynucleotides, wherein each polynucleotide of the first plurality of polynucleotides encodes for a variant sequence encoding for CDR1 on a heavy chain; ii. a second plurality of polynucleotides, wherein each polynucleotide of the second plurality of polynucleotides encodes for a variant sequence encoding for CDR2 on a heavy chain; iii. a third plurality of polynucleotides, wherein each polynucleotide of the third plurality of polynucleotides encodes for a variant sequence encoding for CDR3 on a heavy chain; and (b) mixing the first plurality of polynucleotides, the second plurality of polynucleotides, and the third plurality of polynucleotides to form the nucleic acid library encoding for the adenosine A2A receptor antibody or antibody fragment thereof. Further provided herein are methods for generating a nucleic acid library encoding for an adenosine A2A receptor antibody or antibody fragment thereof, wherein the adenosine A2A receptor antibody or antibody fragment thereof is a single domain antibody. Further provided herein are methods for generating a nucleic acid library encoding for an adenosine A2A receptor antibody or antibody fragment thereof, wherein the single domain antibody comprises one heavy chain variable domain. Further provided herein are methods for generating a nucleic acid library encoding for an adenosine A2A receptor antibody or antibody fragment thereof, wherein the single domain antibody is a VHH antibody. Further provided herein are methods for generating a nucleic acid library encoding for an adenosine A2A receptor antibody or antibody fragment thereof, wherein the nucleic acid library comprises at least 50,000 variant sequences. Further provided herein are methods for generating a nucleic acid library encoding for an adenosine A2A receptor antibody or antibody fragment thereof, wherein the nucleic acid library comprises at least 100,000 variant sequences. Further provided herein are methods for generating a nucleic acid library encoding for an adenosine A2A receptor antibody or antibody fragment thereof, wherein the nucleic acid library comprises at least $10^5$ non-identical nucleic acids. Further provided herein are methods for generating a nucleic acid library encoding for an adenosine A2A receptor antibody or antibody fragment thereof, wherein the nucleic acid library comprises at least one sequence encoding for the adenosine A2A receptor antibody or antibody fragment that binds to adenosine A2A receptor with a $K_D$ of less than 100 nM. Further provided herein are methods for generating a nucleic acid library encoding for an adenosine A2A receptor antibody or antibody fragment thereof, wherein the nucleic acid library comprises at least one sequence encoding for the adenosine A2A receptor antibody or antibody fragment that binds to adenosine A2A receptor with a $K_D$ of less than 50 nM. Further provided herein are methods for generating a nucleic acid library encoding for an adenosine A2A receptor antibody or antibody fragment thereof, wherein the nucleic acid library comprises at least one sequence encoding for the adenosine A2A receptor antibody or antibody fragment that binds to adenosine A2A receptor with a $K_D$ of less than 10 nM. Further provided herein are methods for generating a nucleic acid library encoding for an adenosine A2A receptor antibody or antibody fragment thereof, wherein the nucleic acid library comprises at least 500 variant sequences. Further provided herein are methods for generating a nucleic acid library encoding for an adenosine A2A receptor antibody or antibody fragment thereof, wherein the nucleic acid library comprises at least five sequences encoding for the adenosine A2A receptor antibody or antibody fragment that binds to adenosine A2A receptor with a $K_D$ of less than 100 nM. Further provided herein are methods for generating a nucleic acid library encoding for an adenosine A2A receptor antibody or antibody fragment thereof, wherein the nucleic acid library comprises at least 500 variant sequences.

Provided herein are nucleic acid libraries comprising a plurality of nucleic acids, wherein each nucleic acid of the plurality of nucleic acids encodes for a sequence that when translated encodes for an antibody or antibody fragment thereof, wherein the antibody or antibody fragment thereof comprises a variable region of a heavy chain (VH) that comprises an adenosine A2A receptor binding domain, and wherein each nucleic acid of the plurality of nucleic acids comprises a sequence encoding for a sequence variant of the adenosine A2A receptor binding domain. Further provided herein are nucleic acid libraries comprising a plurality of nucleic acids, wherein a length of the VH is about 90 to about 100 amino acids. Further provided herein are nucleic acid libraries comprising a plurality of nucleic acids, wherein a length of the VH is about 100 to about 400 amino acids. Further provided herein are nucleic acid libraries comprising a plurality of nucleic acids, wherein a length of the VH is about 270 to about 300 base pairs. Further provided herein are nucleic acid libraries comprising a plurality of nucleic acids, wherein a length of the VH is about 300 to about 1200 base pairs. Further provided herein are nucleic acid libraries comprising a plurality of nucleic acids, wherein the library comprises at least $10^5$ non-identical nucleic acids.

Provided herein are protein libraries comprising a plurality of proteins, wherein each of the proteins of the plurality of proteins comprise a variable region of a heavy chain (VH) that comprises a sequence variant of an adenosine A2A receptor binding domain. Further provided herein are protein libraries comprising a plurality of proteins, wherein a length of the VH is about 90 to about 100 amino acids. Further provided herein are protein libraries comprising a plurality of proteins, wherein a length of the VH is about 100 to about 400 amino acids. Further provided herein are protein libraries comprising a plurality of proteins, wherein a length of the VH is about 270 to about 300 base pairs. Further provided herein are protein libraries comprising a plurality of proteins, wherein a length of the VH is about 300 to about 1200 base pairs. Further provided herein are protein libraries comprising a plurality of proteins, wherein the library comprises at least $10^5$ non-identical nucleic acids. Further provided herein are protein libraries comprising a plurality of proteins, wherein the plurality of proteins are used to generate a peptidomimetic library. Further provided herein are protein libraries comprising a plurality of proteins, wherein the protein library comprises antibodies. Further provided herein are protein libraries comprising a plurality of proteins, wherein the protein library comprises at least 500 variant sequences. Further provided herein are protein libraries comprising a plurality of proteins, wherein the protein library comprises at least 5000 variant sequences. Further provided herein are protein libraries comprising a plurality of proteins, wherein the protein library comprises at least 10000 variant sequences.

Provided herein are protein libraries comprising a plurality of proteins, wherein the plurality of proteins comprises sequences encoding for different adenosine A2A receptor binding domains, and wherein the length of each adenosine A2A receptor binding domain is about 100 to about 400 amino acids. Further provided herein are protein libraries comprising a plurality of proteins, wherein the protein library comprises peptides. Further provided herein are protein libraries comprising a plurality of proteins, wherein the protein library comprises immunoglobulins. Further provided herein are protein libraries comprising a plurality of proteins, wherein the protein library comprises antibodies. Further provided herein are protein libraries comprising a plurality of proteins, wherein the protein library comprises single domain antibodies. Further provided herein are protein libraries comprising a plurality of proteins, wherein the plurality of proteins is used to generate a peptidomimetic library. Further provided herein are protein libraries comprising a plurality of proteins, wherein the protein library comprises at least 500 variant sequences. Further provided herein are protein libraries comprising a plurality of proteins, wherein the protein library comprises at least 5000 variant sequences. Further provided herein are protein libraries comprising a plurality of proteins, wherein the protein library comprises at least 10000 variant sequences.

Provided herein are nucleic acid libraries comprising: a plurality of nucleic acids, wherein each of the nucleic acids encodes for a sequence that when translated encodes for an adenosine A2A receptor binding immunoglobulin, wherein the adenosine A2A receptor binding immunoglobulin comprises a variant of an adenosine A2A receptor binding domain, wherein the adenosine A2A receptor binding domain is a ligand for the adenosine A2A receptor, and wherein the nucleic acid library comprises at least 10,000 variant immunoglobulin heavy chains and at least 10,000 variant immunoglobulin light chains. Further provided herein are nucleic acid libraries comprising: a plurality of nucleic acids, wherein the nucleic acid library comprises at least 50,000 variant immunoglobulin heavy chains and at least 50,000 variant immunoglobulin light chains. Further provided herein are nucleic acid libraries comprising: a plurality of nucleic acids, wherein the nucleic acid library comprises at least 100,000 variant immunoglobulin heavy chains and at least 100,000 variant immunoglobulin light chains. Further provided herein are nucleic acid libraries comprising: a plurality of nucleic acids, wherein the nucleic acid library comprises at least $10^5$ non-identical nucleic acids. Further provided herein are nucleic acid libraries comprising: a plurality of nucleic acids, wherein a length of the immunoglobulin heavy chain when translated is about 90 to about 100 amino acids. Further provided herein are nucleic acid libraries comprising: a plurality of nucleic acids, wherein a length of the immunoglobulin heavy chain when translated is about 100 to about 400 amino acids.

Provided herein are nucleic acid libraries comprising: a plurality of nucleic acids, wherein each of the nucleic acids encodes for a sequence that when translated encodes for an adenosine A2A receptor single domain antibody, wherein each sequence of the plurality of sequences comprises a variant sequence encoding for at least one of a CDR1, CDR2, and CDR3 on a variable region of a heavy chain (VH); wherein the library comprises at least 30,000 variant sequences; and wherein the antibody or antibody fragments bind to its antigen with a $K_D$ of less than 100 nM. Further provided herein are nucleic acid libraries comprising: a plurality of nucleic acids, wherein a length of the VH when translated is about 90 to about 100 amino acids. Further provided herein are nucleic acid libraries comprising: a plurality of nucleic acids, wherein a length of the VH when translated is about 100 to about 400 amino acids. Further provided herein are nucleic acid libraries comprising: a plurality of nucleic acids, wherein a length of the VH is about 270 to about 300 base pairs. Further provided herein are nucleic acid libraries comprising: a plurality of nucleic acids, wherein a length of the VH is about 300 to about 1200 base pairs.

Provided herein are vector libraries comprising the nucleic acid libraries as described herein. Provided herein are cell libraries comprising the nucleic acid libraries as described herein. Provided herein are cell libraries comprising the protein libraries as described herein.

Provided herein are nucleic acid libraries comprising: a plurality of nucleic acids, wherein each of the nucleic acids encodes for a sequence that when translated encodes for an adenosine A2A receptor binding immunoglobulin, wherein the adenosine A2A receptor binding immunoglobulin comprises a variant of an adenosine A2A receptor binding domain, wherein the adenosine A2A receptor binding domain is a ligand for the adenosine A2A receptor, and wherein the nucleic acid library comprises at least 10,000 variant immunoglobulin heavy chains and at least 10,000 variant immunoglobulin light chains. Further provided herein are nucleic acid libraries, wherein the nucleic acid library comprises at least 50,000 variant immunoglobulin heavy chains and at least 50,000 variant immunoglobulin light chains. Further provided herein are nucleic acid libraries, wherein the nucleic acid library comprises at least 100,000 variant immunoglobulin heavy chains and at least 100,000 variant immunoglobulin light chains. Further provided herein are nucleic acid libraries, wherein the nucleic acid library comprises at least $10^5$ non-identical nucleic acids. Further provided herein are nucleic acid libraries, wherein a length of the immunoglobulin heavy chain when translated is about 90 to about 100 amino acids. Further provided herein are nucleic acid libraries, wherein a length of the immunoglobulin heavy chain when translated is about 100 to about 400 amino acids. Further provided herein are nucleic acid libraries, wherein the variant immunoglobulin heavy chain when translated comprises at least about 90% sequence identity to any one of SEQ ID NO: 540-628. Further provided herein are nucleic acid libraries, wherein the variant immunoglobulin light chain when translated comprises at least about 90% sequence identity to any one of SEQ ID NO: 629-717. Further provided herein are nucleic acid libraries, wherein the variant immunoglobulin heavy chain when translated comprises any one of SEQ ID NO: 540-628. Further provided herein are nucleic acid libraries, wherein the variant immunoglobulin light chain when translated comprises any one of SEQ ID NO: 629-717.

Provided herein are nucleic acid libraries comprising a plurality of nucleic acids, wherein each nucleic acid of the plurality of nucleic acids encodes for a sequence that when translated encodes for an antibody or antibody fragment thereof, wherein the antibody or antibody fragment thereof comprises a variable region of a heavy chain (VH) that comprises an adenosine A2A receptor binding domain, wherein each nucleic acid of the plurality of nucleic acids comprises a sequence encoding for a sequence variant of the adenosine A2A receptor binding domain, and wherein the antibody or antibody fragment binds to its antigen with a $K_D$ of less than 100 nM. Further provided herein are nucleic acid libraries, wherein a length of the VH is about 90 to about 100 amino acids. Further provided herein are nucleic acid libraries, wherein a length of the VH is about 100 to about 400 amino acids. Further provided herein are nucleic acid libraries, wherein a length of the VH is about 270 to about 300 base pairs. Further provided herein are nucleic acid libraries, wherein a length of the VH is about 300 to about 1200 base pairs. Further provided herein are nucleic acid libraries, wherein the library comprises at least $10^5$ non-identical nucleic acids.

Provided herein are nucleic acid libraries comprising: a plurality of nucleic acids, wherein each of the nucleic acids encodes for a sequence that when translated encodes for an adenosine A2A receptor single domain antibody, wherein each sequence of the plurality of sequences comprises a variant sequence encoding for a CDR1, CDR2, or CDR3 on a variable region of a heavy chain (VH); wherein the library comprises at least 30,000 variant sequences; and wherein the adenosine A2A receptor single domain antibody binds to its antigen with a $K_D$ of less than 100 nM. Further provided herein are nucleic acid libraries, wherein a length of the VH when translated is about 90 to about 100 amino acids. Further provided herein are nucleic acid libraries, wherein a length of the VH when translated is about 100 to about 400 amino acids. Further provided herein are nucleic acid libraries, wherein a length of the VH is about 270 to about 300 base pairs. Further provided herein are nucleic acid libraries, wherein a length of the VH is about 300 to about 1200 base pairs. Further provided herein are nucleic acid libraries, wherein the variant library comprises a variant sequence encoding for a CDR1, CDR2, and CDR3. Further provided herein are nucleic acid libraries, wherein the VH when translated comprises at least 90% sequence identity to any one of SEQ ID NO: 540-628. Further provided herein are nucleic acid libraries, wherein the VH when translated comprises any one of SEQ ID NO: 540-628.

Provided herein are antibodies or antibody fragments that bind adenosine A2A receptor, comprising an immunoglobulin heavy chain and an immunoglobulin light chain: wherein the immunoglobulin heavy chain comprises an amino acid sequence at least about 90% identical to that set forth in any one of SEQ ID NOs: 540-628; and wherein the immunoglobulin light chain comprises an amino acid sequence at least about 90% identical to that set forth in any one of SEQ ID NOs: 629-717. Further provided herein are antibodies or antibody fragments, wherein the immunoglobulin heavy chain comprises an amino acid sequence at least about 95% identical to that set forth in any one of SEQ ID NOs: 540-628; and wherein the immunoglobulin light chain comprises an amino acid sequence at least about 95% identical to that set forth in any one of SEQ ID NOs: 629-717. Further provided herein are antibodies or antibody fragments, wherein the immunoglobulin heavy chain comprises an amino acid sequence as set forth in any one of SEQ ID NOs: 540-628; and wherein the immunoglobulin light chain comprises an amino acid sequence at least about 90% identical to that set forth in any one of SEQ ID NOs: 629-717. Further provided herein are antibodies or antibody fragments, wherein the antibody is a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv), a single chain antibody, a Fab fragment, a F(ab')2 fragment, a Fd fragment, a Fv fragment, a single-domain antibody, an isolated complementarity determining region (CDR), a diabody, a fragment comprised of only a single monomeric variable domain, disulfide-linked Fvs (sdFv), an intrabody, an anti-idiotypic (anti-Id) antibody, or ab antigen-binding fragments thereof. Further provided herein are antibodies or antibody fragments, wherein the antibody or antibody fragment thereof is chimeric or humanized. Further provided herein are antibodies or antibody fragments, wherein the antibody has an EC50 less than about 25 nanomolar in a cAMP assay. Further provided herein are antibodies or antibody fragments, wherein the antibody has an EC50 less than about 20 nanomolar in a cAMP assay. Further provided herein are antibodies or antibody fragments, wherein the antibody has an EC50 less than about 10 nanomolar in a cAMP assay.

Provided herein are antibodies or antibody fragments, wherein the antibody or antibody fragment comprises a complementarity determining region (CDR) comprising an amino acid sequence at least about 90% identical to that set forth in any one of SEQ ID NOs: 6-539.

Provided herein are antibodies or antibody fragments, wherein the antibody or antibody fragment comprises a variable heavy chain complementarity determining region (CDRH) comprising an amino acid sequence at least about 90% identical to that set forth in any one of SEQ ID NOs: 6-272.

Provided herein are antibodies or antibody fragments, wherein the antibody or antibody fragment comprises a variable light chain complementarity determining region (CDRH) comprising an amino acid sequence at least about 90% identical to that set forth in any one of SEQ ID NOs: 273-539.

Provided herein are antibodies or antibody fragments, wherein the antibody or antibody fragment comprises a sequence of any one of SEQ ID NOs: 6-539 and wherein the antibody is a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv), a single chain antibody, a Fab fragment, a F(ab')2 fragment, a Fd fragment, a Fv fragment, a single-domain antibody, an isolated complementarity determining region (CDR), a diabody, a fragment comprised of only a single monomeric variable domain, disulfide-linked Fvs (sdFv), an intrabody, an anti-idiotypic (anti-Id) antibody, or ab antigen-binding fragments thereof.

Provided herein are methods of treating cancer, comprising administering the antibody or antibody fragment described herein.

Provided herein are methods of treating a neurological disease or disorder, comprising administering the antibody or antibody fragment described herein.

Provided herein are methods for generating a nucleic acid library encoding for an adenosine A2A receptor antibody or antibody fragment thereof comprising: (a) providing predetermined sequences encoding for: i. a first plurality of polynucleotides, wherein each polynucleotide of the first plurality of polynucleotides encodes for at least 1000 variant sequence encoding for CDR1 on a heavy chain; ii. a second plurality of polynucleotides, wherein each polynucleotide of the second plurality of polynucleotides encodes for at least 1000 variant sequence encoding for CDR2 on a heavy chain; iii. a third plurality of polynucleotides, wherein each polynucleotide of the third plurality of polynucleotides encodes for at least 1000 variant sequence encoding for CDR3 on a heavy chain; and (b) mixing the first plurality of polynucleotides, the second plurality of polynucleotides, and the third plurality of polynucleotides to form the nucleic acid library of variant nucleic acids encoding for the adenosine A2A receptor antibody or antibody fragment thereof, and wherein at least about 70% of the variant nucleic acids encode for an antibody or antibody fragment that binds to adenosine A2A receptor with a $K_D$ of less than 100 nM. Further provided herein are methods, wherein the adenosine A2A receptor antibody or antibody fragment thereof is a single domain antibody. Further provided herein are methods, wherein the single domain antibody comprises one heavy chain variable domain. Further provided herein are methods, wherein the single domain antibody is a VHH antibody. Further provided herein are methods, wherein the nucleic acid library comprises at least 50,000 variant sequences. Further provided herein are methods, wherein the nucleic acid library comprises at least 100,000 variant sequences. Further provided herein are methods, wherein the nucleic acid library comprises at least $10^5$ non-identical nucleic acids. Further provided herein are methods, wherein the nucleic acid library comprises at least one sequence encoding for the adenosine A2A receptor antibody or antibody fragment that binds to adenosine A2A receptor with a $K_D$ of less than 75 nM. Further provided herein are methods, wherein the nucleic acid library comprises at least one sequence encoding for the adenosine A2A receptor antibody or antibody fragment that binds to adenosine A2A receptor with a $K_D$ of less than 50 nM. Further provided herein are methods, wherein the nucleic acid library comprises at least one sequence encoding for the adenosine A2A receptor antibody or antibody fragment that binds to adenosine A2A receptor with a $K_D$ of less than 10 nM. Further provided herein are methods, wherein the nucleic acid library comprises at least 500 variant sequences. Further provided herein are methods, wherein the nucleic acid library comprises at least five sequences encoding for the adenosine A2A receptor antibody or antibody fragment that binds to adenosine A2A receptor with a $K_D$ of less than 75 nM.

Provided herein are protein libraries encoded by the nucleic acid library described herein, wherein the protein library comprises peptides. Further provided herein are protein libraries, wherein the protein library comprises immunoglobulins. Further provided herein are protein libraries, wherein the protein library comprises antibodies. Further provided herein are protein libraries, wherein the protein library is a peptidomimetic library.

Provided herein are vector libraries comprising the nucleic acid library described herein.

Provided herein are cell libraries comprising the nucleic acid library described herein.

Provided herein are cell libraries comprising the protein library described herein.

BRIEF DESCRIPTION OF THE DRAWINGS

FIG. 12 depicts the clone, ELISA value, Library, ProA value, and $K_D$ value for VHH-Fc.

DETAILED DESCRIPTION

Figure 1A:
FIG. 1A depicts a first schematic of an immunoglobulin scaffold.
Figure 1B:
FIG. 1B depicts a second schematic of an immunoglobulin scaffold.
Figure 2:
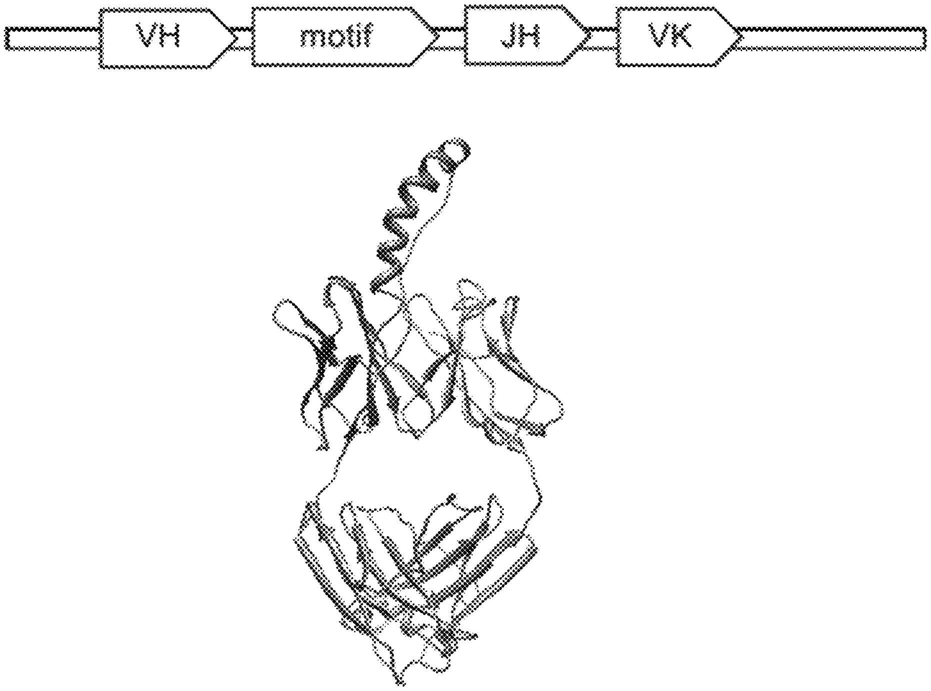
FIG. 2 depicts a schematic of a motif for placement in a scaffold.

The present disclosure employs, unless otherwise indicated, conventional molecular biology techniques, which are within the skill of the art. Unless defined otherwise, all technical and scientific terms used herein have the same meaning as is commonly understood by one of ordinary skill in the art.

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms “a,” “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one or more other features, integers, steps, operations, elements, components, and/or groups thereof. As used herein, the term “and/or” includes any and all combinations of one or more of the associated listed items.

Unless specifically stated or obvious from context, as used herein, the term “about” in reference to a number or range of numbers is understood to mean the stated number and numbers +/−10% thereof, or 10% below the lower listed limit and 10% above the higher listed limit for the values listed for a range.

Unless specifically stated, as used herein, the term “nucleic acid” encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands). Nucleic acid sequences, when provided, are listed in the 5' to 3' direction, unless stated otherwise. Methods described herein provide for the generation of isolated nucleic acids. Methods described herein additionally provide for the generation of isolated and purified nucleic acids. A “nucleic acid” as referred to herein can comprise at least 5, 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more bases in length. Moreover, provided herein are methods for the synthesis of any number of polypeptide-segments encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. cDNA encoding for a gene or gene fragment referred herein may comprise at least one region encoding for exon sequences without an intervening intron sequence in the genomic equivalent sequence.

Adenosine A2A Receptor Libraries

Provided herein are methods and compositions relating to G protein-coupled receptor (GPCR) binding libraries for adenosine A2A receptor (ADORA2) comprising nucleic acids encoding for a scaffold comprising an adenosine A2A receptor binding domain. Scaffolds as described herein can stably support an adenosine A2A receptor binding domain. The adenosine A2A receptor binding domain may be designed based on surface interactions of an adenosine A2A receptor ligand and adenosine A2A receptor. Libraries as described herein may be further variegated to provide for variant libraries comprising nucleic acids each encoding for a predetermined variant of at least one predetermined reference nucleic acid sequence. Further described herein are protein libraries that may be generated when the nucleic acid libraries are translated. In some instances, nucleic acid libraries as described herein are transferred into cells to generate a cell library. Also provided herein are downstream applications for the libraries synthesized using methods described herein. Downstream applications include identification of variant nucleic acids or protein sequences with enhanced biologically relevant functions, e.g., improved stability, affinity, binding, functional activity, and for the treatment or prevention of a disease state associated with adenosine A2A receptor signaling.

Methods, compositions, and systems described herein for the optimization of adenosine A2A receptor immunoglobulins or antibodies comprise a ratio-variant approach that mirror the natural diversity of antibody sequences. In some instances, libraries of optimized adenosine A2A receptor immunoglobulins or antibodies comprise variant adenosine A2A receptor immunoglobulin or antibody sequences. In some instances, the variant adenosine A2A receptor immunoglobulin or antibody sequences are designed comprising variant CDR regions. In some instances, the variant adenosine A2A receptor immunoglobulin or antibody sequences comprising variant CDR regions are generated by shuffling the natural CDR sequences in a llama, humanized, or chimeric framework. In some instances, such libraries are synthesized, cloned into expression vectors, and translation products (antibodies) evaluated for activity. In some instances, fragments of sequences are synthesized and subsequently assembled. In some instances, expression vectors are used to display and enrich desired antibodies, such as phage display. In some instances, the phage vector is a Fab phagemid vector. Selection pressures used during enrichment in some instances includes binding affinity, toxicity, immunological tolerance, stability, or other factor. Such expression vectors allow antibodies with specific properties to be selected ("panning"), and subsequent propagation or amplification of such sequences enriches the library with these sequences. Panning rounds can be repeated any number of times, such as 1, 2, 3, 4, 5, 6, 7, or more than 7 rounds. In some instances, each round of panning involves a number of washes. In some instances, each round of panning involves at least or about 1, 2, 3, 4, 5, 6, 7, 8, 9, 10, 11, 12, 13, 14, 15, 16, or more than 16 washes.

Described herein are methods and systems of in-silico library design. Libraries as described herein, in some instances, are designed based on a database comprising a variety of antibody sequences. In some instances, the database comprises a plurality of variant antibody sequences against various targets. In some instances, the database comprises at least 100, 500, 1000, 1500, 2000, 2500, 3000, 3500, 4000, 4500, 5000, or more than 5000 antibody sequences. An exemplary database is an iCAN database. In some instances, the database comprises naïve and memory B-cell receptor sequences. In some instances, the naïve and memory B-cell receptor sequences are human, mouse, or primate sequences. In some instances, the naïve and memory B-cell receptor sequences are human sequences. In some instances, the database is analyzed for position specific variation. In some instances, antibodies described herein comprise position specific variations in CDR regions. In some instances, the CDR regions comprise multiple sites for variation.

Scaffold Libraries

Provided herein are libraries comprising nucleic acids encoding for a scaffold, wherein sequences for adenosine A2A receptor binding domains are placed in the scaffold. Scaffold described herein allow for improved stability for a range of adenosine A2A receptor binding domain encoding sequences when inserted into the scaffold, as compared to an unmodified scaffold. Exemplary scaffolds include, but are not limited to, a protein, a peptide, an immunoglobulin, derivatives thereof, or combinations thereof. In some instances, the scaffold is an immunoglobulin. Scaffolds as described herein comprise improved functional activity, structural stability, expression, specificity, or a combination thereof. In some instances, scaffolds comprise long regions for supporting an adenosine A2A receptor binding domain.

Provided herein are libraries comprising nucleic acids encoding for a scaffold, wherein the scaffold is an immunoglobulin. In some instances, the immunoglobulin is an antibody. As used herein, the term antibody will be understood to include proteins having the characteristic two-armed, Y-shape of a typical antibody molecule as well as one or more fragments of an antibody that retain the ability to specifically bind to an antigen. Exemplary antibodies include, but are not limited to, a monoclonal antibody, a polyclonal antibody, a bi-specific antibody, a multispecific antibody, a grafted antibody, a human antibody, a humanized antibody, a synthetic antibody, a chimeric antibody, a camelized antibody, a single-chain Fvs (scFv) (including fragments in which the VL and VH are joined using recombinant methods by a synthetic or natural linker that enables them to be made as a single protein chain in which the VL and VH regions pair to form monovalent molecules, including single chain Fab and scFab), a single chain antibody, a Fab fragment (including monovalent fragments comprising the VL, VH, CL, and CH1 domains), a F(ab')2 fragment (including bivalent fragments comprising two Fab fragments linked by a disulfide bridge at the hinge region), a Fd fragment (including fragments comprising the VH and CH1 fragment), a Fv fragment (including fragments comprising the VL and VH domains of a single arm of an antibody), a single-domain antibody (dAb or sdAb) (including fragments comprising a VH domain), an isolated complementarity determining region (CDR), a diabody (including fragments comprising bivalent dimers such as two VL and VH domains bound to each other and recognizing two different antigens), a fragment comprised of only a single monomeric variable domain, disulfide-linked Fvs (sdFv), an intrabody, an anti-idiotypic (anti-Id) antibody, or ab antigen-binding fragments thereof. In some instances, the libraries disclosed herein comprise nucleic acids encoding for a scaffold, wherein the scaffold is a Fv antibody, including Fv antibodies comprised of the minimum antibody fragment which contains a complete antigen-recognition and antigen-binding site. In some embodiments, the Fv antibody consists of a dimer of one heavy chain and one light chain variable domain in tight, non-covalent association, and the three hypervariable regions of each variable domain interact to define an antigen-binding site on the surface of the VH-VL dimer. In some embodiments, the six hypervariable regions confer antigen-binding specificity to the antibody. In some embodiments, a single variable domain (or half of an Fv comprising only three hypervariable regions specific for an antigen, including single domain antibodies isolated from camelid animals comprising one heavy chain variable domain or variable region of a heavy chain such as VHH antibodies or nanobodies) has the ability to recognize and bind antigen. In some instances, the libraries disclosed herein comprise nucleic acids encoding for a scaffold, wherein the scaffold is a single-chain Fv or scFv, including antibody fragments comprising a VH, a VL, or both a VH and VL domain, wherein both domains are present in a single polypeptide chain. In some embodiments, the Fv polypeptide further comprises a polypeptide linker between the VH and VL domains allowing the scFv to form the desired structure for antigen binding. In some instances, a scFv is linked to the Fc fragment or a VHH is linked to the Fc fragment (including minibodies). In some instances, the antibody comprises immunoglobulin molecules and immunologically active fragments of immunoglobulin molecules, e.g., molecules that contain an antigen binding site. Immunoglobulin molecules are of any type (e.g., IgG, IgE, IgM, IgD, IgA and IgY), class (e.g., IgG 1, IgG 2, IgG 3, IgG 4, IgA 1 and IgA 2) or subclass.

In some embodiments, libraries comprise immunoglobulins that are adapted to the species of an intended therapeutic target. Generally, these methods include "mammalization" and comprises methods for transferring donor antigen-binding information to a less immunogenic mammal antibody acceptor to generate useful therapeutic treatments. In some instances, the mammal is mouse, rat, equine, sheep, cow, primate (e.g., chimpanzee, baboon, gorilla, orangutan, monkey), dog, cat, pig, donkey, rabbit, and human. In some instances, provided herein are libraries and methods for felinization and caninization of antibodies.

"Humanized" forms of non-human antibodies can be chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. In some instances, these modifications are made to further refine antibody performance.

"Caninization" can comprise a method for transferring non-canine antigen-binding information from a donor antibody to a less immunogenic canine antibody acceptor to generate treatments useful as therapeutics in dogs. In some instances, caninized forms of non-canine antibodies provided herein are chimeric antibodies that contain minimal sequence derived from non-canine antibodies. In some instances, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. In some instances, caninized antibodies include residues that are not found in the recipient antibody or in the donor antibody. In some instances, these modifications are made to further refine antibody performance. The caninized antibody may also comprise at least a portion of an immunoglobulin constant region (Fc) of a canine antibody.

"Felinization" can comprise a method for transferring non-feline antigen-binding information from a donor antibody to a less immunogenic feline antibody acceptor to generate treatments useful as therapeutics in cats. In some instances, felinized forms of non-feline antibodies provided herein are chimeric antibodies that contain minimal sequence derived from non-feline antibodies. In some instances, felinized antibodies are feline antibody sequences ("acceptor" or "recipient" antibody) in which hypervariable region residues of the recipient are replaced by hypervariable region residues from a non-feline species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the feline antibody are replaced by corresponding non-feline FR residues. In some instances, felinized antibodies include residues that are not found in the recipient antibody or in the donor antibody. In some instances, these modifications are made to further refine antibody performance. The felinized antibody may also comprise at least a portion of an immunoglobulin constant region (Fc) of a felinize antibody.

Provided herein are libraries comprising nucleic acids encoding for a scaffold, wherein the scaffold is a non-immunoglobulin. In some instances, the scaffold is a non-immunoglobulin binding domain. For example, the scaffold is an antibody mimetic. Exemplary antibody mimetics include, but are not limited to, anticalins, affilins, affibody molecules, affimers, affitins, alphabodies, avimers, atrimers, DARPins, fynomers, Kunitz domain-based proteins, monobodies, anticalins, knottins, armadillo repeat protein-based proteins, and bicyclic peptides.

Libraries described herein comprising nucleic acids encoding for a scaffold, wherein the scaffold is an immunoglobulin, comprise variations in at least one region of the immunoglobulin. Exemplary regions of the antibody for variation include, but are not limited to, a complementarity-determining region (CDR), a variable domain, or a constant domain. In some instances, the CDR is CDR1, CDR2, or CDR3. In some instances, the CDR is a heavy domain including, but not limited to, CDRH1, CDRH2, and CDRH3. In some instances, the CDR is a light domain including, but not limited to, CDRL1, CDRL2, and CDRL3. In some instances, the variable domain is variable domain, light chain (VL) or variable domain, heavy chain (VH). In some instances, the VL domain comprises kappa or lambda chains. In some instances, the constant domain is constant domain, light chain (CL) or constant domain, heavy chain (CH).

Methods described herein provide for synthesis of libraries comprising nucleic acids encoding for a scaffold, wherein each nucleic acid encodes for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the scaffold library comprises varied nucleic acids collectively encoding variations at multiple positions. In some instances, the variant library comprises sequences encoding for variation of at least a single codon of a CDRH1, CDRH2, CDRH3, CDRL1, CDRL2, CDRL3, VL, or VH domain. In some instances, the variant library comprises sequences encoding for variation of multiple codons of a CDRH1, CDRH2, CDRH3, CDRL1, CDRL2, CDRL3, VL, or VH domain. In some instances, the variant library comprises sequences encoding for variation of multiple codons of framework element 1 (FW1), framework element 2 (FW2), framework element 3 (FW3), or framework element 4 (FW4). An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

In some instances, the at least one region of the immunoglobulin for variation is from heavy chain V-gene family, heavy chain D-gene family, heavy chain J-gene family, light chain V-gene family, or light chain J-gene family. In some instances, the light chain V-gene family comprises immunoglobulin kappa (IGK) gene or immunoglobulin lambda (IGL). Exemplary genes include, but are not limited to, IGHV1-18, IGHV1-69, IGHV1-8, IGHV3-21, IGHV3-23, IGHV3-30/33rn, IGHV3-28, IGHV1-69, IGHV3-74, IGHV4-39, IGHV4-59/61, IGKV1-39, IGKV1-9, IGKV2-28, IGKV3-11, IGKV3-15, IGKV3-20, IGKV4-1, IGLV1-51, IGLV2-14, IGLV1-40, and IGLV3-1. In some instances, the gene is IGHV1-69, IGHV3-30, IGHV3-23, IGHV3, IGHV1-46, IGHV3-7, IGHV1, or IGHV1-8. In some instances, the gene is IGHV1-69 and IGHV3-30. In some instances, the gene is IGHJ3, IGHJ6, IGHJ, IGHJ4, IGHJ5, IGHJ2, or IGH1. In some instances, the gene is IGHJ3, IGHJ6, IGHJ, or IGHJ4.

Provided herein are libraries comprising nucleic acids encoding for immunoglobulin scaffolds, wherein the libraries are synthesized with various numbers of fragments. In some instances, the fragments comprise the CDRH1, CDRH2, CDRH3, CDRL1, CDRL2, CDRL3, VL, or VH domain. In some instances, the fragments comprise framework element 1 (FW1), framework element 2 (FW2), framework element 3 (FW3), or framework element 4 (FW4). In some instances, the scaffold libraries are synthesized with at least or about 2 fragments, 3 fragments, 4 fragments, 5 fragments, or more than 5 fragments. The length of each of the nucleic acid fragments or average length of the nucleic acids synthesized may be at least or about 50, 75, 100, 125, 150, 175, 200, 225, 250, 275, 300, 325, 350, 375, 400, 425, 450, 475, 500, 525, 550, 575, 600, or more than 600 base pairs. In some instances, the length is about 50 to 600, 75 to 575, 100 to 550, 125 to 525, 150 to 500, 175 to 475, 200 to 450, 225 to 425, 250 to 400, 275 to 375, or 300 to 350 base pairs.

Libraries comprising nucleic acids encoding for immunoglobulin scaffolds as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 amino acids to about 75 amino acids. In some instances, the immunoglobulin scaffolds comprise at least or about 100, 200, 300, 400, 500, 600, 700, 800, 900, 1000, 2000, 3000, 4000, 5000, or more than 5000 amino acids.

A number of variant sequences for the at least one region of the immunoglobulin for variation are de novo synthesized using methods as described herein. In some instances, a number of variant sequences is de novo synthesized for CDRH1, CDRH2, CDRH3, CDRL1, CDRL2, CDRL3, VL, VH, or combinations thereof. In some instances, a number of variant sequences is de novo synthesized for framework element 1 (FW1), framework element 2 (FW2), framework element 3 (FW3), or framework element 4 (FW4). The number of variant sequences may be at least or about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more than 500 sequences. In some instances, the number of variant sequences is at least or about 500, 600, 700, 800, 900, 1000, 2000, 3000, 4000, 5000, 6000, 7000, 8000, or more than 8000 sequences. In some instances, the number of variant sequences is about 10 to 500, 25 to 475, 50 to 450, 75 to 425, 100 to 400, 125 to 375, 150 to 350, 175 to 325, 200 to 300, 225 to 375, 250 to 350, or 275 to 325 sequences.

Variant sequences for the at least one region of the immunoglobulin, in some instances, vary in length or sequence. In some instances, the at least one region that is de novo synthesized is for CDRH1, CDRH2, CDRH3, CDRL1, CDRL2, CDRL3, VL, VH, or combinations thereof. In some instances, the at least one region that is de novo synthesized is for framework element 1 (FW1), framework element 2 (FW2), framework element 3 (FW3), or framework element 4 (FW4). In some instances, the variant sequence comprises at least or about 1, 2, 3, 4, 5, 6, 7, 8, 9, 10, 15, 20, 25, 30, 35, 40, 45, 50, or more than 50 variant nucleotides or amino acids as compared to wild-type. In some instances, the variant sequence comprises at least or about 1, 2, 3, 4, 5, 6, 7, 8, 9, 10, 15, 20, 25, 30, 35, 40, 45, or 50 additional nucleotides or amino acids as compared to wild-type. In some instances, the variant sequence comprises at least or about 1, 2, 3, 4, 5, 6, 7, 8, 9, 10, 15, 20, 25, 30, 35, 40, 45, or 50 less nucleotides or amino acids as compared to wild-type. In some instances, the libraries comprise at least or about $10^1$, $10^2$, $10^3$, $10^4$, $10^5$, $10^6$, $10^7$, $10^8$, $10^9$, $10^{10}$, or more than $10^{10}$ variants.

Following synthesis of scaffold libraries, scaffold libraries may be used for screening and analysis. For example, scaffold libraries are assayed for library displayability and panning. In some instances, displayability is assayed using a selectable tag. Exemplary tags include, but are not limited to, a radioactive label, a fluorescent label, an enzyme, a chemiluminescent tag, a colorimetric tag, an affinity tag or other labels or tags that are known in the art. In some instances, the tag is histidine, polyhistidine, myc, hemagglutinin (HA), or FLAG. In some instances, scaffold libraries are assayed by sequencing using various methods including, but not limited to, single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

In some instances, the scaffold libraries are assayed for functional activity, structural stability (e.g., thermal stable or pH stable), expression, specificity, or a combination thereof. In some instances, the scaffold libraries are assayed for scaffolds capable of folding. In some instances, a region of the antibody is assayed for functional activity, structural stability, expression, specificity, folding, or a combination thereof. For example, a VH region or VL region is assayed for functional activity, structural stability, expression, specificity, folding, or a combination thereof.

Adenosine A2A Receptor Libraries

Provided herein are adenosine A2A receptor binding libraries comprising nucleic acids encoding for scaffolds comprising sequences for adenosine A2A receptor binding domains. In some instances, the scaffolds are immunoglobulins. In some instances, the scaffolds comprising sequences for adenosine A2A receptor binding domains are determined by interactions between the adenosine A2A receptor binding domains and the adenosine A2A receptor.

Provided herein are libraries comprising nucleic acids encoding scaffolds comprising adenosine A2A receptor binding domains, wherein the adenosine A2A receptor binding domains are designed based on surface interactions on adenosine A2A receptor. In some instances, the adenosine A2A receptor binding domain comprises a sequence as defined by SEQ ID NO: 1. In some instances, the adenosine A2A receptor binding domains interact with the amino- or carboxy-terminus of the adenosine A2A receptor. In some instances, the adenosine A2A receptor binding domains interact with at least one transmembrane domain including, but not limited to, transmembrane domain 1 (TM1), transmembrane domain 2 (TM2), transmembrane domain 3 (TM3), transmembrane domain 4 (TM4), transmembrane domain 5 (TM5), transmembrane domain 6 (TM6), and transmembrane domain 7 (TM7). In some instances, the adenosine A2A receptor binding domains interact with an intracellular surface of the adenosine A2A receptor. For example, the adenosine A2A receptor binding domains interact with at least one intracellular loop including, but not limited to, intracellular loop 1 (ICL1), intracellular loop 2 (ICL2), and intracellular loop 3 (ICL3). In some instances, the adenosine A2A receptor binding domains interact with an extracellular surface of the adenosine A2A receptor For example, the adenosine A2A receptor binding domains interact with at least one extracellular domain (ECD) or extracellular loop (ECL) of the adenosine A2A receptor. The extracellular loops include, but are not limited to, extracellular loop 1 (ECL1), extracellular loop 2 (ECL2), and extracellular loop 3 (ECL3).

Described herein are adenosine A2A receptor binding domains, wherein the adenosine A2A receptor binding domains are designed based on surface interactions between an adenosine A2A receptor ligand and the adenosine A2A receptor. In some instances, the ligand is a peptide. In some instances, the ligand is an adenosine A2A receptor agonist. In some instances, the ligand is an adenosine A2A receptor antagonist. In some instances, the ligand is an adenosine A2A receptor allosteric modulator. In some instances, the allosteric modulator is a negative allosteric modulator. In some instances, the allosteric modulator is a positive allosteric modulator. Exemplary ligands of the adenosine A2A receptor include, but are not limited to DU172, PSB36, ZM241385, XAC, caffeine, T4G, T4E, 6DY, 6DZ, 6DX, 6DV, 8D1b, theophylline, UK-432097, adenosine, NECA, and CGS21680.

Sequences of adenosine A2A receptor binding domains based on surface interactions between an adenosine A2A receptor ligand and the adenosine A2A receptor are analyzed using various methods. For example, multispecies computational analysis is performed. In some instances, a structure analysis is performed. In some instances, a sequence analysis is performed. Sequence analysis can be performed using a database known in the art. Non-limiting examples of databases include, but are not limited to, NCBI BLAST (blast.ncbi.nlm.nih.gov/Blast.cgi), UCSC Genome Browser (genome.ucsc.edu/), UniProt (www.uniprot.org/), and IUPHAR/BPS Guide to PHARMACOLOGY (guidetopharmacology.org/).

Described herein are adenosine A2A receptor binding domains designed based on sequence analysis among various organisms. For example, sequence analysis is performed to identify homologous sequences in different organisms. Exemplary organisms include, but are not limited to, mouse, rat, equine, sheep, cow, primate (e.g., chimpanzee, baboon, gorilla, orangutan, monkey), dog, cat, pig, donkey, rabbit, fish, fly, and human.

Following identification of adenosine A2A receptor binding domains, libraries comprising nucleic acids encoding for the adenosine A2A receptor binding domains may be generated. In some instances, libraries of adenosine A2A receptor binding domains comprise sequences of adenosine A2A receptor binding domains designed based on conformational ligand interactions, peptide ligand interactions, small molecule ligand interactions, extracellular domains of adenosine A2A receptor, or antibodies that target adenosine A2A receptor. In some instances, libraries of adenosine A2A receptor binding domains comprise sequences of adenosine A2A receptor binding domains designed based on peptide ligand interactions. In some instances, the ligand is a not an antibody ligand. Libraries of adenosine A2A receptor binding domains may be translated to generate protein libraries. In some instances, libraries of adenosine A2A receptor binding domains are translated to generate peptide libraries, immunoglobulin libraries, derivatives thereof, or combinations thereof. In some instances, libraries of adenosine A2A receptor binding domains are translated to generate protein libraries that are further modified to generate peptidomimetic libraries. In some instances, libraries of adenosine A2A receptor binding domains are translated to generate protein libraries that are used to generate small molecules.

Methods described herein provide for synthesis of libraries of adenosine A2A receptor binding domains comprising nucleic acids each encoding for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the libraries of adenosine A2A receptor binding domains comprise varied nucleic acids collectively encoding variations at multiple positions. In some instances, the variant library comprises sequences encoding for variation of at least a single codon in an adenosine A2A receptor binding domain. In some instances, the variant library comprises sequences encoding for variation of multiple codons in an adenosine A2A receptor binding domain. An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

Methods described herein provide for synthesis of libraries comprising nucleic acids encoding for the adenosine A2A receptor binding domains, wherein the libraries comprise sequences encoding for variation of length of the adenosine A2A receptor binding domains. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons less as compared to a predetermined reference sequence. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 200, 225, 250, 275, 300, or more than 300 codons more as compared to a predetermined reference sequence.

Following identification of adenosine A2A receptor binding domains, the adenosine A2A receptor binding domains may be placed in scaffolds as described herein. In some instances, the scaffolds are immunoglobulins. In some instances, the adenosine A2A receptor binding domains are placed in the CDRH3 region. Adenosine A2A receptor binding domains that may be placed in scaffolds can also be referred to as a motif. Scaffolds comprising adenosine A2A receptor binding domains may be designed based on binding, specificity, stability, expression, folding, or downstream activity. In some instances, the scaffolds comprising adenosine A2A receptor binding domains enable contact with the adenosine A2A receptor. In some instances, the scaffolds comprising adenosine A2A receptor binding domains enables high affinity binding with the adenosine A2A receptor. An exemplary amino acid sequence of adenosine A2A receptor binding domain is described in Table 1.

TABLE 1

Adenosine A2A receptor binding domain amino acid sequences

| SEQ ID NO | GPCR | Amino Acid Sequence |
|---|---|---|
| 1 | Adenosine A2A receptor | MPIMGSSVYITVELAIAVLAILGNVLVCWAVWLNSNL QNVTNYFVVSLAAADIAVGVLAIPFAITISTGFCAAC HGCLFIACFVLVLTQSSIFSLLAIAIDRYIAIRIPLR YNGLVTGTRAKGIIAICWVLSFAIGLTPMLGWNNCGQ PKEGKNHSQGCGEGQVACLFEDVVPMNYMVYNFFACV LVPLLLMLGVYLRIFLAARRQLKQMESQPLPGERARS TLQKEVHAAKSLAIIVGLFALCWLPLHIINCFTFFCP |

TABLE 1 -continued

Adenosine A2A receptor binding domain amino acid sequences

| SEQ ID NO | GPCR | Amino Acid Sequence |
|---|---|---|
| | | DCSHAPLWLMYLAIVLSHTNSVVNPFIYAYRIREFRQ TFRKIIRSHVLRQQEPFKAAGTSARVLAAHGSDGEQV SLRLNGHPPGVWANGSAPHPERRPNGYALGLVSGGSA QESQGNTGLPDVELLSHELKGVCPEPPGLDDPLAQDG AGVS |

Provided herein are scaffolds or immunoglobulins comprising adenosine A2A receptor binding domains, wherein the sequences of the adenosine A2A receptor binding domains support interaction with adenosine A2A receptor. The sequence may be homologous or identical to a sequence of an adenosine A2A receptor ligand. In some instances, the adenosine A2A receptor binding domain sequence comprises at least or about 70%, 80%, 85%, 90%, 91%, 92%, 93%, 94%, 95%, 96%, 97%, 98%, 99%, or 100% sequence identity to SEQ ID NO: 1. In some instances, the adenosine A2A receptor binding domain sequence comprises at least or about 95% homology to SEQ ID NO: 1. In some instances, the adenosine A2A receptor binding domain sequence comprises at least or about 97% homology to SEQ ID NO: 1. In some instances, the adenosine A2A receptor binding domain sequence comprises at least or about 99% homology to SEQ ID NO: 1. In some instances, the adenosine A2A receptor binding domain sequence comprises at least or about 100% homology to SEQ ID NO: 1. In some instances, the adenosine A2A receptor binding domain sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, or more than 400 amino acids of SEQ ID NO: 1.

Provided herein are antibodies or immunoglobulins, wherein the antibody or immunoglobulin comprises a sequence at least or about 70%, 80%, 85%, 90%, 91%, 92%, 93%, 94%, 95%, 96%, 97%, 98%, 99%, or 100% sequence identity to any one of SEQ ID NOs: 540-717. In some instances, the antibody or immunoglobulin sequence comprises at least or about 95% sequence identity to any one of SEQ ID NOs: 540-717. In some instances, the antibody or immunoglobulin sequence comprises at least or about 97% sequence identity to any one of SEQ ID NOs: 540-717. In some instances, the antibody or immunoglobulin sequence comprises at least or about 99% sequence identity to any one of SEQ ID NOs: 540-717. In some instances, the antibody or immunoglobulin sequence comprises at least or about 100% sequence identity to any one SEQ ID NOs: 540-717. In some instances, the antibody or immunoglobulin sequence comprises at least a portion having at least or about 1, 2, 3, 4, 5, 6, 7, 8, 9, 10, 12, 14, 16, 18, 20, 30, 40, 50, 60, 70, 80, 90, 100, 110, or more than 110 amino acids of any one of SEQ ID NOs: 540-717.

In some embodiments, the antibody or immunoglobulin sequence comprises complementarity determining regions (CDRs) comprising a sequence as set forth in Tables 15-16. In some embodiments, the antibody or immunoglobulin sequence comprises complementarity determining regions (CDRs) comprising at least or about 70%, 80%, 85%, 90%, 91%, 92%, 93%, 94%, 95%, 96%, 97%, 98%, 99%, or 100% sequence identity to any one of SEQ ID NOs: 6-539. In some instances, the antibody or immunoglobulin sequence comprises complementarity determining regions (CDRs) comprising at least or about 95% homology to any one of SEQ ID NOs: 6-539. In some instances, the antibody or immunoglobulin sequence comprises complementarity determining regions (CDRs) comprising at least or about 97% homology to any one of SEQ ID NOs: 6-539. In some instances, the antibody or immunoglobulin sequence comprises complementarity determining regions (CDRs) comprising at least or about 99% homology to any one of SEQ ID NOs: 6-539. In some instances, the antibody or immunoglobulin sequence comprises complementarity determining regions (CDRs) comprising at least or about 100% homology to any one of SEQ ID NOs: 6-539. In some instances, the antibody or immunoglobulin sequence comprises complementarity determining regions (CDRs) comprising at least a portion having at least or about 3, 4, 5, 6, 7, 8, 9, 10, 12, 14, 16, or more than 16 amino acids of any one of SEQ ID NOs: 6-539.

In some embodiments, the antibody or immunoglobulin sequence comprises a CDR1 comprising at least or about 70%, 80%, 85%, 90%, 91%, 92%, 93%, 94%, 95%, 96%, 97%, 98%, 99%, or 100% sequence identity to any one of SEQ ID NOs: 6-94 or 273-361. In some instances, the antibody or immunoglobulin sequence comprises CDR1 comprising at least or about 95% homology of any one of SEQ ID NOs: 6-94 and 273-361. In some instances, the antibody or immunoglobulin sequence comprises CDR1 comprising at least or about 97% homology to any one of SEQ ID NOs: 6-94 or 273-361. In some instances, the antibody or immunoglobulin sequence comprises CDR1 comprising at least or about 99% homology to any one of SEQ ID NOs: 6-94 or 273-361. In some instances, the antibody or immunoglobulin sequence comprises CDR1 comprising at least or about 100% homology to any one of SEQ ID NOs: 6-270 or 273-537. In some instances, the antibody or immunoglobulin sequence comprises CDR1 comprising at least a portion having at least or about 3, 4, 5, 6, 7, 8, 9, 10, 12, 14, 16, or more than 16 amino acids of any one of SEQ ID NOs: 6-94 or 273-361.

In some embodiments, the antibody or immunoglobulin sequence comprises a CDR2 comprising at least or about 70%, 80%, 85%, 90%, 91%, 92%, 93%, 94%, 95%, 96%, 97%, 98%, 99%, or 100% sequence identity to any one of SEQ ID NOs: 95-183 and 362-450. In some instances, the antibody or immunoglobulin sequence comprises CDR2 comprising at least or about 95% homology to any one of SEQ ID NOs: 95-183 and 362-450. In some instances, the antibody or immunoglobulin sequence comprises CDR2 comprising at least or about 97% homology to any one of SEQ ID NOs: 795-183 and 362-450. In some instances, the antibody or immunoglobulin sequence comprises CDR2 comprising at least or about 99% homology to any one of SEQ ID NOs: 95-183 and 362-450. In some instances, the antibody or immunoglobulin sequence comprises CDR2 comprising at least or about 100% homology to any one of SEQ ID NOs: 95-183 and 362-450. In some instances, the antibody or immunoglobulin sequence comprises CDR2 comprising at least a portion having at least or about 3, 4, 5, 6, 7, 8, 9, 10, 12, 14, 16, or more than 16 amino acids of any one of SEQ ID NOs: 95-183 and 362-450.

In some embodiments, the antibody or immunoglobulin sequence comprises a CDR3 comprising at least or about 70%, 80%, 85%, 90%, 91%, 92%, 93%, 94%, 95%, 96%, 97%, 98%, 99%, or 100% sequence identity to any one of SEQ ID NOs: 184-272 and 451-539. In some instances, the antibody or immunoglobulin sequence comprises CDR3 comprising at least or about 95% homology to any one of SEQ ID NOs: 184-272 and 451-539. In some instances, the antibody or immunoglobulin sequence comprises CDR3 comprising at least or about 97% homology to any one of SEQ ID NOs: 184-272 and 451-539. In some instances, the antibody or immunoglobulin sequence comprises CDR3 comprising at least or about 99% homology to any one of SEQ ID NOs: 184-272 and 451-539. In some instances, the antibody or immunoglobulin sequence comprises CDR3 comprising at least or about 100% homology to any one of SEQ ID NOs: 184-272 and 451-539. In some instances, the antibody or immunoglobulin sequence comprises CDR3 comprising at least a portion having at least or about 3, 4, 5, 6, 7, 8, 9, 10, 12, 14, 16, or more than 16 amino acids of any one of SEQ ID NOs: 184-272 and 451-539.

In some embodiments, the antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to any one of SEQ ID NOs: 6-94; a CDRH2 comprising at least or about 70%, 80%, 85%, 90%, 91%, 92%, 93%, 94%, 95%, 96%, 97%, 98%, 99%, or 100% sequence identity to any one of SEQ ID NOs: 95-183; and a CDRH3 comprising at least or about 70%, 80%, 85%, 90%, 91%, 92%, 93%, 94%, 95%, 96%, 97%, 98%, 99%, or 100% sequence identity to any one of SEQ ID NOs: 184-272. In some instances, the antibody or immunoglobulin sequence comprises CDRH1 comprising at least or about 95%, 97%, 99%, or 100% homology to any one of SEQ ID NOs: 6-94; a CDRH2 comprising at least or about 95%, 97%, 99%, or 100% homology to any one of SEQ ID NOs: 95-183; and a CDRH3 comprising at least or about 95%, 97%, 99%, or 100% homology to any one of SEQ ID NOs: 184-272. In some instances, the antibody or immunoglobulin sequence comprises CDRH1 comprising at least a portion having at least or about 3, 4, 5, 6, 7, 8, 9, 10, 12, 14, 16, or more than 16 amino acids of SEQ ID NO: 6-94; a CDRH2 comprising at least a portion having at least or about 3, 4, 5, 6, 7, 8, 9, 10, 12, 14, 16, or more than 16 amino acids of SEQ ID NO: 95-183; and a CDRH3 comprising at least a portion having at least or about 3, 4, 5, 6, 7, 8, 9, 10, 12, 14, 16, or more than 16 amino acids of SEQ ID NO: 184-272.

In some embodiments, the antibody or immunoglobulin sequence comprises a CDRL1 comprising at least or about 70%, 80%, 85%, 90%, 91%, 92%, 93%, 94%, 95%, 96%, 97%, 98%, 99%, or 100% sequence identity to SEQ ID NO: 273-361; a CDRL2 comprising at least or about 70%, 80%, 85%, 90%, 91%, 92%, 93%, 94%, 95%, 96%, 97%, 98%, 99%, or 100% sequence identity to SEQ ID NO: 362-450; and a CDRL3 comprising at least or about 70%, 80%, 85%, 90%, 91%, 92%, 93%, 94%, 95%, 96%, 97%, 98%, 99%, or 100% sequence identity to SEQ ID NO: 451-539. In some instances, the antibody or immunoglobulin sequence comprises CDRL1 comprising at least or about 95%, 97%, 99%, or 100% homology to SEQ ID NO: 273-361; a CDRL2 comprising at least or about 95%, 97%, 99%, or 100% homology to SEQ ID NO: 362-450; and a CDRL3 comprising at least or about 95%, 97%, 99%, or 100% homology to SEQ ID NO: 451-539. In some instances, the antibody or immunoglobulin sequence comprises CDRL1 comprising at least a portion having at least or about 3, 4, 5, 6, 7, 8, 9, 10, 12, 14, 16, or more than 16 amino acids of SEQ ID NO: 273-361; a CDRL2 comprising at least a portion having at least or about 3, 4, 5, 6, 7, 8, 9, 10, 12, 14, 16, or more than 16 amino acids of SEQ ID NO: 362-450; and a CDRL3 comprising at least a portion having at least or about 3, 4, 5, 6, 7, 8, 9, 10, 12, 14, 16, or more than 16 amino acids of SEQ ID NO: 451-539.

In some embodiments, the antibody or immunoglobulin sequence comprises a CDRH1 comprising at least or about 70%, 80%, 85%, 90%, 91%, 92%, 93%, 94%, 95%, 96%, 97%, 98%, 99%, or 100% sequence identity to any one of SEQ ID NOs: 6-94; a CDRH2 comprising at least or about 70%, 80%, 85%, 90%, 91%, 92%, 93%, 94%, 95%, 96%, 97%, 98%, 99%, or 100% sequence identity to any one of SEQ ID NOs: 95-183; a CDRH3 comprising at least or about 70%, 80%, 85%, 90%, 91%, 92%, 93%, 94%, 95%, 96%, 97%, 98%, 99%, or 100% sequence identity to any one of SEQ ID NOs: 184-272, a CDRL1 comprising at least or about 70%, 80%, 85%, 90%, 91%, 92%, 93%, 94%, 95%, 96%, 97%, 98%, 99%, or 100% sequence identity to any one of SEQ ID NOs: 273-362; a CDRL2 comprising at least or about 70%, 80%, 85%, 90%, 91%, 92%, 93%, 94%, 95%, 96%, 97%, 98%, 99%, or 100% sequence identity to any one of SEQ ID NOs: 362-450; and a CDRL3 comprising at least or about 70%, 80%, 85%, 90%, 91%, 92%, 93%, 94%, 95%, 96%, 97%, 98%, 99%, or 100% sequence identity to any one of SEQ ID NOs: 451-539. In some instances, the antibody or immunoglobulin sequence comprises CDRH1 comprising at least or about 95%, 97%, 99%, or 100% homology to any one of SEQ ID NOs: 6-94; a CDRH2 comprising at least or about 95%, 97%, 99%, or 100% homology to any one of SEQ ID NOs: 95-183; a CDRH3 comprising at least or about 95%, 97%, 99%, or 100% homology to any one of SEQ ID NOs: 184-272; a CDRL1 comprising at least or about 95%, 97%, 99%, or 100% homology to any one of SEQ ID NOs: 273-362; a CDRL2 comprising at least or about 95%, 97%, 99%, or 100% homology to any one of SEQ ID NOs: 362-450; and a CDRL3 comprising at least or about 95%, 97%, 99%, or 100% homology to any one of SEQ ID NOs: 451-539. In some instances, the antibody or immunoglobulin sequence comprises CDRH1 comprising at least a portion having at least or about 3, 4, 5, 6, 7, 8, 9, 10, 12, 14, 16, or more than 16 amino acids of any one of SEQ ID NOs: 6-94; a CDRH2 comprising at least a portion having at least or about 3, 4, 5, 6, 7, 8, 9, 10, 12, 14, 16, or more than 16 amino acids of any one of SEQ ID NOs: 95-183; a CDRH3 comprising at least a portion having at least or about 3, 4, 5, 6, 7, 8, 9, 10, 12, 14, 16, or more than 16 amino acids of any one of SEQ ID NOs: 184-272; a CDRL1 comprising at least a portion having at least or about 3, 4, 5, 6, 7, 8, 9, 10, 12, 14, 16, or more than 16 amino acids of any one of SEQ ID NOs: 273-362; a CDRL2 comprising at least a portion having at least or about 3, 4, 5, 6, 7, 8, 9, 10, 12, 14, 16, or more than 16 amino acids of any one of SEQ ID NOs: 362-450; and a CDRL3 comprising at least a portion having at least or about 3, 4, 5, 6, 7, 8, 9, 10, 12, 14, 16, or more than 16 amino acids of any one of SEQ ID NOs: 451-539.

Described herein, in some embodiments, are antibodies or immunoglobulins that bind to the adenosine A2A receptor. In some instances, the adenosine A2A receptor antibody or immunoglobulin sequence comprises a heavy chain variable domain comprising at least or about 70%, 80%, 85%, 90%, 91%, 92%, 93%, 94%, 95%, 96%, 97%, 98%, 99%, or 100% sequence identity to any one of SEQ ID NOs: 540-628. In some instances, the adenosine A2A receptor antibody or immunoglobulin sequence comprises a heavy chain variable domain comprising at least or about 95% sequence identity to any one of SEQ ID NOs: 540-628. In some instances, the adenosine A2A receptor antibody or immunoglobulin sequence comprises a heavy chain variable domain comprising at least or about 97% sequence identity to any one of SEQ ID NOs: 540-628. In some instances, the adenosine A2A receptor antibody or immunoglobulin sequence comprises a heavy chain variable domain comprising at least or about 99% sequence identity to any one of SEQ ID NOs: 540-628. In some instances, the adenosine A2A receptor antibody or immunoglobulin sequence comprises a heavy chain variable domain comprising at least or about 100% sequence identity to any one of SEQ ID NOs: 540-628. In some instances, the adenosine A2A receptor antibody or immunoglobulin sequence comprises a heavy chain variable domain comprising at least a portion having at least or about 1, 2, 3, 4, 5, 6, 7, 8, 9, 10, 12, 14, 16, 18, 20, 30, 40, 50, 60, 70, 80, 90, 100, 110, or more than 110 amino acids of SEQ ID NOs: 540-628.

In some instances, the adenosine A2A receptor antibody or immunoglobulin sequence comprises a light chain variable domain comprising at least or about 70%, 80%, 85%, 90%, 91%, 92%, 93%, 94%, 95%, 96%, 97%, 98%, 99%, or 100% sequence identity to any one of SEQ ID NOs: 629-717. In some instances, the adenosine A2A receptor antibody or immunoglobulin sequence comprises a light chain variable domain comprising at least or about 95% sequence identity to any one of SEQ ID NOs: 629-717. In some instances, the adenosine A2A receptor antibody or immunoglobulin sequence comprises a light chain variable domain comprising at least or about 97% sequence identity to any one of SEQ ID NOs: 629-717. In some instances, the adenosine A2A receptor antibody or immunoglobulin sequence comprises a light chain variable domain comprising at least or about 99% sequence identity to any one of SEQ ID NOs: 629-717. In some instances, the adenosine A2A receptor antibody or immunoglobulin sequence comprises a light chain variable domain comprising at least or about 100% sequence identity to any one of SEQ ID NOs: 629-717. In some instances, the adenosine A2A receptor antibody or immunoglobulin sequence comprises a light chain variable domain comprising at least a portion having at least or about 1, 2, 3, 4, 5, 6, 7, 8, 9, 10, 12, 14, 16, 18, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, or more than 400 amino acids of SEQ ID NOs: 629-717.

In some embodiments, the immunoglobulin heavy chain comprises an amino acid sequence at least about 90% identical to that set forth in SEQ ID NO: 540; and the immunoglobulin light chain comprises an amino acid sequence at least about 90% identical to that set forth in SEQ ID NO: 629. In some embodiments, the immunoglobulin heavy chain comprises an amino acid sequence at least about 90% identical to that set forth in SEQ ID NO: 541; and the immunoglobulin light chain comprises an amino acid sequence at least about 90% identical to that set forth in SEQ ID NO: 630. In some embodiments, the immunoglobulin heavy chain comprises an amino acid sequence at least about 90% identical to that set forth in SEQ ID NO: 542; and the immunoglobulin light chain comprises an amino acid sequence at least about 90% identical to that set forth in SEQ ID NO: 631. In some embodiments, the immunoglobulin heavy chain comprises an amino acid sequence at least about 90% identical to that set forth in SEQ ID NO: 543; and the immunoglobulin light chain comprises an amino acid sequence at least about 90% identical to that set forth in SEQ ID NO: 632. In some embodiments, the immunoglobulin heavy chain comprises an amino acid sequence at least about 90% identical to that set forth in SEQ ID NO: 544; and the immunoglobulin light chain comprises an amino acid sequence at least about 90% identical to that set forth in SEQ ID NO: 633. In some embodiments, the immunoglobulin heavy chain comprises an amino acid sequence at least about 90% identical to that set forth in SEQ ID NO: 545; and the immunoglobulin light chain comprises an amino acid sequence at least about 90% identical to that set forth in SEQ ID NO: 634. In some embodiments, the immunoglobulin heavy chain comprises an amino acid sequence at least about 90% identical to that set forth in SEQ ID NO: 546; and the immunoglobulin light chain comprises an amino acid sequence at least about 90% identical to that set forth in SEQ ID NO: 635. In some embodiments, the immunoglobulin heavy chain comprises an amino acid sequence at least about 90% identical to that set forth in SEQ ID NO: 547; and the immunoglobulin light chain comprises an amino acid sequence at least about 90% identical to that set forth in SEQ ID NO: 636. In some embodiments, the immunoglobulin heavy chain comprises an amino acid sequence at least about 90% identical to that set forth in SEQ ID NO: 548; and the immunoglobulin light chain comprises an amino acid sequence at least about 90% identical to that set forth in SEQ ID NO: 637. In some embodiments, the immunoglobulin heavy chain comprises an amino acid sequence at least about 90% identical to that set forth in SEQ ID NO: 549; and the immunoglobulin light chain comprises an amino acid sequence at least about 90% identical to that set forth in SEQ ID NO: 638. In some embodiments, the immunoglobulin heavy chain comprises an amino acid sequence at least about 90% identical to that set forth in SEQ ID NO: 550; and the immunoglobulin light chain comprises an amino acid sequence at least about 90% identical to that set forth in SEQ ID NO: 639. In some embodiments, the immunoglobulin heavy chain comprises an amino acid sequence at least about 90% identical to that set forth in SEQ ID NO: 551; and the immunoglobulin light chain comprises an amino acid sequence at least about 90% identical to that set forth in SEQ ID NO: 640. In some embodiments, the immunoglobulin heavy chain comprises an amino acid sequence at least about 90% identical to that set forth in SEQ ID NO: 552; and the immunoglobulin light chain comprises an amino acid sequence at least about 90% identical to that set forth in SEQ ID NO: 641. In some embodiments, the immunoglobulin heavy chain comprises an amino acid sequence at least about 90% identical to that set forth in SEQ ID NO: 553; and the immunoglobulin light chain comprises an amino acid sequence at least about 90% identical to that set forth in SEQ ID NO: 642. In some embodiments, the immunoglobulin heavy chain comprises an amino acid sequence at least about 90% identical to that set forth in SEQ ID NO: 554; and the immunoglobulin light chain comprises an amino acid sequence at least about 90% identical to that set forth in SEQ ID NO: 643. In some embodiments, the immunoglobulin heavy chain comprises an amino acid sequence at least about 90% identical to that set forth in SEQ ID NO: 555; and the immunoglobulin light chain comprises an amino acid sequence at least about 90% identical to that set forth in SEQ ID NO: 644. In some embodiments, the immunoglobulin heavy chain comprises an amino acid sequence at least about 90% identical to that set forth in SEQ ID NO: 556; and the immunoglobulin light chain comprises an amino acid sequence at least about 90% identical to that set forth in SEQ ID NO: 645. In some embodiments, the immunoglobulin heavy chain comprises an amino acid sequence at least about 90% identical to that set forth in SEQ ID NO: 557; and the immunoglobulin light chain comprises an amino acid sequence at least about 90% identical to that set forth in SEQ ID NO: 646. In some embodiments, the immunoglobulin heavy chain comprises an amino acid sequence at least about 90% identical to that set forth in SEQ ID NO: 558; and the immunoglobulin light chain comprises an amino acid sequence at least about 90% identical to that set forth in SEQ ID NO: 647. In some embodiments, the immunoglobulin heavy chain comprises an amino acid sequence at least about 90% identical to that set forth in SEQ ID NO: 559; and the immunoglobulin light chain comprises an amino acid sequence at least about 90% identical to that set forth in SEQ ID NO: 648. In some embodiments, the immunoglobulin heavy chain comprises an amino acid sequence at least about 90% identical to that set forth in SEQ ID NO: 560; and the immunoglobulin light chain comprises an amino acid sequence at least about 90% identical to that set forth in SEQ ID NO: 649. In some embodiments, the immunoglobulin heavy chain comprises an amino acid sequence at least about 90% identical to that set forth in SEQ ID NO: 561; and the immunoglobulin light chain comprises an amino acid sequence at least about 90% identical to that set forth in SEQ ID NO: 650. In some embodiments, the immunoglobulin heavy chain comprises an amino acid sequence at least about 90% identical to that set forth in SEQ ID NO: 562; and the immunoglobulin light chain comprises an amino acid sequence at least about 90% identical to that set forth in SEQ ID NO: 651. In some embodiments, the immunoglobulin heavy chain comprises an amino acid sequence at least about 90% identical to that set forth in SEQ ID NO: 563; and the immunoglobulin light chain comprises an amino acid sequence at least about 90% identical to that set forth in SEQ ID NO: 652. In some embodiments, the immunoglobulin heavy chain comprises an amino acid sequence at least about 90% identical to that set forth in SEQ ID NO: 564; and the immunoglobulin light chain comprises an amino acid sequence at least about 90% identical to that set forth in SEQ ID NO: 653. In some embodiments, the immunoglobulin heavy chain comprises an amino acid sequence at least about 90% identical to that set forth in SEQ ID NO: 565; and the immunoglobulin light chain comprises an amino acid sequence at least about 90% identical to that set forth in SEQ ID NO: 654. In some embodiments, the immunoglobulin heavy chain comprises an amino acid sequence at least about 90% identical to that set forth in SEQ ID NO: 566; and the immunoglobulin light chain comprises an amino acid sequence at least about 90% identical to that set forth in SEQ ID NO: 655. In some embodiments, the immunoglobulin heavy chain comprises an amino acid sequence at least about 90% identical to that set forth in SEQ ID NO: 567; and the immunoglobulin light chain comprises an amino acid sequence at least about 90% identical to that set forth in SEQ ID NO: 656. In some embodiments, the immunoglobulin heavy chain comprises an amino acid sequence at least about 90% identical to that set forth in SEQ ID NO: 568; and the immunoglobulin light chain comprises an amino acid sequence at least about 90% identical to that set forth in SEQ ID NO: 657. In some embodiments, the immunoglobulin heavy chain comprises an amino acid sequence at least about 90% identical to that set forth in SEQ ID NO: 569; and the immunoglobulin light chain comprises an amino acid sequence at least about 90% identical to that set forth in SEQ ID NO: 658. In some embodiments, the immunoglobulin heavy chain comprises an amino acid sequence at least about 90% identical to that set forth in SEQ ID NO: 570; and the immunoglobulin light chain comprises an amino acid sequence at least about 90% identical to that set forth in SEQ ID NO: 659. In some embodiments, the immunoglobulin heavy chain comprises an amino acid sequence at least about 90% identical to that set forth in SEQ ID NO: 571; and the immunoglobulin light chain comprises an amino acid sequence at least about 90% identical to that set forth in SEQ ID NO: 660. In some embodiments, the immunoglobulin heavy chain comprises an amino acid sequence at least about 90% identical to that set forth in SEQ ID NO: 572; and the immunoglobulin light chain comprises an amino acid sequence at least about 90% identical to that set forth in SEQ ID NO: 661. In some embodiments, the immunoglobulin heavy chain comprises an amino acid sequence at least about 90% identical to that set forth in SEQ ID NO: 573; and the immunoglobulin light chain comprises an amino acid sequence at least about 90% identical to that set forth in SEQ ID NO: 662. In some embodiments, the immunoglobulin heavy chain comprises an amino acid sequence at least about 90% identical to that set forth in SEQ ID NO: 574; and the immunoglobulin light chain comprises an amino acid sequence at least about 90% identical to that set forth in SEQ ID NO: 663. In some embodiments, the immunoglobulin heavy chain comprises an amino acid sequence at least about 90% identical to that set forth in SEQ ID NO: 575; and the immunoglobulin light chain comprises an amino acid sequence at least about 90% identical to that set forth in SEQ ID NO: 664. In some embodiments, the immunoglobulin heavy chain comprises an amino acid sequence at least about 90% identical to that set forth in SEQ ID NO: 576; and the immunoglobulin light chain comprises an amino acid sequence at least about 90% identical to that set forth in SEQ ID NO: 665. In some embodiments, the immunoglobulin heavy chain comprises an amino acid sequence at least about 90% identical to that set forth in SEQ ID NO: 577; and the immunoglobulin light chain comprises an amino acid sequence at least about 90% identical to that set forth in SEQ ID NO: 666. In some embodiments, the immunoglobulin heavy chain comprises an amino acid sequence at least about 90% identical to that set forth in SEQ ID NO: 578; and the immunoglobulin light chain comprises an amino acid sequence at least about 90% identical to that set forth in SEQ ID NO: 667. In some embodiments, the immunoglobulin heavy chain comprises an amino acid sequence at least about 90% identical to that set forth in SEQ ID NO: 579; and the immunoglobulin light chain comprises an amino acid sequence at least about 90% identical to that set forth in SEQ ID NO: 668. In some embodiments, the immunoglobulin heavy chain comprises an amino acid sequence at least about 90% identical to that set forth in SEQ ID NO: 580; and the immunoglobulin light chain comprises an amino acid sequence at least about 90% identical to that set forth in SEQ ID NO: 669. In some embodiments, the immunoglobulin heavy chain comprises an amino acid sequence at least about 90% identical to that set forth in SEQ ID NO: 581; and the immunoglobulin light chain comprises an amino acid sequence at least about 90% identical to that set forth in SEQ ID NO: 670. In some embodiments, the immunoglobulin heavy chain comprises an amino acid sequence at least about 90% identical to that set forth in SEQ ID NO: 582; and the immunoglobulin light chain comprises an amino acid sequence at least about 90% identical to that set forth in SEQ ID NO: 671. In some embodiments, the immunoglobulin heavy chain comprises an amino acid sequence at least about 90% identical to that set forth in SEQ ID NO: 583; and the immunoglobulin light chain comprises an amino acid sequence at least about 90% identical to that set forth in SEQ ID NO: 672. In some embodiments, the immunoglobulin heavy chain comprises an amino acid sequence at least about 90% identical to that set forth in SEQ ID NO: 584; and the immunoglobulin light chain comprises an amino acid sequence at least about 90% identical to that set forth in SEQ ID NO: 673. In some embodiments, the immunoglobulin heavy chain comprises an amino acid sequence at least about 90% identical to that set forth in SEQ ID NO: 585; and the immunoglobulin light chain comprises an amino acid sequence at least about 90% identical to that set forth in SEQ ID NO: 674. In some embodiments, the immunoglobulin heavy chain comprises an amino acid sequence at least about 90% identical to that set forth in SEQ ID NO: 586; and the immunoglobulin light chain comprises an amino acid sequence at least about 90% identical to that set forth in SEQ ID NO: 675. In some embodiments, the immunoglobulin heavy chain comprises an amino acid sequence at least about 90% identical to that set forth in SEQ ID NO: 587; and the immunoglobulin light chain comprises an amino acid sequence at least about 90% identical to that set forth in SEQ ID NO: 676. In some embodiments, the immunoglobulin heavy chain comprises an amino acid sequence at least about 90% identical to that set forth in SEQ ID NO: 588; and the immunoglobulin light chain comprises an amino acid sequence at least about 90% identical to that set forth in SEQ ID NO: 677. In some embodiments, the immunoglobulin heavy chain comprises an amino acid sequence at least about 90% identical to that set forth in SEQ ID NO: 589; and the immunoglobulin light chain comprises an amino acid sequence at least about 90% identical to that set forth in SEQ ID NO: 678. In some embodiments, the immunoglobulin heavy chain comprises an amino acid sequence at least about 90% identical to that set forth in SEQ ID NO: 590; and the immunoglobulin light chain comprises an amino acid sequence at least about 90% identical to that set forth in SEQ ID NO: 679. In some embodiments, the immunoglobulin heavy chain comprises an amino acid sequence at least about 90% identical to that set forth in SEQ ID NO: 591; and the immunoglobulin light chain comprises an amino acid sequence at least about 90% identical to that set forth in SEQ ID NO: 680. In some embodiments, the immunoglobulin heavy chain comprises an amino acid sequence at least about 90% identical to that set forth in SEQ ID NO: 592; and the immunoglobulin light chain comprises an amino acid sequence at least about 90% identical to that set forth in SEQ ID NO: 681. In some embodiments, the immunoglobulin heavy chain comprises an amino acid sequence at least about 90% identical to that set forth in SEQ ID NO: 593; and the immunoglobulin light chain comprises an amino acid sequence at least about 90% identical to that set forth in SEQ ID NO: 682. In some embodiments, the immunoglobulin heavy chain comprises an amino acid sequence at least about 90% identical to that set forth in SEQ ID NO: 594; and the immunoglobulin light chain comprises an amino acid sequence at least about 90% identical to that set forth in SEQ ID NO: 683. In some embodiments, the immunoglobulin heavy chain comprises an amino acid sequence at least about 90% identical to that set forth in SEQ ID NO: 595; and the immunoglobulin light chain comprises an amino acid sequence at least about 90% identical to that set forth in SEQ ID NO: 684. In some embodiments, the immunoglobulin heavy chain comprises an amino acid sequence at least about 90% identical to that set forth in SEQ ID NO: 596; and the immunoglobulin light chain comprises an amino acid sequence at least about 90% identical to that set forth in SEQ ID NO: 685. In some embodiments, the immunoglobulin heavy chain comprises an amino acid sequence at least about 90% identical to that set forth in SEQ ID NO: 597; and the immunoglobulin light chain comprises an amino acid sequence at least about 90% identical to that set forth in SEQ ID NO: 686. In some embodiments, the immunoglobulin heavy chain comprises an amino acid sequence at least about 90% identical to that set forth in SEQ ID NO: 598; and the immunoglobulin light chain comprises an amino acid sequence at least about 90% identical to that set forth in SEQ ID NO: 687. In some embodiments, the immunoglobulin heavy chain comprises an amino acid sequence at least about 90% identical to that set forth in SEQ ID NO: 599; and the immunoglobulin light chain comprises an amino acid sequence at least about 90% identical to that set forth in SEQ ID NO: 688. In some embodiments, the immunoglobulin heavy chain comprises an amino acid sequence at least about 90% identical to that set forth in SEQ ID NO: 600; and the immunoglobulin light chain comprises an amino acid sequence at least about 90% identical to that set forth in SEQ ID NO: 689. In some embodiments, the immunoglobulin heavy chain comprises an amino acid sequence at least about 90% identical to that set forth in SEQ ID NO: 601; and the immunoglobulin light chain comprises an amino acid sequence at least about 90% identical to that set forth in SEQ ID NO: 690. In some embodiments, the immunoglobulin heavy chain comprises an amino acid sequence at least about 90% identical to that set forth in SEQ ID NO: 602; and the immunoglobulin light chain comprises an amino acid sequence at least about 90% identical to that set forth in SEQ ID NO: 691. In some embodiments, the immunoglobulin heavy chain comprises an amino acid sequence at least about 90% identical to that set forth in SEQ ID NO: 603; and the immunoglobulin light chain comprises an amino acid sequence at least about 90% identical to that set forth in SEQ ID NO: 692. In some embodiments, the immunoglobulin heavy chain comprises an amino acid sequence at least about 90% identical to that set forth in SEQ ID NO: 604; and the immunoglobulin light chain comprises an amino acid sequence at least about 90% identical to that set forth in SEQ ID NO: 693. In some embodiments, the immunoglobulin heavy chain comprises an amino acid sequence at least about 90% identical to that set forth in SEQ ID NO: 605; and the immunoglobulin light chain comprises an amino acid sequence at least about 90% identical to that set forth in SEQ ID NO: 694. In some embodiments, the immunoglobulin heavy chain comprises an amino acid sequence at least about 90% identical to that set forth in SEQ ID NO: 606; and the immunoglobulin light chain comprises an amino acid sequence at least about 90% identical to that set forth in SEQ ID NO: 695. In some embodiments, the immunoglobulin heavy chain comprises an amino acid sequence at least about 90% identical to that set forth in SEQ ID NO: 607; and the immunoglobulin light chain comprises an amino acid sequence at least about 90% identical to that set forth in SEQ ID NO: 696. In some embodiments, the immunoglobulin heavy chain comprises an amino acid sequence at least about 90% identical to that set forth in SEQ ID NO: 608; and the immunoglobulin light chain comprises an amino acid sequence at least about 90% identical to that set forth in SEQ ID NO: 697. In some embodiments, the immunoglobulin heavy chain comprises an amino acid sequence at least about 90% identical to that set forth in SEQ ID NO: 609; and the immunoglobulin light chain comprises an amino acid sequence at least about 90% identical to that set forth in SEQ ID NO: 698. In some embodiments, the immunoglobulin heavy chain comprises an amino acid sequence at least about 90% identical to that set forth in SEQ ID NO: 610; and the immunoglobulin light chain comprises an amino acid sequence at least about 90% identical to that set forth in SEQ ID NO: 699. In some embodiments, the immunoglobulin heavy chain comprises an amino acid sequence at least about 90% identical to that set forth in SEQ ID NO: 611; and the immunoglobulin light chain comprises an amino acid sequence at least about 90% identical to that set forth in SEQ ID NO: 700. In some embodiments, the immunoglobulin heavy chain comprises an amino acid sequence at least about 90% identical to that set forth in SEQ ID NO: 612; and the immunoglobulin light chain comprises an amino acid sequence at least about 90% identical to that set forth in SEQ ID NO: 701. In some embodiments, the immunoglobulin heavy chain comprises an amino acid sequence at least about 90% identical to that set forth in SEQ ID NO: 613; and the immunoglobulin light chain comprises an amino acid sequence at least about 90% identical to that set forth in SEQ ID NO: 702. In some embodiments, the immunoglobulin heavy chain comprises an amino acid sequence at least about 90% identical to that set forth in SEQ ID NO: 614; and the immunoglobulin light chain comprises an amino acid sequence at least about 90% identical to that set forth in SEQ ID NO: 703. In some embodiments, the immunoglobulin heavy chain comprises an amino acid sequence at least about 90% identical to that set forth in SEQ ID NO: 615; and the immunoglobulin light chain comprises an amino acid sequence at least about 90% identical to that set forth in SEQ ID NO: 704. In some embodiments, the immunoglobulin heavy chain comprises an amino acid sequence at least about 90% identical to that set forth in SEQ ID NO: 616; and the immunoglobulin light chain comprises an amino acid sequence at least about 90% identical to that set forth in SEQ ID NO: 705. In some embodiments, the immunoglobulin heavy chain comprises an amino acid sequence at least about 90% identical to that set forth in SEQ ID NO: 617; and the immunoglobulin light chain comprises an amino acid sequence at least about 90% identical to that set forth in SEQ ID NO: 706. In some embodiments, the immunoglobulin heavy chain comprises an amino acid sequence at least about 90% identical to that set forth in SEQ ID NO: 618; and the immunoglobulin light chain comprises an amino acid sequence at least about 90% identical to that set forth in SEQ ID NO: 707. In some embodiments, the immunoglobulin heavy chain comprises an amino acid sequence at least about 90% identical to that set forth in SEQ ID NO: 619; and the immunoglobulin light chain comprises an amino acid sequence at least about 90% identical to that set forth in SEQ ID NO: 708. In some embodiments, the immunoglobulin heavy chain comprises an amino acid sequence at least about 90% identical to that set forth in SEQ ID NO: 620; and the immunoglobulin light chain comprises an amino acid sequence at least about 90% identical to that set forth in SEQ ID NO: 709. In some embodiments, the immunoglobulin heavy chain comprises an amino acid sequence at least about 90% identical to that set forth in SEQ ID NO: 621; and the immunoglobulin light chain comprises an amino acid sequence at least about 90% identical to that set forth in SEQ ID NO: 710. In some embodiments, the immunoglobulin heavy chain comprises an amino acid sequence at least about 90% identical to that set forth in SEQ ID NO: 622; and the immunoglobulin light chain comprises an amino acid sequence at least about 90% identical to that set forth in SEQ ID NO: 711. In some embodiments, the immunoglobulin heavy chain comprises an amino acid sequence at least about 90% identical to that set forth in SEQ ID NO: 623; and the immunoglobulin light chain comprises an amino acid sequence at least about 90% identical to that set forth in SEQ ID NO: 712. In some embodiments, the immunoglobulin heavy chain comprises an amino acid sequence at least about 90% identical to that set forth in SEQ ID NO: 624; and the immunoglobulin light chain comprises an amino acid sequence at least about 90% identical to that set forth in SEQ ID NO: 713. In some embodiments, the immunoglobulin heavy chain comprises an amino acid sequence at least about 90% identical to that set forth in SEQ ID NO: 625; and the immunoglobulin light chain comprises an amino acid sequence at least about 90% identical to that set forth in SEQ ID NO: 714. In some embodiments, the immunoglobulin heavy chain comprises an amino acid sequence at least about 90% identical to that set forth in SEQ ID NO: 626; and the immunoglobulin light chain comprises an amino acid sequence at least about 90% identical to that set forth in SEQ ID NO: 715. In some embodiments, the immunoglobulin heavy chain comprises an amino acid sequence at least about 90% identical to that set forth in SEQ ID NO: 627; and the immunoglobulin light chain comprises an amino acid sequence at least about 90% identical to that set forth in SEQ ID NO: 716. In some embodiments, the immunoglobulin heavy chain comprises an amino acid sequence at least about 90% identical to that set forth in SEQ ID NO: 628; and the immunoglobulin light chain comprises an amino acid sequence at least about 90% identical to that set forth in SEQ ID NO: 717.

Provided herein are adenosine A2A receptor binding libraries comprising nucleic acids encoding for scaffolds or immunoglobulins comprising adenosine A2A receptor binding domains comprise variation in domain type, domain length, or residue variation. In some instances, the domain is a region in the scaffold comprising the adenosine A2A receptor binding domains. For example, the region is the VH, CDRH3, or VL domain. In some instances, the domain is the adenosine A2A receptor binding domain.

Methods described herein provide for synthesis of an adenosine A2A receptor binding library of nucleic acids each encoding for a predetermined variant of at least one predetermined reference nucleic acid sequence. In some cases, the predetermined reference sequence is a nucleic acid sequence encoding for a protein, and the variant library comprises sequences encoding for variation of at least a single codon such that a plurality of different variants of a single residue in the subsequent protein encoded by the synthesized nucleic acid are generated by standard translation processes. In some instances, the adenosine A2A receptor binding library comprises varied nucleic acids collectively encoding variations at multiple positions. In some instances, the variant library comprises sequences encoding for variation of at least a single codon of a VH, CDRH3, or VL domain. In some instances, the variant library comprises sequences encoding for variation of at least a single codon in an adenosine A2A receptor binding domain. For example, at least one single codon of an adenosine A2A receptor binding domain as listed in Table 1 is varied. In some instances, the variant library comprises sequences encoding for variation of multiple codons of a VH, CDRH3, or VL domain. In some instances, the variant library comprises sequences encoding for variation of multiple codons in an adenosine A2A receptor binding domain. An exemplary number of codons for variation include, but are not limited to, at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons.

Methods described herein provide for synthesis of an adenosine A2A receptor binding library of nucleic acids each encoding for a predetermined variant of at least one predetermined reference nucleic acid sequence, wherein the adenosine A2A receptor binding library comprises sequences encoding for variation of length of a domain. In some instances, the domain is VH, CDRH3, or VL domain. In some instances, the domain is the adenosine A2A receptor binding domain. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 225, 250, 275, 300, or more than 300 codons less as compared to a predetermined reference sequence. In some instances, the library comprises sequences encoding for variation of length of at least or about 1, 5, 10, 15, 20, 25, 30, 35, 40, 45, 50, 55, 60, 65, 70, 75, 80, 85, 90, 95, 100, 125, 150, 175, 200, 225, 250, 275, 300, or more than 300 codons more as compared to a predetermined reference sequence.

Provided herein are adenosine A2A receptor binding libraries comprising nucleic acids encoding for scaffolds comprising adenosine A2A receptor binding domains, wherein the adenosine A2A receptor binding libraries are synthesized with various numbers of fragments. In some instances, the fragments comprise the VH, CDRH3, or VL domain. In some instances, the adenosine A2A receptor binding libraries are synthesized with at least or about 2 fragments, 3 fragments, 4 fragments, 5 fragments, or more than 5 fragments. The length of each of the nucleic acid fragments or average length of the nucleic acids synthesized may be at least or about 50, 75, 100, 125, 150, 175, 200, 225, 250, 275, 300, 325, 350, 375, 400, 425, 450, 475, 500, 525, 550, 575, 600, or more than 600 base pairs. In some instances, the length is about 50 to 600, 75 to 575, 100 to 550, 125 to 525, 150 to 500, 175 to 475, 200 to 450, 225 to 425, 250 to 400, 275 to 375, or 300 to 350 base pairs.

Adenosine A2A receptor binding libraries comprising nucleic acids encoding for scaffolds comprising adenosine A2A receptor binding domains as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 to about 75 amino acids.

Adenosine A2A receptor binding libraries comprising de novo synthesized variant sequences encoding for scaffolds comprising adenosine A2A receptor binding domains comprise a number of variant sequences. In some instances, a number of variant sequences is de novo synthesized for a CDRH1, CDRH2, CDRH3, CDRL1, CDRL2, CDRL3, VL, VH, or a combination thereof. In some instances, a number of variant sequences is de novo synthesized for framework element 1 (FW1), framework element 2 (FW2), framework element 3 (FW3), or framework element 4 (FW4). In some instances, a number of variant sequences is de novo synthesized for an adenosine A2A receptor binding domain. For example, the number of variant sequences is about 1 to about 10 sequences for the VH domain, about $10^8$ sequences for the adenosine A2A receptor binding domain, and about 1 to about 44 sequences for the VK domain. The number of variant sequences may be at least or about 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, or more than 500 sequences. In some instances, the number of variant sequences is about 10 to 300, 25 to 275, 50 to 250, 75 to 225, 100 to 200, or 125 to 150 sequences.

Adenosine A2A receptor binding libraries comprising de novo synthesized variant sequences encoding for scaffolds comprising adenosine A2A receptor binding domains comprise improved diversity. For example, variants are generated by placing adenosine A2A receptor binding domain variants in immunoglobulin scaffold variants comprising N-terminal CDRH3 variations and C-terminal CDRH3 variations. In some instances, variants include affinity maturation variants. Alternatively or in combination, variants include variants in other regions of the immunoglobulin including, but not limited to, CDRH1, CDRH2, CDRL1, CDRL2, and CDRL3. In some instances, the number of variants of the adenosine A2A receptor binding libraries is least or about $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more than $10^{20}$ non-identical sequences. For example, a library comprising about 10 variant sequences for a VH region, about 237 variant sequences for a CDRH3 region, and about 43 variant sequences for a VL and CDRL3 region comprises $10^5$ non-identical sequences (10×237×43).

Provided herein are libraries comprising nucleic acids encoding for an adenosine A2A receptor antibody comprising variation in at least one region of the antibody, wherein the region is the CDR region. In some instances, the adenosine A2A receptor antibody is a single domain antibody comprising one heavy chain variable domain such as a VHH antibody. In some instances, the VHH antibody comprises variation in one or more CDR regions. In some instances, libraries described herein comprise at least or about 1, 10, 20, 30, 40, 50, 60, 70, 80, 90, 100, 200, 300, 400, 500, 600, 700, 800, 900, 1000, 1200, 1400, 1600, 1800, 2000, 2400, 2600, 2800, 3000, or more than 3000 sequences of a CDR1, CDR2, or CDR3. In some instances, libraries described herein comprise at least or about $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more than $10^{20}$ sequences of a CDR1, CDR2, or CDR3. For example, the libraries comprise at least 2000 sequences of a CDR1, at least 1200 sequences for CDR2, and at least 1600 sequences for CDR3. In some instances, each sequence is non-identical.

In some instances, the CDR1, CDR2, or CDR3 is of a variable domain, light chain (VL). CDR1, CDR2, or CDR3 of a variable domain, light chain (VL) can be referred to as CDRL1, CDRL2, or CDRL3, respectively. In some instances, libraries described herein comprise at least or about 1, 2, 3, 4, 5, 6, 7, 8, 9, 10, 20, 30, 40, 50, 60, 70, 80, 90, 100, 200, 300, 400, 500, 600, 700, 800, 900, 1000, 1200, 1400, 1600, 1800, 2000, 2400, 2600, 2800, 3000, or more than 3000 sequences of a CDR1, CDR2, or CDR3 of the VL. In some instances, libraries described herein comprise at least or about $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more than $10^{20}$ sequences of a CDR1, CDR2, or CDR3 of the VL. For example, the libraries comprise at least 20 sequences of a CDR1 of the VL, at least 4 sequences of a CDR2 of the VL, and at least 140 sequences of a CDR3 of the VL. In some instances, the libraries comprise at least 2 sequences of a CDR1 of the VL, at least 1 sequence of CDR2 of the VL, and at least 3000 sequences of a CDR3 of the VL. In some instances, the VL is IGKV1-39, IGKV1-9, IGKV2-28, IGKV3-11, IGKV3-15, IGKV3-20, IGKV4-1, IGLV1-51, IGLV2-14, IGLV1-40, or IGLV3-1. In some instances, the VL is IGKV2-28. In some instances, the VL is IGLV1-51.

In some instances, the CDR1, CDR2, or CDR3 is of a variable domain, heavy chain (VH). CDR1, CDR2, or CDR3 of a variable domain, heavy chain (VH) can be referred to as CDRH1, CDRH2, or CDRH3, respectively. In some instances, libraries described herein comprise at least or about 1, 2, 3, 4, 5, 6, 7, 8, 9, 10, 20, 30, 40, 50, 60, 70, 80, 90, 100, 200, 300, 400, 500, 600, 700, 800, 900, 1000, 1200, 1400, 1600, 1800, 2000, 2400, 2600, 2800, 3000, or more than 3000 sequences of a CDR1, CDR2, or CDR3 of the VH. In some instances, libraries described herein comprise at least or about $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more than $10^{20}$ sequences of a CDR1, CDR2, or CDR3 of the VH. For example, the libraries comprise at least 30 sequences of a CDR1 of the VH, at least 570 sequences of a CDR2 of the VH, and at least $10^8$ sequences of a CDR3 of the VH. In some instances, the libraries comprise at least 30 sequences of a CDR1 of the VH, at least 860 sequences of a CDR2 of the VH, and at least $10^7$ sequences of a CDR3 of the VH. In some instances, the VH is IGHV1-18, IGHV1-69, IGHV1-8 IGHV3-21, IGHV3-23, IGHV3-30/33m, IGHV3-28, IGHV3-74, IGHV4-39, or IGHV4-59/61. In some instances, the VH is IGHV1-69, IGHV3-30, IGHV3-23, IGHV3, IGHV1-46, IGHV3-7, IGHV1, or IGHV1-8. In some instances, the VH is IGHV1-69 and IGHV3-30. In some instances, the VH is IGHV3-23.

Libraries as described herein, in some embodiments, comprise varying lengths of a CDRL1, CDRL2, CDRL3, CDRH1, CDRH2, or CDRH3. In some instances, the length of the CDRL1, CDRL2, CDRL3, CDRH1, CDRH2, or CDRH3 comprises at least or about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or more than 90 amino acids in length. For example, the CDRH3 comprises at least or about 12, 15, 16, 17, 20, 21, or 23 amino acids in length. In some instances, the CDRL1, CDRL2, CDRL3, CDRH1, CDRH2, or CDRH3 comprises a range of about 1 to about 10, about 5 to about 15, about 10 to about 20, or about 15 to about 30 amino acids in length.

Libraries comprising nucleic acids encoding for antibodies having variant CDR sequences as described herein comprise various lengths of amino acids when translated. In some instances, the length of each of the amino acid fragments or average length of the amino acid synthesized may be at least or about 15, 20, 25, 30, 35, 40, 45, 50, 55, 60, 65, 70, 75, 80, 85, 90, 95, 100, 105, 110, 115, 120, 125, 130, 135, 140, 145, 150, or more than 150 amino acids. In some instances, the length of the amino acid is about 15 to 150, 20 to 145, 25 to 140, 30 to 135, 35 to 130, 40 to 125, 45 to 120, 50 to 115, 55 to 110, 60 to 110, 65 to 105, 70 to 100, or 75 to 95 amino acids. In some instances, the length of the amino acid is about 22 amino acids to about 75 amino acids. In some instances, the antibodies comprise at least or about 100, 200, 300, 400, 500, 600, 700, 800, 900, 1000, 2000, 3000, 4000, 5000, or more than 5000 amino acids.

Ratios of the lengths of a CDRL1, CDRL2, CDRL3, CDRH1, CDRH2, or CDRH3 may vary in libraries described herein. In some instances, a CDRL1, CDRL2, CDRL3, CDRH1, CDRH2, or CDRH3 comprising at least or about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or more than 90 amino acids in length comprises about 10%, 20%, 30%, 40%, 50%, 60%, 70%, 80%, 90%, or more than 90% of the library. For example, a CDRH3 comprising about 23 amino acids in length is present in the library at 40%, a CDRH3 comprising about 21 amino acids in length is present in the library at 30%, a CDRH3 comprising about 17 amino acids in length is present in the library at 20%, and a CDRH3 comprising about 12 amino acids in length is present in the library at 10%. In some instances, a CDRH3 comprising about 20 amino acids in length is present in the library at 40%, a CDRH3 comprising about 16 amino acids in length is present in the library at 30%, a CDRH3 comprising about 15 amino acids in length is present in the library at 20%, and a CDRH3 comprising about 12 amino acids in length is present in the library at 10%.

Libraries as described herein encoding for a VHH antibody comprise variant CDR sequences that are shuffled to generate a library with a theoretical diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more than $10^{20}$ sequences. In some instances, the library has a final library diversity of at least or about $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$, or more than $10^{20}$ sequences.

Provided herein are adenosine A2A receptor binding libraries encoding for an immunoglobulin. In some instances, the adenosine A2A receptor immunoglobulin is an antibody. In some instances, the adenosine A2A receptor immunoglobulin is a VHH antibody. In some instances, the adenosine A2A receptor immunoglobulin comprises a binding affinity (e.g., $K_D$) to adenosine A2A receptor of less than 1 nM, less than 1.2 nM, less than 2 nM, less than 5 nM, less than 10 nM, less than 11 nm, less than 13.5 nM, less than 15 nM, less than 20 nM, less than 25 nM, or less than 30 nM. In some instances, the adenosine A2A receptor immunoglobulin comprises a $K_D$ of less than 1 nM. In some instances, the adenosine A2A receptor immunoglobulin comprises a $K_D$ of less than 1.2 nM. In some instances, the adenosine A2A receptor immunoglobulin comprises a $K_D$ of less than 2 nM. In some instances, the adenosine A2A receptor immunoglobulin comprises a $K_D$ of less than 5 nM. In some instances, the adenosine A2A receptor immunoglobulin comprises a $K_D$ of less than 10 nM. In some instances, the adenosine A2A receptor immunoglobulin comprises a $K_D$ of less than 13.5 nM. In some instances, the adenosine A2A receptor immunoglobulin comprises a $K_D$ of less than 15 nM. In some instances, the adenosine A2A receptor immunoglobulin comprises a $K_D$ of less than 20 nM. In some instances, the adenosine A2A receptor immunoglobulin comprises a $K_D$ of less than 25 nM. In some instances, the adenosine A2A receptor immunoglobulin comprises a $K_D$ of less than 30 nM.

In some instances, the adenosine A2A receptor immunoglobulin is an adenosine A2A receptor agonist. In some instances, the adenosine A2A receptor immunoglobulin is an adenosine A2A receptor antagonist. In some instances, the adenosine A2A receptor immunoglobulin is an adenosine A2A receptor allosteric modulator. In some instances, the allosteric modulator is a negative allosteric modulator. In some instances, the allosteric modulator is a positive allosteric modulator. In some instances, the adenosine A2A receptor immunoglobulin results in agonistic, antagonistic, or allosteric effects at a concentration of at least or about 1 nM, 2 nM, 4 nM, 6 nM, 8 nM, 10 nM, 20 nM, 30 nM, 40 nM, 50 nM, 60 nM, 70 nM, 80 nM, 90 nM, 100 nM, 120 nM, 140 nM, 160 nM, 180 nM, 200 nM, 300 nM, 400 nM, 500 nM, 600 nM, 700 nM, 800 nM, 900 nM, 1000 nM, or more than 1000 nM. In some instances, the adenosine A2A receptor immunoglobulin is a negative allosteric modulator. In some instances, the adenosine A2A receptor immunoglobulin is a negative allosteric modulator at a concentration of at least or about 0.001, 0.005, 0.01, 0.05, 0.1, 0.5, 1 nM, 2 nM, 4 nM, 6 nM, 8 nM, 10 nM, 20 nM, 30 nM, 40 nM, 50 nM, 60 nM, 70 nM, 80 nM, 90 nM, 100 nM, or more than 100 nM. In some instances, the adenosine A2A receptor immunoglobulin is a negative allosteric modulator at a concentration in a range of about 0.001 to about 100, 0.01 to about 90, about 0.1 to about 80, 1 to about 50, about 10 to about 40 nM, or about 1 to about 10 nM. In some instances, the adenosine A2A receptor immunoglobulin comprises an EC50 or IC50 of at least or about 0.001, 0.0025, 0.005, 0.01, 0.025, 0.05, 0.06, 0.07, 0.08, 0.9, 0.1, 0.5, 1, 2, 3, 4, 5, 6, or more than 6 nM. In some instances, the adenosine A2A receptor immunoglobulin comprises an EC50 or IC50 of at least or about 1 nM, 2 nM, 4 nM, 6 nM, 8 nM, 10 nM, 20 nM, 30 nM, 40 nM, 50 nM, 60 nM, 70 nM, 80 nM, 90 nM, 100 nM, or more than 100 nM.

Adenosine A2A receptor immunoglobulins as described herein may comprise improved properties. In some instances, the adenosine A2A receptor immunoglobulins are monomeric. In some instances, the adenosine A2A receptor immunoglobulins are not prone to aggregation. In some instances, at least or about 70%, 75%, 80%, 85%, 90%, 95%, or 99% of the adenosine A2A receptor immunoglobulins are monomeric. In some instances, the adenosine A2A receptor immunoglobulins are thermostable. In some instances, the adenosine A2A receptor immunoglobulins result in reduced non-specific binding.

Following synthesis of adenosine A2A receptor binding libraries comprising nucleic acids encoding scaffolds comprising adenosine A2A receptor binding domains, libraries may be used for screening and analysis. For example, libraries are assayed for library displayability and panning. In some instances, displayability is assayed using a selectable tag. Exemplary tags include, but are not limited to, a radioactive label, a fluorescent label, an enzyme, a chemiluminescent tag, a colorimetric tag, an affinity tag or other labels or tags that are known in the art. In some instances, the tag is histidine, polyhistidine, myc, hemagglutinin (HA), or FLAG. The adenosine A2A receptor binding libraries may comprise nucleic acids encoding scaffolds comprising adenosine A2A receptor binding domains with multiple tags such as GFP, FLAG, and Lucy as well as a DNA barcode. In some instances, libraries are assayed by sequencing using various methods including, but not limited to, single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis.

Expression Systems

Provided herein are libraries comprising nucleic acids encoding for scaffolds comprising adenosine A2A receptor binding domains, wherein the libraries have improved specificity, stability, expression, folding, or downstream activity. In some instances, libraries described herein are used for screening and analysis.

Provided herein are libraries comprising nucleic acids encoding for scaffolds comprising adenosine A2A receptor binding domains, wherein the nucleic acid libraries are used for screening and analysis. In some instances, screening and analysis comprises in vitro, in vivo, or ex vivo assays. Cells for screening include primary cells taken from living subjects or cell lines. Cells may be from prokaryotes (e.g., bacteria and fungi) or eukaryotes (e.g., animals and plants). Exemplary animal cells include, without limitation, those from a mouse, rabbit, primate, and insect. In some instances, cells for screening include a cell line including, but not limited to, Chinese Hamster Ovary (CHO) cell line, human embryonic kidney (HEK) cell line, or baby hamster kidney (BHK) cell line. In some instances, nucleic acid libraries described herein may also be delivered to a multicellular organism. Exemplary multicellular organisms include, without limitation, a plant, a mouse, rabbit, primate, and insect.

Nucleic acid libraries or protein libraries encoded thereof described herein may be screened for various pharmacological or pharmacokinetic properties. In some instances, the libraries are screened using in vitro assays, in vivo assays, or ex vivo assays. For example, in vitro pharmacological or pharmacokinetic properties that are screened include, but are not limited to, binding affinity, binding specificity, and binding avidity. Exemplary in vivo pharmacological or pharmacokinetic properties of libraries described herein that are screened include, but are not limited to, therapeutic efficacy, activity, preclinical toxicity properties, clinical efficacy properties, clinical toxicity properties, immunogenicity, potency, and clinical safety properties.

Pharmacological or pharmacokinetic properties that may be screened include, but are not limited to, cell binding affinity and cell activity. For example, cell binding affinity assays or cell activity assays are performed to determine agonistic, antagonistic, or allosteric effects of libraries described herein. In some instances, the cell activity assay is a cAMP assay. In some instances, libraries as described herein are compared to cell binding or cell activity of ligands of adenosine A2A receptor.

Libraries as described herein may be screened in cell-based assays or in non-cell-based assays. Examples of non-cell-based assays include, but are not limited to, using viral particles, using in vitro translation proteins, and using protealiposomes with adenosine A2A receptor.

Nucleic acid libraries as described herein may be screened by sequencing. In some instances, next generation sequence is used to determine sequence enrichment of adenosine A2A receptor binding variants. In some instances, V gene distribution, J gene distribution, V gene family, CDR3 counts per length, or a combination thereof is determined. In some instances, clonal frequency, clonal accumulation, lineage accumulation, or a combination thereof is determined. In some instances, number of sequences, sequences with VH clones, clones, clones greater than 1, clonotypes, clonotypes greater than 1, lineages, simpsons, or a combination thereof is determined. In some instances, a percentage of non-identical CDR3s is determined. For example, the percentage of non-identical CDR3s is calculated as the number of non-identical CDR3s in a sample divided by the total number of sequences that had a CDR3 in the sample.

Provided herein are nucleic acid libraries, wherein the nucleic acid libraries may be expressed in a vector. Expression vectors for inserting nucleic acid libraries disclosed herein may comprise eukaryotic or prokaryotic expression vectors. Exemplary expression vectors include, without limitation, mammalian expression vectors: pSF-CMV-NEO-NH2-PPT-3XFLAG, pSF-CMV-NEO-COOH-3XFLAG, pSF-CMV-PURO-NH2-GST-TEV, pSF-OXB20-COOH-TEV-FLAG(R)-6His, pCEP4 pDEST27, pSF-CMV-Ub-KrYFP, pSF-CMV-FMDV-daGFP, pEF1a-mCherry-N1 Vector, pEF1a-tdTomato Vector, pSF-CMV-FMDV-Hygro, pSF-CMV-PGK-Puro, pMCP-tag(m), and pSF-CMV-PURO-NH2-CMYC; bacterial expression vectors: pSF-OXB20-BetaGal, pSF-OXB20-Fluc, pSF-OXB20, and pSF-Tac; plant expression vectors: pRI 101-AN DNA and pCambia2301; and yeast expression vectors: pTYB21 and pKLAC2, and insect vectors: pAc5.1/V5-His A and pDEST8. In some instances, the vector is pcDNA3 or pcDNA3.1.

Described herein are nucleic acid libraries that are expressed in a vector to generate a construct comprising a scaffold comprising sequences of adenosine A2A receptor binding domains. In some instances, a size of the construct varies. In some instances, the construct comprises at least or about 500, 600, 700, 800, 900, 1000, 1100, 1300, 1400, 1500, 1600, 1700, 1800, 2000, 2400, 2600, 2800, 3000, 3200, 3400, 3600, 3800, 4000, 4200, 4400, 4600, 4800, 5000, 6000, 7000, 8000, 9000, 10000, or more than 10000 bases. In some instances, a the construct comprises a range of about 300 to 1,000, 300 to 2,000, 300 to 3,000, 300 to 4,000, 300 to 5,000, 300 to 6,000, 300 to 7,000, 300 to 8,000, 300 to 9,000, 300 to 10,000, 1,000 to 2,000, 1,000 to 3,000, 1,000 to 4,000, 1,000 to 5,000, 1,000 to 6,000, 1,000 to 7,000, 1,000 to 8,000, 1,000 to 9,000, 1,000 to 10,000, 2,000 to 3,000, 2,000 to 4,000, 2,000 to 5,000, 2,000 to 6,000, 2,000 to 7,000, 2,000 to 8,000, 2,000 to 9,000, 2,000 to 10,000, 3,000 to 4,000, 3,000 to 5,000, 3,000 to 6,000, 3,000 to 7,000, 3,000 to 8,000, 3,000 to 9,000, 3,000 to 10,000, 4,000 to 5,000, 4,000 to 6,000, 4,000 to 7,000, 4,000 to 8,000, 4,000 to 9,000, 4,000 to 10,000, 5,000 to 6,000, 5,000 to 7,000, 5,000 to 8,000, 5,000 to 9,000, 5,000 to 10,000, 6,000 to 7,000, 6,000 to 8,000, 6,000 to 9,000, 6,000 to 10,000, 7,000 to 8,000, 7,000 to 9,000, 7,000 to 10,000, 8,000 to 9,000, 8,000 to 10,000, or 9,000 to 10,000 bases.

Provided herein are libraries comprising nucleic acids encoding for scaffolds comprising adenosine A2A receptor binding domains, wherein the nucleic acid libraries are expressed in a cell. In some instances, the libraries are synthesized to express a reporter gene. Exemplary reporter genes include, but are not limited to, acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), cerulean fluorescent protein, citrine fluorescent protein, orange fluorescent protein, cherry fluorescent protein, turquoise fluorescent protein, blue fluorescent protein, horseradish peroxidase (HRP), luciferase (Luc), nopaline synthase (NOS), octopine synthase (OCS), luciferase, and derivatives thereof. Methods to determine modulation of a reporter gene are well known in the art, and include, but are not limited to, fluorometric methods (e.g. fluorescence spectroscopy, Fluorescence Activated Cell Sorting (FACS), fluorescence microscopy), and antibiotic resistance determination.

Diseases and Disorders

Provided herein are adenosine A2A receptor binding libraries comprising nucleic acids encoding for scaffolds comprising adenosine A2A receptor binding domains that may have therapeutic effects. In some instances, the adenosine A2A receptor binding libraries result in protein when translated that is used to treat a disease or disorder. In some instances, the protein is an immunoglobulin. In some instances, the protein is a peptidomimetic. Exemplary diseases include, but are not limited to, cancer, inflammatory diseases or disorders, a metabolic disease or disorder, a cardiovascular disease or disorder, a respiratory disease or disorder, pain, a digestive disease or disorder, a reproductive disease or disorder, an endocrine disease or disorder, or a neurological disease or disorder. In some instances, the neurological disease or disorder is a neurodegenerative disease or disorder. In some instances, the neurological disease or disorder is Parkinson's disease, Alzheimer's disease, or multiple sclerosis. In some instances, the cancer is a solid cancer or a hematologic cancer. In some instances, the A2AR immunoglobulins described herein are used as a monotherapy for treating cancer. In some instances, the A2AR immunoglobulins described herein are used in combination with other therapeutic agents for treating cancer. In some instances, the A2AR immunoglobulins described herein enhance tumor vaccines, checkpoint blockade and adoptive T cell therapy. In some instances, an inhibitor of adenosine A2A receptor as described herein is used for treatment of a disease or disorder of the central nervous system, kidney, intestine, lung, hair, skin, bone, or cartilage.

In some instances, an inhibitor of adenosine A2A receptor as described herein is used for sleep regulation, angiogenesis, or modulation of the immune system. In some instances, the subject is a mammal. In some instances, the subject is a mouse, rabbit, dog, or human. Subjects treated by methods described herein may be infants, adults, or children. Pharmaceutical compositions comprising antibodies or antibody fragments as described herein may be administered intravenously or subcutaneously.

Variant Libraries

Codon Variation

Variant nucleic acid libraries described herein may comprise a plurality of nucleic acids, wherein each nucleic acid encodes for a variant codon sequence compared to a reference nucleic acid sequence. In some instances, each nucleic acid of a first nucleic acid population contains a variant at a single variant site. In some instances, the first nucleic acid population contains a plurality of variants at a single variant site such that the first nucleic acid population contains more than one variant at the same variant site. The first nucleic acid population may comprise nucleic acids collectively encoding multiple codon variants at the same variant site. The first nucleic acid population may comprise nucleic acids collectively encoding up to 19 or more codons at the same position. The first nucleic acid population may comprise nucleic acids collectively encoding up to 60 variant triplets at the same position, or the first nucleic acid population may comprise nucleic acids collectively encoding up to 61 different triplets of codons at the same position. Each variant may encode for a codon that results in a different amino acid during translation. Table 3 provides a listing of each codon possible (and the representative amino acid) for a variant site.

TABLE 2

List of codons and amino acids

| Amino Acids | One letter code | Three letter code | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Iso | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

A nucleic acid population may comprise varied nucleic acids collectively encoding up to 20 codon variations at multiple positions. In such cases, each nucleic acid in the population comprises variation for codons at more than one position in the same nucleic acid. In some instances, each nucleic acid in the population comprises variation for codons at 1, 2, 3, 4, 5, 6, 7, 8, 9, 10, 11, 12, 13, 14, 15, 16, 17, 18, 19, 20 or more codons in a single nucleic acid. In some instances, each variant long nucleic acid comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single long nucleic acid. In some instances, the variant nucleic acid population comprises variation for codons at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more codons in a single nucleic acid. In some instances, the variant nucleic acid population comprises variation for codons in at least about 10, 20, 30, 40, 50, 60, 70, 80, 90, 100 or more codons in a single long nucleic acid.

Highly Parallel Nucleic Acid Synthesis

Provided herein is a platform approach utilizing miniaturization, parallelization, and vertical integration of the end-to-end process from polynucleotide synthesis to gene assembly within nanowells on silicon to create a revolutionary synthesis platform. Devices described herein provide, with the same footprint as a 96-well plate, a silicon synthesis platform is capable of increasing throughput by a factor of up to 1,000 or more compared to traditional synthesis methods, with production of up to approximately 1,000,000 or more polynucleotides, or 10,000 or more genes in a single highly-parallelized run.

With the advent of next-generation sequencing, high resolution genomic data has become an important factor for studies that delve into the biological roles of various genes in both normal biology and disease pathogenesis. At the core of this research is the central dogma of molecular biology and the concept of "residue-by-residue transfer of sequential information." Genomic information encoded in the DNA is transcribed into a message that is then translated into the protein that is the active product within a given biological pathway.

Another exciting area of study is on the discovery, development and manufacturing of therapeutic molecules focused on a highly-specific cellular target. High diversity DNA sequence libraries are at the core of development pipelines for targeted therapeutics. Gene mutants are used to express proteins in a design, build, and test protein engineering cycle that ideally culminates in an optimized gene for high expression of a protein with high affinity for its therapeutic target. As an example, consider the binding pocket of a receptor. The ability to test all sequence permutations of all residues within the binding pocket simultaneously will allow for a thorough exploration, increasing chances of success. Saturation mutagenesis, in which a researcher attempts to generate all possible mutations at a specific site within the receptor, represents one approach to this development challenge. Though costly and time and labor-intensive, it enables each variant to be introduced into each position. In contrast, combinatorial mutagenesis, where a few selected positions or short stretch of DNA may be modified extensively, generates an incomplete repertoire of variants with biased representation.

To accelerate the drug development pipeline, a library with the desired variants available at the intended frequency in the right position available for testing—in other words, a precision library, enables reduced costs as well as turnaround time for screening. Provided herein are methods for synthesizing nucleic acid synthetic variant libraries which provide for precise introduction of each intended variant at the desired frequency. To the end user, this translates to the ability to not only thoroughly sample sequence space but also be able to query these hypotheses in an efficient manner, reducing cost and screening time. Genome-wide editing can elucidate important pathways, libraries where each variant and sequence permutation can be tested for optimal functionality, and thousands of genes can be used to reconstruct entire pathways and genomes to re-engineer biological systems for drug discovery.

In a first example, a drug itself can be optimized using methods described herein. For example, to improve a specified function of an antibody, a variant polynucleotide library encoding for a portion of the antibody is designed and synthesized. A variant nucleic acid library for the antibody can then be generated by processes described herein (e.g., PCR mutagenesis followed by insertion into a vector). The antibody is then expressed in a production cell line and screened for enhanced activity. Example screens include examining modulation in binding affinity to an antigen, stability, or effector function (e.g., ADCC, complement, or apoptosis). Exemplary regions to optimize the antibody include, without limitation, the Fc region, Fab region, variable region of the Fab region, constant region of the Fab region, variable domain of the heavy chain or light chain (VH or VL), and specific complementarity-determining regions (CDRs) of VII or VL.

Nucleic acid libraries synthesized by methods described herein may be expressed in various cells associated with a disease state. Cells associated with a disease state include cell lines, tissue samples, primary cells from a subject, cultured cells expanded from a subject, or cells in a model system. Exemplary model systems include, without limitation, plant and animal models of a disease state.

To identify a variant molecule associated with prevention, reduction or treatment of a disease state, a variant nucleic acid library described herein is expressed in a cell associated with a disease state, or one in which a cell a disease state can be induced. In some instances, an agent is used to induce a disease state in cells. Exemplary tools for disease state induction include, without limitation, a Cre/Lox recombination system, LPS inflammation induction, and streptozotocin to induce hypoglycemia. The cells associated with a disease state may be cells from a model system or cultured cells, as well as cells from a subject having a particular disease condition. Exemplary disease conditions include a bacterial, fungal, viral, autoimmune, or proliferative disorder (e.g., cancer). In some instances, the variant nucleic acid library is expressed in the model system, cell line, or primary cells derived from a subject, and screened for changes in at least one cellular activity. Exemplary cellular activities include, without limitation, proliferation, cycle progression, cell death, adhesion, migration, reproduction, cell signaling, energy production, oxygen utilization, metabolic activity, and aging, response to free radical damage, or any combination thereof Substrates Devices used as a surface for polynucleotide synthesis may be in the form of substrates which include, without limitation, homogenous array surfaces, patterned array surfaces, channels, beads, gels, and the like. Provided herein are substrates comprising a plurality of clusters, wherein each cluster comprises a plurality of loci that support the attachment and synthesis of polynucleotides. In some instances, substrates comprise a homogenous array surface. For example, the homogenous array surface is a homogenous plate. The term "locus" as used herein refers to a discrete region on a structure which provides support for polynucleotides encoding for a single predetermined sequence to extend from the surface. In some instances, a locus is on a two dimensional surface, e.g., a substantially planar surface. In some instances, a locus is on a three-dimensional surface, e.g., a well, microwell, channel, or post. In some instances, a surface of a locus comprises a material that is actively functionalized to attach to at least one nucleotide for polynucleotide synthesis, or preferably, a population of identical nucleotides for synthesis of a population of polynucleotides. In some instances, polynucleotide refers to a population of polynucleotides encoding for the same nucleic acid sequence. In some cases, a surface of a substrate is inclusive of one or a plurality of surfaces of a substrate. The average error rates for polynucleotides synthesized within a library described here using the systems and methods provided are often less than 1 in 1000, less than about 1 in 2000, less than about 1 in 3000 or less often without error correction.

Provided herein are surfaces that support the parallel synthesis of a plurality of polynucleotides having different predetermined sequences at addressable locations on a common support. In some instances, a substrate provides support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the surfaces provide support for the synthesis of more than 50, 100, 200, 400, 600, 800, 1000, 1200, 1400, 1600, 1800, 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the substrate provides a surface environment for the growth of polynucleotides having at least 80, 90, 100, 120, 150, 175, 200, 225, 250, 275, 300, 325, 350, 375, 400, 425, 450, 475, 500 bases or more.

Provided herein are methods for polynucleotide synthesis on distinct loci of a substrate, wherein each locus supports the synthesis of a population of polynucleotides. In some cases, each locus supports the synthesis of a population of polynucleotides having a different sequence than a population of polynucleotides grown on another locus. In some instances, each polynucleotide sequence is synthesized with 1, 2, 3, 4, 5, 6, 7, 8, 9 or more redundancy across different loci within the same cluster of loci on a surface for polynucleotide synthesis. In some instances, the loci of a substrate are located within a plurality of clusters. In some instances, a substrate comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a substrate comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some instances, a substrate comprises about 10,000 distinct loci. The amount of loci within a single cluster is varied in different instances. In some cases, each cluster includes 1, 2, 3, 4, 5, 6, 7, 8, 9, 10, 20, 30, 40, 50, 60, 70, 80, 90, 100, 120, 130, 150, 200, 300, 400, 500 or more loci. In some instances, each cluster includes about 50-500 loci. In some instances, each cluster includes about 100-200 loci. In some instances, each cluster includes about 100-150 loci. In some instances, each cluster includes about 109, 121, 130 or 137 loci. In some instances, each cluster includes about 19, 20, 61, 64 or more loci. Alternatively or in combination, polynucleotide synthesis occurs on a homogenous array surface.

In some instances, the number of distinct polynucleotides synthesized on a substrate is dependent on the number of distinct loci available in the substrate. In some instances, the density of loci within a cluster or surface of a substrate is at least or about 1, 10, 25, 50, 65, 75, 100, 130, 150, 175, 200, 300, 400, 500, 1,000 or more loci per $mm^2$. In some cases, a substrate comprises 10-500, 25-400, 50-500, 100-500, 150-500, 10-250, 50-250, 10-200, or 50-200 $mm^2$. In some instances, the distance between the centers of two adjacent loci within a cluster or surface is from about 10-500, from about 10-200, or from about 10-100 um. In some instances, the distance between two centers of adjacent loci is greater than about 10, 20, 30, 40, 50, 60, 70, 80, 90 or 100 um. In some instances, the distance between the centers of two adjacent loci is less than about 200, 150, 100, 80, 70, 60, 50, 40, 30, 20 or 10 um. In some instances, each locus has a width of about 0.5, 1, 2, 3, 4, 5, 6, 7, 8, 9, 10, 20, 30, 40, 50, 60, 70, 80, 90 or 100 um. In some cases, each locus has a width of about 0.5-100, 0.5-50, 10-75, or 0.5-50 um.

In some instances, the density of clusters within a substrate is at least or about 1 cluster per 100 $mm^2$, 1 cluster per 10 $mm^2$, 1 cluster per 5 $mm^2$, 1 cluster per 4 $mm^2$, 1 cluster per 3 $mm^2$, 1 cluster per 2 $mm^2$, 1 cluster per 1 $mm^2$, 2 clusters per 1 $mm^2$, 3 clusters per 1 $mm^2$, 4 clusters per 1 $mm^2$, 5 clusters per 1 $mm^2$, 10 clusters per 1 $mm^2$, 50 clusters per 1 $mm^2$ or more. In some instances, a substrate comprises from about 1 cluster per 10 $mm^2$ to about 10 clusters per 1 $mm^2$. In some instances, the distance between the centers of two adjacent clusters is at least or about 50, 100, 200, 500, 1000, 2000, or 5000 um. In some cases, the distance between the centers of two adjacent clusters is between about 50-100, 50-200, 50-300, 50-500, and 100-2000 um. In some cases, the distance between the centers of two adjacent clusters is between about 0.05-50, 0.05-10, 0.05-5, 0.05-4, 0.05-3, 0.05-2, 0.1-10, 0.2-10, 0.3-10, 0.4-10, 0.5-10, 0.5-5, or 0.5-2 mm. In some cases, each cluster has a cross section of about 0.5 to about 2, about 0.5 to about 1, or about 1 to about 2 mm. In some cases, each cluster has a cross section of about 0.5, 0.6, 0.7, 0.8, 0.9, 1, 1.1, 1.2, 1.3, 1.4, 1.5, 1.6, 1.7, 1.8, 1.9 or 2 mm. In some cases, each cluster has an interior cross section of about 0.5, 0.6, 0.7, 0.8, 0.9, 1, 1.1, 1.15, 1.2, 1.3, 1.4, 1.5, 1.6, 1.7, 1.8, 1.9 or 2 mm.

In some instances, a substrate is about the size of a standard 96 well plate, for example between about 100 and about 200 mm by between about 50 and about 150 mm. In some instances, a substrate has a diameter less than or equal to about 1000, 500, 450, 400, 300, 250, 200, 150, 100 or 50 mm. In some instances, the diameter of a substrate is between about 25-1000, 25-800, 25-600, 25-500, 25-400, 25-300, or 25-200 mm. In some instances, a substrate has a planar surface area of at least about 100; 200; 500; 1,000; 2,000; 5,000; 10,000; 12,000; 15,000; 20,000; 30,000; 40,000; 50,000 $mm^2$ or more. In some instances, the thickness of a substrate is between about 50-2000, 50-1000, 100-1000, 200-1000, or 250-1000 mm.

Surface Materials

Substrates, devices, and reactors provided herein are fabricated from any variety of materials suitable for the methods, compositions, and systems described herein. In certain instances, substrate materials are fabricated to exhibit a low level of nucleotide binding. In some instances, substrate materials are modified to generate distinct surfaces that exhibit a high level of nucleotide binding. In some instances, substrate materials are transparent to visible and/or UV light. In some instances, substrate materials are sufficiently conductive, e.g., are able to form uniform electric fields across all or a portion of a substrate. In some instances, conductive materials are connected to an electric ground. In some instances, the substrate is heat conductive or insulated. In some instances, the materials are chemical resistant and heat resistant to support chemical or biochemical reactions, for example polynucleotide synthesis reaction processes. In some instances, a substrate comprises flexible materials. For flexible materials, materials can include, without limitation: nylon, both modified and unmodified, nitrocellulose, polypropylene, and the like. In some instances, a substrate comprises rigid materials. For rigid materials, materials can include, without limitation: glass; fuse silica; silicon, plastics (for example polytetraflouroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

Surface Architecture

Provided herein are substrates for the methods, compositions, and systems described herein, wherein the substrates have a surface architecture suitable for the methods, compositions, and systems described herein. In some instances, a substrate comprises raised and/or lowered features. One benefit of having such features is an increase in surface area to support polynucleotide synthesis. In some instances, a substrate having raised and/or lowered features is referred to as a three-dimensional substrate. In some cases, a three-dimensional substrate comprises one or more channels. In some cases, one or more loci comprise a channel. In some cases, the channels are accessible to reagent deposition via a deposition device such as a material deposition device. In some cases, reagents and/or fluids collect in a larger well in fluid communication one or more channels. For example, a substrate comprises a plurality of channels corresponding to a plurality of loci with a cluster, and the plurality of channels are in fluid communication with one well of the cluster. In some methods, a library of polynucleotides is synthesized in a plurality of loci of a cluster.

Provided herein are substrates for the methods, compositions, and systems described herein, wherein the substrates are configured for polynucleotide synthesis. In some instances, the structure is configured to allow for controlled flow and mass transfer paths for polynucleotide synthesis on a surface. In some instances, the configuration of a substrate allows for the controlled and even distribution of mass transfer paths, chemical exposure times, and/or wash efficacy during polynucleotide synthesis. In some instances, the configuration of a substrate allows for increased sweep efficiency, for example by providing sufficient volume for a growing polynucleotide such that the excluded volume by the growing polynucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing the polynucleotide. In some instances, a three-dimensional structure allows for managed flow of fluid to allow for the rapid exchange of chemical exposure.

Provided herein are substrates for the methods, compositions, and systems described herein, wherein the substrates comprise structures suitable for the methods, compositions, and systems described herein. In some instances, segregation is achieved by physical structure. In some instances, segregation is achieved by differential functionalization of the surface generating active and passive regions for polynucleotide synthesis. In some instances, differential functionalization is achieved by alternating the hydrophobicity across the substrate surface, thereby creating water contact angle effects that cause beading or wetting of the deposited reagents. Employing larger structures can decrease splashing and cross-contamination of distinct polynucleotide synthesis locations with reagents of the neighboring spots. In some cases, a device, such as a material deposition device, is used to deposit reagents to distinct polynucleotide synthesis locations. Substrates having three-dimensional features are configured in a manner that allows for the synthesis of a large number of polynucleotides (e.g., more than about 10,000) with a low error rate (e.g., less than about 1:500, 1:1000, 1:1500, 1:2,000, 1:3,000, 1:5,000, or 1:10,000). In some cases, a substrate comprises features with a density of about or greater than about 1, 5, 10, 20, 30, 40, 50, 60, 70, 80, 100, 110, 120, 130, 140, 150, 160, 170, 180, 190, 200, 300, 400 or 500 features per $mm^2$.

A well of a substrate may have the same or different width, height, and/or volume as another well of the substrate. A channel of a substrate may have the same or different width, height, and/or volume as another channel of the substrate. In some instances, the diameter of a cluster or the diameter of a well comprising a cluster, or both, is between about 0.05-50, 0.05-10, 0.05-5, 0.05-4, 0.05-3, 0.05-2, 0.05-1, 0.05-0.5, 0.05-0.1, 0.1-10, 0.2-10, 0.3-10, 0.4-10, 0.5-10, 0.5-5, or 0.5-2 mm. In some instances, the diameter of a cluster or well or both is less than or about 5, 4, 3, 2, 1, 0.5, 0.1, 0.09, 0.08, 0.07, 0.06, or 0.05 mm. In some instances, the diameter of a cluster or well or both is between about 1.0 and 1.3 mm. In some instances, the diameter of a cluster or well, or both is about 1.150 mm. In some instances, the diameter of a cluster or well, or both is about 0.08 mm. The diameter of a cluster refers to clusters within a two-dimensional or three-dimensional substrate.

In some instances, the height of a well is from about 20-1000, 50-1000, 100-1000, 200-1000, 300-1000, 400-1000, or 500-1000 um. In some cases, the height of a well is less than about 1000, 900, 800, 700, or 600 um.

In some instances, a substrate comprises a plurality of channels corresponding to a plurality of loci within a cluster, wherein the height or depth of a channel is 5-500, 5-400, 5-300, 5-200, 5-100, 5-50, or 10-50 um. In some cases, the height of a channel is less than 100, 80, 60, 40, or 20 um.

In some instances, the diameter of a channel, locus (e.g., in a substantially planar substrate) or both channel and locus (e.g., in a three-dimensional substrate wherein a locus corresponds to a channel) is from about 1-1000, 1-500, 1-200, 1-100, 5-100, or 10-100 um, for example, about 90, 80, 70, 60, 50, 40, 30, 20 or 10 um. In some instances, the diameter of a channel, locus, or both channel and locus is less than about 100, 90, 80, 70, 60, 50, 40, 30, 20 or 10 um. In some instances, the distance between the center of two adjacent channels, loci, or channels and loci is from about 1-500, 1-200, 1-100, 5-200, 5-100, 5-50, or 5-30, for example, about 20 um.

Surface Modifications

Provided herein are methods for polynucleotide synthesis on a surface, wherein the surface comprises various surface modifications. In some instances, the surface modifications are employed for the chemical and/or physical alteration of a surface by an additive or subtractive process to change one or more chemical and/or physical properties of a substrate surface or a selected site or region of a substrate surface. For example, surface modifications include, without limitation, (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

In some cases, the addition of a chemical layer on top of a surface (referred to as adhesion promoter) facilitates structured patterning of loci on a surface of a substrate. Exemplary surfaces for application of adhesion promotion include, without limitation, glass, silicon, silicon dioxide and silicon nitride. In some cases, the adhesion promoter is a chemical with a high surface energy. In some instances, a second chemical layer is deposited on a surface of a substrate. In some cases, the second chemical layer has a low surface energy. In some cases, surface energy of a chemical layer coated on a surface supports localization of droplets on the surface. Depending on the patterning arrangement selected, the proximity of loci and/or area of fluid contact at the loci are alterable.

In some instances, a substrate surface, or resolved loci, onto which nucleic acids or other moieties are deposited, e.g., for polynucleotide synthesis, are smooth or substantially planar (e.g., two-dimensional) or have irregularities, such as raised or lowered features (e.g., three-dimensional features). In some instances, a substrate surface is modified with one or more different layers of compounds. Such modification layers of interest include, without limitation, inorganic and organic layers such as metals, metal oxides, polymers, small organic molecules and the like.

In some instances, resolved loci of a substrate are functionalized with one or more moieties that increase and/or decrease surface energy. In some cases, a moiety is chemically inert. In some cases, a moiety is configured to support a desired chemical reaction, for example, one or more processes in a polynucleotide synthesis reaction. The surface energy, or hydrophobicity, of a surface is a factor for determining the affinity of a nucleotide to attach onto the surface. In some instances, a method for substrate functionalization comprises: (a) providing a substrate having a surface that comprises silicon dioxide; and (b) silanizing the surface using, a suitable silanizing agent described herein or otherwise known in the art, for example, an organofunctional alkoxysilane molecule. Methods and functionalizing agents are described in U.S. Pat. No. 5,474,796, which is herein incorporated by reference in its entirety.

In some instances, a substrate surface is functionalized by contact with a derivatizing composition that contains a mixture of silanes, under reaction conditions effective to couple the silanes to the substrate surface, typically via reactive hydrophilic moieties present on the substrate surface. Silanization generally covers a surface through self-assembly with organofunctional alkoxysilane molecules. A variety of siloxane functionalizing reagents can further be used as currently known in the art, e.g., for lowering or increasing surface energy. The organofunctional alkoxysilanes are classified according to their organic functions.

Polynucleotide Synthesis

Methods of the current disclosure for polynucleotide synthesis may include processes involving phosphoramidite chemistry. In some instances, polynucleotide synthesis comprises coupling a base with phosphoramidite. Polynucleotide synthesis may comprise coupling a base by deposition of phosphoramidite under coupling conditions, wherein the same base is optionally deposited with phosphoramidite more than once, i.e., double coupling. Polynucleotide synthesis may comprise capping of unreacted sites. In some instances, capping is optional. Polynucleotide synthesis may also comprise oxidation or an oxidation step or oxidation steps. Polynucleotide synthesis may comprise deblocking, detritylation, and sulfurization. In some instances, polynucleotide synthesis comprises either oxidation or sulfurization. In some instances, between one or each step during a polynucleotide synthesis reaction, the device is washed, for example, using tetrazole or acetonitrile. Time frames for any one step in a phosphoramidite synthesis method may be less than about 2 min, 1 min, 50 sec, 40 sec, 30 sec, 20 sec and 10 sec.

Polynucleotide synthesis using a phosphoramidite method may comprise a subsequent addition of a phosphoramidite building block (e.g., nucleoside phosphoramidite) to a growing polynucleotide chain for the formation of a phosphite triester linkage. Phosphoramidite polynucleotide synthesis proceeds in the 3' to 5' direction. Phosphoramidite polynucleotide synthesis allows for the controlled addition of one nucleotide to a growing nucleic acid chain per synthesis cycle. In some instances, each synthesis cycle comprises a coupling step. Phosphoramidite coupling involves the formation of a phosphite triester linkage between an activated nucleoside phosphoramidite and a nucleoside bound to the substrate, for example, via a linker. In some instances, the nucleoside phosphoramidite is provided to the device activated. In some instances, the nucleoside phosphoramidite is provided to the device with an activator. In some instances, nucleoside phosphoramidites are provided to the device in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition of a nucleoside phosphoramidite, the device is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the device is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step is useful to block unreacted substrate-bound 5'-OH groups after coupling from further chain elongation, preventing the formation of polynucleotides with internal base deletions. Further, phosphoramidites activated with 1H-tetrazole may react, to a small extent, with the O6 position of guanosine. Without being bound by theory, upon oxidation with 12/water, this side product, possibly via O6-N7 migration, may undergo depurination. The apurinic sites may end up being cleaved in the course of the final deprotection of the polynucleotide thus reducing the yield of the full-length product. The O6 modifications may be removed by treatment with the capping reagent prior to oxidation with 12/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the device is optionally washed.

In some instances, following addition of a nucleoside phosphoramidite, and optionally after capping and one or more wash steps, the device bound growing nucleic acid is oxidized. The oxidation step comprises the phosphite triester is oxidized into a tetracoordinated phosphate triester, a protected precursor of the naturally occurring phosphate diester internucleoside linkage. In some instances, oxidation of the growing polynucleotide is achieved by treatment with iodine and water, optionally in the presence of a weak base (e.g., pyridine, lutidine, collidine). Oxidation may be carried out under anhydrous conditions using, e.g. tert-Butyl hydroperoxide or (1S)-(+)-(10-camphorsulfonyl)-oxaziridine (CSO). In some methods, a capping step is performed following oxidation. A second capping step allows for device drying, as residual water from oxidation that may persist can inhibit subsequent coupling. Following oxidation, the device and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including but not limited to 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, the protected 5' end of the device bound growing polynucleotide is removed so that the primary hydroxyl group is reactive with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound polynucleotide and thus reduces the yield of the desired full-length product. Methods and compositions of the disclosure described herein provide for controlled deblocking conditions limiting undesired depurination reactions. In some instances, the device bound polynucleotide is washed after deblocking. In some instances, efficient washing after deblocking contributes to synthesized polynucleotides having a low error rate.

Methods for the synthesis of polynucleotides typically involve an iterating sequence of the following steps: application of a protected monomer to an actively functionalized surface (e.g., locus) to link with either the activated surface, a linker or with a previously deprotected monomer; deprotection of the applied monomer so that it is reactive with a subsequently applied protected monomer; and application of another protected monomer for linking. One or more intermediate steps include oxidation or sulfurization. In some instances, one or more wash steps precede or follow one or all of the steps.

Methods for phosphoramidite-based polynucleotide synthesis comprise a series of chemical steps. In some instances, one or more steps of a synthesis method involve reagent cycling, where one or more steps of the method comprise application to the device of a reagent useful for the step. For example, reagents are cycled by a series of liquid deposition and vacuum drying steps. For substrates comprising three-dimensional features such as wells, microwells, channels and the like, reagents are optionally passed through one or more regions of the device via the wells and/or channels.

Methods and systems described herein relate to polynucleotide synthesis devices for the synthesis of polynucleotides. The synthesis may be in parallel. For example, at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 75000, 100000 or more polynucleotides can be synthesized in parallel. The total number polynucleotides that may be synthesized in parallel may be from 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150, 22-100, 23-50, 24-45, 25-40, 30-35. Those of skill in the art appreciate that the total number of polynucleotides synthesized in parallel may fall within any range bound by any of these values, for example 25-100. The total number of polynucleotides synthesized in parallel may fall within any range defined by any of the values serving as endpoints of the range. Total molar mass of polynucleotides synthesized within the device or the molar mass of each of the polynucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the polynucleotides or average length of the polynucleotides within the device may be at least or about at least 10, 15, 20, 25, 30, 35, 40, 45, 50, 100, 150, 200, 300, 400, 500 nucleotides, or more. The length of each of the polynucleotides or average length of the polynucleotides within the device may be at most or about at most 500, 400, 300, 200, 150, 100, 50, 45, 35, 30, 25, 20, 19, 18, 17, 16, 15, 14, 13, 12, 11, 10 nucleotides, or less. The length of each of the polynucleotides or average length of the polynucleotides within the device may fall from 10-500, 9-400, 11-300, 12-200, 13-150, 14-100, 15-50, 16-45, 17-40, 18-35, 19-25. Those of skill in the art appreciate that the length of each of the polynucleotides or average length of the polynucleotides within the device may fall within any range bound by any of these values, for example 100-300. The length of each of the polynucleotides or average length of the polynucleotides within the device may fall within any range defined by any of the values serving as endpoints of the range.

Methods for polynucleotide synthesis on a surface provided herein allow for synthesis at a fast rate. As an example, at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more are synthesized. Nucleotides include adenine, guanine, thymine, cytosine, uridine building blocks, or analogs/modified versions thereof. In some instances, libraries of polynucleotides are synthesized in parallel on substrate. For example, a device comprising about or at least about 100; 1,000; 10,000; 30,000; 75,000; 100,000; 1,000,000; 2,000,000; 3,000,000; 4,000,000; or 5,000,000 resolved loci is able to support the synthesis of at least the same number of distinct polynucleotides, wherein polynucleotide encoding a distinct sequence is synthesized on a resolved locus. In some instances, a library of polynucleotides is synthesized on a device with low error rates described herein in less than about three months, two months, one month, three weeks, 15, 14, 13, 12, 11, 10, 9, 8, 7, 6, 5, 4, 3, 2 days, 24 hours or less. In some instances, larger nucleic acids assembled from a polynucleotide library synthesized with low error rate using the substrates and methods described herein are prepared in less than about three months, two months, one month, three weeks, 15, 14, 13, 12, 11, 10, 9, 8, 7, 6, 5, 4, 3, 2 days, 24 hours or less.

In some instances, methods described herein provide for generation of a library of nucleic acids comprising variant nucleic acids differing at a plurality of codon sites. In some instances, a nucleic acid may have 1 site, 2 sites, 3 sites, 4 sites, 5 sites, 6 sites, 7 sites, 8 sites, 9 sites, 10 sites, 11 sites, 12 sites, 13 sites, 14 sites, 15 sites, 16 sites, 17 sites 18 sites, 19 sites, 20 sites, 30 sites, 40 sites, 50 sites, or more of variant codon sites.

In some instances, the one or more sites of variant codon sites may be adjacent. In some instances, the one or more sites of variant codon sites may not be adjacent and separated by 1, 2, 3, 4, 5, 6, 7, 8, 9, 10, or more codons.

In some instances, a nucleic acid may comprise multiple sites of variant codon sites, wherein all the variant codon sites are adjacent to one another, forming a stretch of variant codon sites. In some instances, a nucleic acid may comprise multiple sites of variant codon sites, wherein none the variant codon sites are adjacent to one another. In some instances, a nucleic acid may comprise multiple sites of variant codon sites, wherein some the variant codon sites are adjacent to one another, forming a stretch of variant codon sites, and some of the variant codon sites are not adjacent to one another.

Figure 3:
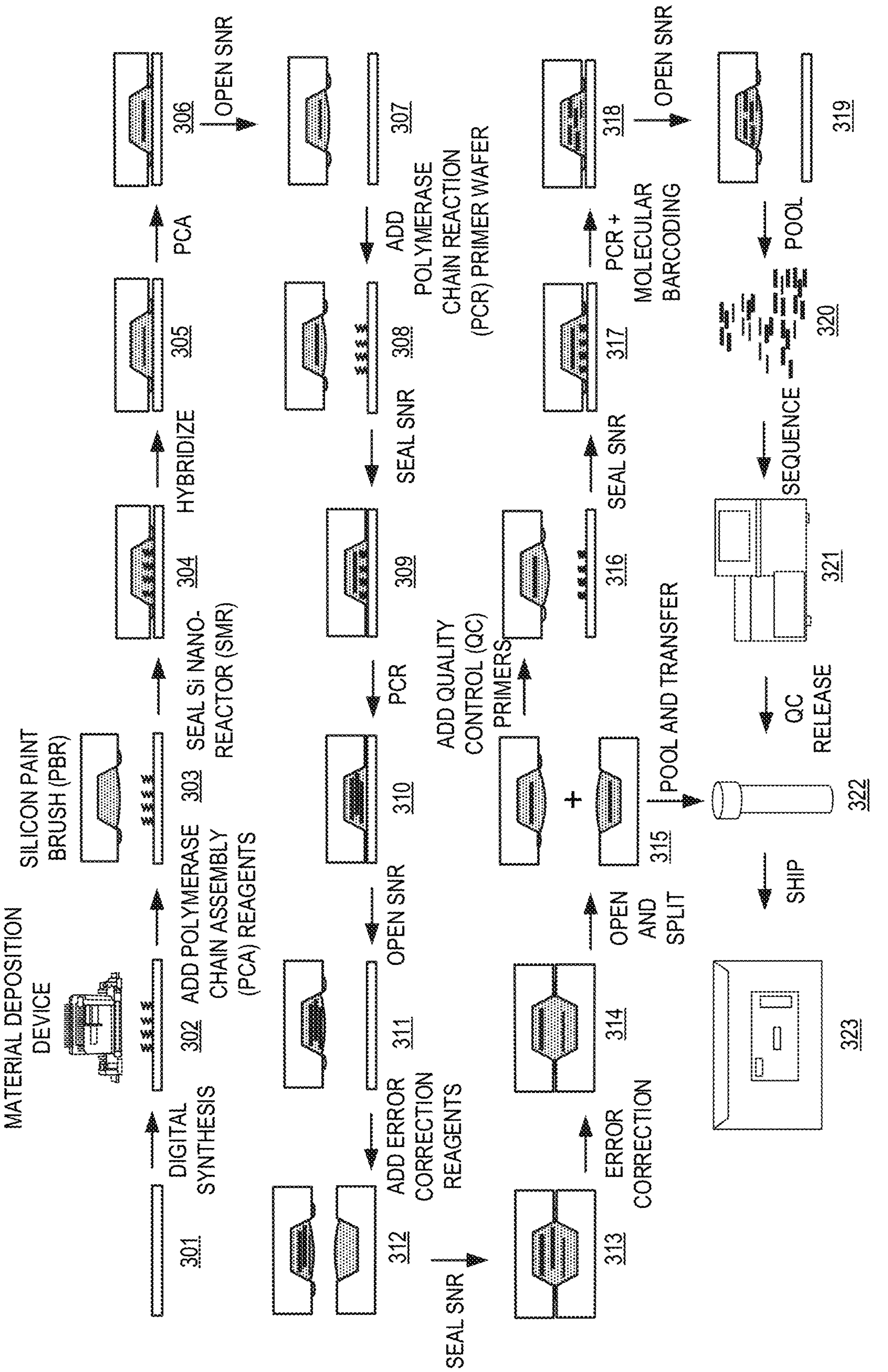
FIG. 3 presents a diagram of steps demonstrating an exemplary process workflow for gene synthesis as disclosed herein.

Referring to the Figures, FIG. 3 illustrates an exemplary process workflow for synthesis of nucleic acids (e.g., genes) from shorter nucleic acids. The workflow is divided generally into phases: (1) de novo synthesis of a single stranded nucleic acid library, (2) joining nucleic acids to form larger fragments, (3) error correction, (4) quality control, and (5) shipment. Prior to de novo synthesis, an intended nucleic acid sequence or group of nucleic acid sequences is preselected. For example, a group of genes is preselected for generation.

Once large nucleic acids for generation are selected, a predetermined library of nucleic acids is designed for de novo synthesis. Various suitable methods are known for generating high density polynucleotide arrays. In the workflow example, a device surface layer is provided. In the example, chemistry of the surface is altered in order to improve the polynucleotide synthesis process. Areas of low surface energy are generated to repel liquid while areas of high surface energy are generated to attract liquids. The surface itself may be in the form of a planar surface or contain variations in shape, such as protrusions or microwells which increase surface area. In the workflow example, high surface energy molecules selected serve a dual function of supporting DNA chemistry, as disclosed in International Patent Application Publication WO/2015/021080, which is herein incorporated by reference in its entirety.

In situ preparation of polynucleotide arrays is generated on a solid support and utilizes single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 302. In some instances, polynucleotides are cleaved from the surface at this stage. Cleavage includes gas cleavage, e.g., with ammonia or methylamine.

The generated polynucleotide libraries are placed in a reaction chamber. In this exemplary workflow, the reaction chamber (also referred to as "nanoreactor") is a silicon coated well, containing PCR reagents and lowered onto the polynucleotide library 303. Prior to or after the sealing 304 of the polynucleotides, a reagent is added to release the polynucleotides from the substrate. In the exemplary workflow, the polynucleotides are released subsequent to sealing of the nanoreactor 305. Once released, fragments of single stranded polynucleotides hybridize in order to span an entire long range sequence of DNA. Partial hybridization 305 is possible because each synthesized polynucleotide is designed to have a small portion overlapping with at least one other polynucleotide in the pool.

After hybridization, a PCA reaction is commenced. During the polymerase cycles, the polynucleotides anneal to complementary fragments and gaps are filled in by a polymerase. Each cycle increases the length of various fragments randomly depending on which polynucleotides find each other. Complementarity amongst the fragments allows for forming a complete large span of double stranded DNA 306.

After PCA is complete, the nanoreactor is separated from the device 307 and positioned for interaction with a device having primers for PCR 308. After sealing, the nanoreactor is subject to PCR 309 and the larger nucleic acids are amplified. After PCR 310, the nanochamber is opened 311, error correction reagents are added 312, the chamber is sealed 313 and an error correction reaction occurs to remove mismatched base pairs and/or strands with poor complementarity from the double stranded PCR amplification products 314. The nanoreactor is opened and separated 315. Error corrected product is next subject to additional processing steps, such as PCR and molecular bar coding, and then packaged 322 for shipment 323.

In some instances, quality control measures are taken. After error correction, quality control steps include for example interaction with a wafer having sequencing primers for amplification of the error corrected product 316, sealing the wafer to a chamber containing error corrected amplification product 317, and performing an additional round of amplification 318. The nanoreactor is opened 319 and the products are pooled 320 and sequenced 321. After an acceptable quality control determination is made, the packaged product 322 is approved for shipment 323.

In some instances, a nucleic acid generated by a workflow such as that in FIG. 3 is subject to mutagenesis using overlapping primers disclosed herein. In some instances, a library of primers are generated by in situ preparation on a solid support and utilize single nucleotide extension process to extend multiple oligomers in parallel. A deposition device, such as a material deposition device, is designed to release reagents in a step wise fashion such that multiple polynucleotides extend, in parallel, one residue at a time to generate oligomers with a predetermined nucleic acid sequence 302.

Computer Systems

Any of the systems described herein, may be operably linked to a computer and may be automated through a computer either locally or remotely. In various instances, the methods and systems of the disclosure may further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the disclosure. The computer systems may be programmed to interface between the user specified base sequence and the position of a material deposition device to deliver the correct reagents to specified regions of the substrate.

Figure 4:
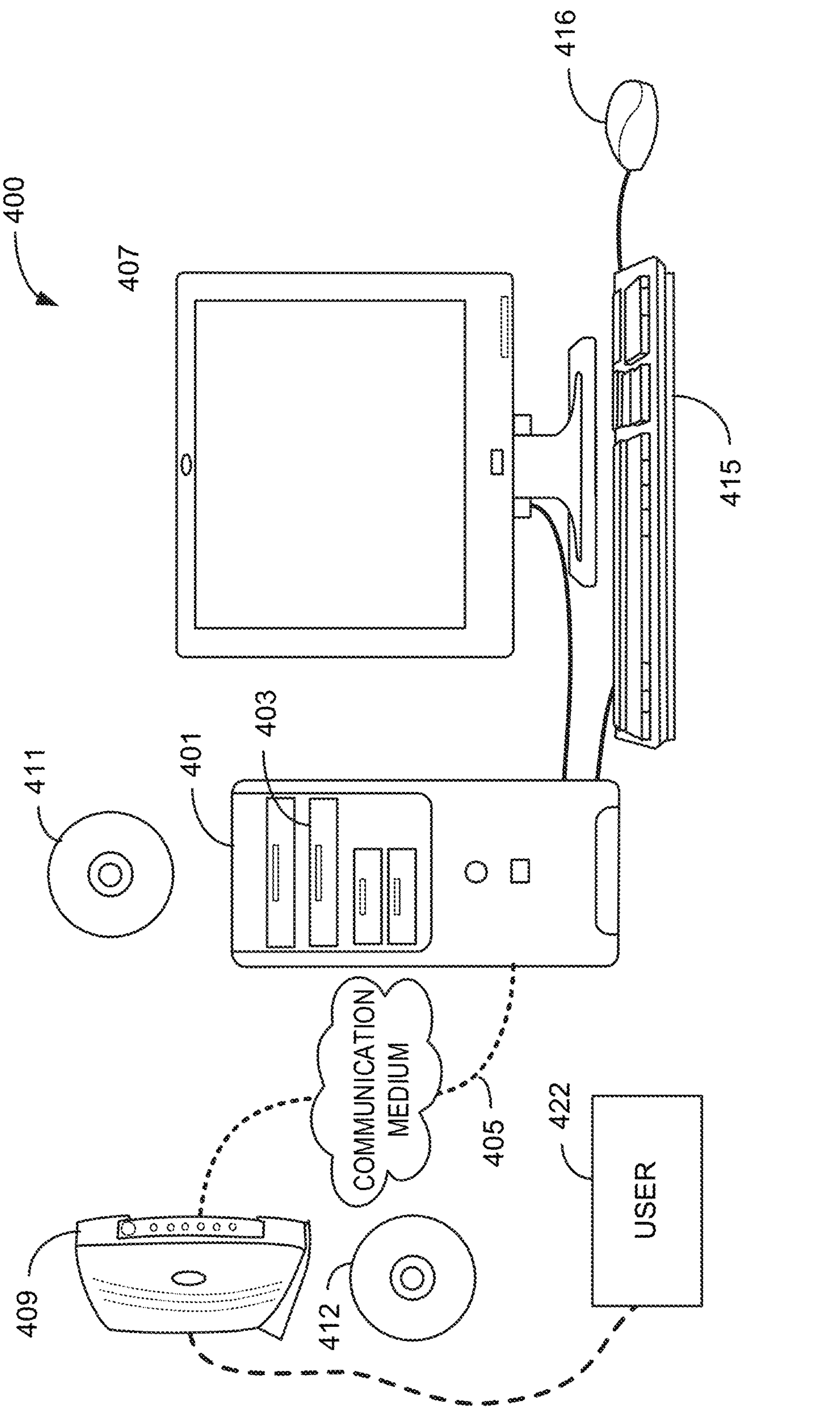
FIG. 4 illustrates an example of a computer system.

The computer system 400 illustrated in FIG. 4 may be understood as a logical apparatus that can read instructions from media 411 and/or a network port 405, which can optionally be connected to server 409 having fixed media 412. The system, such as shown in FIG. 4 can include a CPU 401, disk drives 403, optional input devices such as keyboard 415 and/or mouse 416 and optional monitor 407. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 422 as illustrated in FIG. 4.

Figure 5:
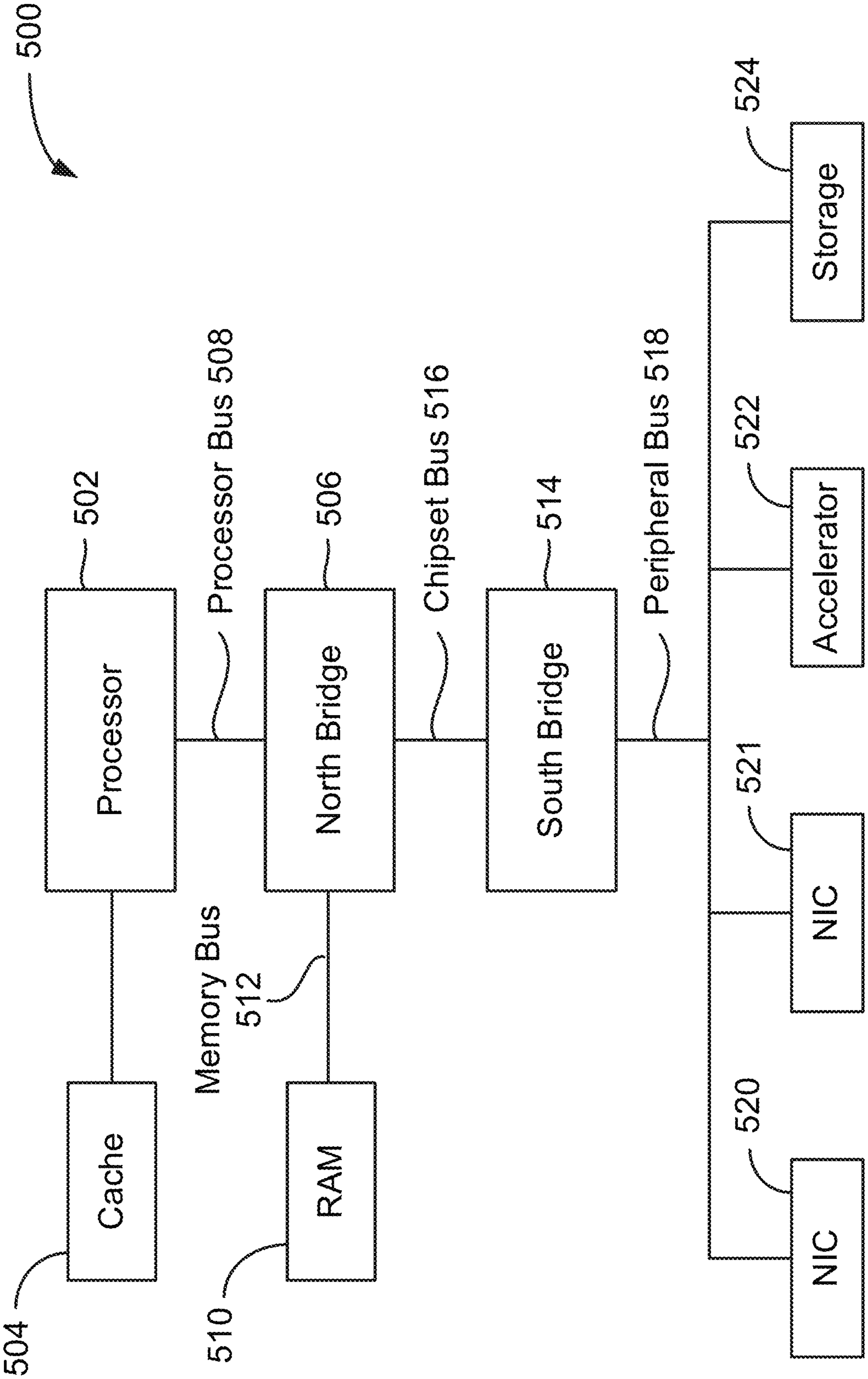
FIG. 5 is a block diagram illustrating an architecture of a computer system.

As illustrated in FIG. 5, a high speed cache 504 can be connected to, or incorporated in, the processor 502 to provide a high speed memory for instructions or data that have been recently, or are frequently, used by processor 502. The processor 502 is connected to a north bridge 506 by a processor bus 508. The north bridge 506 is connected to random access memory (RAM) 510 by a memory bus 512 and manages access to the RAM 510 by the processor 502. The north bridge 506 is also connected to a south bridge 514 by a chipset bus 516. The south bridge 514 is, in turn, connected to a peripheral bus 518. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 518. In some alternative architectures, the functionality of the north bridge can be incorporated into the processor instead of using a separate north bridge chip. In some instances, system 500 can include an accelerator card 522 attached to the peripheral bus 518. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 524 and can be loaded into RAM 510 and/or cache 504 for use by the processor. The system 500 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present disclosure. In this example, system 500 also includes network interface cards (NICs) 520 and 521 connected to the peripheral bus for providing network interfaces to external storage, such as Network Attached Storage (NAS) and other computer systems that can be used for distributed parallel processing.

Figure 6:
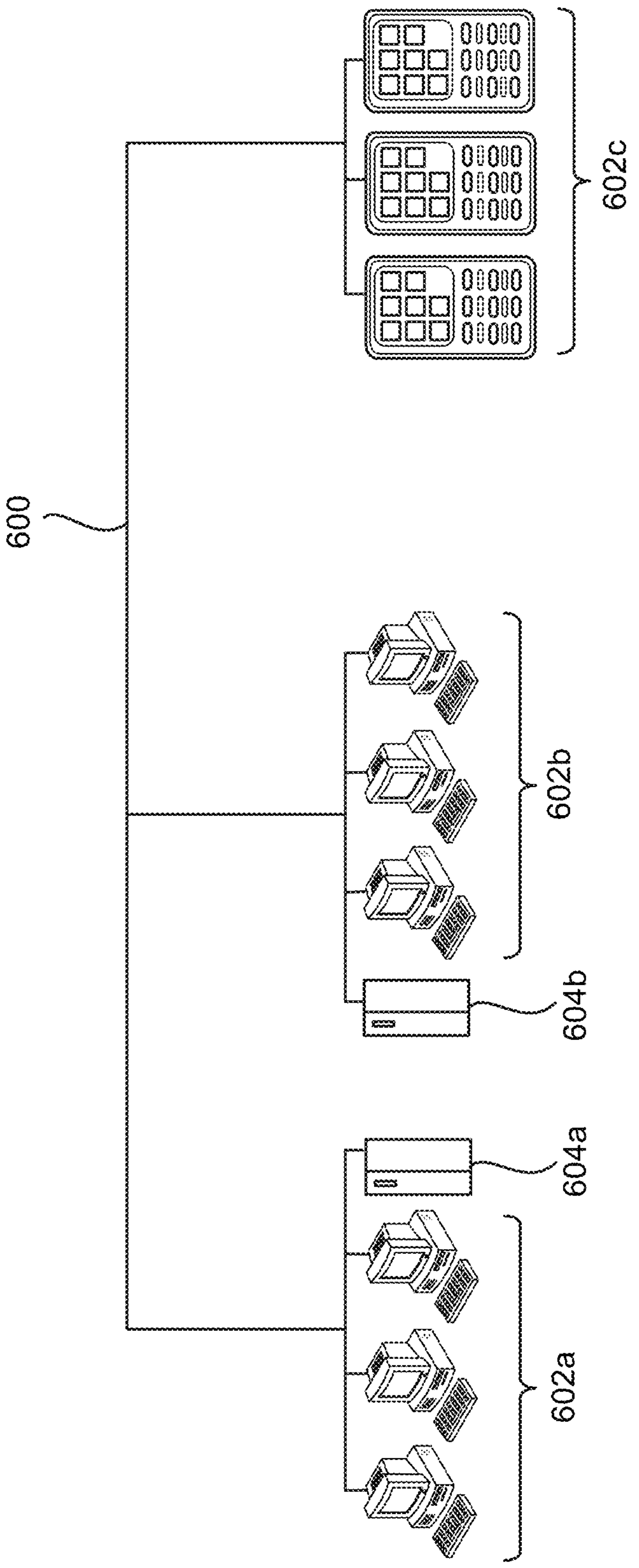
FIG. 6 is a diagram demonstrating a network configured to incorporate a plurality of computer systems, a plurality of cell phones and personal data assistants, and Network Attached Storage (NAS).

FIG. 6 is a diagram showing a network 600 with a plurality of computer systems 602*a*, and 602*b*, a plurality of cell phones and personal data assistants 602*c*, and Network Attached Storage (NAS) 604*a*, and 604*b*. In example instances, systems 602$a$, 602$b$, and 602$c$ can manage data storage and optimize data access for data stored in Network Attached Storage (NAS) 604$a$ and 604$b$. A mathematical model can be used for the data and be evaluated using distributed parallel processing across computer systems 602$a$, and 602$b$, and cell phone and personal data assistant systems 602$c$. Computer systems 602$a$, and 602$b$, and cell phone and personal data assistant systems 602$c$ can also provide parallel processing for adaptive data restructuring of the data stored in Network Attached Storage (NAS) 604$a$ and 604$b$. FIG. 6 illustrates an example only, and a wide variety of other computer architectures and systems can be used in conjunction with the various instances of the present disclosure. For example, a blade server can be used to provide parallel processing. Processor blades can be connected through a back plane to provide parallel processing. Storage can also be connected to the back plane or as Network Attached Storage (NAS) through a separate network interface. In some example instances, processors can maintain separate memory spaces and transmit data through network interfaces, back plane or other connectors for parallel processing by other processors. In other instances, some or all of the processors can use a shared virtual address memory space.

Figure 7:
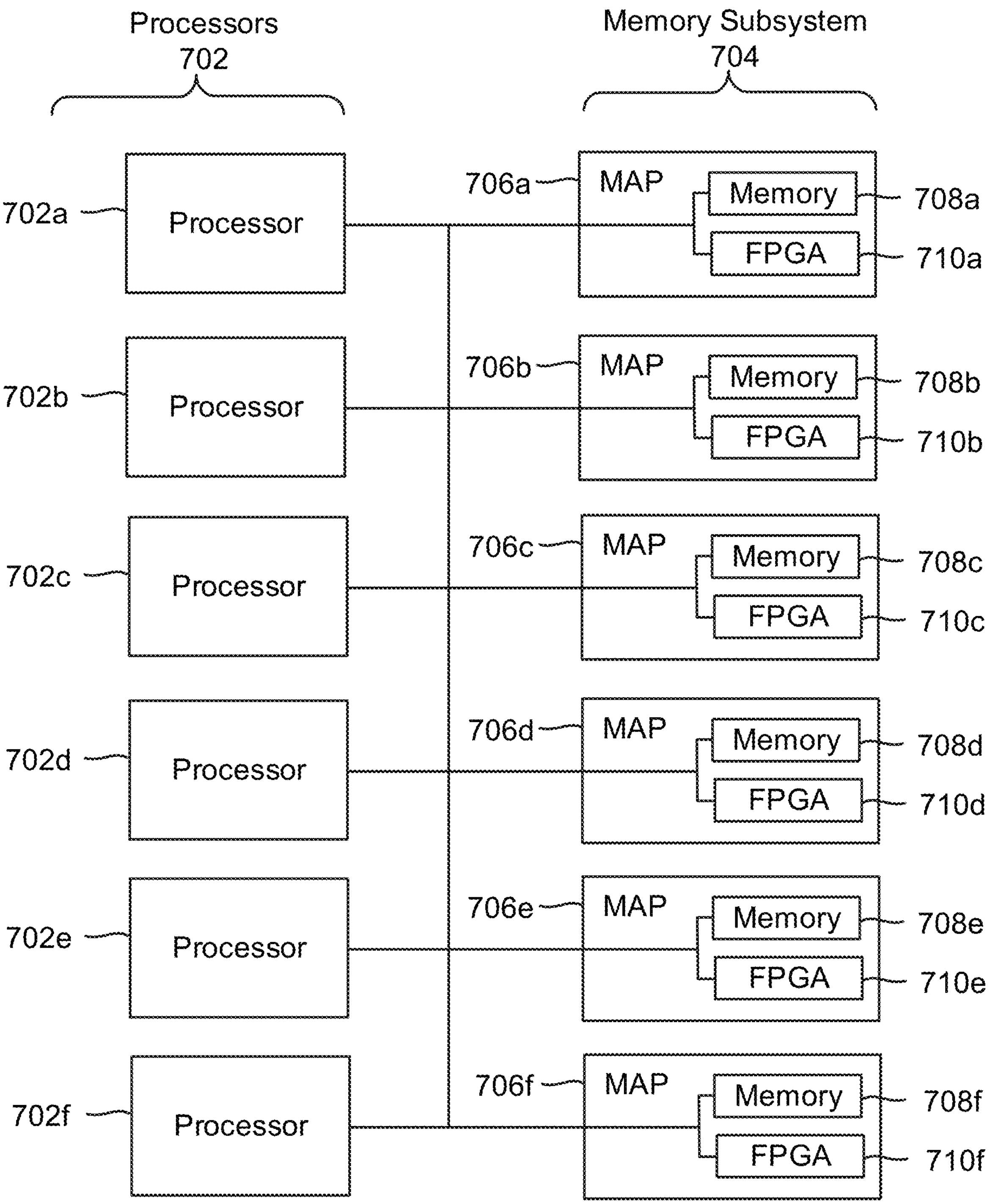
FIG. 7 is a block diagram of a multiprocessor computer system using a shared virtual address memory space.
Figure 8A:
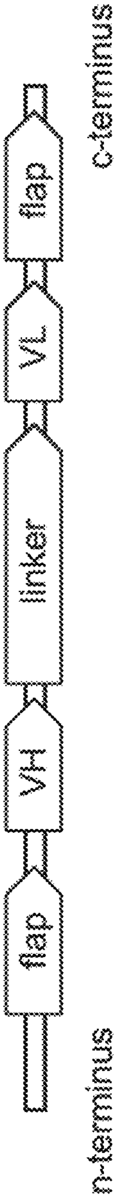
FIG. 8A depicts a schematic of an immunoglobulin scaffold comprising a VH domain attached to a VL domain using a linker.
Figure 8B:
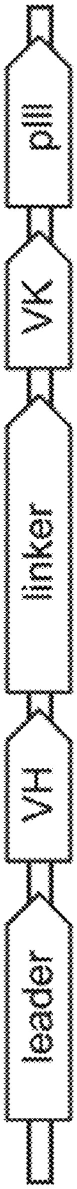
FIG. 8B depicts a schematic of a full-domain architecture of an immunoglobulin scaffold comprising a VH domain attached to a VL domain using a linker, a leader sequence, and pIII sequence.
Figure 8C:
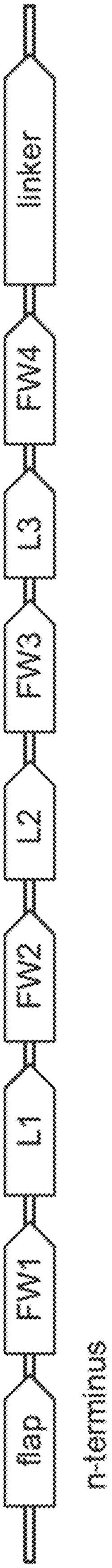
FIG. 8C depicts a schematic of four framework elements (FW1, FW2, FW3, FW4) and the variable 3 CDR (L1, L2, L3) elements for a VL or VH domain.
Figure 9A:
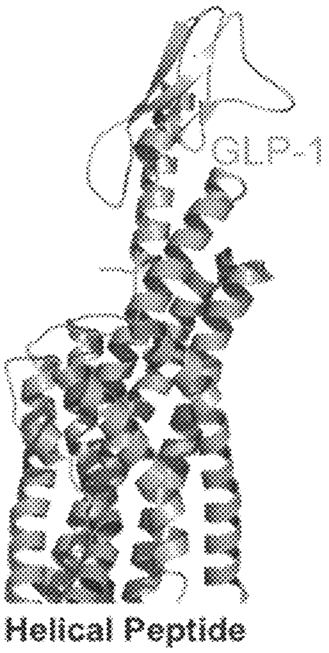
FIG. 9A depicts a structure of Glucagon-like peptide 1 (GLP-1, cyan) in complex with GLP-1 receptor (GLP-1R, grey), PDB entry 5VAI.
Figure 9B:
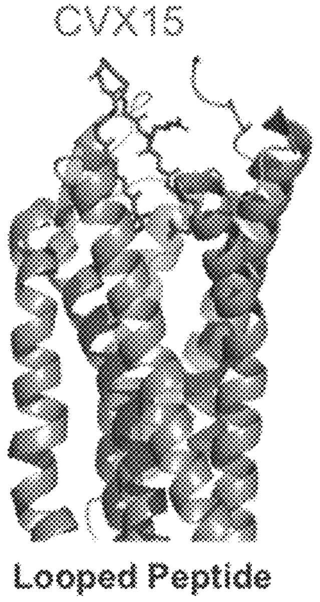
FIG. 9B depicts a crystal structure of CXCR4 chemokine receptor (grey) in complex with a cyclic peptide antagonist CVX15 (blue), PDB entry 3OR0.
Figure 9C:
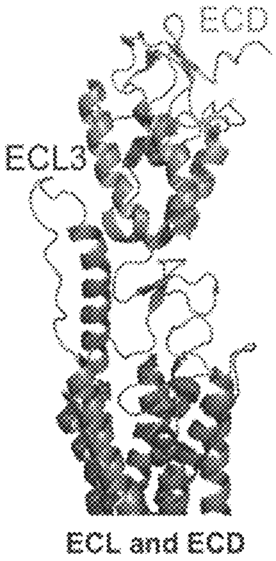
FIG. 9C depicts a crystal structure of human smoothened with the transmembrane domain in grey and extracellular domain (ECD) in orange, PDB entry 5L7D. The ECD contacts the TMD through extracellular loop 3 (ECL3).
Figure 9D:
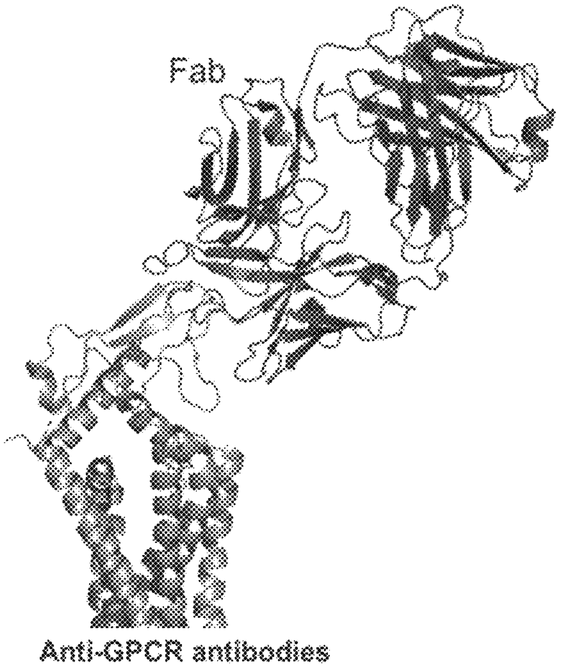
FIG. 9D depicts a structure of GLP-1R (grey) in complex with a Fab (magenta), PDB entry 6LN2.
Figure 9E:
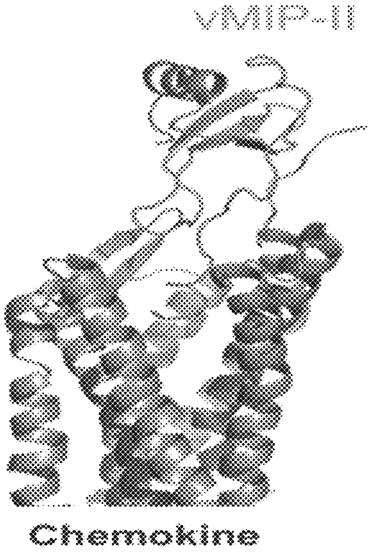
FIG. 9E depicts a crystal structure of CXCR4 (grey) in complex with a viral chemokine antagonist Viral macrophage inflammatory protein 2 (vMIP-II, green), PDB entry 4RWS.

FIG. 7 is a block diagram of a multiprocessor computer system 700 using a shared virtual address memory space in accordance with an example instance. The system includes a plurality of processors 702$a$-$f$ that can access a shared memory subsystem 704. The system incorporates a plurality of programmable hardware memory algorithm processors (MAPs) 706$a$-$f$ in the memory subsystem 704. Each MAP 706$a$-$f$ can comprise a memory 708$a$-$f$ and one or more field programmable gate arrays (FPGAs) 710$a$-$f$. The MAP provides a configurable functional unit and particular algorithms or portions of algorithms can be provided to the FPGAs 710$a$-$f$ for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 708$a$-$f$, allowing it to execute tasks independently of, and asynchronously from the respective microprocessor 702$a$-$f$. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 5, system on chips (SOCs), application specific integrated circuits (ASICs), or other processing and logic elements. For example, the Set Processor and Optimizer can be implemented with hardware acceleration through the use of a hardware accelerator card, such as accelerator card 522 illustrated in FIG. 5.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Functionalization of a Device Surface

A device was functionalized to support the attachment and synthesis of a library of polynucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The device surface was resist coated using a Brewer Science 200X spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min in MSF 26A. Remaining developer was rinsed with the handgun and the device soaked in water for 5 min. The device was baked for 30 min at 100° C. in the oven, followed by visual inspection for lithography defects using a Nikon L200. A descum process was used to remove residual resist using the SAMCO PC-300 instrument to $O_2$ plasma etch at 250 watts for 1 min.

The device surface was passively functionalized with a 1004 solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for polynucleotide synthesis.

Example 2: Synthesis of a 50-Mer Sequence on an Oligonucleotide Synthesis Device A two dimensional oligonucleotide synthesis device was assembled into a flowcell, which was connected to a flowcell (Applied Biosystems (ABI394 DNA Synthesizer"). The two-dimensional oligonucleotide synthesis device was uniformly functionalized with N-(3-TRIETHOXYSILYLPROPYL)-4-HYDROXYBUTYRAMIDE (Gelest) was used to synthesize an exemplary polynucleotide of 50 bp ("50-mer polynucleotide") using polynucleotide synthesis methods described herein.

The sequence of the 50-mer was as described in SEQ ID NO.: 2. 5'AGACAATCAACCATTTGGGGTGGACAGCCTTGACCTCTAGACTTCGGCAT##TTTTTTT TTT3' (SEQ ID NO.: 2), where # denotes Thymidine-succinyl hexamide CED phosphoramidite (CLP-2244 from ChemGenes), which is a cleavable linker enabling the release of oligos from the surface during deprotection.

The synthesis was done using standard DNA synthesis chemistry (coupling, capping, oxidation, and deblocking) according to the protocol in Table 3 and an ABI synthesizer.

TABLE 3

Synthesis protocols

| General DNA Synthesis Process Name | Table 3 Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |

TABLE 3-continued

Synthesis protocols

| General DNA Synthesis Process Name | Table 3 Process Step | Time (sec) |
|---|---|---|
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After polynucleotide synthesis, the chip was deprotected in gaseous ammonia overnight at 75 psi. Five drops of water were applied to the surface to recover polynucleotides. The recovered polynucleotides were then analyzed on a BioAnalyzer small RNA chip.

Example 3: Synthesis of a 100-Mer Sequence on an Oligonucleotide Synthesis Device The same process as described in Example 2 for the synthesis of the 50-mer sequence was used for the synthesis of a 100-mer polynucleotide ("100-mer polynucleotide"; 5' CGGGATCCTTATCGTCATCGTCGTACAGATCCCGACCCATTTGCTGTCCACCAGTCATGCTAGCCATACCATGATGATGATGATGATGAGAACCCCGCAT##TTTTTTTTTT3', where # denotes Thymidine-succinyl hexamide CED phosphoramidite (CLP-2244 from ChemGenes); SEQ ID NO.: 3) on two different silicon chips, the first one uniformly functionalized with N-(3-TRIETHOXYSILYLPROPYL)-4-HYDROXYBUTYRAMIDE and the second one functionalized with 5/95 mix of 11-acetoxyundecyltriethoxysilane and n-decyltriethoxysilane, and the polynucleotides extracted from the surface were analyzed on a BioAnalyzer instrument.

All ten samples from the two chips were further PCR amplified using a forward (5'ATGCGGGGTTCTCATCATC3; SEQ ID NO.: 4) and a reverse (5'CGGGATCCTTATCGTCATCG3'; SEQ ID NO.: 5) primer in a 50 uL PCR mix (25 uL NEB Q5 mastermix, 2.5 uL 10 uM Forward primer, 2.5 uL 10 uM Reverse primer, 1 uL polynucleotide extracted from the surface, and water up to 50 uL) using the following thermalcycling program:

98° C., 30 sec

98° C., 10 sec; 63° C., 10 sec; 72° C., 10 sec; repeat 12 cycles

72° C., 2 min

The PCR products were also run on a BioAnalyzer, demonstrating sharp peaks at the 100-mer position. Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

| Sequencing results | | |
|---|---|---|
| Spot | Error rate | Cycle efficiency |
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized polynucleotides were repeated on two chips with different surface chemistries. Overall, 89% of the 100-mers that were sequenced were perfect sequences with no errors, corresponding to 233 out of 262.

Table 5 summarizes error characteristics for the sequences obtained from the polynucleotide samples from spots 1-10.

TABLE 5

| Error characteristics | | | | | |
|---|---|---|---|---|---|
| | Spot no. | | | | |
| Sample ID | OSA_0046/ 1 | OSA_0047/ 2 | OSA_0048/ 3 | OSA_0049/ 4 | OSA_0050/ 5 |
| Total Sequences | 32 | 32 | 32 | 32 | 32 |
| Sequencing Quality | 25 of 28 | 27 of 27 | 26 of 30 | 21 of 23 | 25 of 26 |
| Oligo Quality | 23 of 25 | 25 of 27 | 22 of 26 | 18 of 21 | 24 of 25 |
| ROI Match Count | 2500 | 2698 | 2561 | 2122 | 2499 |
| ROI Mutation | 2 | 2 | 1 | 3 | 1 |
| ROI Multi Base Deletion | 0 | 0 | 0 | 0 | 0 |
| ROI Small Insertion | 1 | 0 | 0 | 0 | 0 |
| ROI Single Base Deletion | 0 | 0 | 0 | 0 | 0 |
| Large Deletion Count | 0 | 0 | 1 | 0 | 0 |
| Mutation: G > A | 2 | 2 | 1 | 2 | 1 |
| Mutation: T > C | 0 | 0 | 0 | 1 | 0 |
| ROI Error Count | 3 | 2 | 2 | 3 | 1 |
| ROI Error Rate | Err: ~1 in 834 | Err: ~1 in 1350 | Err: ~1 in 1282 | Err: ~1 in 708 | Err: ~1 in 2500 |

TABLE 5-continued

| Error characteristics | | | | | |
|---|---|---|---|---|---|
| ROI Minus Primer Error Rate | MP Err: ~1 in 763 | MP Err: ~1 in 824 | MP Err: ~1 in 780 | MP Err: ~1 in 429 | MP Err: ~1 in 1525 |
| | Spot no. | | | | |
| Sample ID | OSA_0051/ 6 | OSA_0052/ 7 | OSA_0053/ 8 | OSA_0054/ 9 | OSA_ 0055/ 10 |
| Total Sequences | 32 | 32 | 32 | 32 | 32 |
| Sequencing Quality | 29 of 30 | 27 of 31 | 29 of 31 | 28 of 29 | 25 of 28 |
| Oligo Quality | 25 of 29 | 22 of 27 | 28 of 29 | 26 of 28 | 20 of 25 |
| ROI Match Count | 2666 | 2625 | 2899 | 2798 | 2348 |
| ROI Mutation | 0 | 2 | 1 | 2 | 1 |
| ROI Multi Base Deletion | 0 | 0 | 0 | 0 | 0 |
| ROI Small Insertion | 0 | 0 | 0 | 0 | 0 |
| ROI Single Base Deletion | 0 | 0 | 0 | 0 | 0 |
| Large Deletion Count | 1 | 1 | 0 | 0 | 0 |
| Mutation: G > A | 0 | 2 | 1 | 2 | 1 |
| Mutation: T > C | 0 | 0 | 0 | 0 | 0 |
| ROI Error Count | 1 | 3 | 1 | 2 | 1 |
| ROI Error Rate | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 1615 | MP Err: ~1 in 531 | MP Err: ~1 in 1769 | MP Err: ~1 in 854 | MP Err: ~1 in 1451 |

Example 4: Design of Antibody Scaffolds

To generate scaffolds, structural analysis, repertoire sequencing analysis of the heavy chain, and specific analysis of heterodimer high-throughput sequencing datasets were performed. Each heavy chain was associated with each light chain scaffold. Each heavy chain scaffold was assigned 5 different long CDRH3 loop options. Each light chain scaffold was assigned 5 different L3 scaffolds. The heavy chain CDRH3 stems were chosen from the frequently observed long H3 loop stems (10 amino acids on the N-terminus and the C-terminus) found both across individuals and across V-gene segments. The light chain scaffold L3s were chosen from heterodimers comprising long H3s. Direct heterodimers based on information from the Protein Data Bank (PDB) and deep sequencing datasets were used in which CDR H1, H2, L1, L2, L3, and CDRH3 stems were fixed. The various scaffolds were then formatted for display on phage to assess for expression.

Structural Analysis

About 2,017 antibody structures were analyzed from which 22 structures with long CDRH3s of at least 25 amino acids in length were observed. The heavy chains included the following: IGHV1-69, IGHV3-30, IGHV4-49, and IGHV3-21. The light chains identified included the following: IGLV3-21, IGKV3-11, IGKV2-28, IGKV1-5, IGLV1-51, IGLV1-44, and IGKV1-13. In the analysis, four heterodimer combinations were observed multiple times including: IGHV4-59/61-IGLV3-21, IGHV3-21-IGKV2-28, IGHV1-69-IGKV3-11, and IGHV1-69-IGKV1-5. An analysis of sequences and structures identified intra-CDRH3 disulfide bonds in a few structures with packing of bulky side chains such as tyrosine in the stem providing support for long H3 stability. Secondary structures including beta-turn-beta sheets and a “hammerhead” subdomain were also observed.

Repertoire Analysis

A repertoire analysis was performed on 1,083,875 IgM+/CD27-naïve B cell receptor (BCR) sequences and 1,433,011 CD27+ sequences obtained by unbiased 5'RACE from 12 healthy controls. The 12 healthy controls comprised equal numbers of male and female and were made up of 4 Caucasian, 4 Asian, and 4 Hispanic individuals. The repertoire analysis demonstrated that less than 1% of the human repertoire comprises BCRs with CDRH3s longer than 21 amino acids. A V-gene bias was observed in the long CDR3 subrepertoire, with IGHV1-69, IGHV4-34, IGHV1-18, and IGHV1-8 showing preferential enrichment in BCRs with long H3 loops. A bias against long loops was observed for IGHV3-23, IGHV4-59/61, IGHV5-51, IGHV3-48, IGHV3-53/66, IGHV3-15, IGHV3-74, IGHV3-73, IGHV3-72, and IGHV2-70. The IGHV4-34 scaffold was demonstrated to be autoreactive and had a short half-life.

Viable N-terminal and C-terminal CDRH3 scaffold variation for long loops were also designed based on the 5'RACE reference repertoire. About 81,065 CDRH3s of amino acid length 22 amino acids or greater were observed. By comparing across V-gene scaffolds, scaffold-specific H3 stem variation was avoided as to allow the scaffold diversity to be cloned into multiple scaffold references.

Heterodimer Analysis

Heterodimer analysis was performed on scaffolds. Variant sequences and lengths of the scaffolds were assayed.

Structural Analysis

Structural analysis was performed using GPCR scaffolds of variant sequences and lengths were assayed.

Example 5: Generation of GPCR Antibody Libraries

Based on GPCR-ligand interaction surfaces and scaffold arrangements, libraries were designed and de novo synthesized. See Example 4. 10 variant sequences were designed for the variable domain, heavy chain, 237 variant sequences were designed for the heavy chain complementarity determining region 3, and 44 variant sequences were designed for the variable domain, light chain. The fragments were synthesized as three fragments following similar methods as described in Examples 1-3.

Following de novo synthesis, 10 variant sequences were generated for the variable domain, heavy chain, 236 variant sequences were generated for the heavy chain complementarity determining region 3, and 43 variant sequences were designed for a region comprising the variable domain, light chain and CDRL3 and of which 9 variants for variable domain, light chain were designed. This resulted in a library with about $10^5$ diversity (10×236×43). This was confirmed using next generation sequencing (NGS) with 16 million reads.

The various light and heavy chains were then tested for expression and protein folding. The 10 variant sequences for variable domain, heavy chain included the following: IGHV1-18, IGHV1-69, IGHV1-8 IGHV3-21, IGHV3-23, IGHV3-30/33rn, IGHV3-28, IGHV3-74, IGHV4-39, and IGHV4-59/61. Of the 10 variant sequences, IGHV1-18, IGHV1-69, and IGHV3-30/33rn exhibited improved characteristics such as improved thermostability. 9 variant sequences for variable domain, light chain included the following: IGKV1-39, IGKV1-9, IGKV2-28, IGKV3-11, IGKV3-15, IGKV3-20, IGKV4-1, IGLV1-51, and IGLV2-14. Of the 9 variant sequences, IGKV1-39, IGKV3-15, IGLV1-51, and IGLV2-14 exhibited improved characteristics such as improved thermostability.

Example 6: GPCR Libraries

This example describes the generation of GPCR libraries.

Materials and Method

Stable Cell Line and Phage Library Generation

The full length human GLP-1R gene (UniProt-P43220) with an N-terminal FLAG tag and C-terminal GFP tag cloned into pCDNA3.1(+) vector (ThermoFisher) was transfected into suspension Chinese Hamster Ovary (CHO) cells to generate the stable cell line expressing GLP-1R. Target expression was confirmed by FACS. Cells expressing >80% of GLP-1R by GFP were then directly used for cell-based selections.

Germline heavy chain IGHV1-69, IGHV3-30 and germline light chain IGKV1-39, IGKV3-15, IGLV1-51, IGLV2-14 framework combinations were used in the GPCR-focused phage-displayed library, and all six CDR diversities were encoded by oligo pools synthesized similar to Examples 1-3 above. The CDRs were also screened to ensure they did not contain manufacturability liabilities, cryptic splice sites, or commonly used nucleotide restriction sites. The heavy chain variable region (VH) and light chain variable region (VL) were linked by (G4S)3 linker (SEQ ID NO: 718). The resulting scFv (VH-linker-VL) gene library was cloned into a pADL 22-2c (Antibody Design Labs) phage display vector by NotI restriction digestion and electroporated into TG1 electro-competent *E. coli* cells. (Lucigen). The final library has a diversity of $1.1\times10^{10}$ size which was verified by NGS.

Panning and Screening Strategy Used to Isolate Agonist GLP-1R scFv Clones

Before panning on GLP-1R expressing CHO cells, phage particles were blocked with 5% BSA/PBS and depleted for non-specific binders on CHO parent cells. For CHO parent cell depletion, the input phage aliquot was rotated at 14 rpm/min with $1\times10^8$ CHO parent cells for 1 hour at room temperature (RT). The cells were then pelleted by centrifuging at 1,200 rpm for 10 mins in a tabletop Eppendorf centrifuge 5920RS/4×1000 rotor to deplete the non-specific CHO cell binders. The phage supernatant, depleted of CHO cell binders, was then transferred to $1\times10^8$ GLP-1R expressing CHO cells. The phage supernatant and GLP-1R expressing CHO cells were rotated at 14 rpm/min for 1 hour at RT to select for GLP-1R binders. After incubation, the cells were washed several times with 1×PBS/0.5% Tween to remove non-binding clones. To elute the phage bound to the GLP-1R cells, the cells were incubated with trypsin in PBS buffer for 30 minutes at 37° C. The cells were pelleted by centrifuging at 1,200 rpm for 10 mins. The output supernatant enriched in GLP-1R binding clones was amplified in TG1 *E. coli* cells to use as input phage for the next round of selection. This selection strategy was repeated for five rounds. Every round was depleted against the CHO parent background. Amplified output phage from a round was used as the input phage for the subsequent round, and the stringency of washes were increased in each subsequent round of selections with more washes. After five rounds of selection, 500 clones from each of round 4 and round 5 were Sanger sequenced to identify unique clones.

Next-Generation Sequencing Analysis

The phagemid DNA was miniprepped from the output bacterial stocks of all panning rounds. The variable heavy chain (VH) was PCR amplified from the phagemid DNA using the Forward Primer ACAGAATTCATTAAAGAGGAGAAATTAACC (SEQ ID NO: 719) and reverse primer TGAACCGCCTCCACCGCTAG (SEQ ID NO: 720). The PCR product was directly used for library preparation using the KAPA HyperPlus Library Preparation Kit (Kapa Biosystems, product #KK8514). To add diversity in the library, the samples were spiked with 15% PhiX Control purchased from Illumina, Inc. (product #FC-110-3001). The library was then loaded onto Illumina's 600 cycle MiSeq Reagent Kit v3 (Illumina, product #MS-102-3003) and run on the MiSeq instrument.

Reformatting and High Throughput (HT) IgG Purification

Expi293 cells were transfected using Expifectamine (ThermoFisher, A14524) with the heavy chain and light chain DNA at a 2:1 ratio and supernatants were harvested 4 days post-transfection before cell viability dropped below 80%. Purifications were undertaken using either King Fisher (ThermoFisher) with protein A magnetic beads or Phynexus protein A column tips (Hamilton). For large scale production of IgG clones that were evaluated in in vivo mouse studies an Akta HPLC purification system (GE) was used.

IgG characterization and quality control. The purified IgGs for the positive GLP-1R binders (hits) were subjected to characterization for their purity by LabChip GXII Touch HT Protein Express high-sensitivity assay. Dithiothreitol (DTT) was used to reduce the IgG into VH and VL. IgG concentrations were measured using Lunatic (UnChain). IgG for in vivo mouse studies were further characterized by HPLC and tested for endotoxin levels (Endosafe® nexgen-PTS™ Endotoxin Testing, Charles River), with less than 5 EU per kg dosing.

Binding Assays and Flow Cytometry

GLP-1R IgG clones were tested in a binding assay coupled to flow cytometry analysis as follows: FLAG-GLP-1R-GFP expressing CHO cells (CHO-GLP-1R) and CHO-parent cells were incubated with 100 nM IgG for 1 h on ice, washed three times and incubated with Alexa 647 conjugated goat-anti-human antibody (1:200) (Jackson ImmunoResearch Laboratories, 109-605-044) for 30 min on ice, followed by three washes, centrifuging to pellet the cells between each washing step. All incubations and washes were in buffer containing PBS+1% BSA. For titrations, IgG was serially diluted 1:3 starting from 100 nM down to 0.046 nM. Cells were analyzed by flow cytometry and hits (a hit is an IgG that specifically binds to CHO-GLP-1R) were identified by measuring the GFP signal against the Alexa 647 signal. Flow cytometry data of binding assays with 100 nM IgG are presented as dot plots. Analyses of binding assays with IgG titrations are presented as binding curves plotting IgG concentrations against MFI (mean fluorescence intensity).

Ligand Competition Assay

Ligand competition assays involved co-incubating the primary IgG with 1 μM GLP-1 (7-36). For each data point, IgG (600 nM) was prepared in Flow buffer (PBS+1% BSA) and diluted 1:3 down for 8 titration points. Peptide GLP-1 7-36 (2 μM) was prepared similarly with the Flow buffer (PBS+1% BSA). Each well contained 100,000 cells to which 50 μL of IgG and 504 of peptide (=plus) or buffer alone without peptide (=minus) were added. Cells and IgG/peptide mix were incubated for 1 hr on ice, and after washing, secondary antibody (goat anti-human APC, Jackson ImmunoResearch Laboratories, product #109-605-044) diluted 1:200 in PBS+1% BSA was added. This was incubated on ice for 30 mins (504 per well), before washing and resuspending in 60 μL buffer. Finally, the assay read-out was measured on an Intellicyt® IQue3 Screener at a rate of 4 seconds per well.

Results

Design of GPCR Focused Antibody Library is Based on GPCR Binding Motifs and GPCR Antibodies All known GPCR interactions, which include interactions of GPCRs with ligands, peptides, antibodies, endogenous extracellular loops and small molecules were analyzed to map the GPCR binding molecular determinants. Crystal structures of almost 150 peptides, ligand or antibodies bound to ECDs of around 50 GPCRs (http://www.gperdb.org) were used to identify GPCR binding motifs. Over 1000 GPCR binding motifs were extracted from this analysis. In addition, by analysis of all solved structures of GPCRs (zhanglab.ccmb.med.umich.edu/GPCR-EXP/), over 2000 binding motifs from endogenous extracellular loops of GPCRs were identified. Finally, by analysis of structures of over 100 small molecule ligands bound to GPCR, a reduced amino acid library of 5 amino acids (Tyr, Phe, His, Pro and Gly) that may be able to recapitulate many of the structural contacts of these ligands was identified. A sub-library with this reduced amino acid diversity was placed within a CxxxxxC motif. In total, over 5000 GPCR binding motifs were identified (FIGS. 9A-9E). These binding motifs were placed in one of five different stem regions: CARDLRELECEEWTxxxxxSRGPCVDPRGVAGSFDVW (SEQ ID NO: 721), CARDMYYDFxxxxxEVVPADDAFDIW (SEQ ID NO: 722), CARDGRGSLPRPKGGPxxxxxYDSSEDSGGAFDIW (SEQ ID NO: 723) (SEQ ID NO: 724), CARANQHFxxxxxGYHYYGMDVW, CAKHMSMQxxxxxRADLVGDAFDVW (SEQ ID NO: 725).

These stem regions were selected from structural antibodies with ultra-long HCDR3s. Antibody germlines were specifically chosen to tolerate these ultra-long HCDR3s. Structure and sequence analysis of human antibodies with longer than 21 amino acids revealed a V-gene bias in antibodies with long CDR3s. Finally, the germline IGHV (IGHV1-69 and IGHV3-30), IGKV (IGKV1-39 and IGKV3-15) and IGLV (IGLV1-51 and IGLV2-14) genes were chosen based on this analysis.

Figure 10:
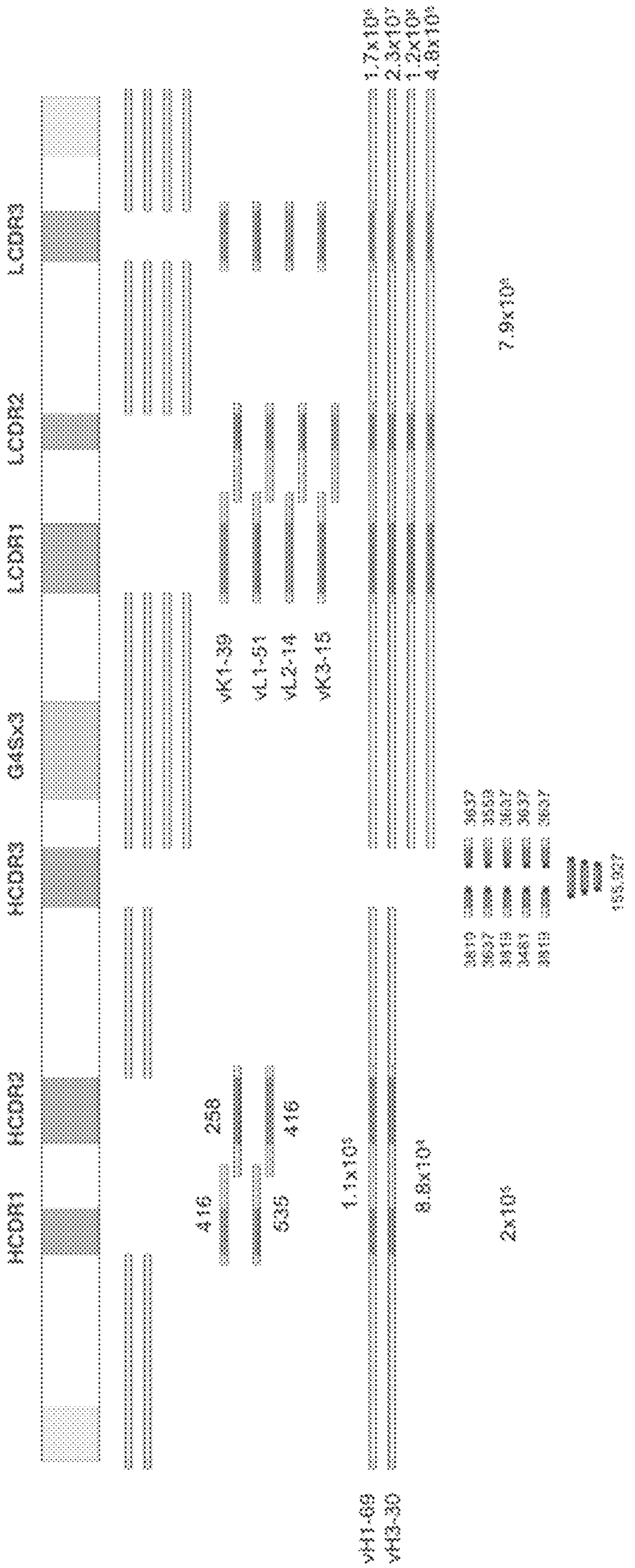
FIG. 10 depicts a schema of the GPCR focused library design. Two germline heavy chain VH1-69 and VH3-30; 4 germline light chain IGKV1-39 and IGKV3-15, and IGLV1-51 and IGLV2-14.
Figure 11:
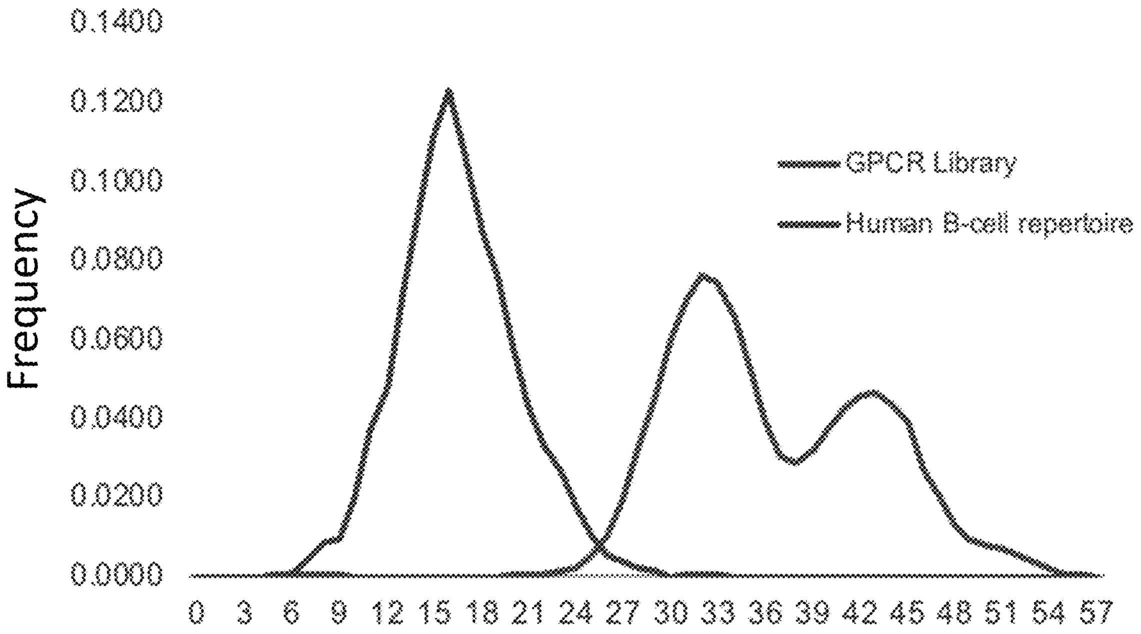
FIG. 11 depicts a graph of HCDR3 length distribution in the GPCR-focused library compared to the HCDR3 length distribution in B-cell populations from three healthy adult donors. In total, 2,444,718 unique VH sequences from the GPCR library and 2,481,511 unique VH sequences from human B-cell repertoire were analyzed to generate the length distribution plot.

In addition to HCDR3 diversity, limited diversity was also introduced in the other 5 CDRs. There were 416 HCDR1 and 258 HCDR2 variants in the IGHV1-69 domain; 535 HCDR1 and 416 HCDR2 variants in the IGHV3-30 domain; 490 LCDR1, 420 LCDR2 and 824 LCDR3 variants in the IGKV1-39 domain; 490 LCDR1, 265 LCDR2 and 907 LCDR3 variants in the IGKV3-15 domain; 184 LCDR1, 151 LCDR2 and 824 LCDR3 variants in the IGLV1-51 domain; 967 LCDR1, 535 LCDR2 and 922 LCDR3 variants in the IGLV2-14 domain (FIG. 10). These CDR variants were selected by comparing the germline CDRs with the near-germline space of single, double and triple mutations observed in the CDRs within the V-gene repertoire of at least two out of 12 human donors. All CDRs have were pre-screened to remove manufacturability liabilities, cryptic splice sites or nucleotide restriction sites. The CDRs were synthesized as an oligo pool and incorporated into the selected antibody scaffolds. The heavy chain (VH) and light chain (VL) genes were linked by $(G_4S)_3$ linker (SEQ ID NO: 718). The resulting scFv (VH-linker-VL) gene pool was cloned into a phagemid display vector at the N-terminal of the M13 gene-3 minor coat protein. The final size of the GPCR library is $1\times10^{10}$ in a scFv format. Next-generation sequencing (NGS) was performed on the final phage library to analyze the HCDR3 length distribution in the library for comparison with the HCDR3 length distribution in B-cell populations from three healthy adult donors. The HCDR3 sequences from the three healthy donors used were derived from a publicly available database with over 37 million B-cell receptor sequences[31]. The HCDR3 length in the GPCR library is much longer than the HCDR3 length observed in B-cell repertoire sequences. On average, the median HCDR3 length in the GPCR library (which shows a biphasic pattern of distribution) is two or three times longer (33 to 44 amino acids) than the median lengths observed in natural B-cell repertoire sequences (15 to 17 amino acids) (FIG. 11). The biphasic length distribution of HCDR3 in the GPCR library is mainly caused by the two groups of stems (8aa, 9aaxxxxx10aa, 12aa) and (14aa, 16aa xxxxx18aa, 14aa) used to present the motifs within HCDR3.

Example 7: VHH Libraries

Synthetic VHH libraries were developed. For the 'VHH Ratio' library with tailored CDR diversity, 2391 VHH sequences (iCAN database) were aligned using Clustal Omega to determine the consensus at each position and the framework was derived from the consensus at each position. The CDRs of all of the 2391 sequences were analyzed for position-specific variation, and this diversity was introduced in the library design. For the 'VHH Shuffle' library with shuffled CDR diversity, the iCAN database was scanned for unique CDRs in the nanobody sequences. 1239 unique CDR1's, 1600 unique CDR2's, and 1608 unique CDR3's were identified and the framework was derived from the consensus at each framework position amongst the 2391 sequences in the iCAN database. Each of the unique CDR's was individually synthesized and shuffled in the consensus framework to generate a library with theoretical diversity of 3.2×10^9. The library was then cloned in the phagemid vector using restriction enzyme digest. For the 'VHH hShuffle' library (a synthetic "human" VHH library with shuffled CDR diversity), the iCAN database was scanned for unique CDRs in the nanobody sequences. 1239 unique CDR1's, 1600 unique CDR2's, and 1608 unique CDR3's were identified and framework 1, 3, and 4 was derived from the human germline DP-47 framework. Framework 2 was derived from the consensus at each framework position amongst the 2391 sequences in the iCAN database. Each of the unique CDR's was individually synthesized and shuffled in the partially humanized framework using the NUGE tool to generate a library with theoretical diversity of 3.2×10^9. The library was then cloned in the phagemid vector using the NUGE tool.

The Carterra SPR system was used to assess binding affinity and affinity distribution for VHH-Fc variants. VHH-Fc demonstrate a range of affinities for TIGIT, with a low end of 12 nM $K_D$ and a high end of 1685 nM $K_D$ (data not shown). FIG. 12 provides specific values for the VHH-Fc clones for ELISA, Protein A (mg/ml), and $K_D$ (nM).

Example 8. Hyperimmune Immunoglobulin Library for A2A Receptor

Figure 13:
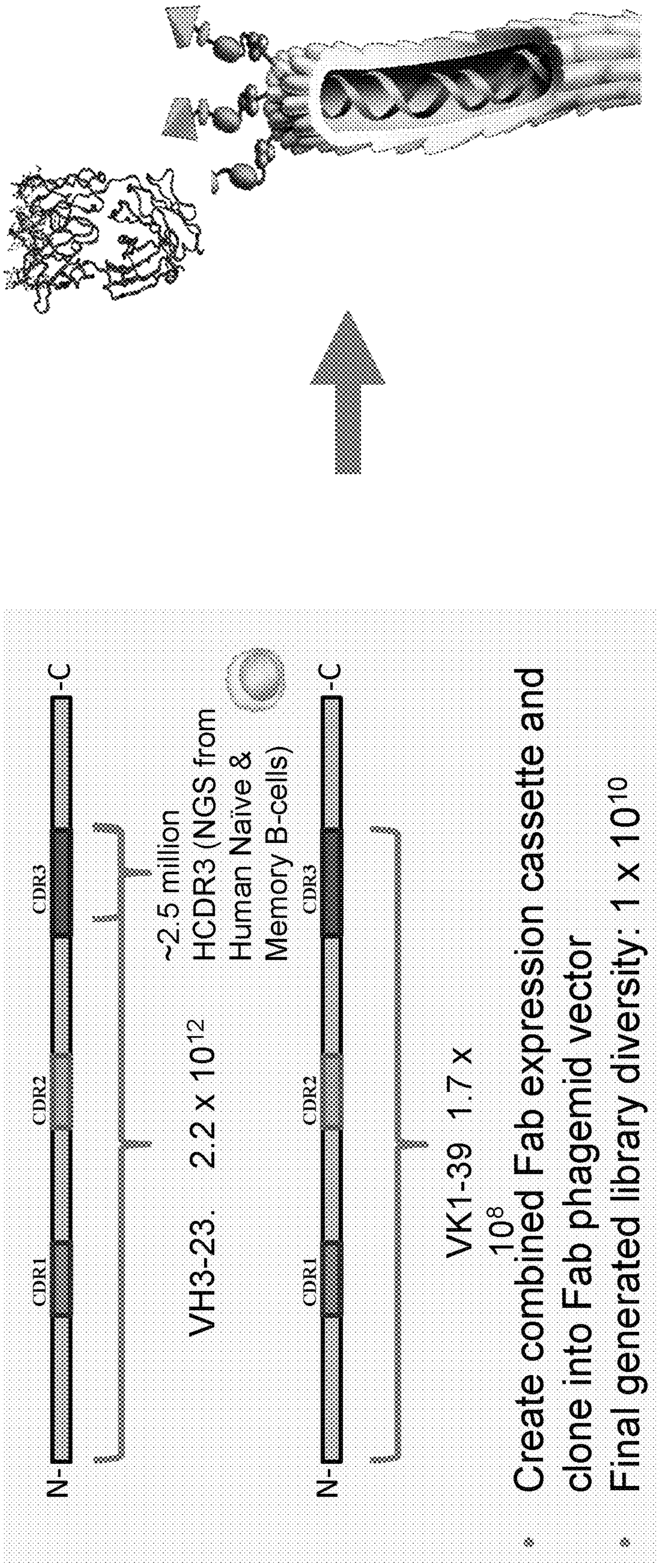
FIG. 13 depicts a schema of design of phage-displayed hyperimmune libraries generated herein.

A hyperimmune immunoglobulin (IgG) library was created using similar methods as described in Example 7. Briefly, the hyperimmune IgG library was generated from analysis of databases of human naïve and memory B-cell receptor sequences consisting of more than 37 million unique IgH sequences from each of 3 healthy donors. More than two million CDRH3 sequences were gathered from the analysis and individually constructed using methods similar to Examples 1-3. The CDRH3 sequences were incorporated into the VHH hShuffle library described in Example 9. The final library diversity was determined to be $1.3\times10^{10}$. A schematic of the design can be seen in FIG. 13.

Figure 14A:
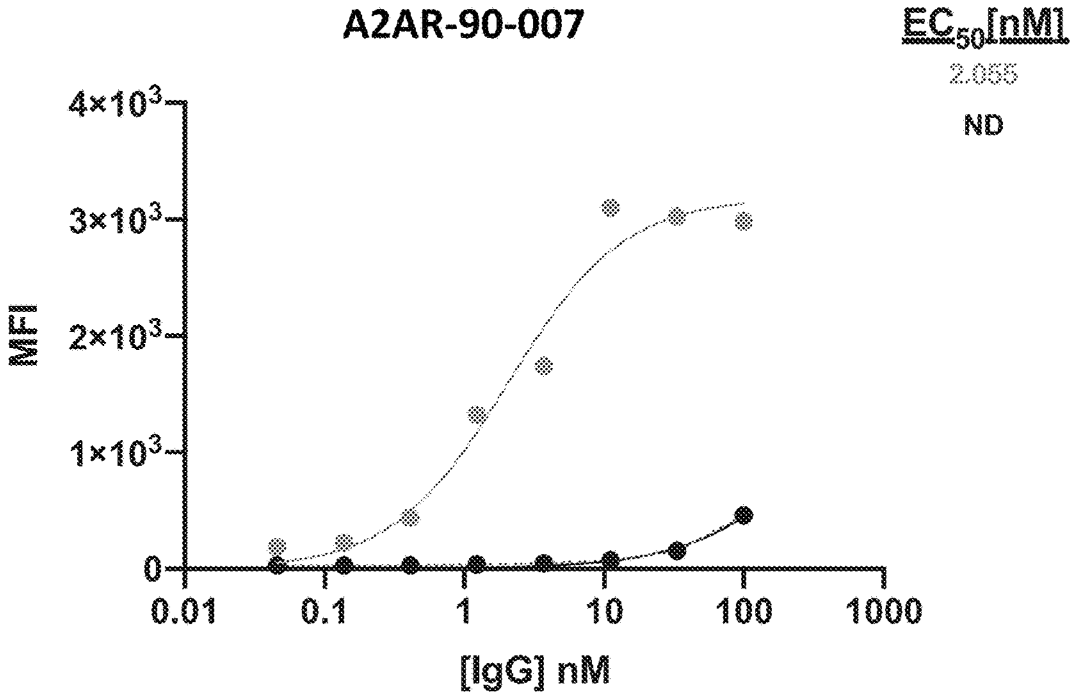
FIGS. 14A-14B depict graphs of a dose curve (FIG. 14A) and FACS analysis (FIG. 14B) of A2AR-90-007.
Figure 14B:
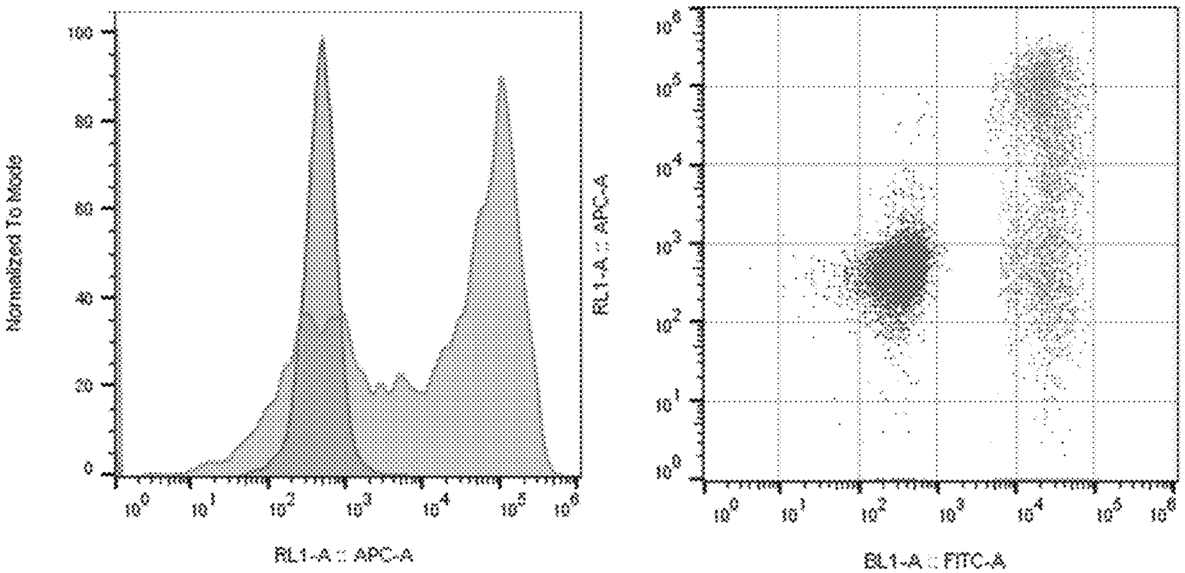

73 out of 88 unique clones had a target cell MFI values 2 fold over parental cells. 15 out of 88 unique Clones with target cell MFI values 20 fold over parental cells. Data for adenosine A2A receptor variant A2AR-90-007 is seen in FIGS. 14A-14B.

This Example shows generation of a VHH library for the A2AR with high affinity and $K_D$ values in the sub-nanomolar range.

Example 9. GPCR Libraries with Varied CDR's

A GPCR library was created using a CDR randomization scheme.

Briefly, GPCR libraries were designed based on GPCR antibody sequences. Over sixty different GPCR antibodies were analyzed and sequences from these GPCRs were modified using a CDR randomization scheme.

Figure 15A:
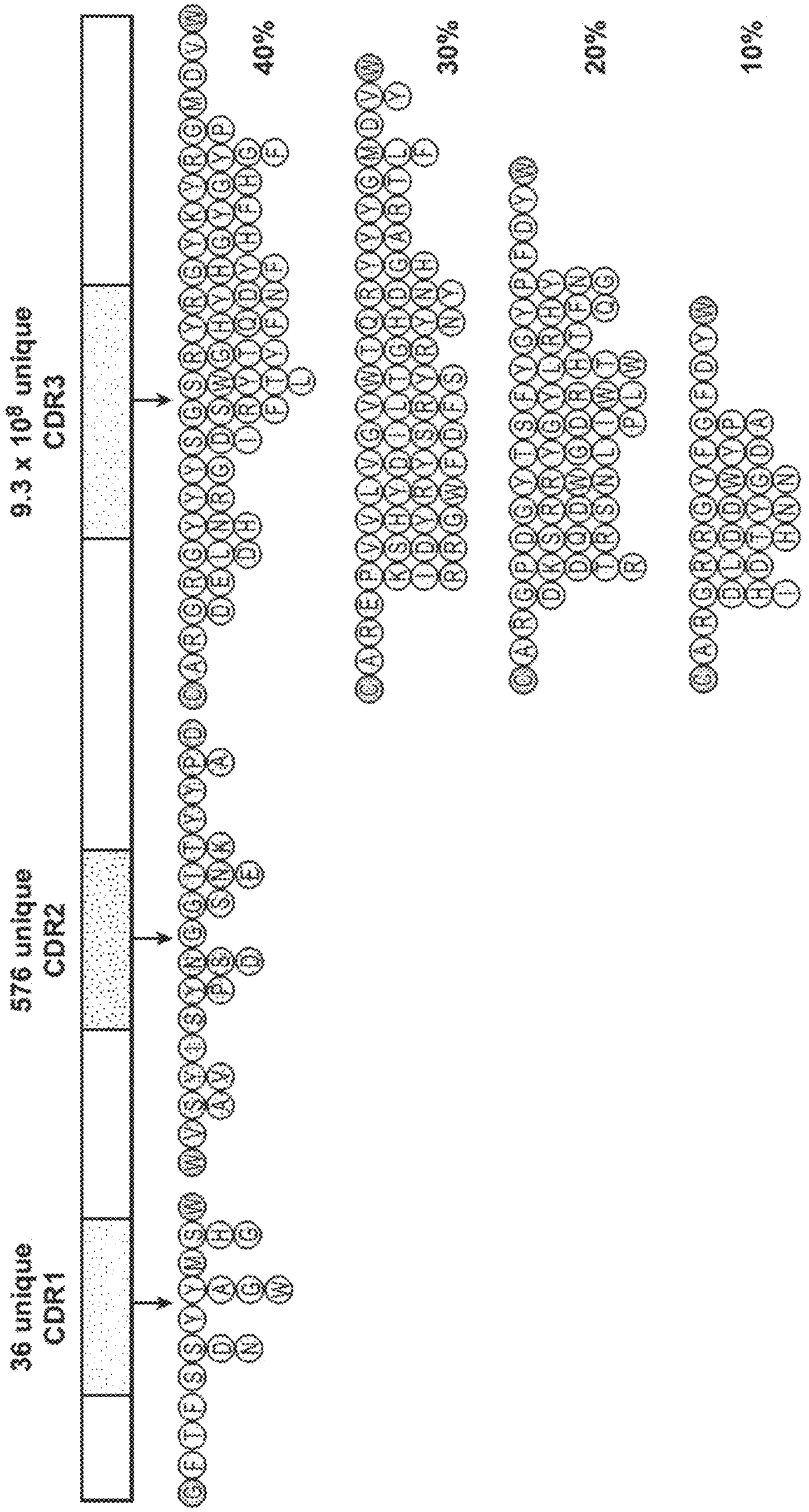
FIG. 15A depicts a schema of heavy chain IGHV3-23 design. Figure discloses SEQ ID NOS 726-731, respectively, in order of appearance.

The heavy chain IGHV3-23 design is seen in FIG. 15A. As seen in FIG. 15A, IGHV3-23 CDRH3's had four distinctive lengths: 23 amino acids, 21 amino acids, 17 amino acids, and 12 amino acids, with each length having its residue diversity. The ratio for the four lengths were the following: 40% for the CDRH3 23 amino acids in length, 30% for the CDRH3 21 amino acids in length, 20% for the CDRH3 17 amino acids in length, and 10% for the CDRH3 12 amino acids in length. The CDRH3 diversity was determined to be $9.3\times10^8$, and the full heavy chain IGHV3-23 diversity was $1.9\times10^{13}$.

Figure 15B:
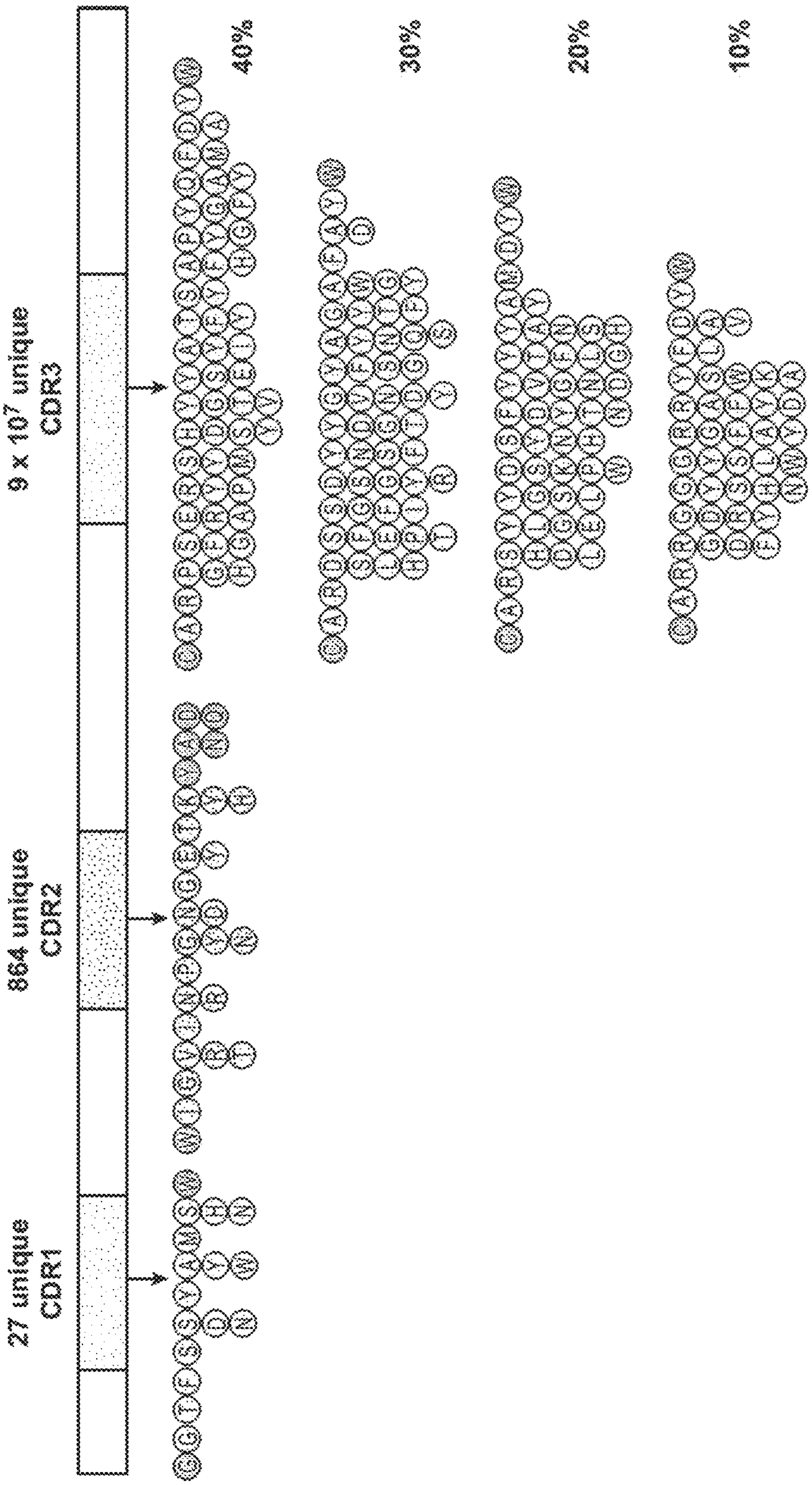
FIG. 15B depicts a schema of heavy chain IGHV1-69 design. Figure discloses SEQ ID NOS 732-737, respectively, in order of appearance.

The heavy chain IGHV1-69 design is seen in FIG. 15B. As seen in FIG. 15B, IGHV1-69 CDRH3's had four distinctive lengths: 20 amino acids, 16 amino acids, 15 amino acids, and 12 amino acids, with each length having its residue diversity. The ratio for the four lengths were the following: 40% for the CDRH3 20 amino acids in length, 30% for the CDRH3 16 amino acids in length, 20% for the CDRH3 15 amino acids in length, and 10% for the CDRH3 12 amino acids in length. The CDRH3 diversity was determined to be $9\times10^7$, and the full heavy chain IGHV-69 diversity is $4.1\times10^{12}$.

Figure 15C:
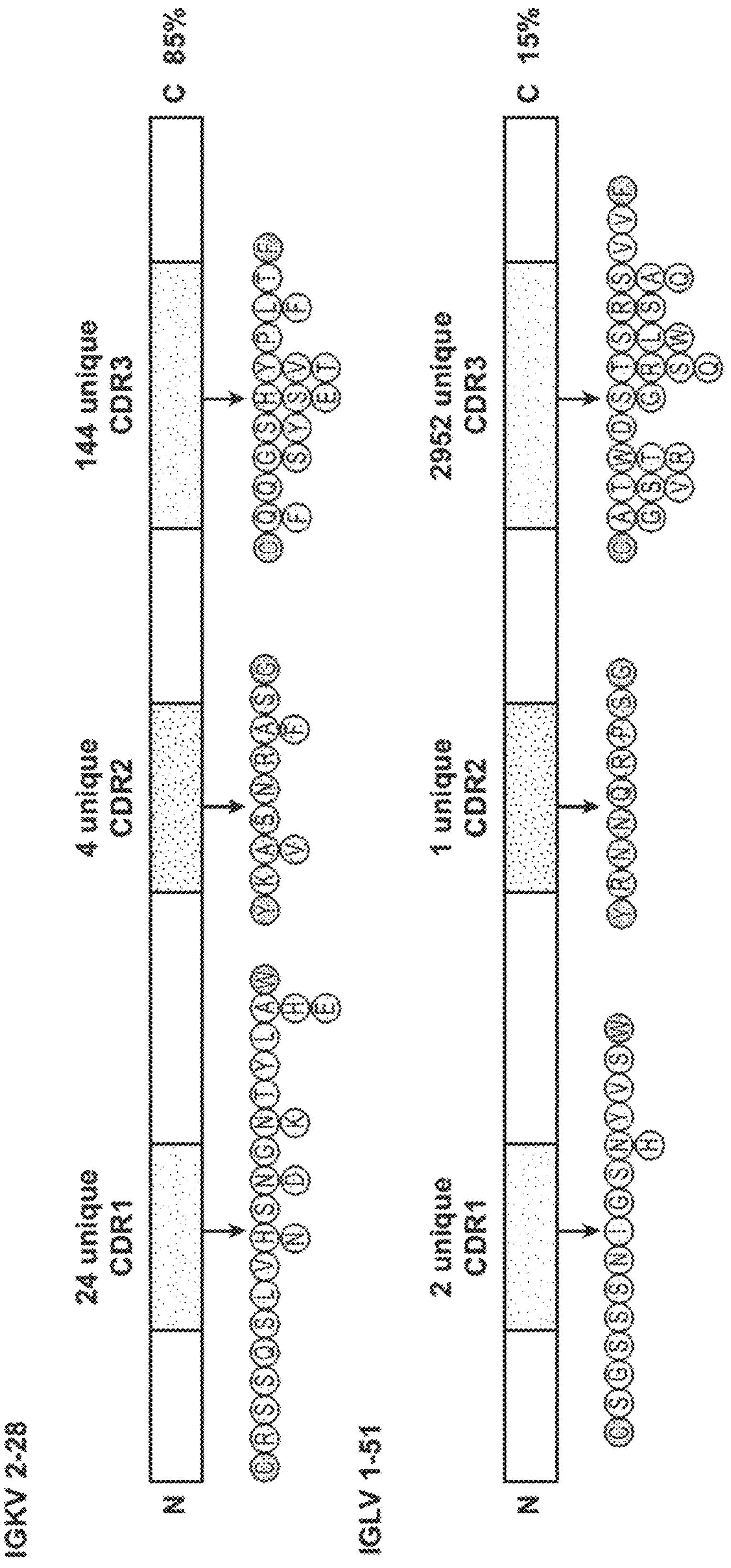
FIG. 15C depicts a schema of light chains IGKV 2-28 and IGLV 1-51 design. Figure discloses SEQ ID NOS 738-743, respectively, in order of appearance.

The light chains IGKV 2-28 and IGLV 1-51 design is seen in FIG. 15C. Antibody light chain CDR sequences were analyzed for position-specific variation. Two light chain frameworks were selected with fixed CDR lengths. The theoretical diversities were determined to be 13800 and 5180 for kappa and light chains, respectively.

Figure 15D:
FIG. 15D depicts a schema of the theoretical diversity and final diversity of a GPCR library.

The final theoretical diversity was determined to be $4.7\times10^{17}$ and the final, generated Fab library had a diversity of $6\times10^9$. See FIG. 15D.

Example 10. Adenosine A2A Receptor Libraries with Varied CDR's

An adenosine A2A receptor library is created using a CDR randomization scheme similarly described in Example 9.

Briefly, adenosine A2A receptor libraries are designed based on GPCR antibody sequences. Over sixty different GPCR antibodies are analyzed and sequences from these GPCRs are modified using a CDR randomization scheme. Adenosine A2A receptor variant IgGs designed using the CDR randomization scheme are purified and are assayed to determine cell-based affinity measurements and for functional analysis.

Example 11. A2A Variant Immunoglobulins

A2AR variant immunoglobulins generated were assayed in various functional assays.

First, A2AR immunoglobulin scFv phage libraries were panned on cells and immobilized A2a proteins, and screened. The output phage numbers from each round of selection are seen in Tables 7-8.

TABLE 7

| Target | Library | Round 1 | Round 2 | Round 3 | Round 4 | Round 5 |
|---|---|---|---|---|---|---|
| HEK293-A2a Cells | Mouse Immune | $2.7 \times 10^6$ | $4.1 \times 10^7$ | $5.0 \times 10^7$ | $5.0 \times 10^7$ | $1.2 \times 10^8$ |
| A2a protein | Humanized Synthetic | $4.1 \times 10^6$ | $8.0 \times 10^7$ | $2.3 \times 10^8$ | $1.2 \times 10^7$ | $5.8 \times 10^7$ |
| A2a protein + ZM241385 | Humanized Synthetic | $5.2 \times 10^6$ | $4.5 \times 10^7$ | $1.3 \times 10^8$ | $3.0 \times 10^7$ | $6.7 \times 10^7$ |
| A2a protein | Mouse Immune | $4.3 \times 10^7$ | $5.8 \times 10^7$ | $3.0 \times 10^7$ | $4.8 \times 10^7$ | $3.2 \times 10^7$ |
| A2a protein + ZM241385 | Mouse Immune | $2.4 \times 10^7$ | $3.7 \times 10^7$ | $1.9 \times 10^8$ | $6.0 \times 10^7$ | $6.0 \times 10^6$ |

TABLE 8

| Target | Library | Round 1 | Round 2 | Round 3 | Round 4 | Round 5 |
|---|---|---|---|---|---|---|
| HEK293-A2a Cells | Immune | $1.3 \times 10^6$ | $3.1 \times 10^7$ | $5.0 \times 10^7$ | $5.0 \times 10^7$ | $1.3 \times 10^8$ |
| A2a protein | Synthetic | $5.2 \times 10^6$ | $3.7 \times 10^7$ | $1.5 \times 10^8$ | $1.2 \times 10^7$ | $4.9 \times 10^7$ |
| A2a protein + ZM241385 | Synthetic | $6.7 \times 10^6$ | $2.9 \times 10^7$ | $6.0 \times 10^7$ | $2.0 \times 10^7$ | $6.0 \times 10^7$ |
| A2a protein | Immune | $8.0 \times 10^6$ | $2.0 \times 10^7$ | $9.0 \times 10^7$ | $2.3 \times 10^7$ | $2.8 \times 10^7$ |
| A2a protein + ZM241385 | Immune | $6.0 \times 10^6$ | $1.7 \times 10^7$ | $1.3 \times 10^8$ | $4.6 \times 10^7$ | $1.9 \times 10^7$ |

Example 12. Screening Antibody Binding

Selected A2AR immunoglobulins from the groups listed in Tables 15-18 were assayed for binding to the targets as listed in the tables.

HEK293-A2a Cells

Figure 16B:
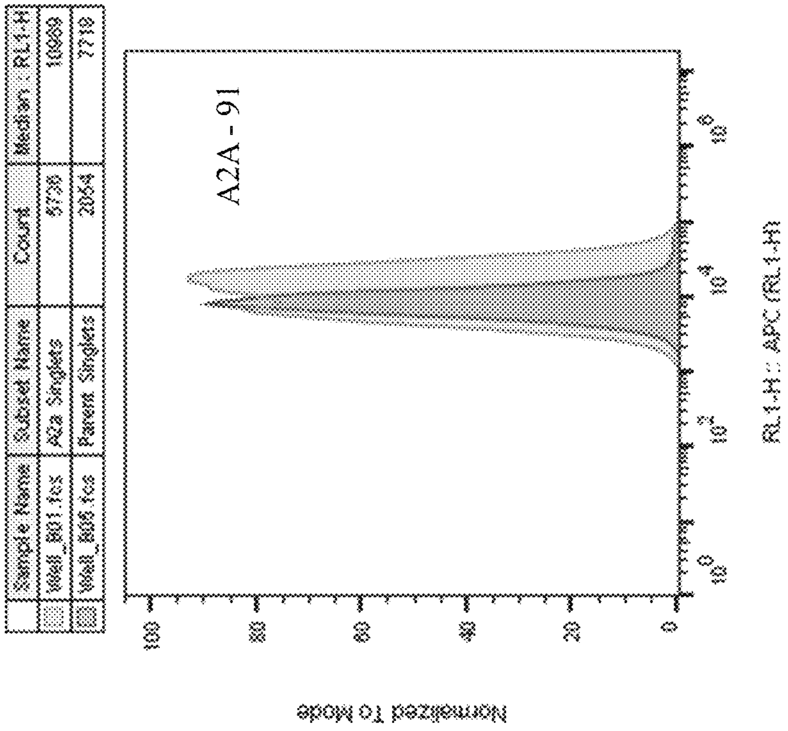
FIGS. 16A-16O depict flow cytometry data using variant A2A receptor immunoglobulins (FIGS. 16A-16N) and control (FIG. 16O).
Figure 16A:
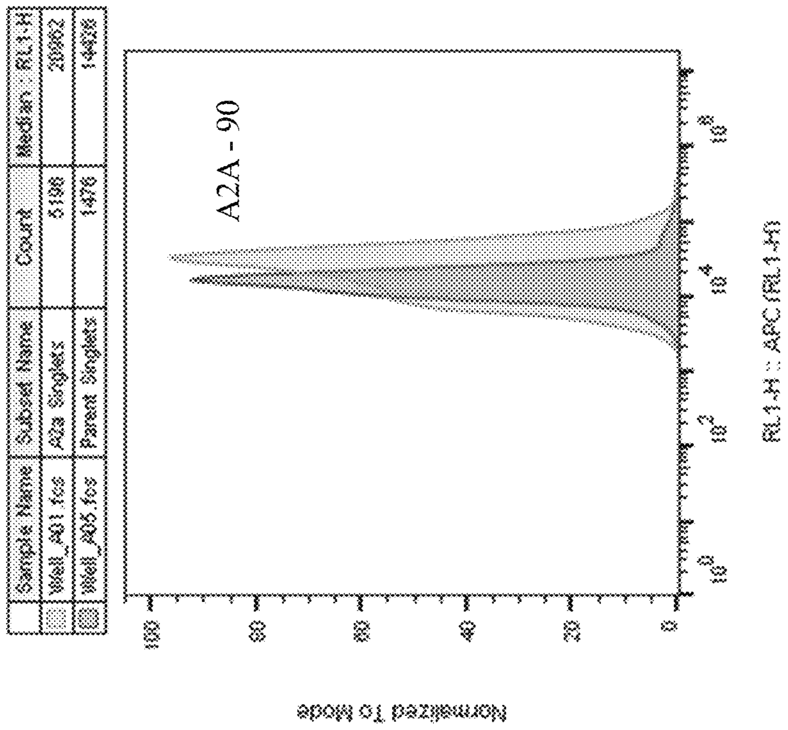
Figure 16C:
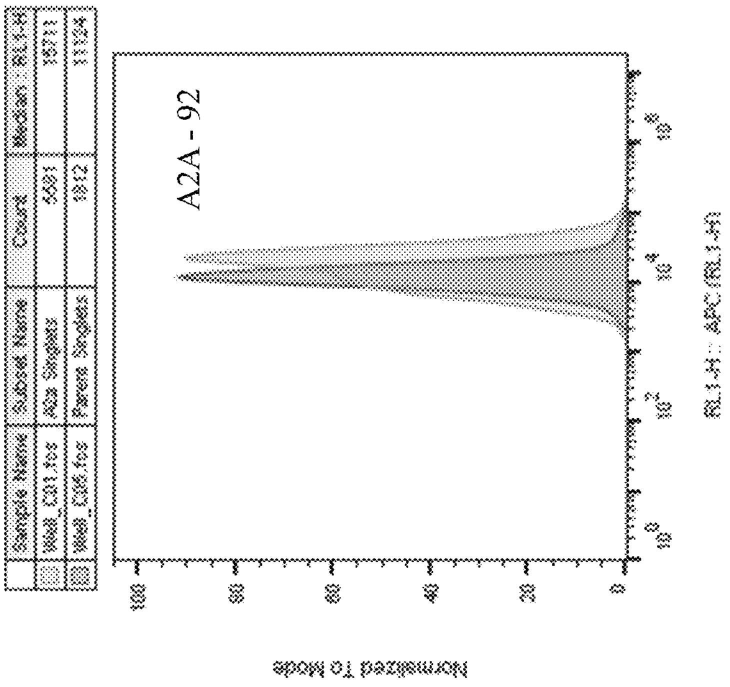
Figure 16D:
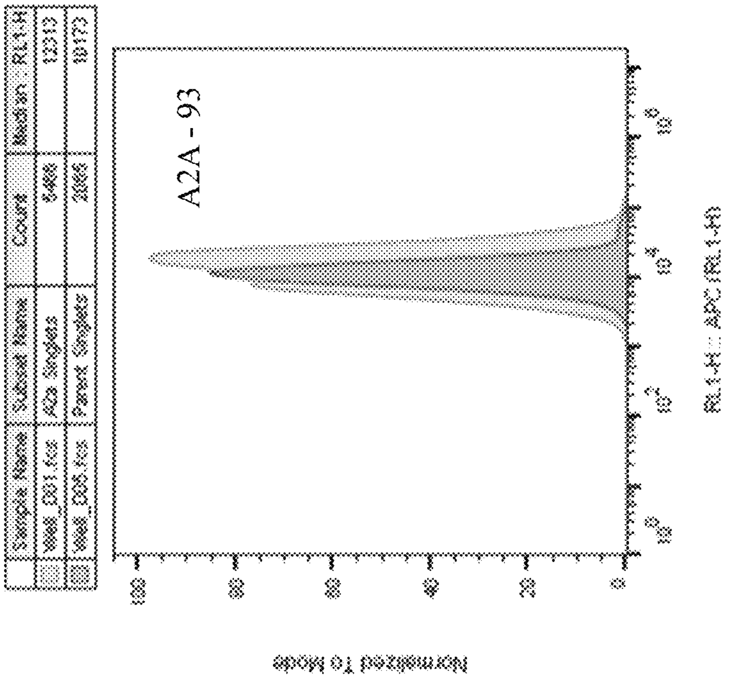
Figure 16E:
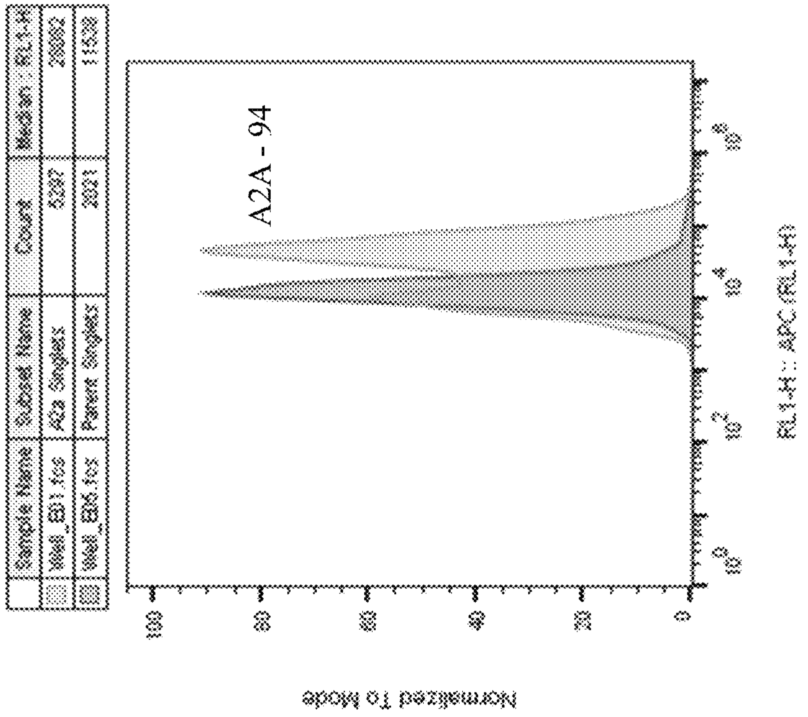
Figure 16F:
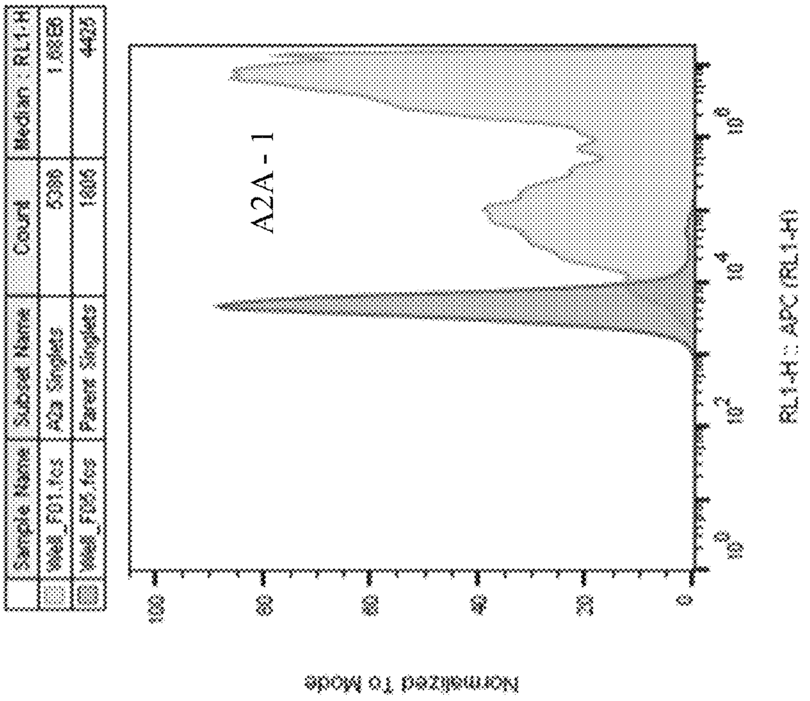
Figure 16H:
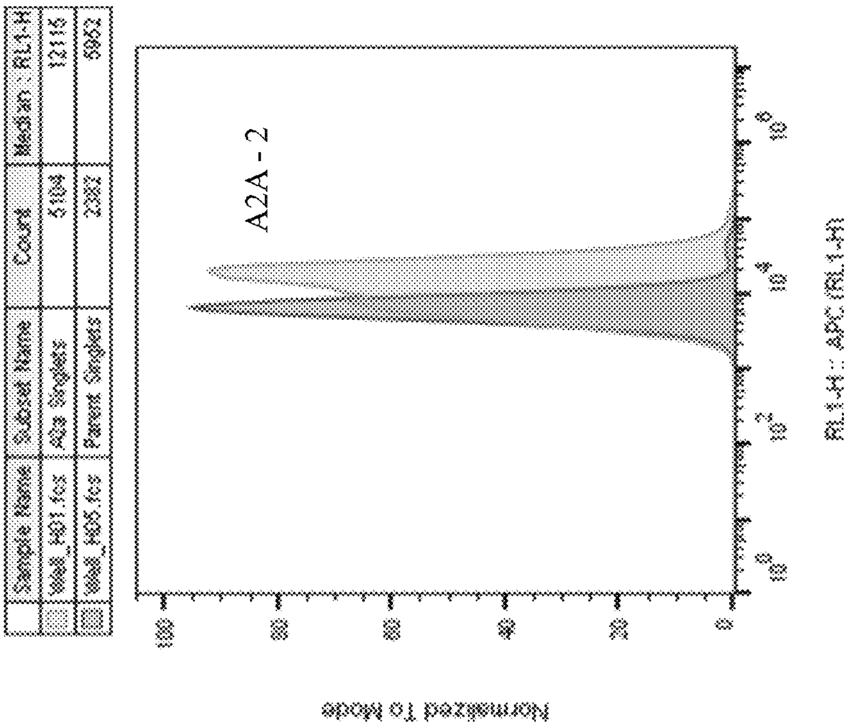
Figure 16G:
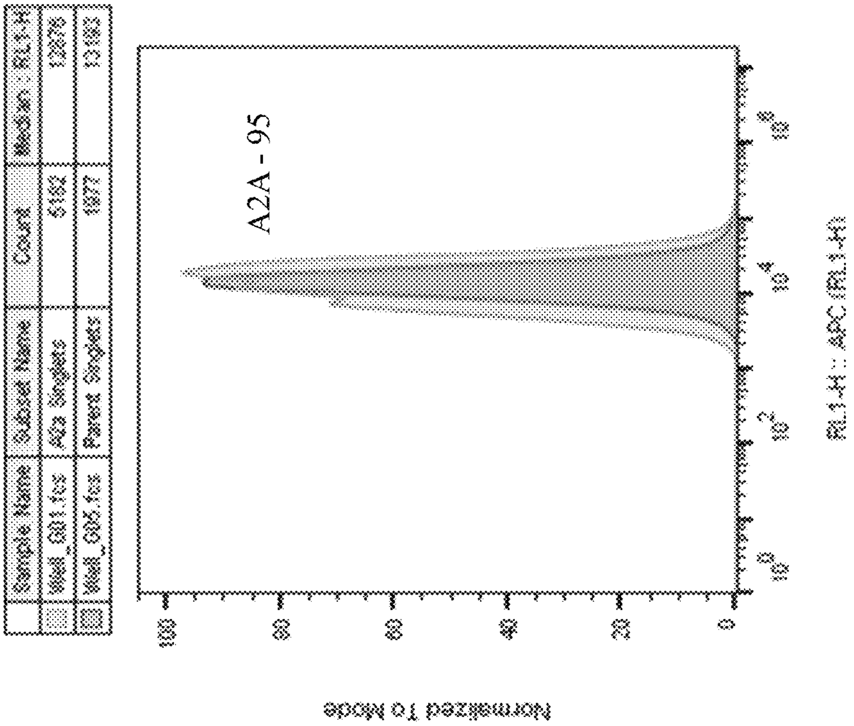
Figure 16J:
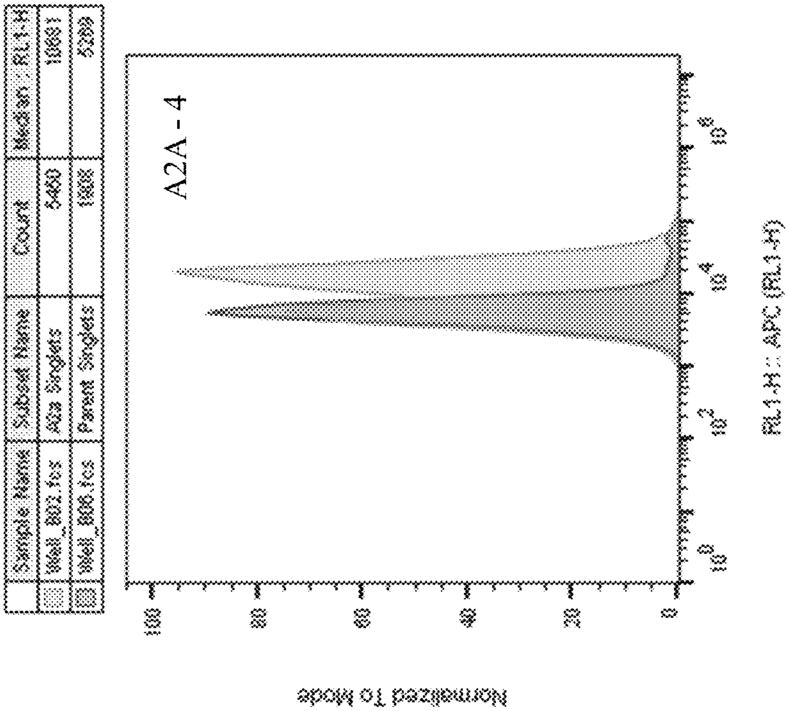
Figure 16I:
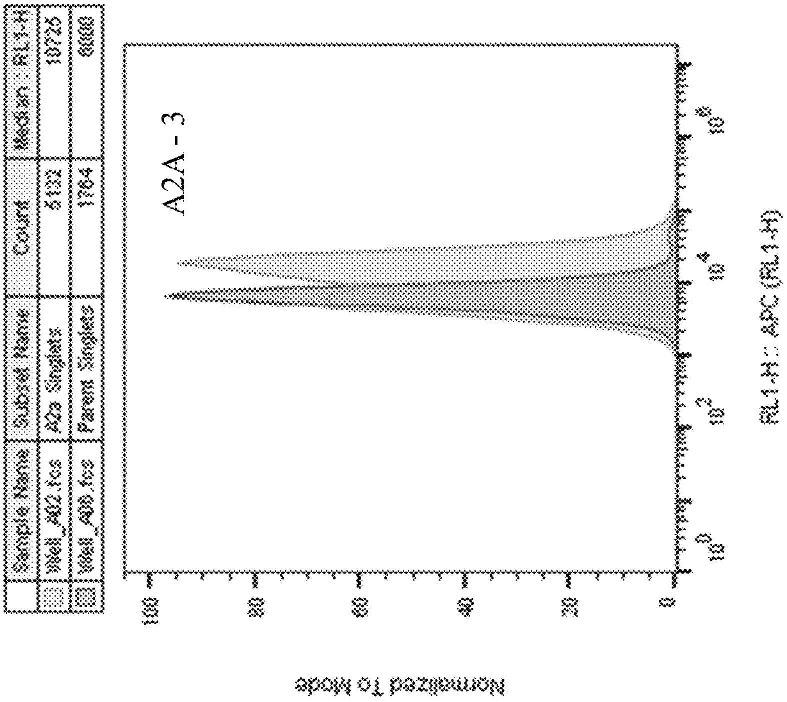
Figure 16L:
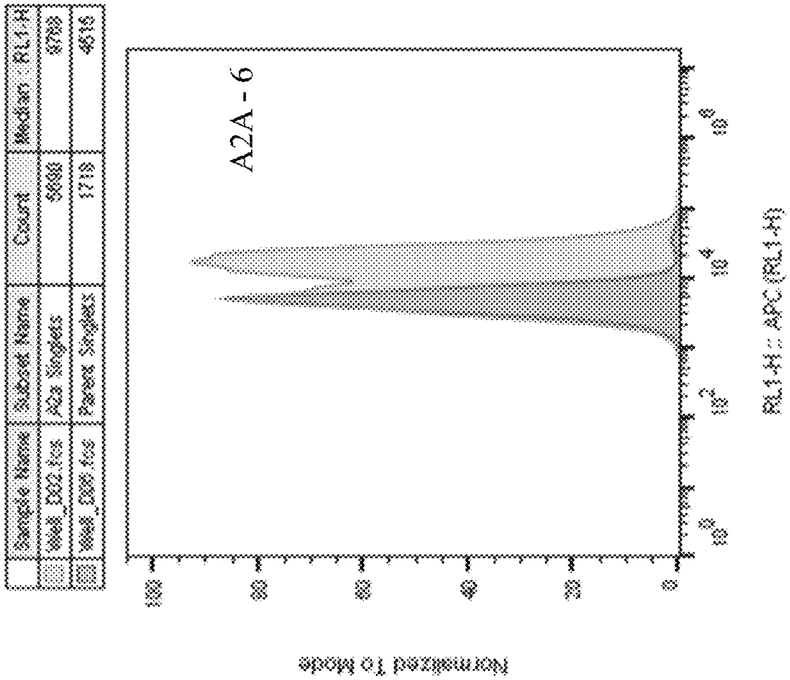
Figure 16K:
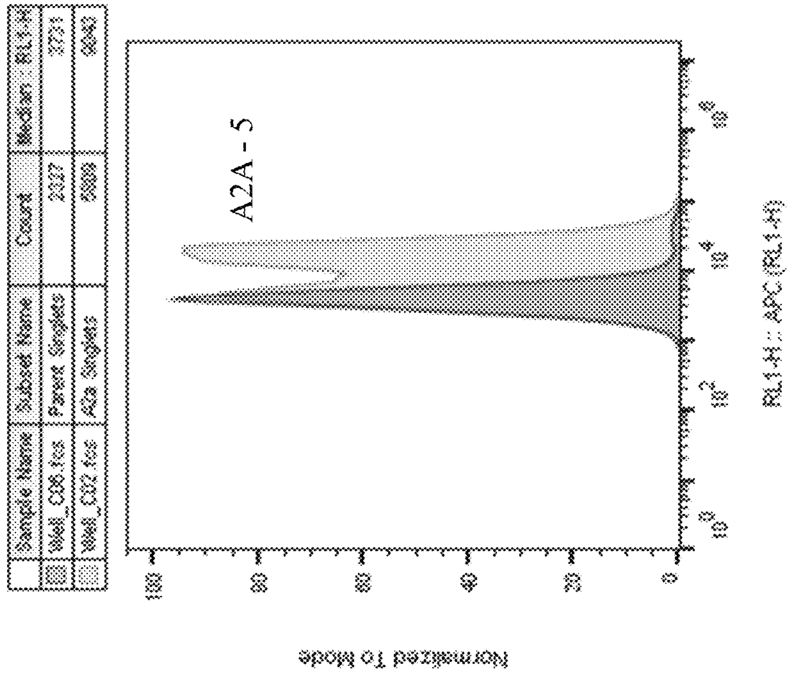
Figure 16M:
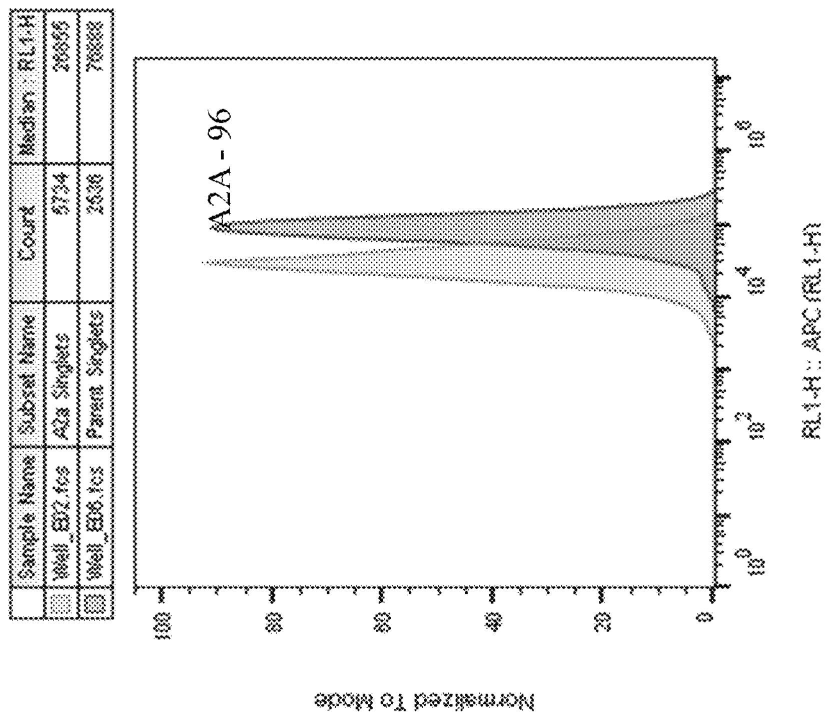
Figure 16N:
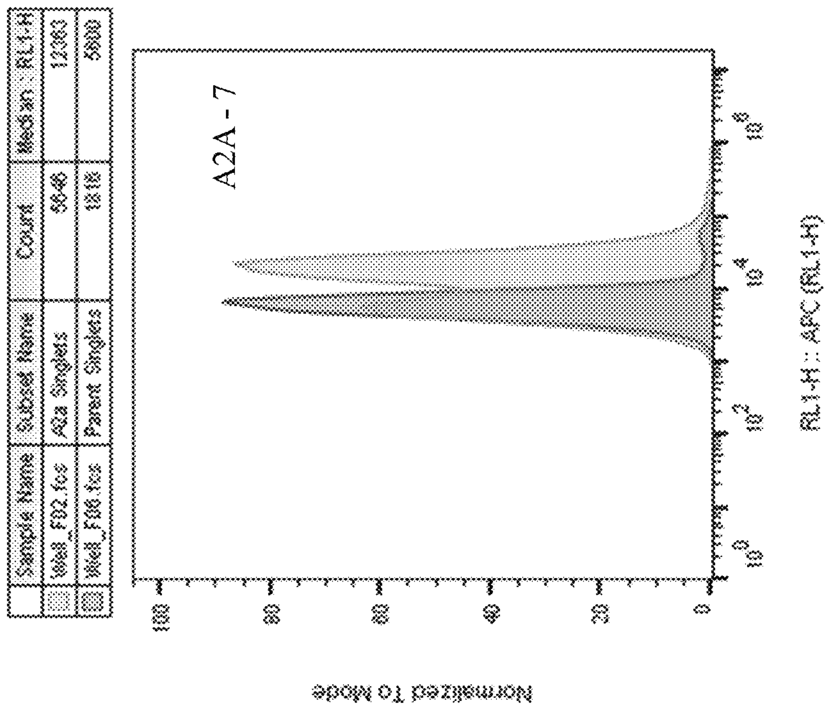
Figure 16O:
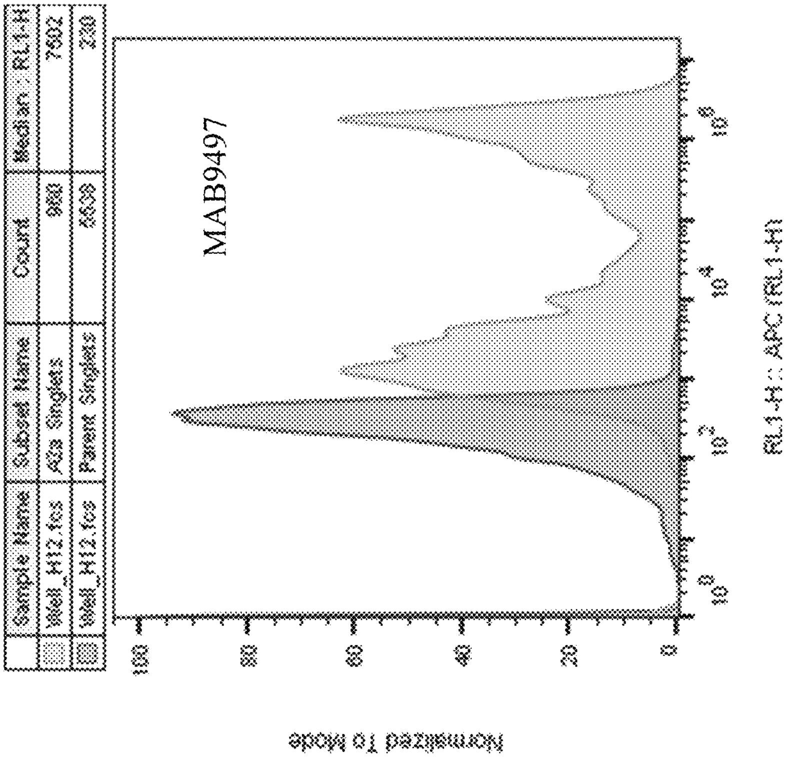
Figure 17A:
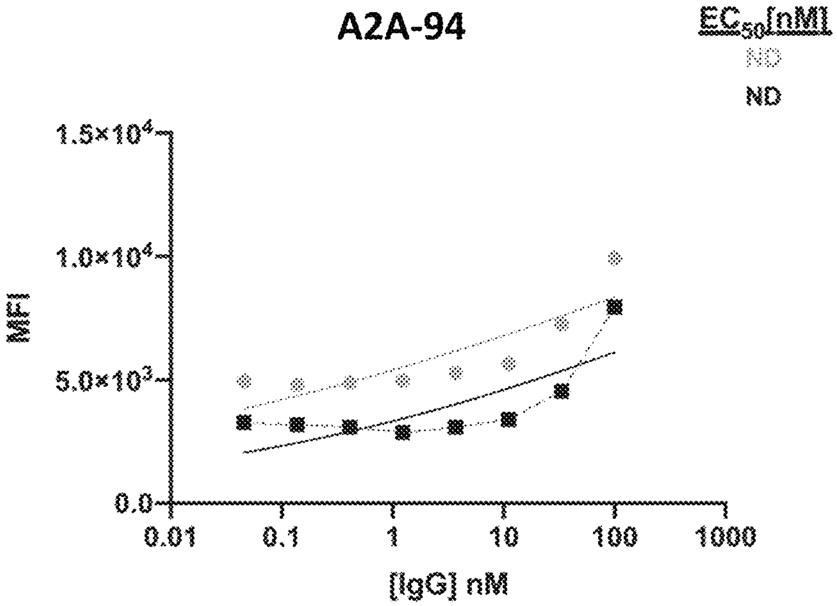
FIGS. 17A-17H depict graphs of binding curves. Binding curves are plotted with IgG concentration vs. MFI (mean fluorescence intensity).
Figure 17B:
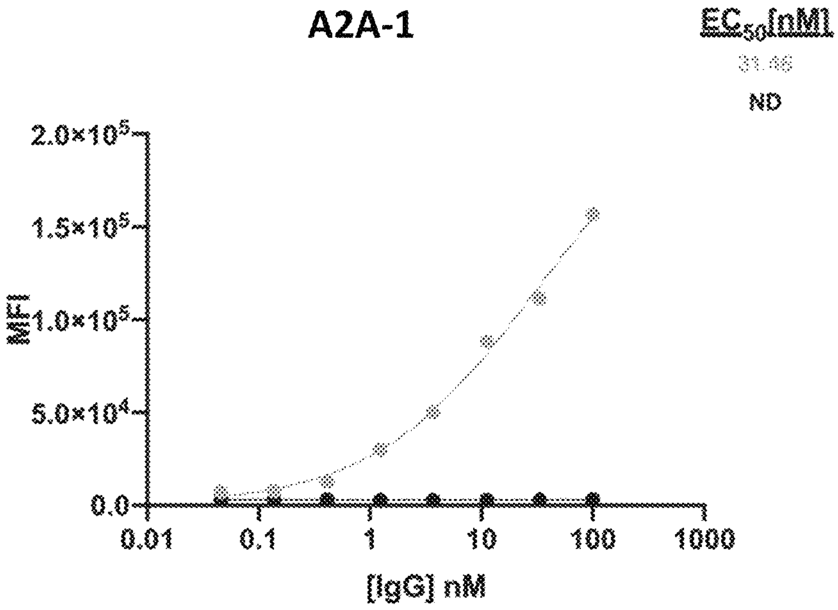
Figure 17C:
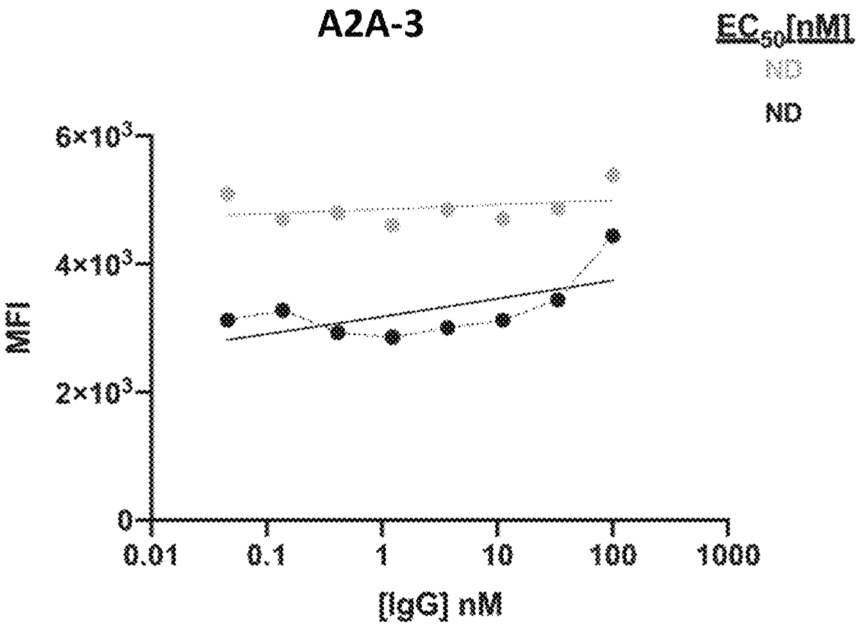
Figure 17D:
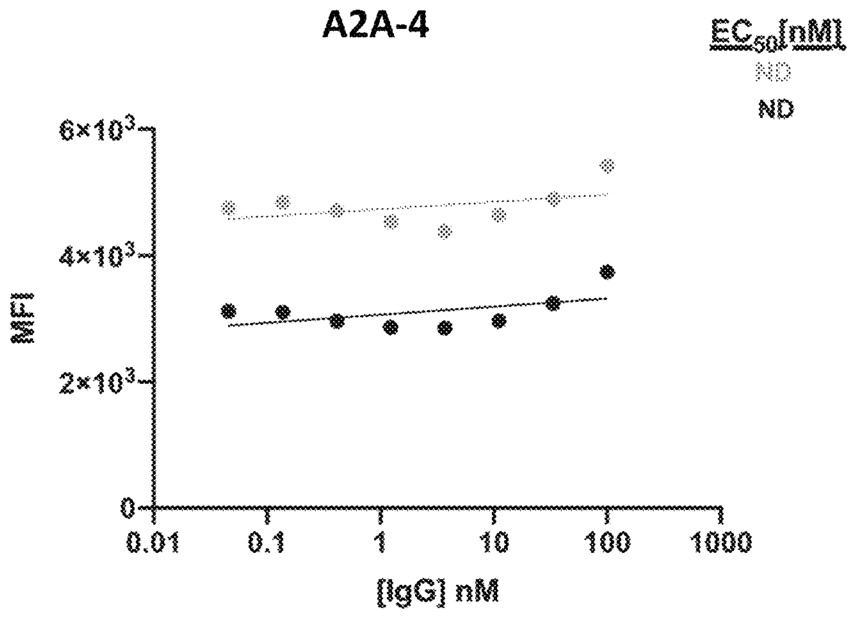
Figure 17E:
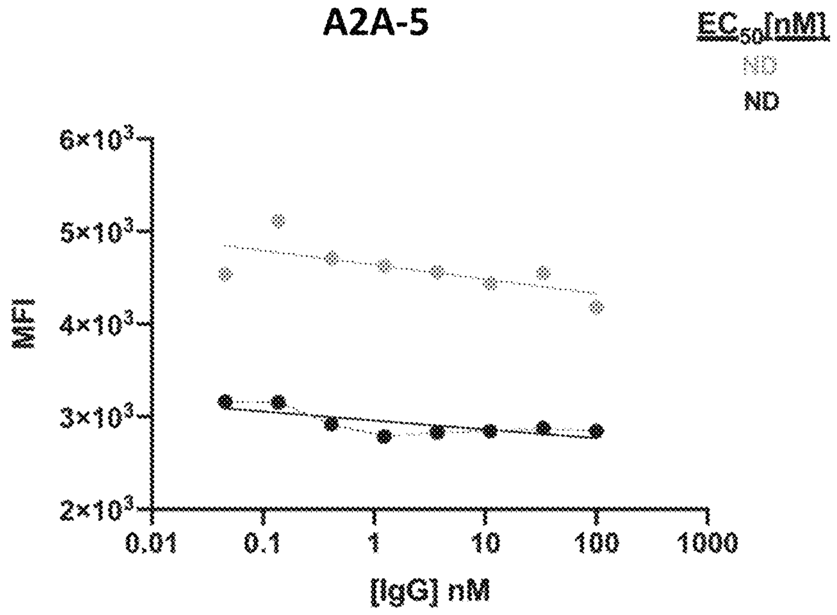
Figure 17F:
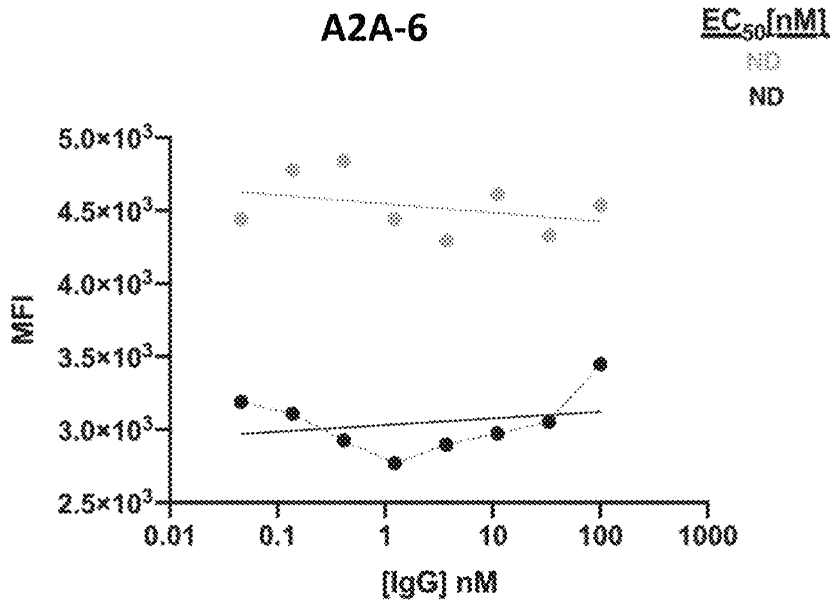
Figure 17G:
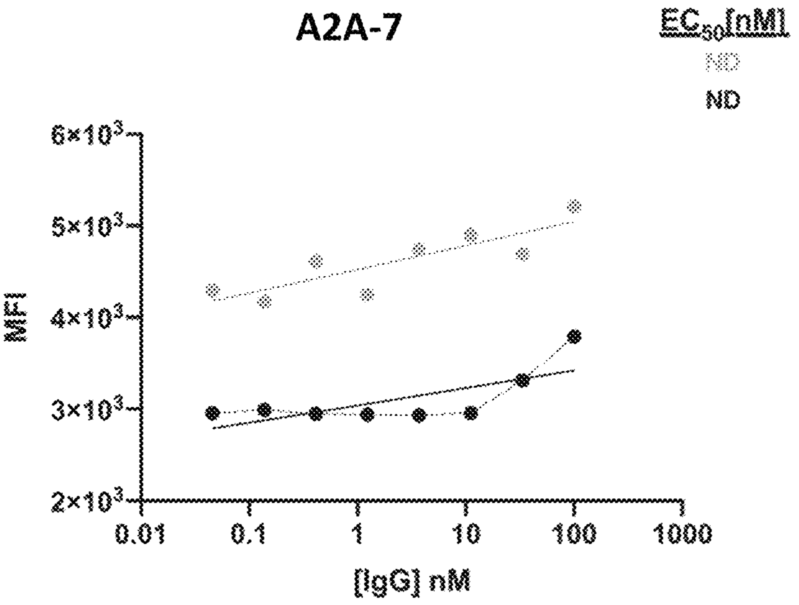
Figure 17H:
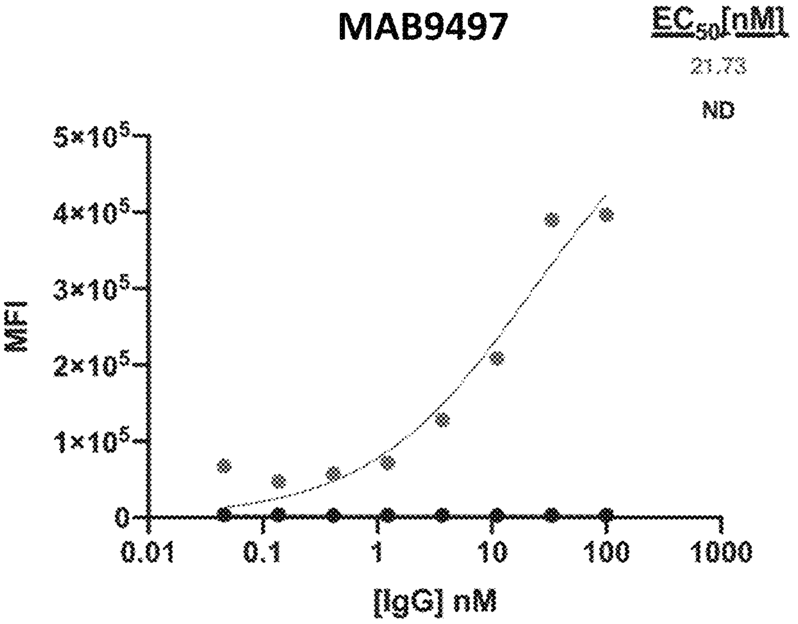
Figure 18B:
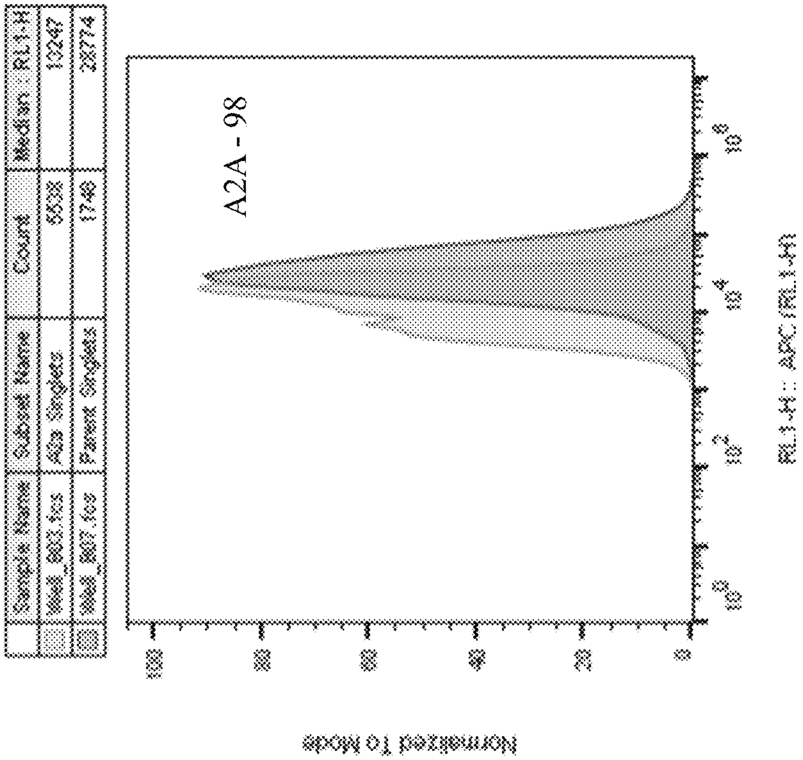
FIGS. 18A-18O depict graphs of binding curves using variants from a mouse immune library (FIGS. 18A-18N) and using a control (FIG. 18O).
Figure 18A:
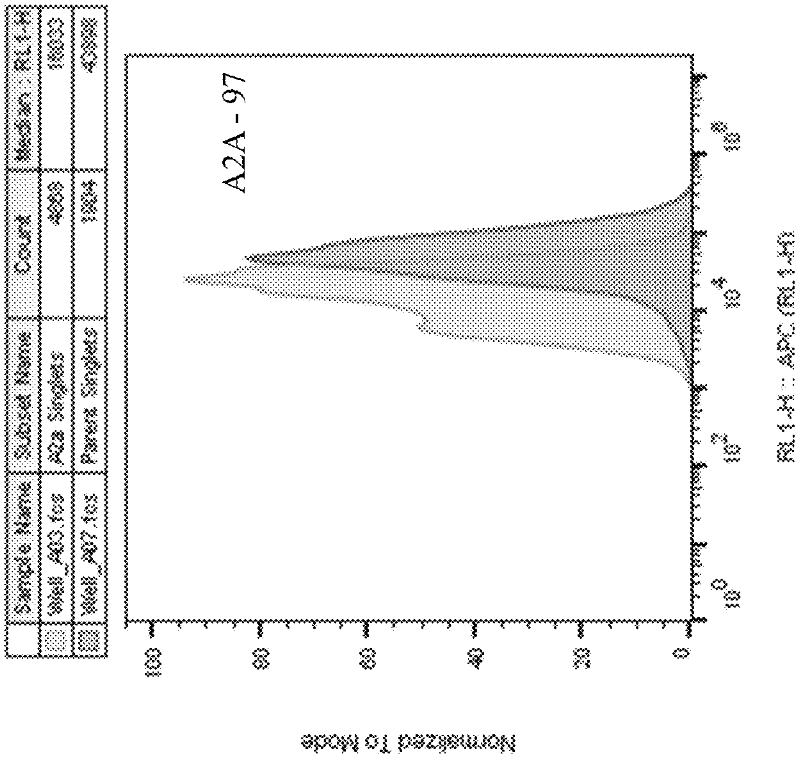
Figure 18D:
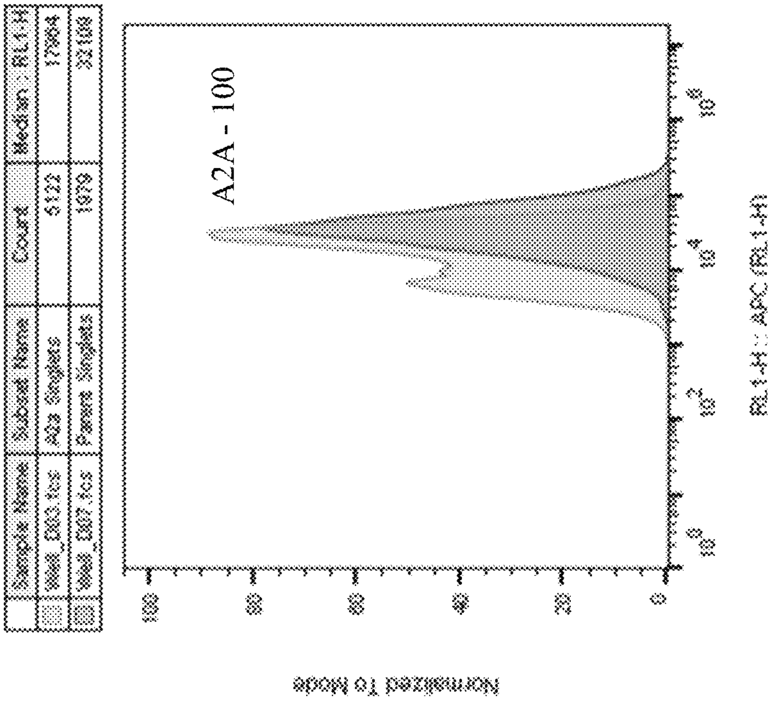
Figure 18C:
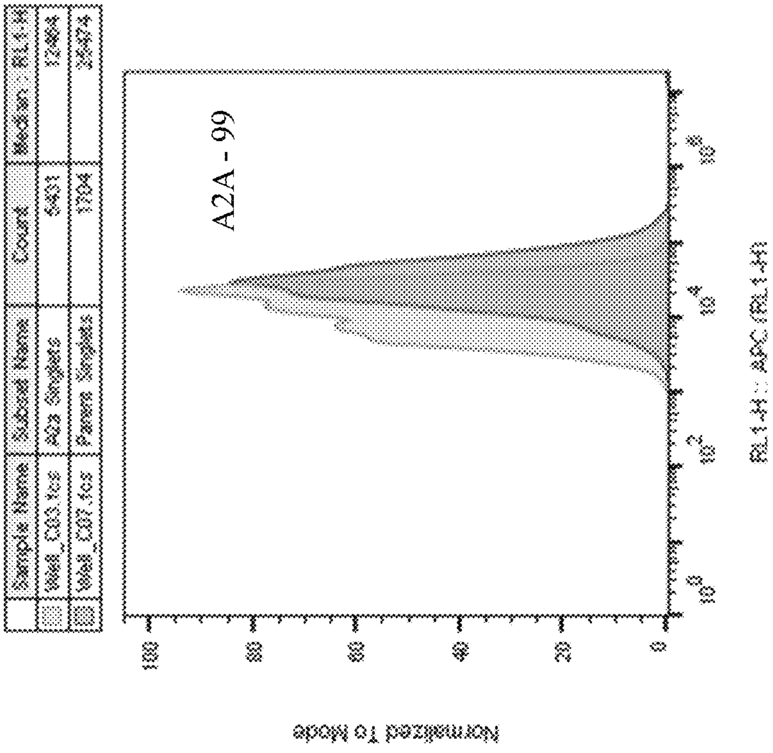
Figure 18F:
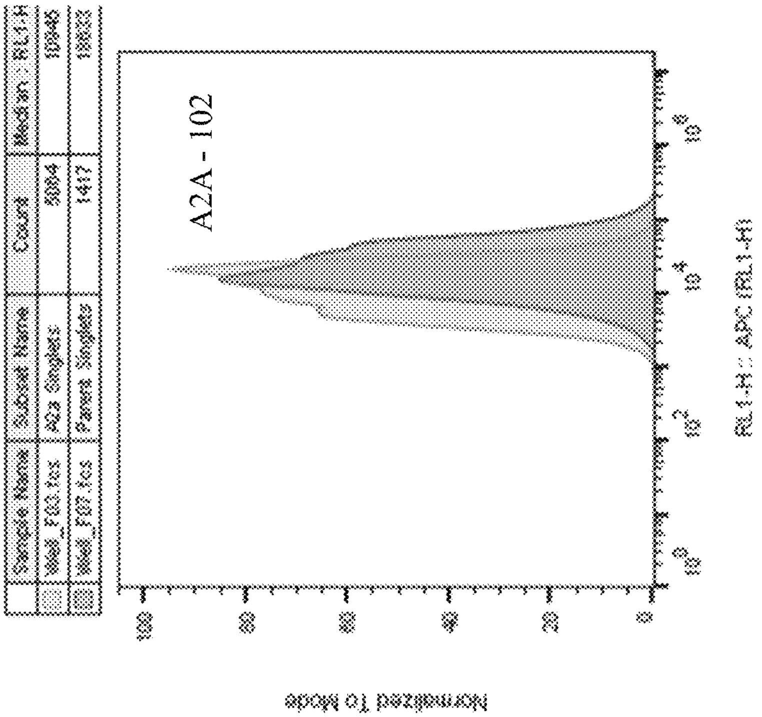
Figure 18E:
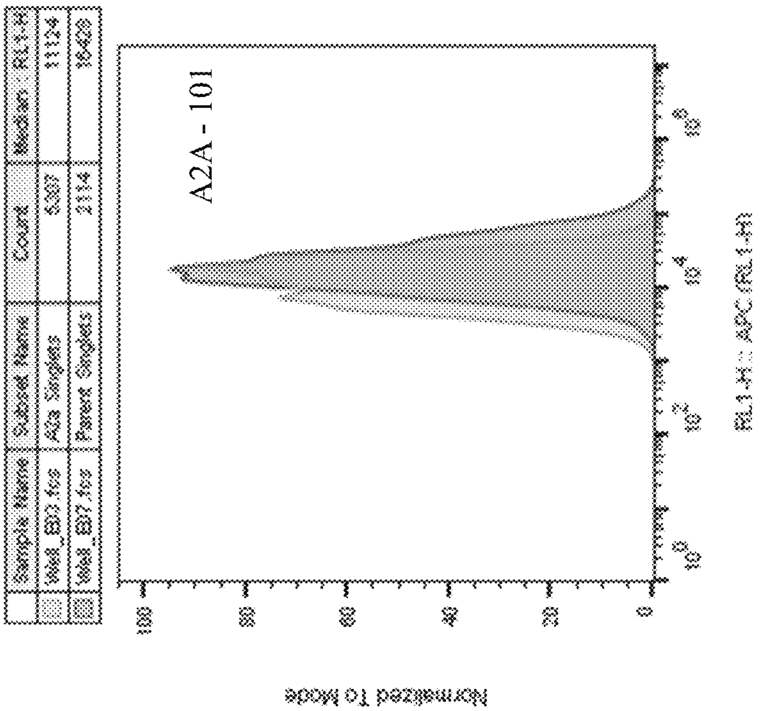
Figure 18H:
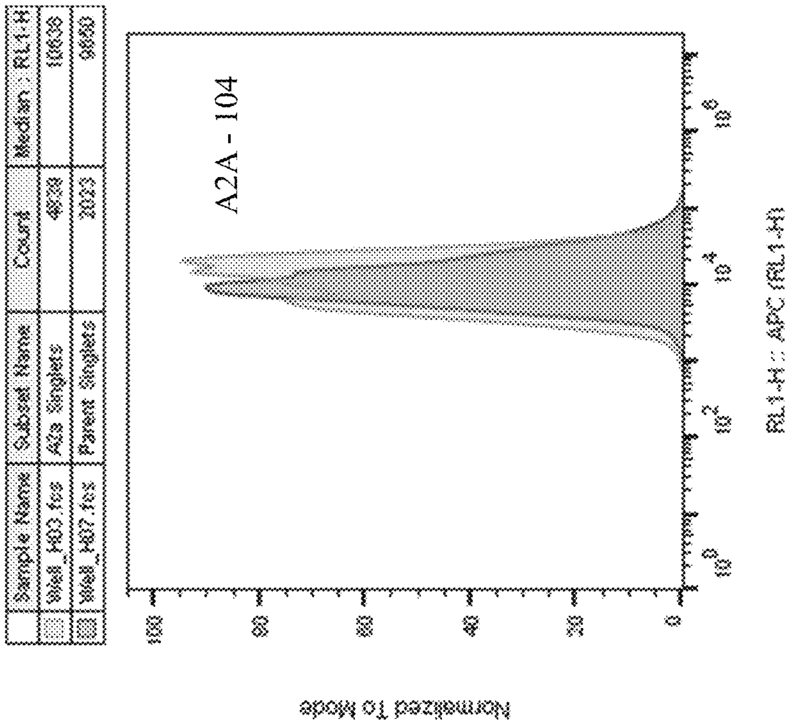
Figure 18G:
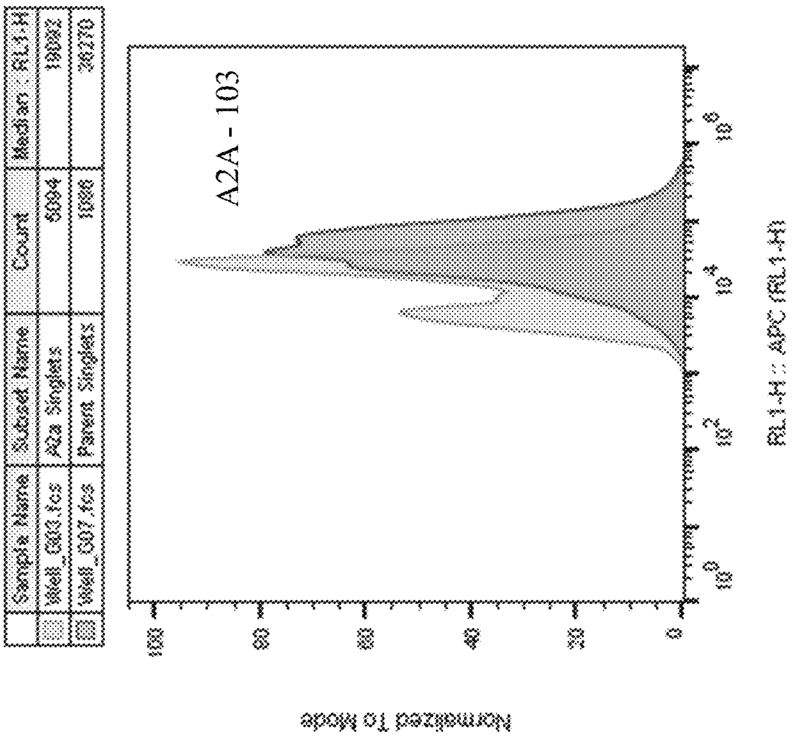
Figure 18I:
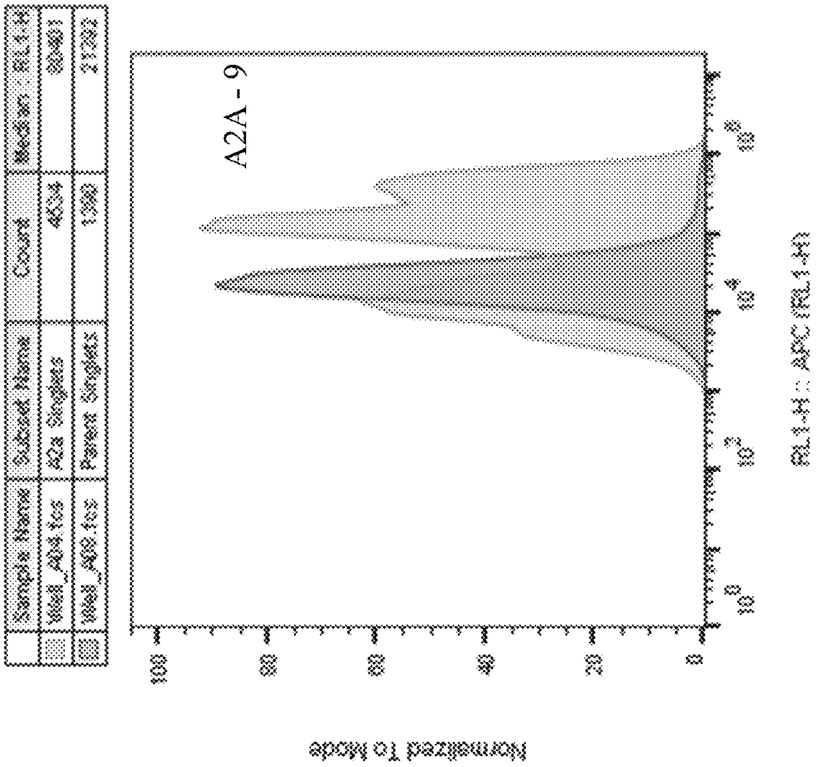
Figure 18J:
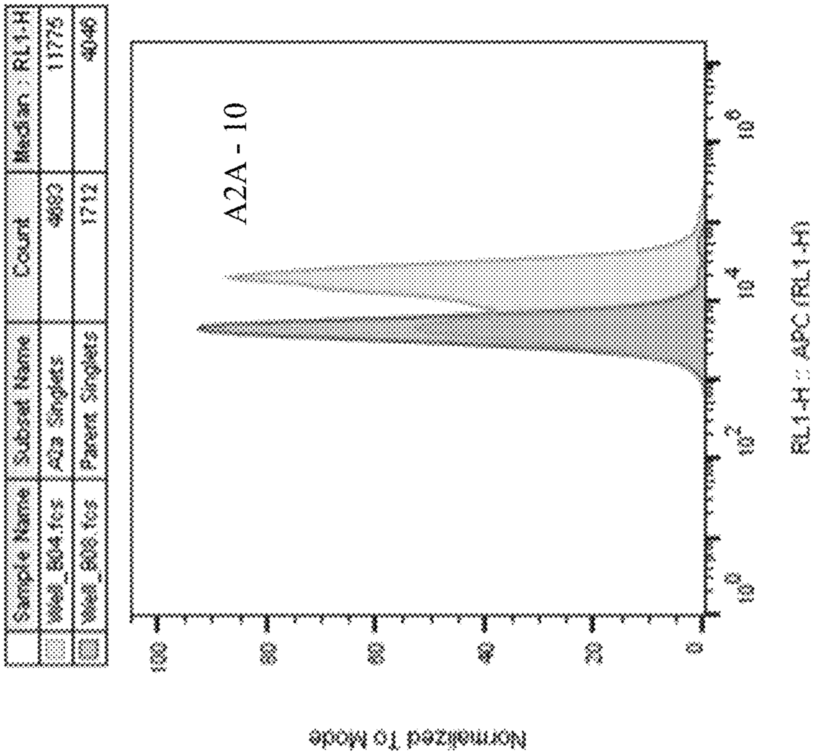
Figure 18K:
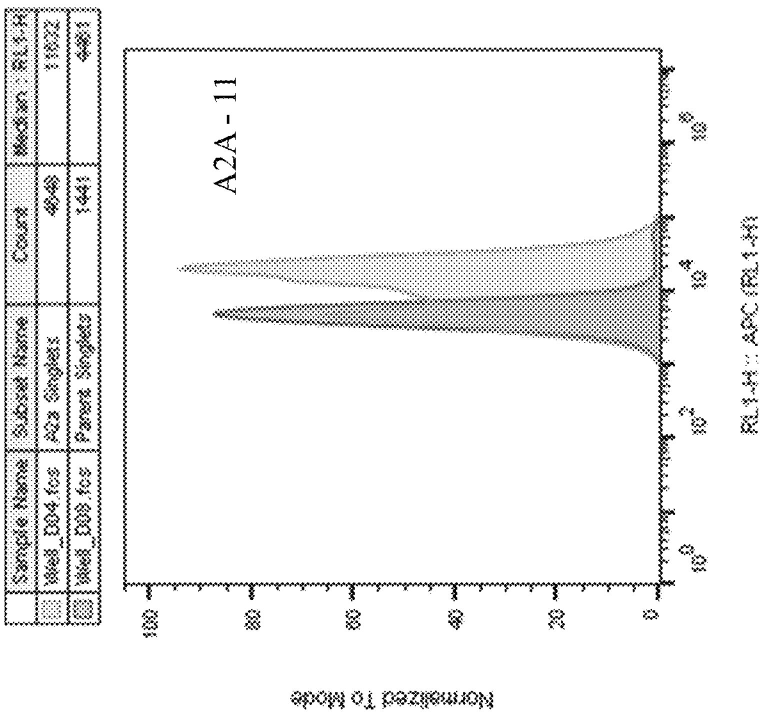
Figure 18L:
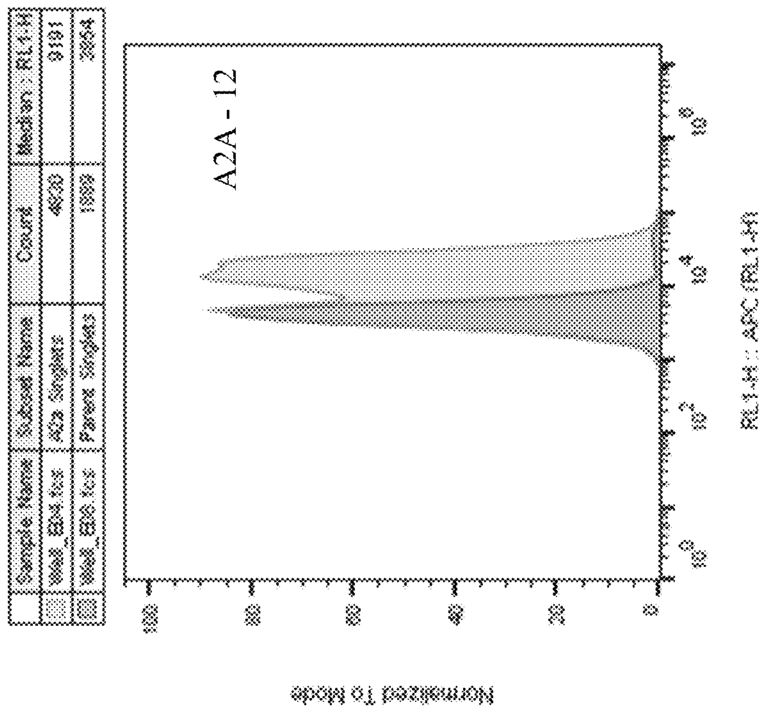
Figure 18N:
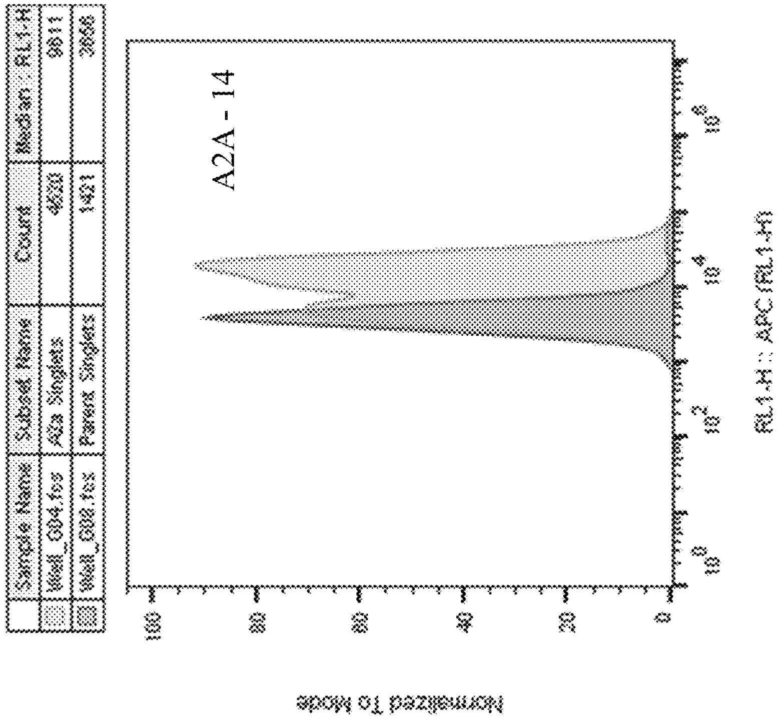
Figure 18M:
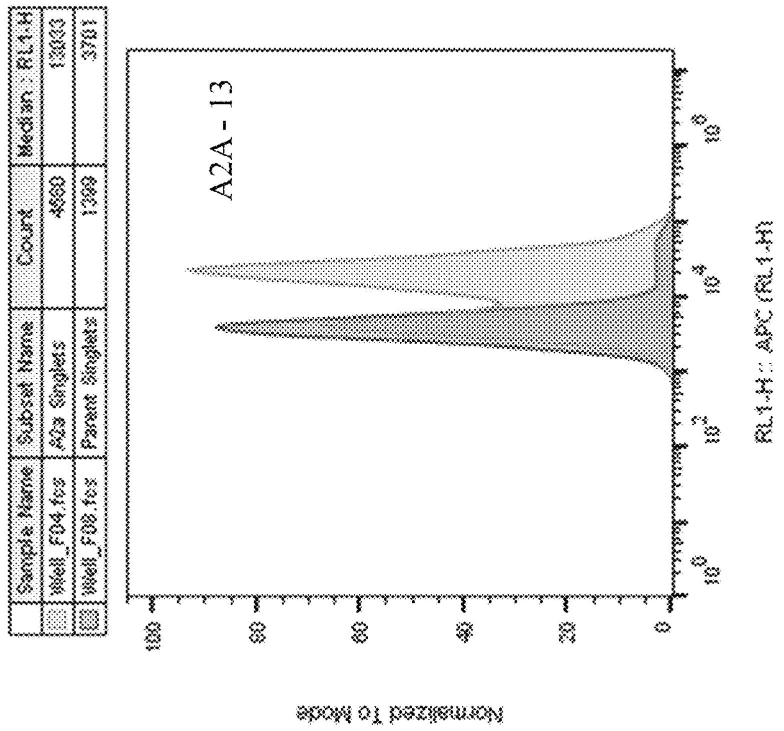
Figure 18O:
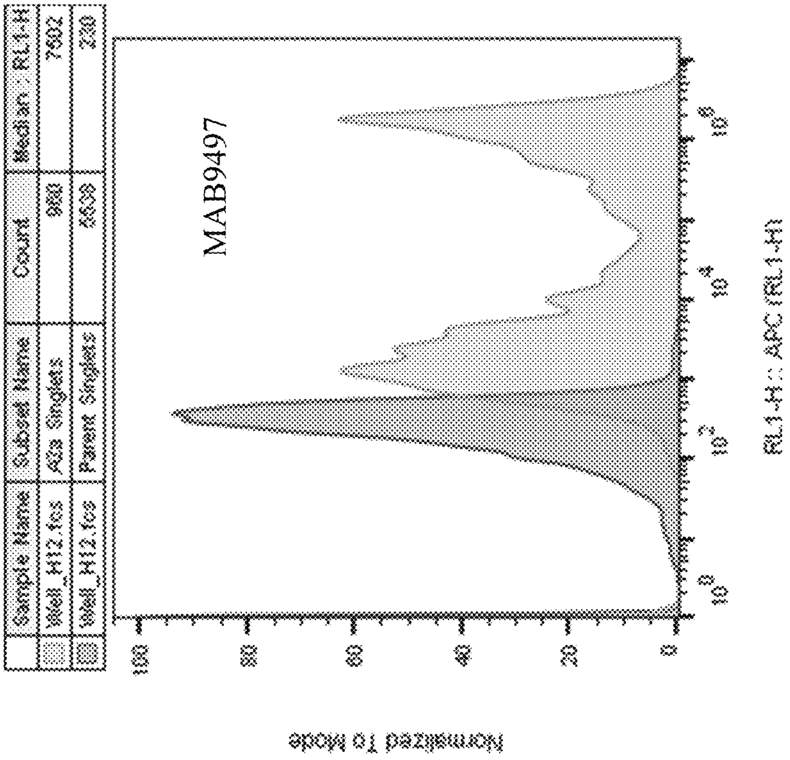
Figure 19A:
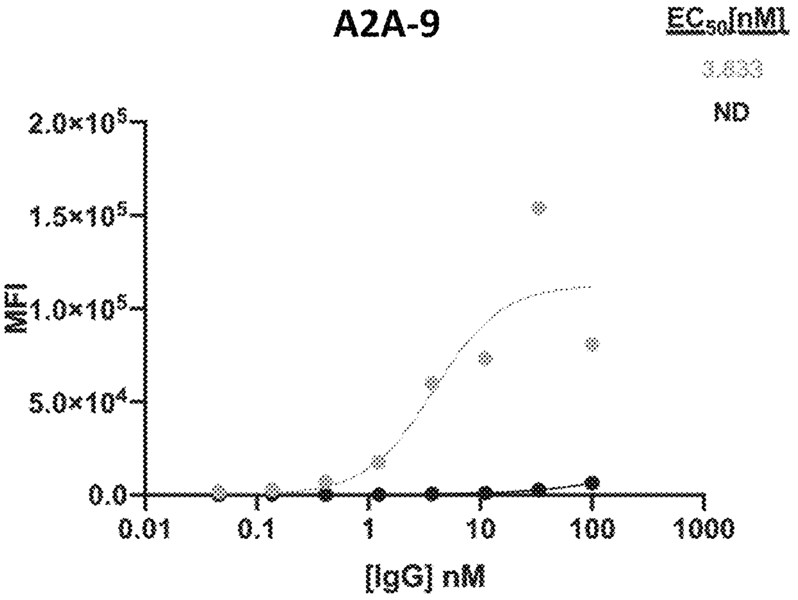
FIGS. 19A-19G depict graph of cell binding with adenosine A2aR monoclonal (MAB9497) and selected variants. Binding curves are plotted with IgG concentration vs. MFI (mean fluorescence intensity).
Figure 19B:
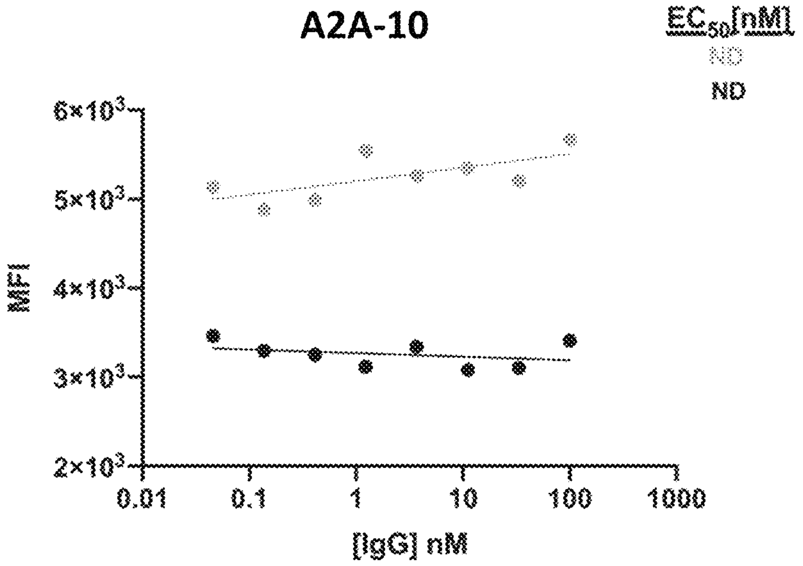
Figure 19C:
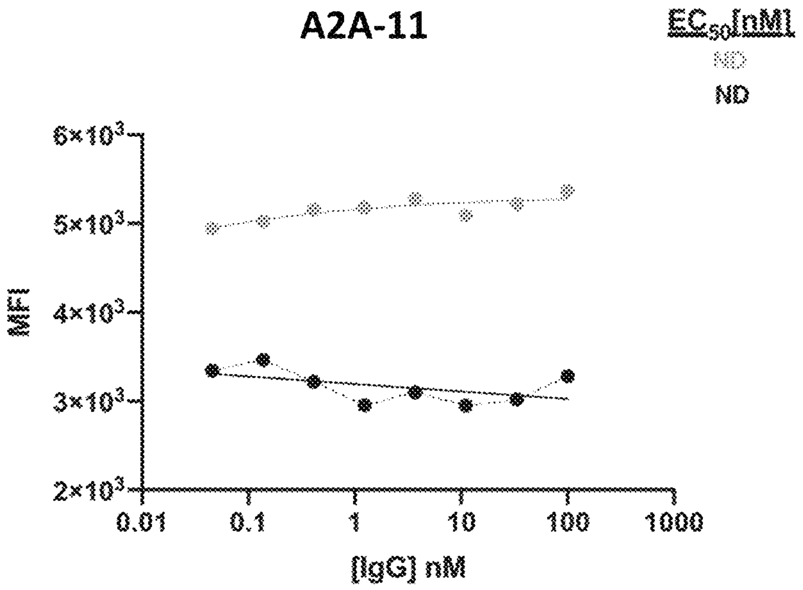
Figure 19D:
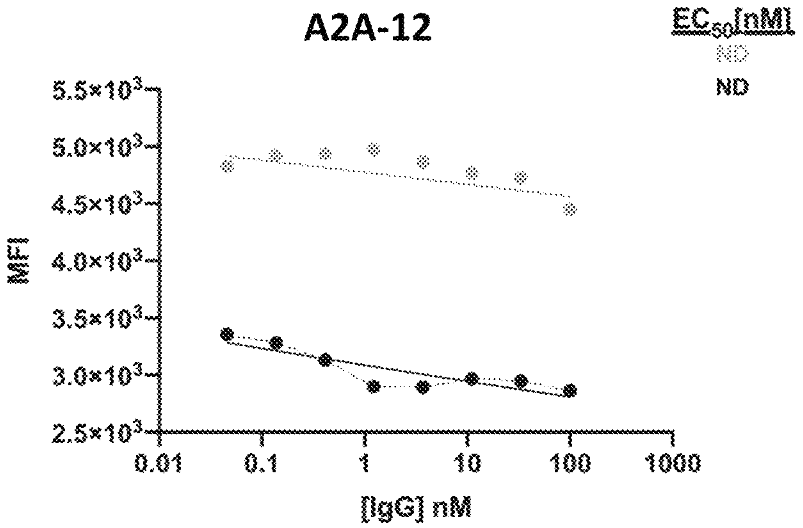
Figure 19E:
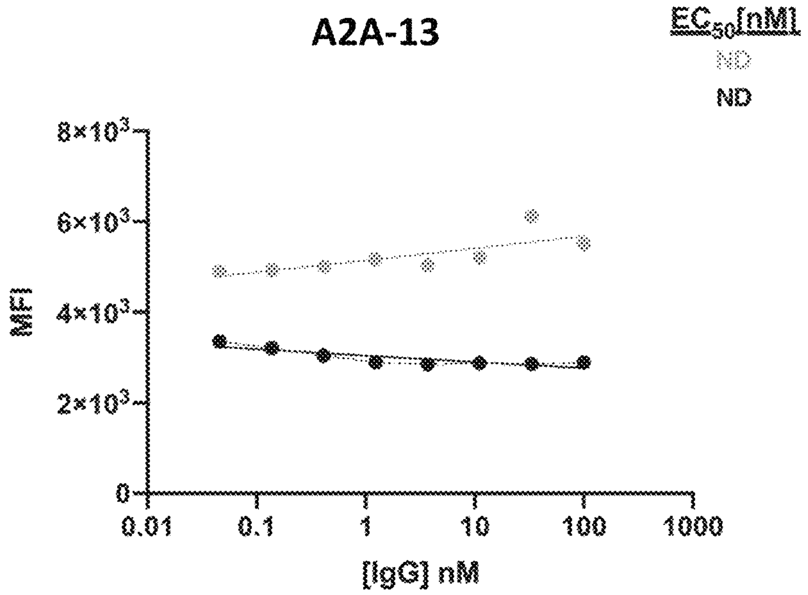
Figure 19F:
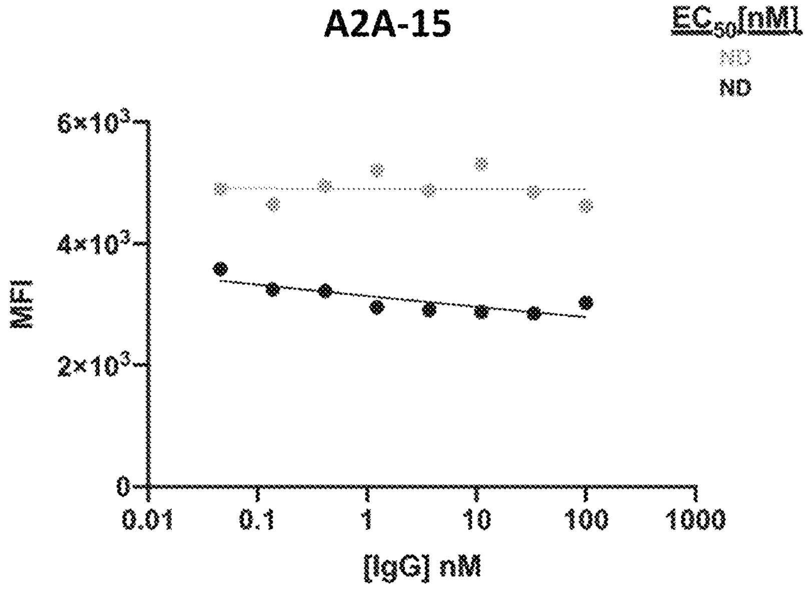
Figure 19G:
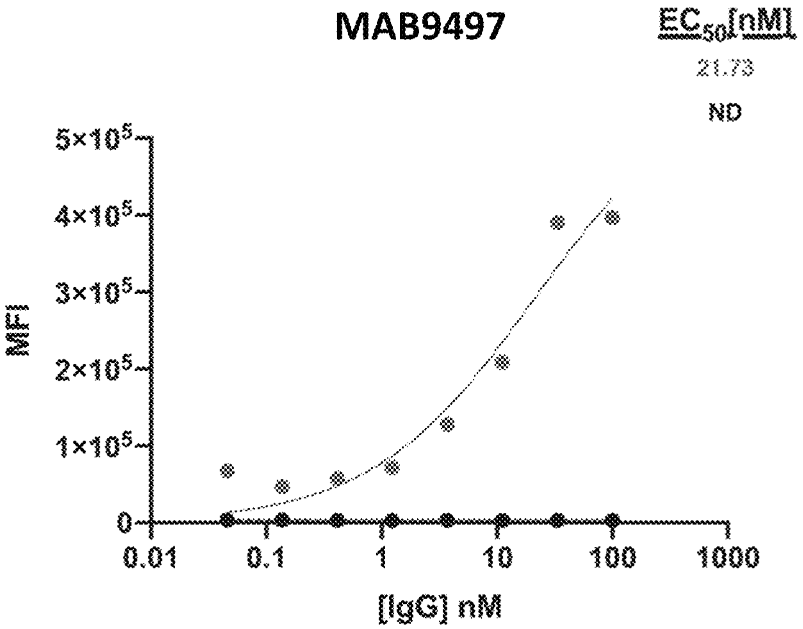
Figure 20A:
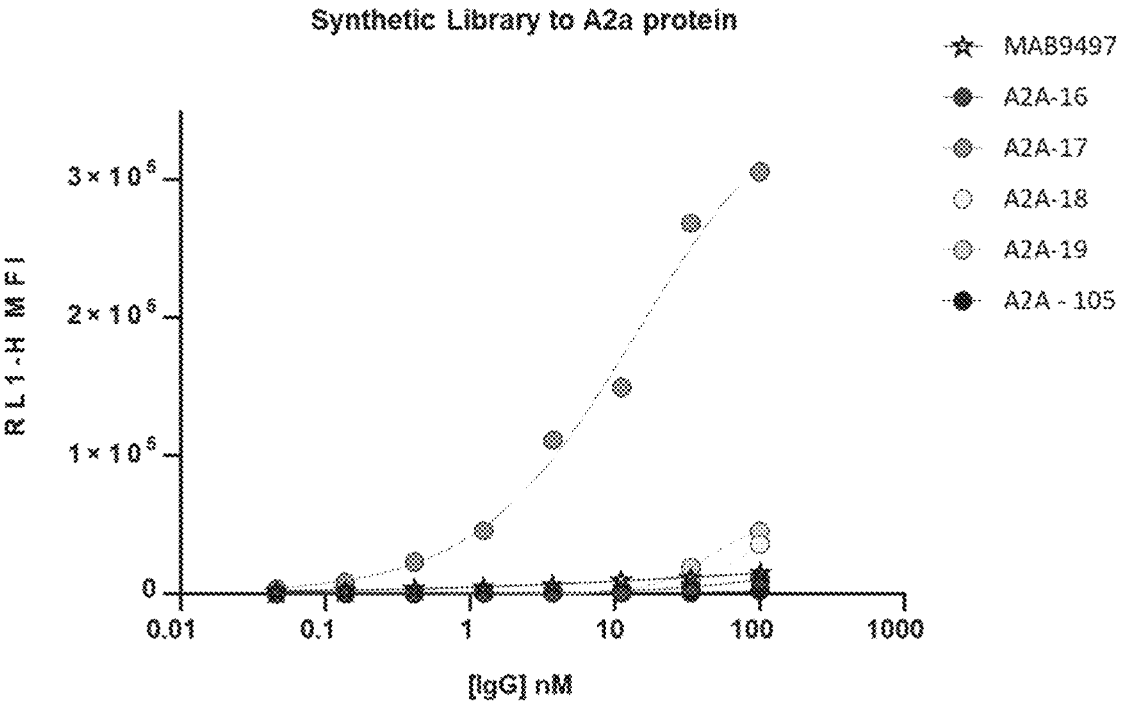
FIGS. 20A-20G depict graphs of cell binding in a titration assay from 100 nM.
Figure 20B:
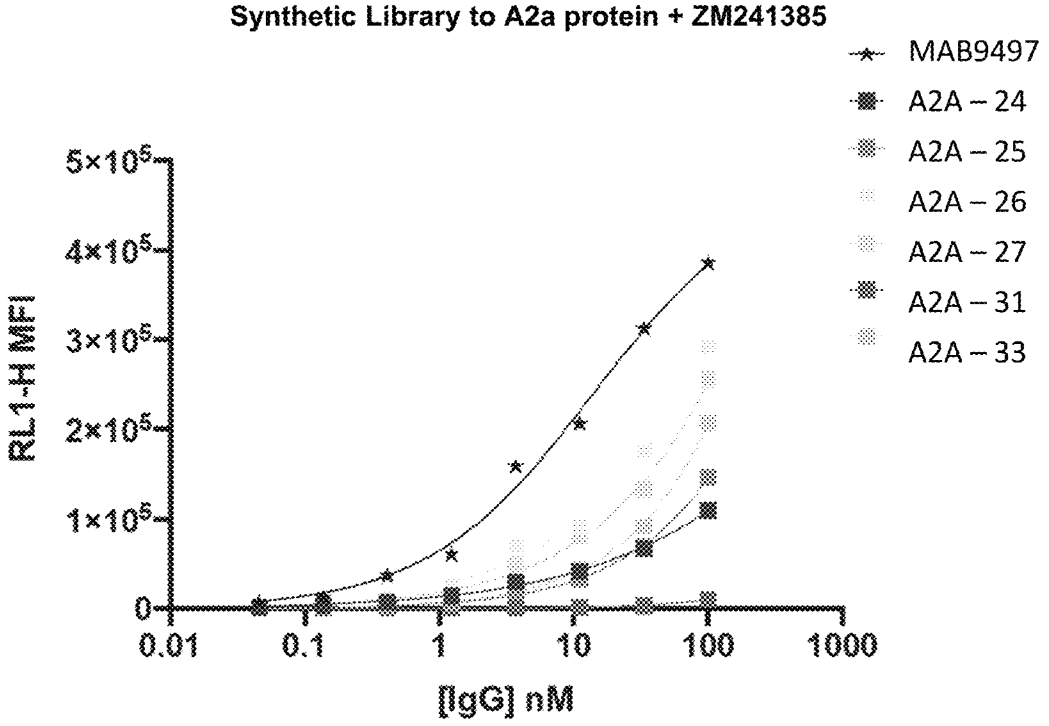
Figure 20C:
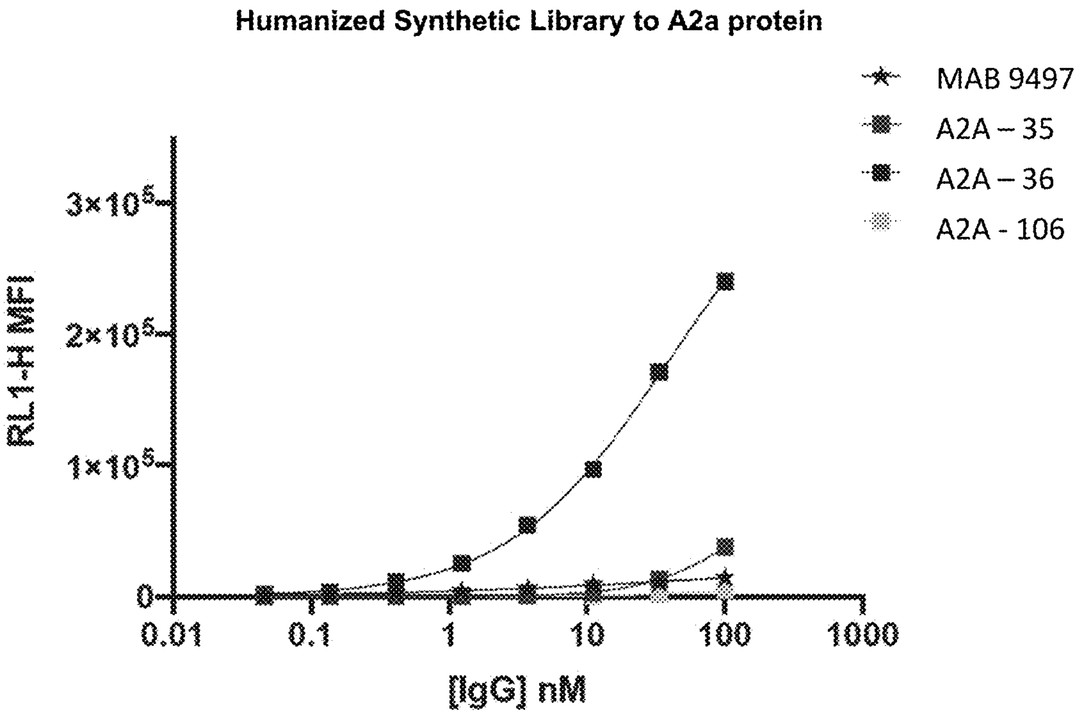
Figure 20D:
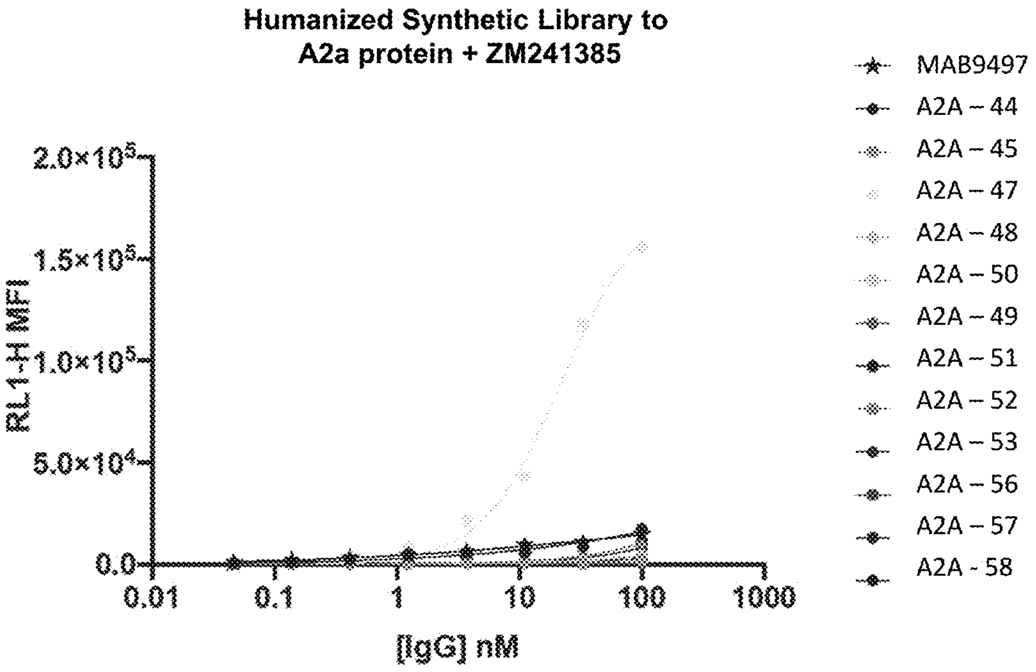
Figure 20E:
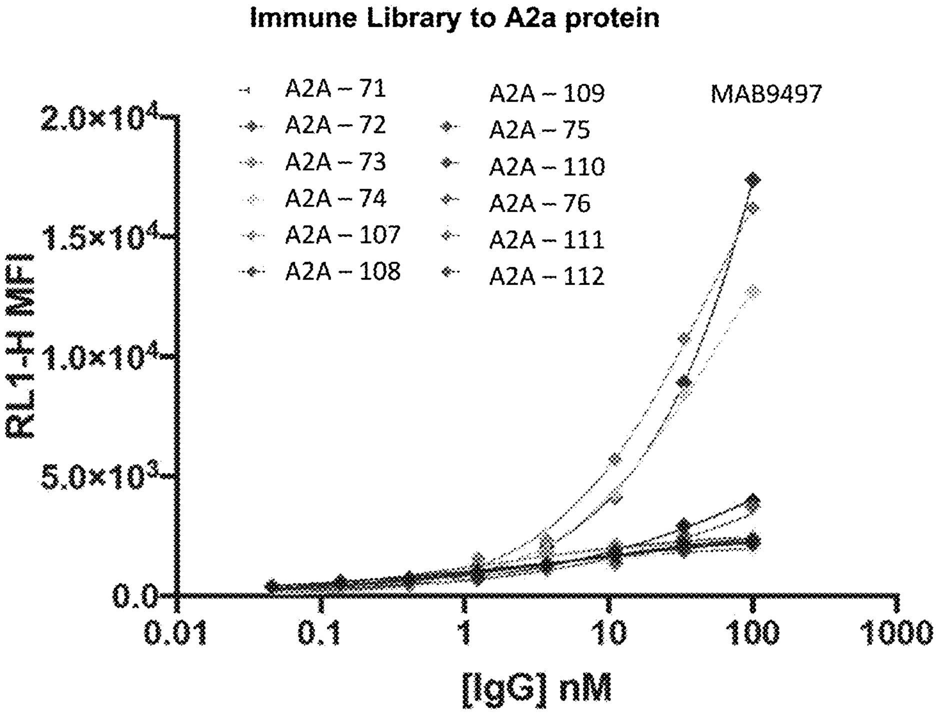
Figure 20F:
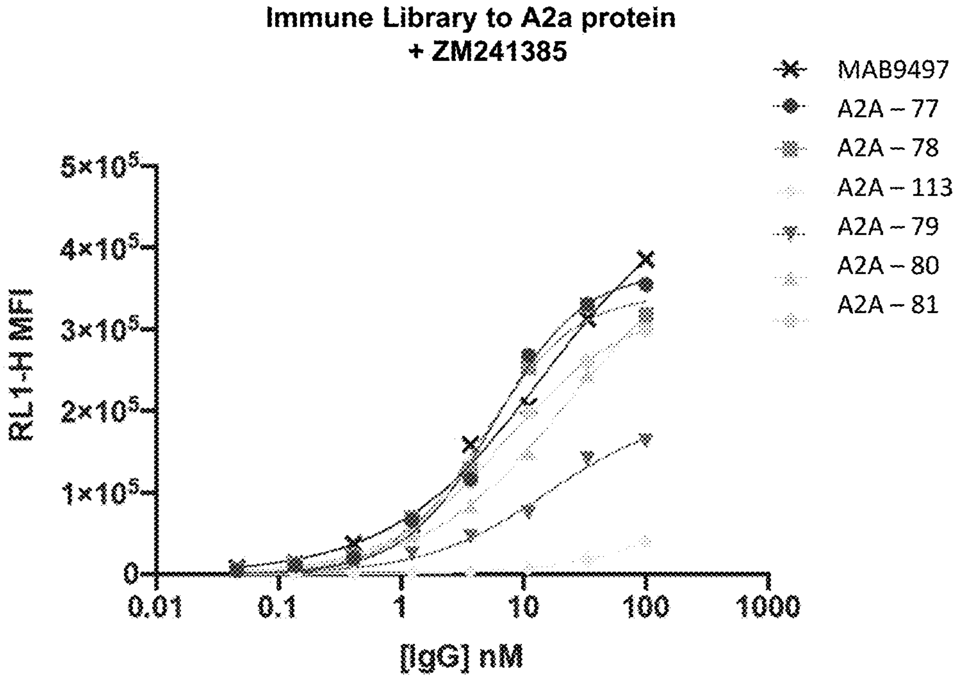
Figure 20G:
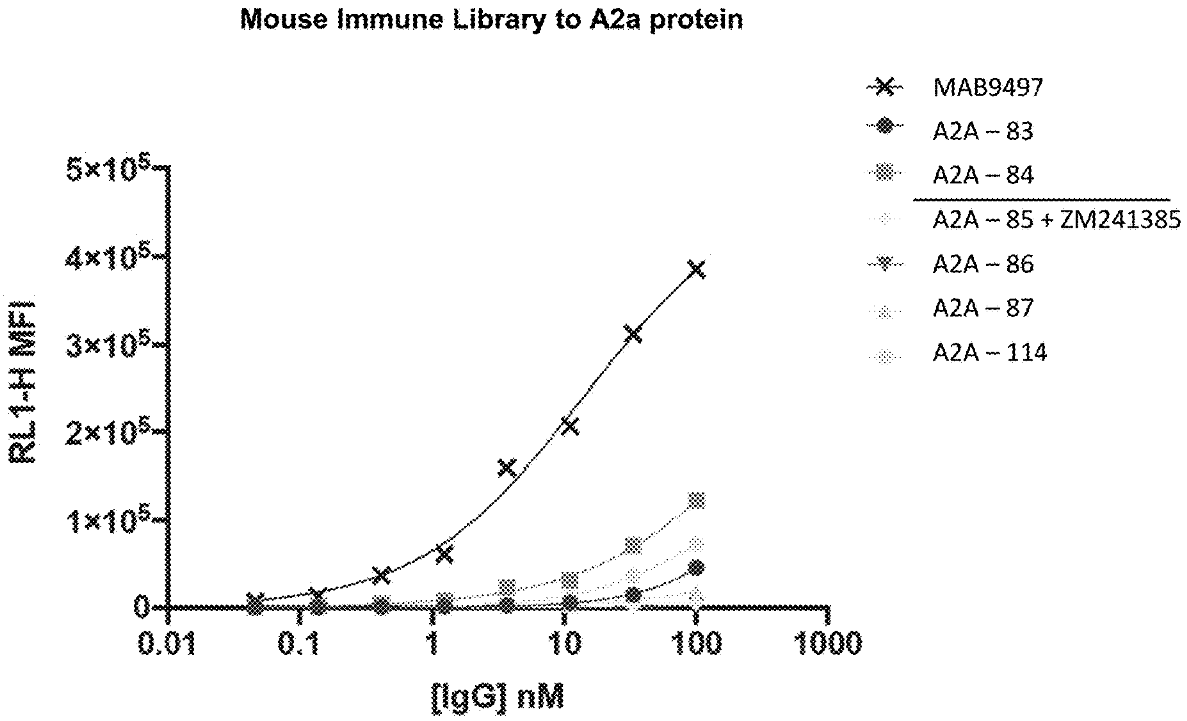

Flow cytometry data showing binding to HEK293-A2a cells using immunoglobulins from variant libraries were generated using 100 nM IgG and compared to detected binding in parent cells. Binding using variants from an immune library are shown in FIGS. 16A-16N. A control is shown in FIG. 16O, showing cell binding with Human Adenosine A2aR monoclonal (MAB9497). Selected variants were assessed for binding at concentrations titrated from 100 nM. Resulting curves are show in FIGS. 17A-17H. Binding curves are plotted with IgG concentration vs. MFI (mean fluorescence intensity). Binding using variants from a mouse immune library are shown in FIGS. 18A-18N. A control is shown in FIG. 18O, showing cell binding with Human Adenosine A2aR monoclonal (MAB9497). Selected variants were assessed for binding at concentrations titrated from 100 nM. Resulting curves are show in FIGS. 19A-19G. Binding curves are plotted with IgG concentration vs. MFI (mean fluorescence intensity).

Protein Bindings

Purified A2a immunoglobulins from Tables 15-18 were assayed for binding in a titration from 100 nM. Results of selected variants are shown in FIGS. 20A-20G.

Example 13. Agonist Response in LANCE® cAMP Assay

Figure 21:
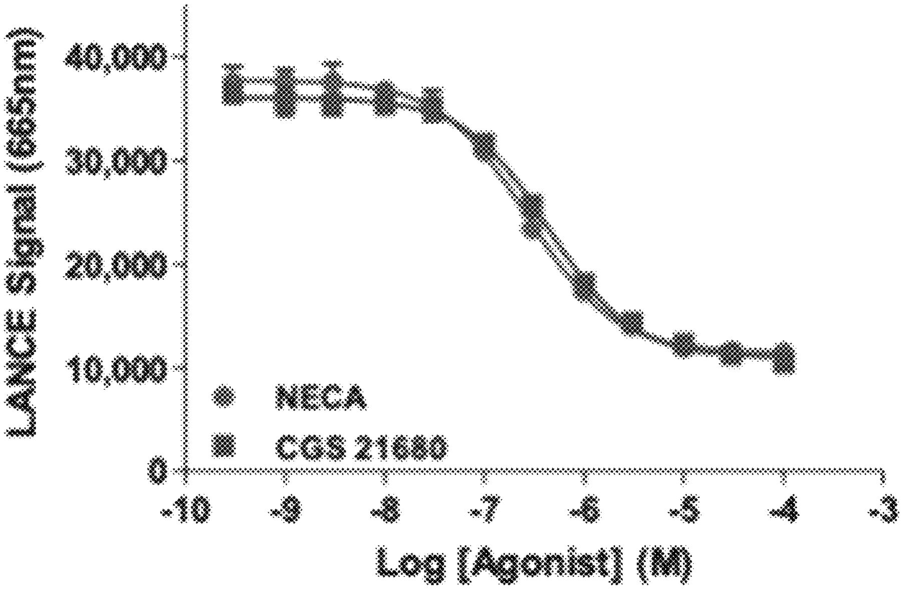
FIG. 21 depicts data from an agonist dose-response assay measured using a cAMP assay.

An agonist dose-response assay was performed using a LANCE® cAMP assay in 384-well format using 2500 cells/well according to manufacturer's instructions. Cell stimulation with NECA and CGS 21680 was performed for 30 min at room temperature. Readings were taken on a EnVision plate reader in Laser mode. Data is shown in FIG. 21. The Z'-factor was calculated for NECA with at least 16 background and 16 maximal signal points (Z'=0.80). Calculated $EC_{50}$ (M) for NECA=$2.7\times10^{-7}$ and for CGS 21680=$4.3\times10^{-7}$.

Example 14. Antagonist Response in LANCE® cAMP Assay

Figure 22:
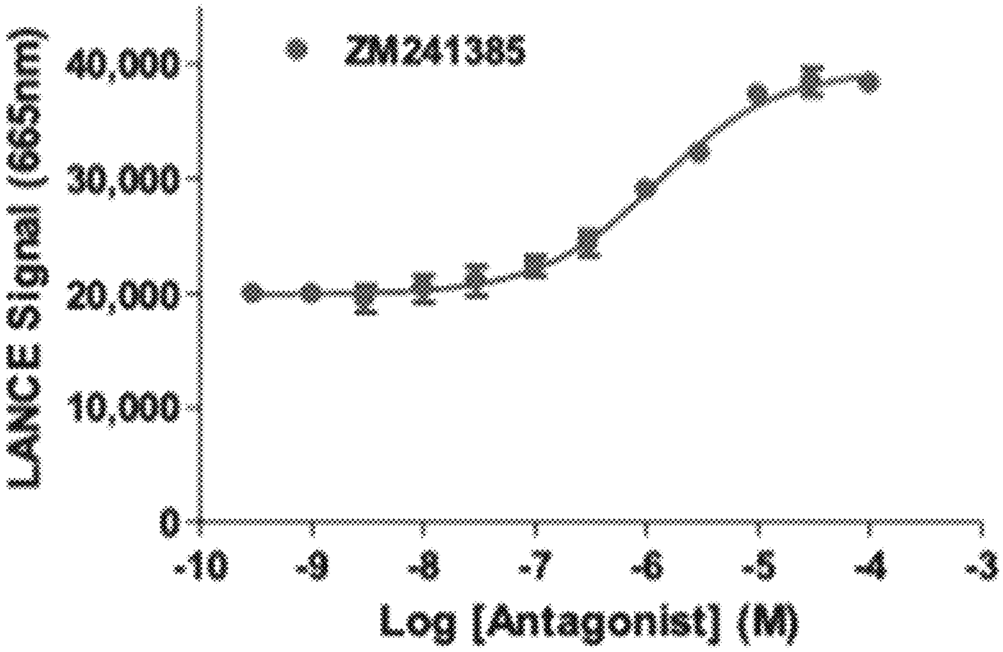
FIG. 22 depicts data from an antagonist dose-response assay measured using a cAMP assay.

An antagonist dose-response assay was performed using a LANCE® cAMP assay in 384-well format using 2500 cells/well and 1 μM NECA (reference agonist) according to manufacturer's instruction. Cell stimulation with ZM241385 was performed for 30 min at room temperature. Readings were taken on a EnVision plate reader in Laser mode. Data is shown in FIG. 22. Calculated $IC_{50}$ (M) for ZM241385=$1.25\times10^{-5}$.

Example 15. A2A cAMP Antagonist Titration

Figure 23:
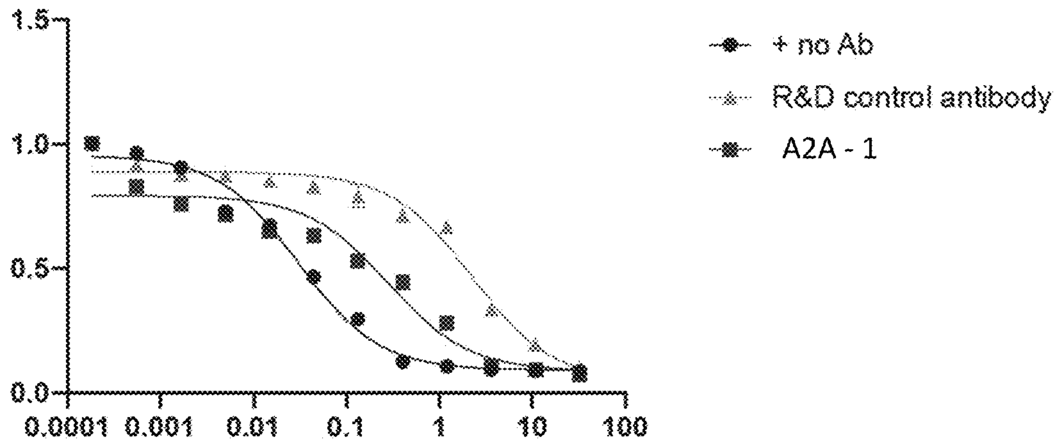
FIG. 23 depicts results from a cAMP antagonist titration assay.

Cells were plated at 3000/well and pre-incubated with fixed 100 nM IgG for 1 hr at room temperature, followed by stimulation with NECA titration for 30 min at room temperature according to manufacturer's instructions. Buffer was PBS+0.1% BSA+0.5 mM IBMX. Results shown in FIG. 23. Absolute IC50 is shown in Table 9, indicating A2A-1 is a negative allosteric modulator.

TABLE 9

| | +no Ab | A2A - 1 | R&D control antibody |
|---|---|---|---|
| IC50 | 0.03040 | 0.2816 | 2.253 |

Example 16. LANCE® Allosteric cAMP Assay

Figure 24:
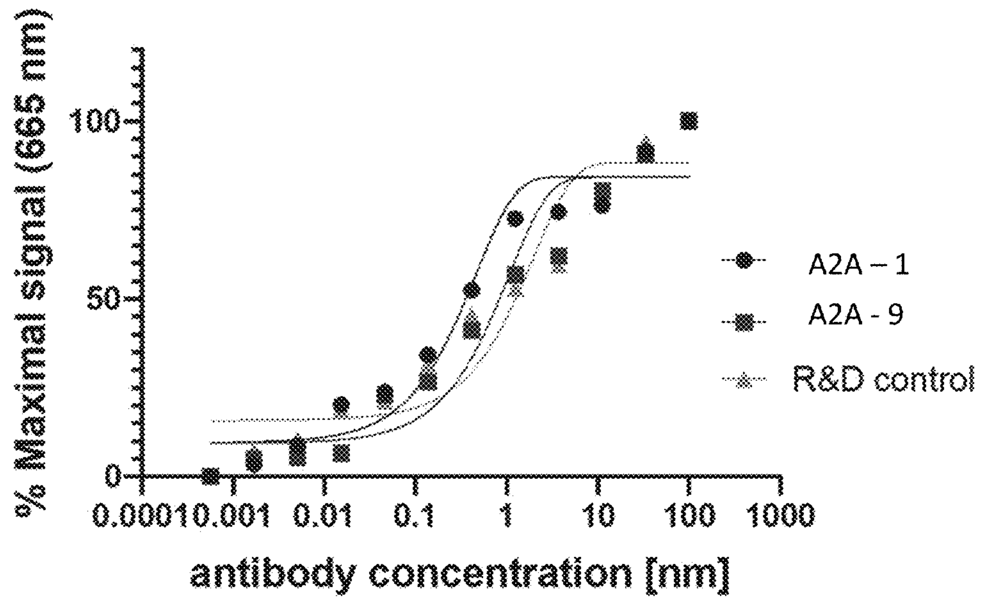
FIG. 24 depicts data from variant A2A-1 and A2A-9 from a cAMP assay.

A2A-1 and A2A-9 were assayed for allosteric modulation. Cells were pre-incubated with titrated IgG for 1 hr at room temperature, followed by stimulation with fixed NECA concentration. Results are shown in FIG. 24. IC50 values are shown in Table 10, indicating A2A-1 is a negative allosteric modulator.

TABLE 10

| | A2A - 1 | A2A - 9 | R&D control antibody |
|---|---|---|---|
| Absolute IC50 | 1.833 | 4.106 | 9.432 |

Example 17. cAMP Allosteric A2A Perkin Elmer

Figure 25:
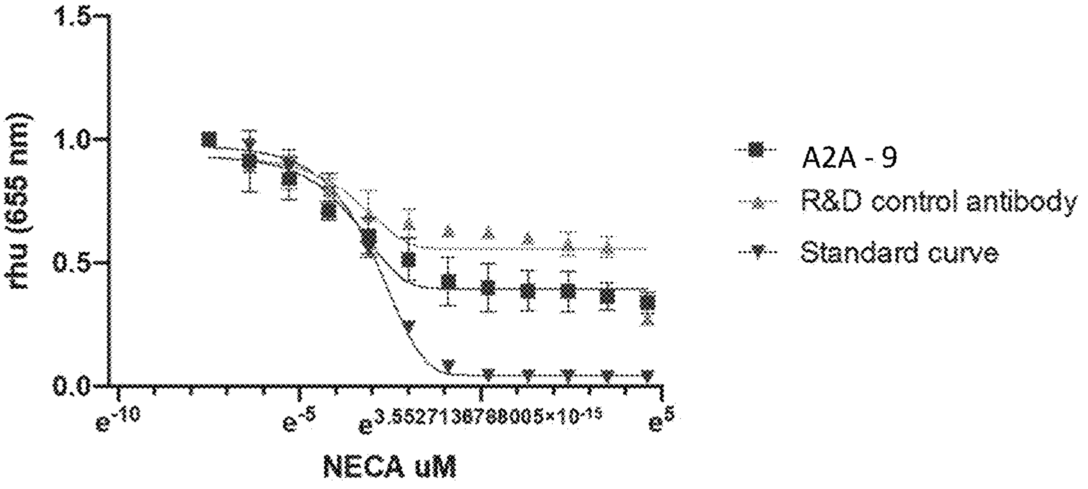
FIG. 25 depicts data for variant A2A9 using a cAMP assay.

A2A-9 was assayed as described in Example 15. Resulting response curves are shown in FIG. 25. Calculated IC50 for A2A-9 is shown in Table 11.

TABLE 11

| | A2A - 9 | R&D control antibody | No antibody |
|---|---|---|---|
| Absolute IC50 | ~0.4513 | ~0.5126 | ~0.2556 |

Example 18. A2A cAMP Antagonist Titration

Figure 26:
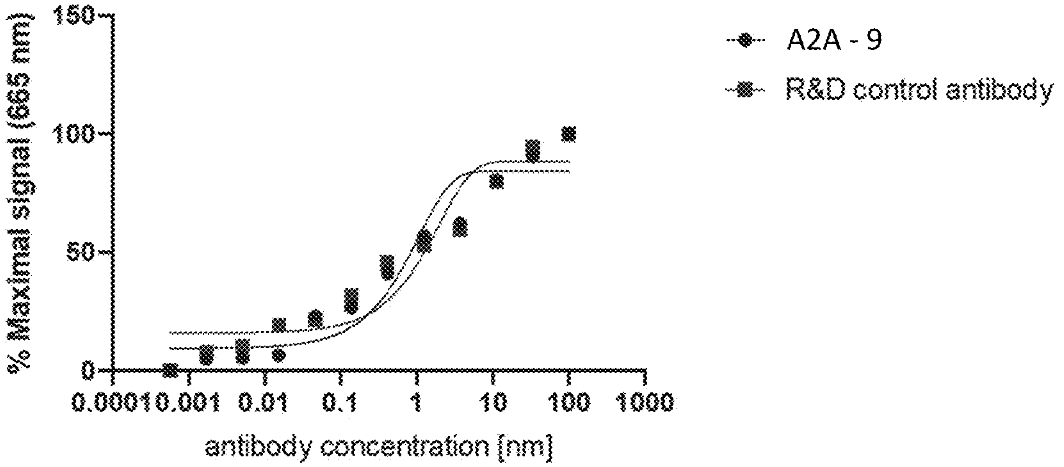
FIG. 26 depicts data for variant A2A9 using a cAMP antagonist titration assay.

A2A-9 was assayed as described in Example 16. Resulting response curves are shown in FIG. 26. Calculated IC50 values are shown in Table 12. Results indicate A2A-9 is an antagonist.

TABLE 12

| | A2A - 9 | R&D control antibody |
|---|---|---|
| Absolute IC50 | 4.106 | 9.432 |

Example 19. A2A Antagonistic cAMP Assay

Figure 27A:
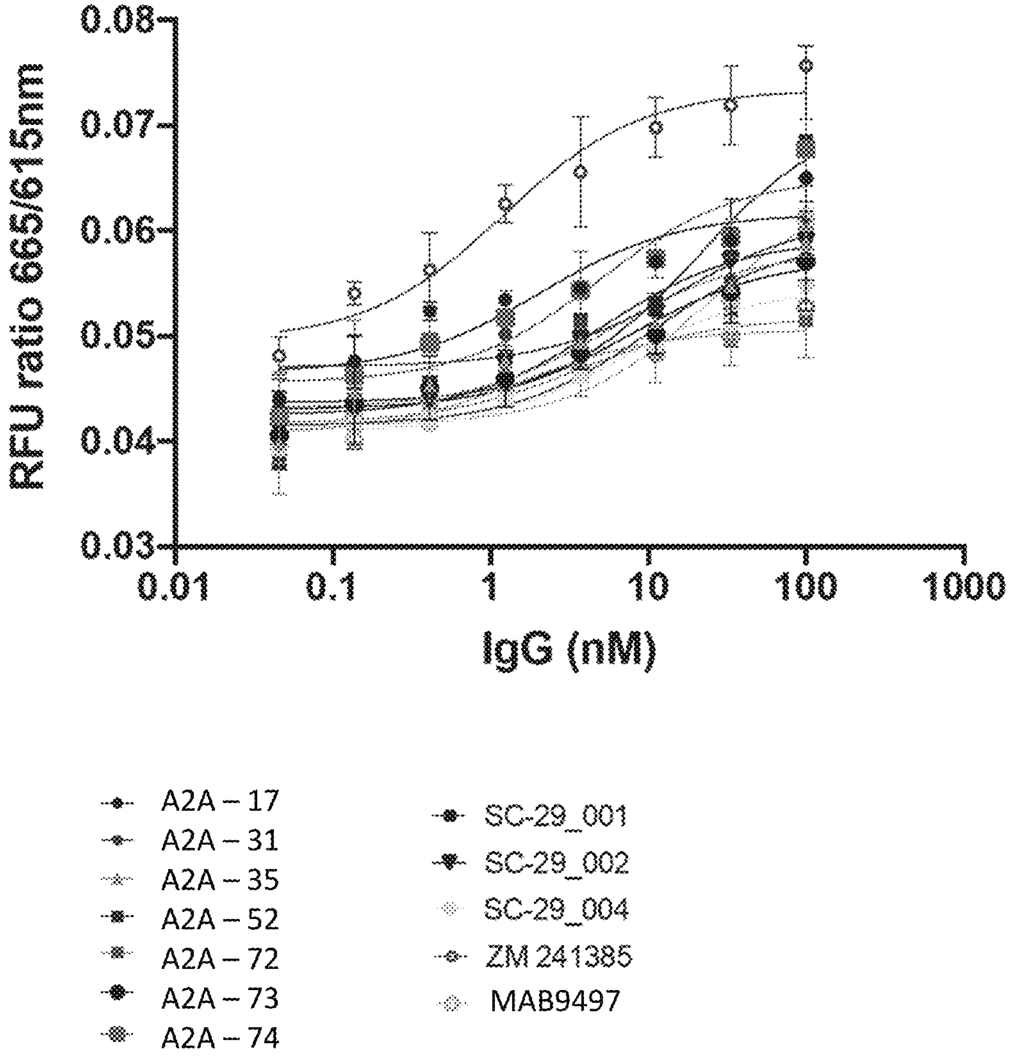
FIGS. 27A-27C depict data for variant A2A receptor immunoglobulins in an antagonistic cAMP assay.
Figure 27B:
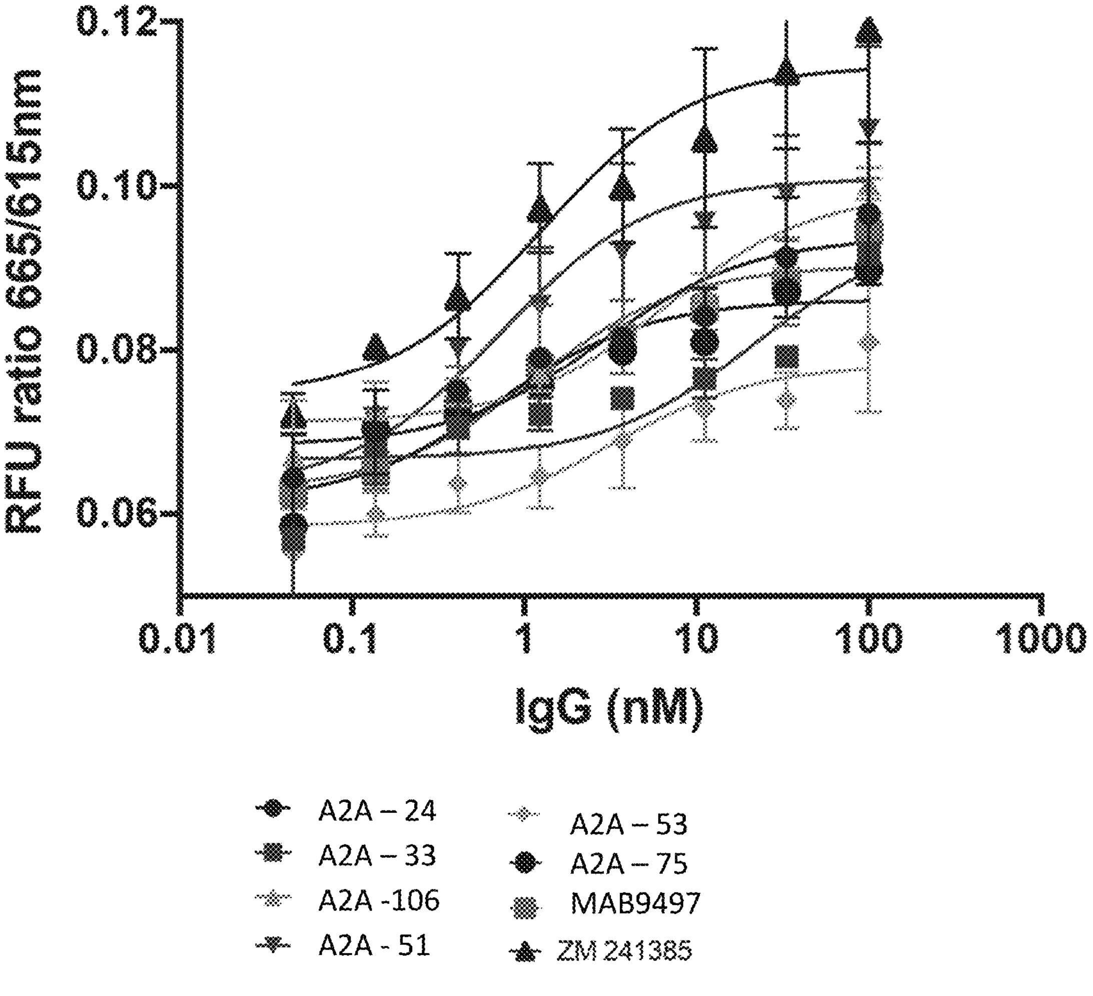
Figure 27C:
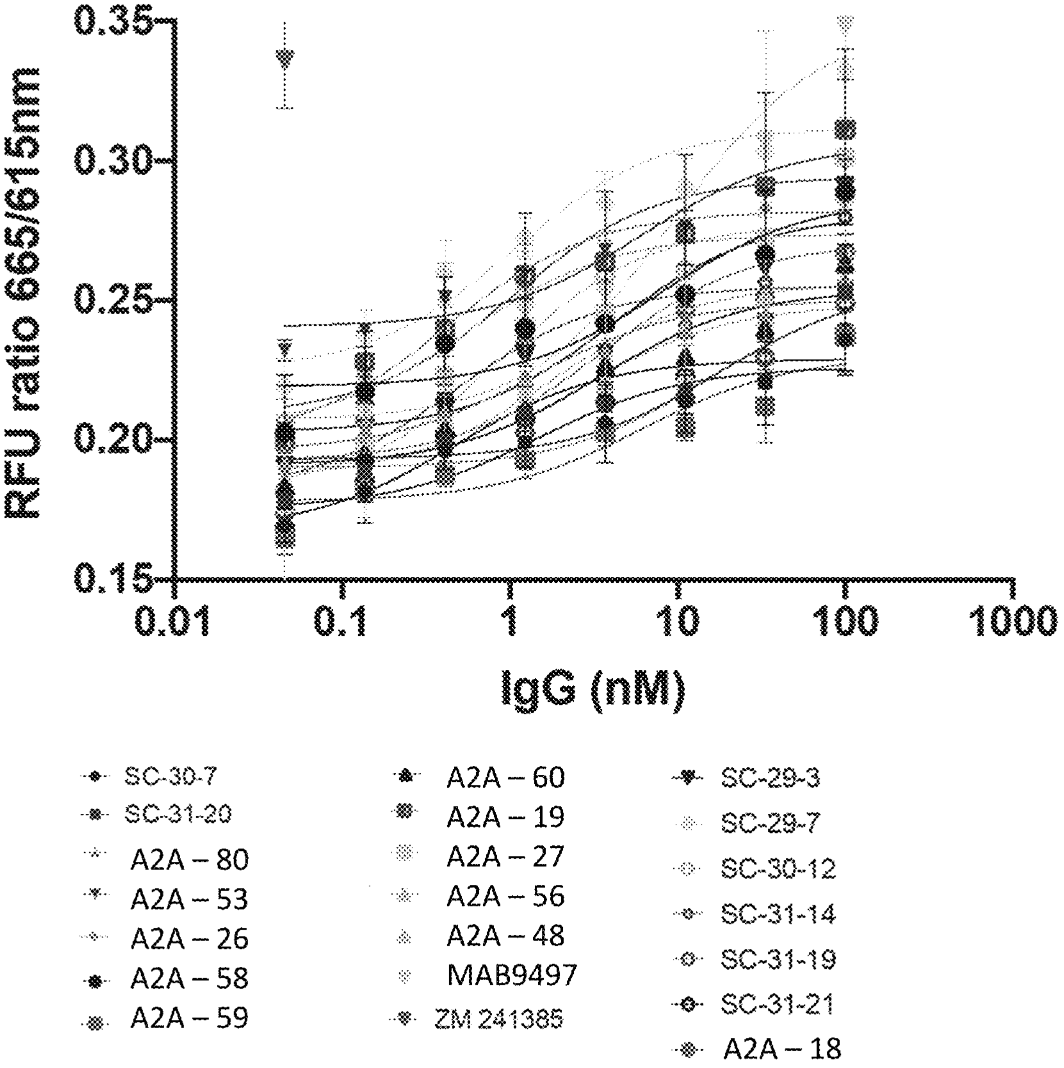

Selected variants were assayed for binding to target. Immunoglobulins were titrated in triplicate and incubated on cells for 1 hour, followed by incubation with 0.5 μM NECA for 30 minutes. Binding curves showing relative fluorescent units (RFU) ratio at 665 nm/615 nm versus nM IgG on a log scale are shown in FIGS. 27A-27C. Final binding studies found functional antibodies in the generated libraries as listed in Table 13 and Table 14.

TABLE 13

| Target | Library | Reformatted | Functional |
|---|---|---|---|
| HEK293-A2a Cells | Mouse Immune | 14 | |
| A2a protein | Humanized Synthetic | 95 | 2 |
| A2a protein + ZM241385 | Humanized Synthetic | 95 | 3 |
| A2a protein | Mouse Immune | 12 | 1 |
| A2a protein + ZM241385 | Mouse Immune | 22 | 0 |

TABLE 14

| Target | Library | Reformatted | Functional |
|---|---|---|---|
| HEK293-A2a Cells | Immune | 14 | |
| A2a protein | Synthetic | 95 | 2 |
| A2a protein + ZM241385 | Synthetic | 95 | 5 |
| A2a protein | Immune | 29 | 4 |
| A2a protein + ZM241385 | Immune | 10 | 5 |

Example 20. A2AR Cell Functional cAMP Assays

Allosteric and Antagonistic cAMP Assays were Performed Using A2A Cell Lines

Figure 28A:
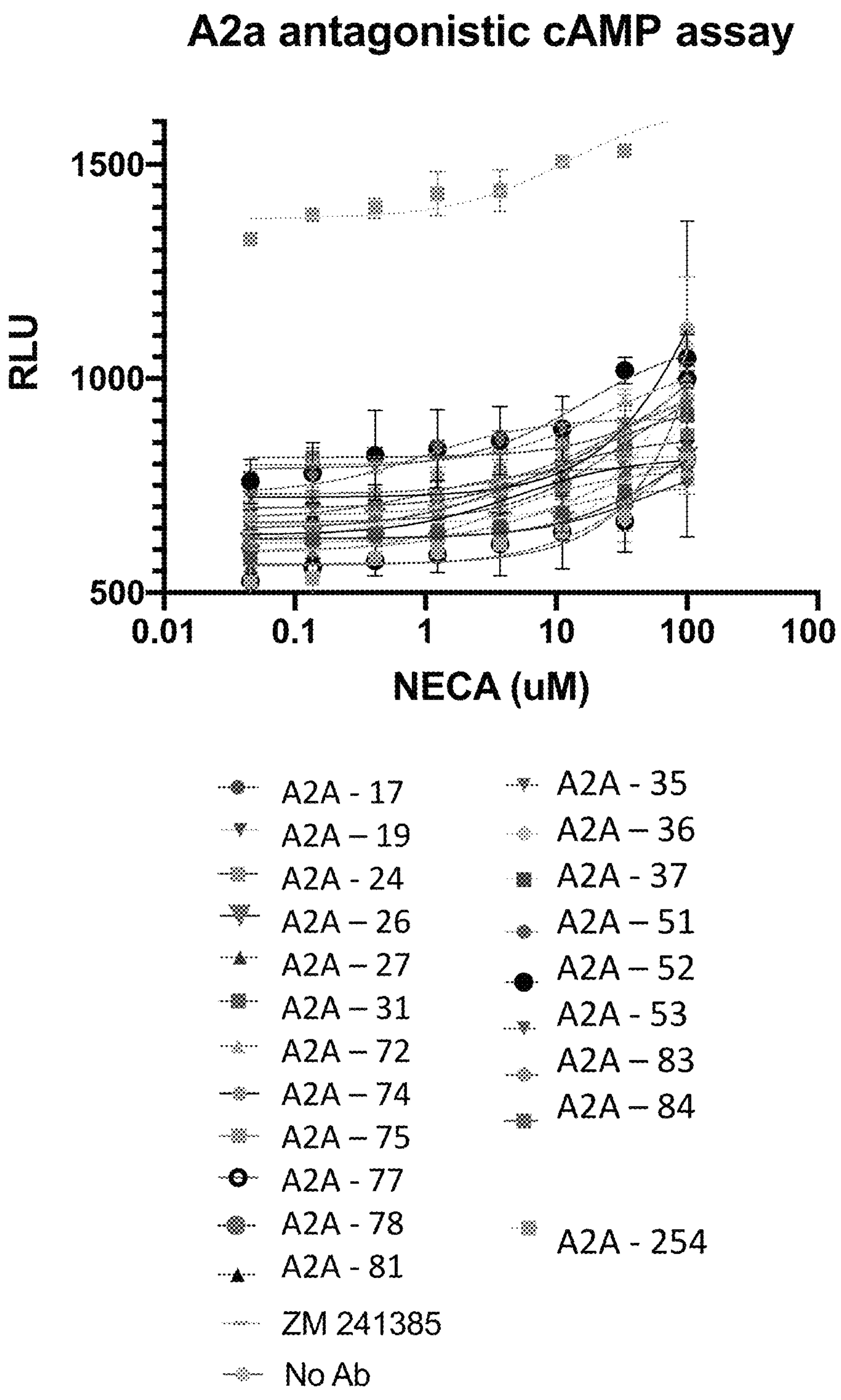
FIGS. 28A-28C depict data for variant A2A receptor immunoglobulins in an allosteric cAMP assay.
Figure 28B:
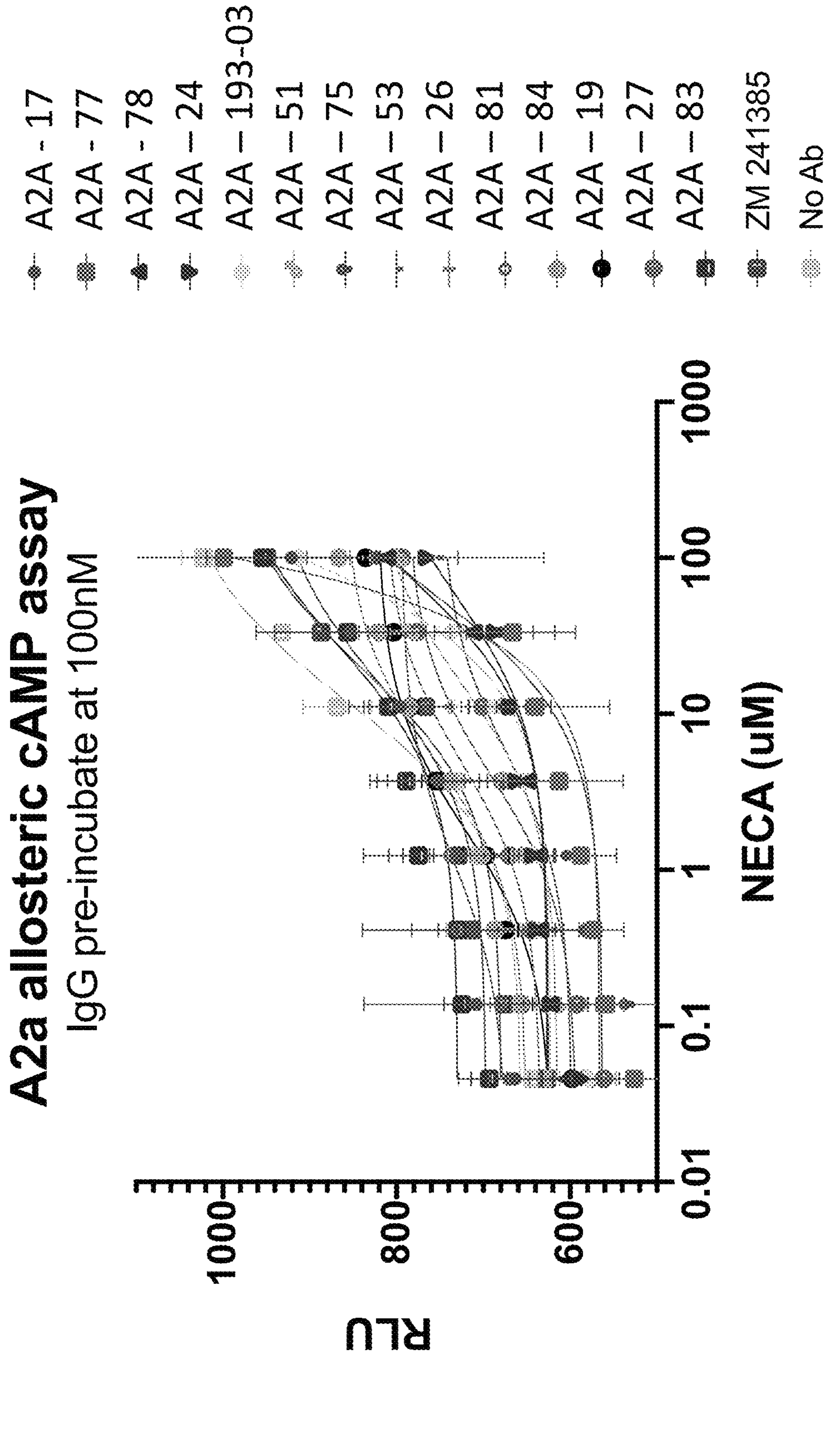
Figure 28C:
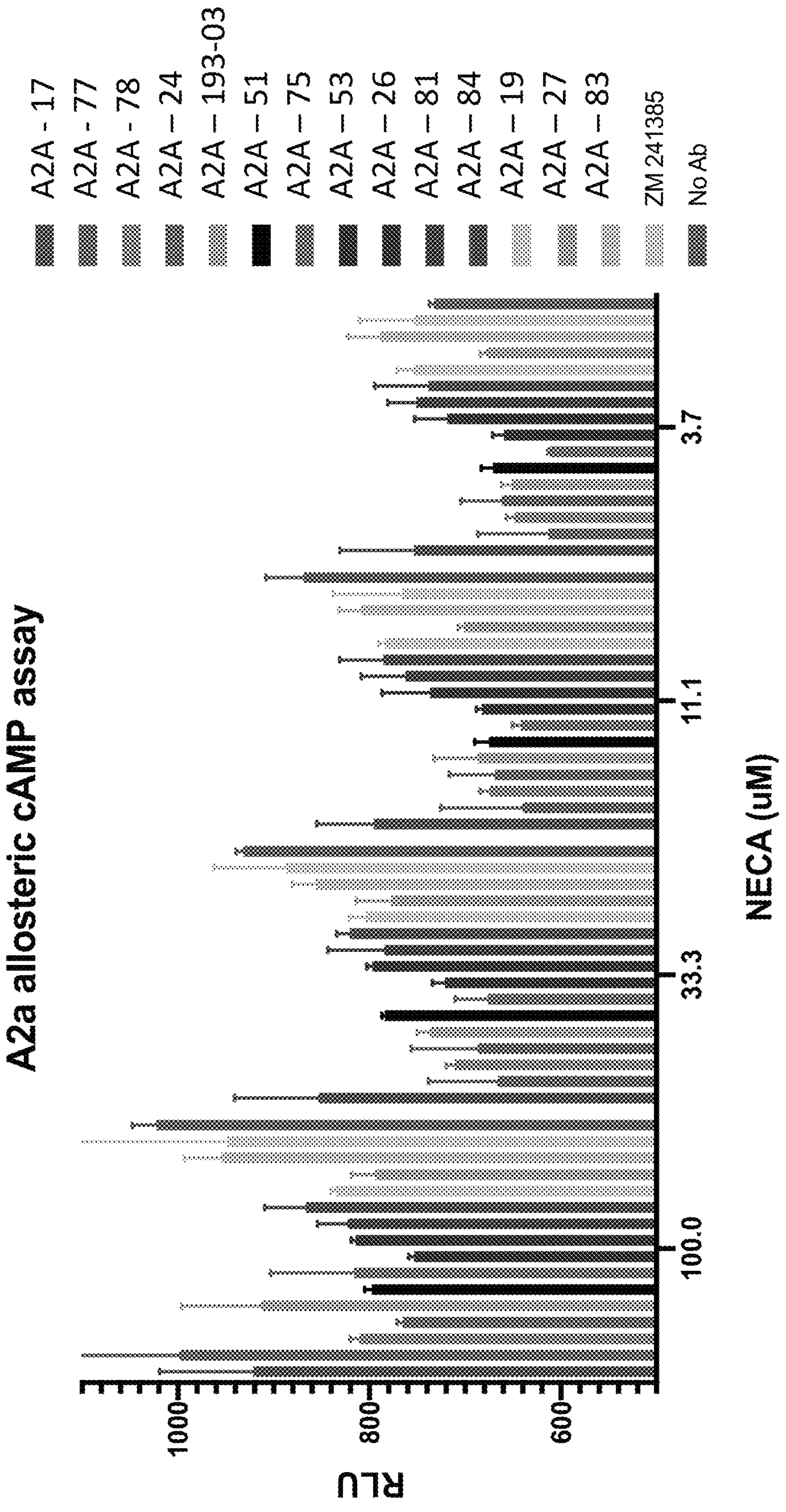

Briefly, cells were pre-incubated with anti-A2AR antibody at 100 nM followed by NECA stimulation 3× titration from 100 uM. Data from a functional allosteric cAMP assay is seen in FIGS. 28A-28C. ZM241385 functioned as an antagonist. "No Ab" functioned as agonist only.

Figure 29A:
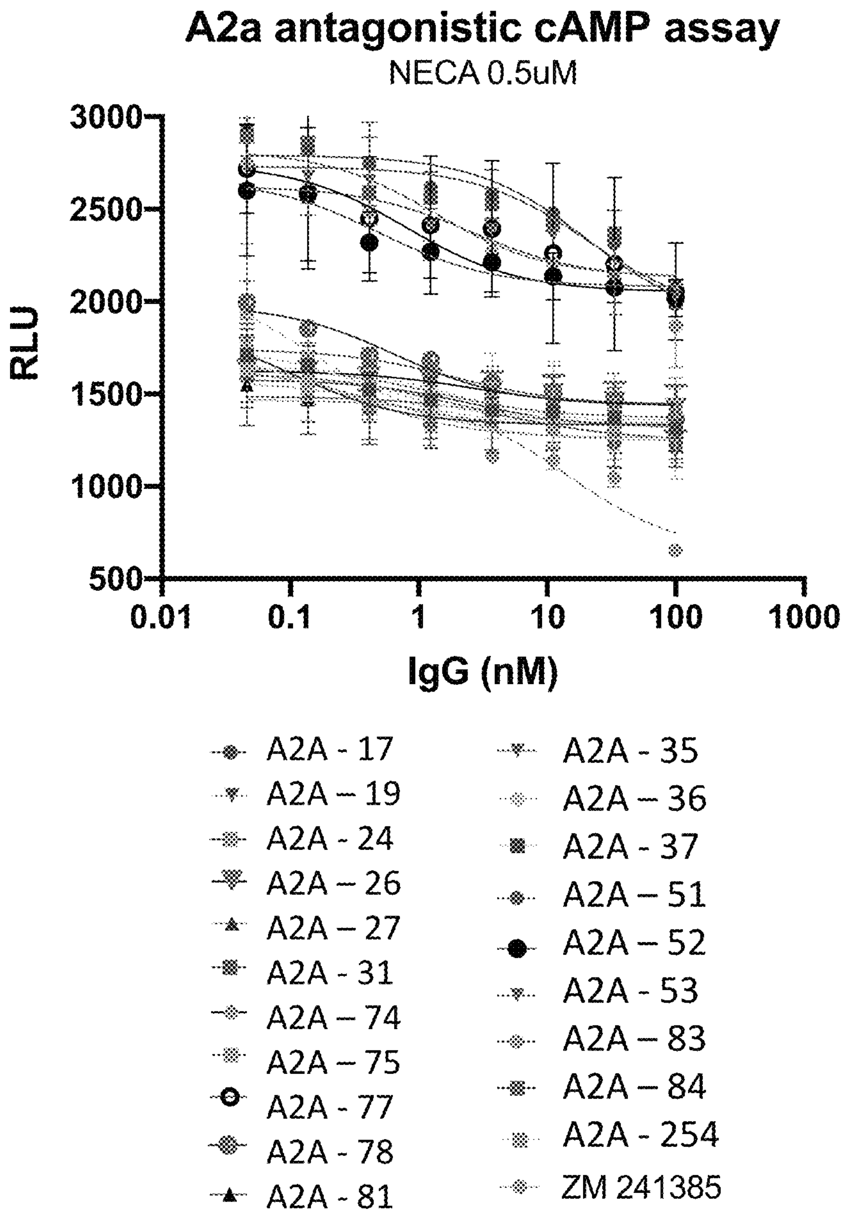
FIGS. 29A-29C depict data for variant A2A receptor immunoglobulins in an antagonistic cAMP assay.
Figure 29B:
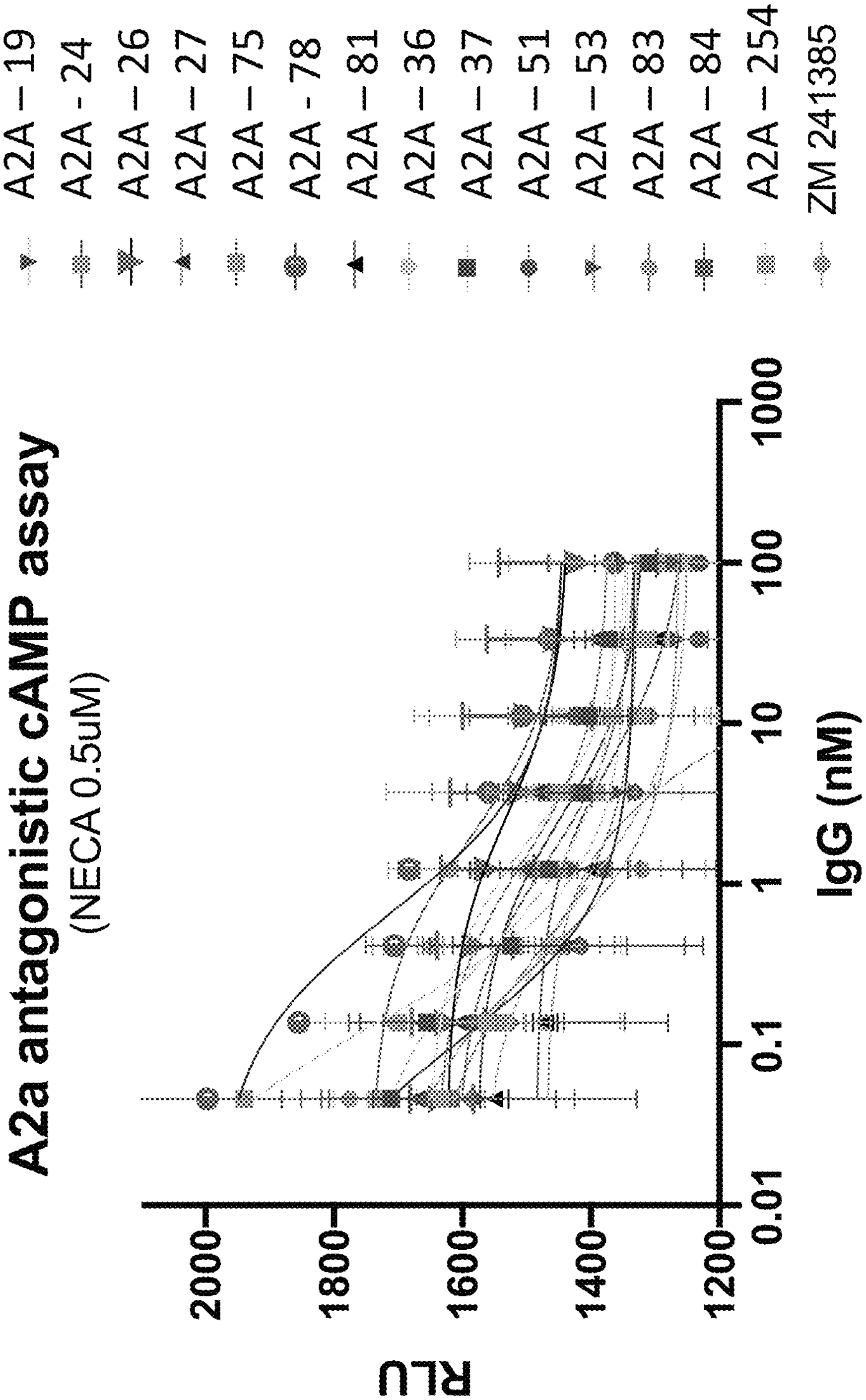
Figure 29C:
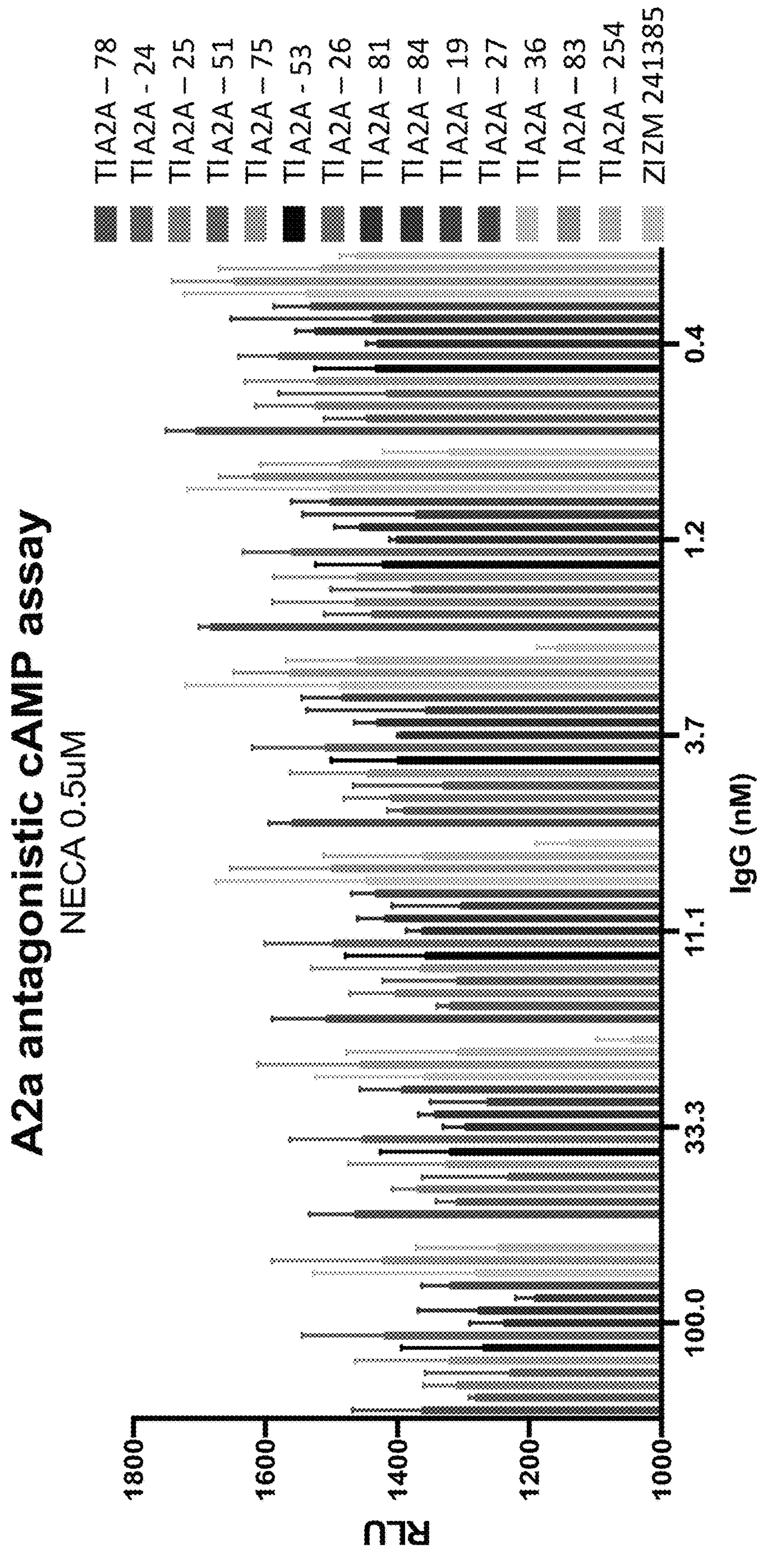
Figure 30A:
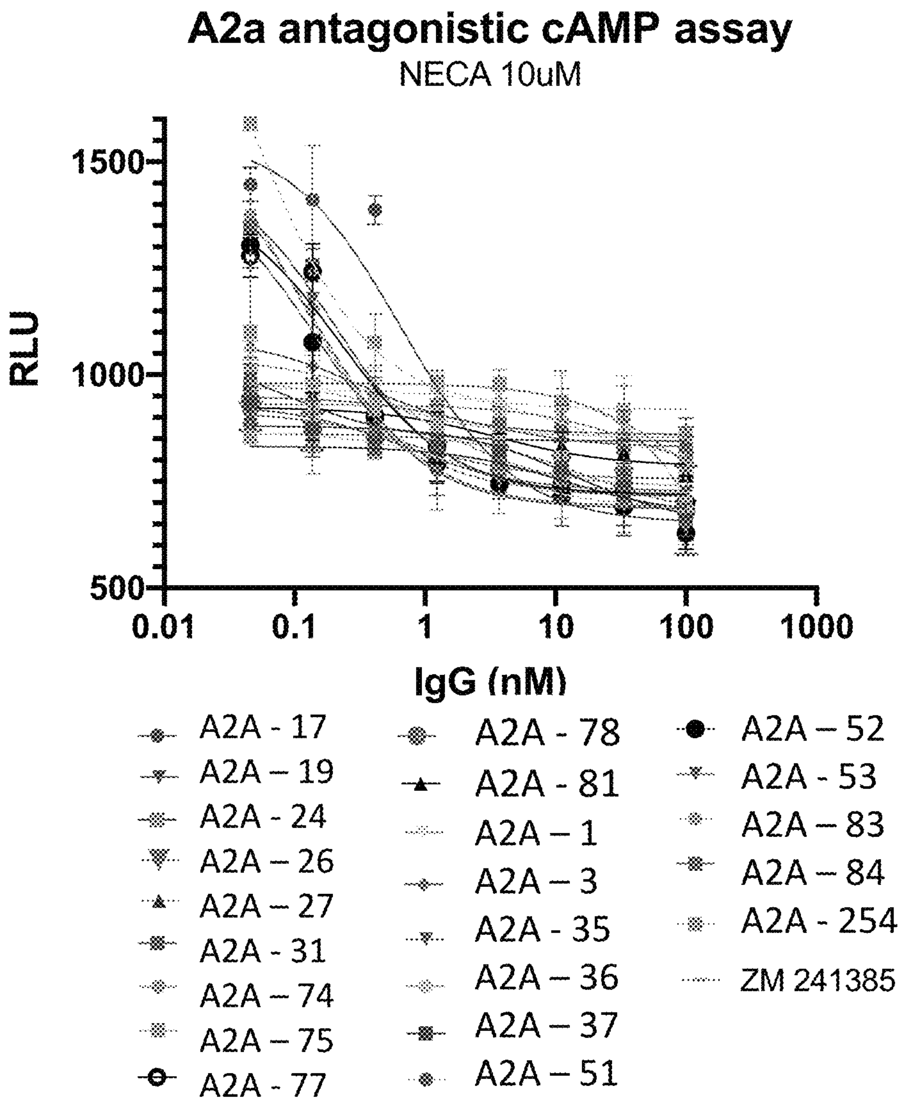
FIGS. 30A-30C depict data for variant A2A receptor immunoglobulins in an antagonistic cAMP assay.
Figure 30B:
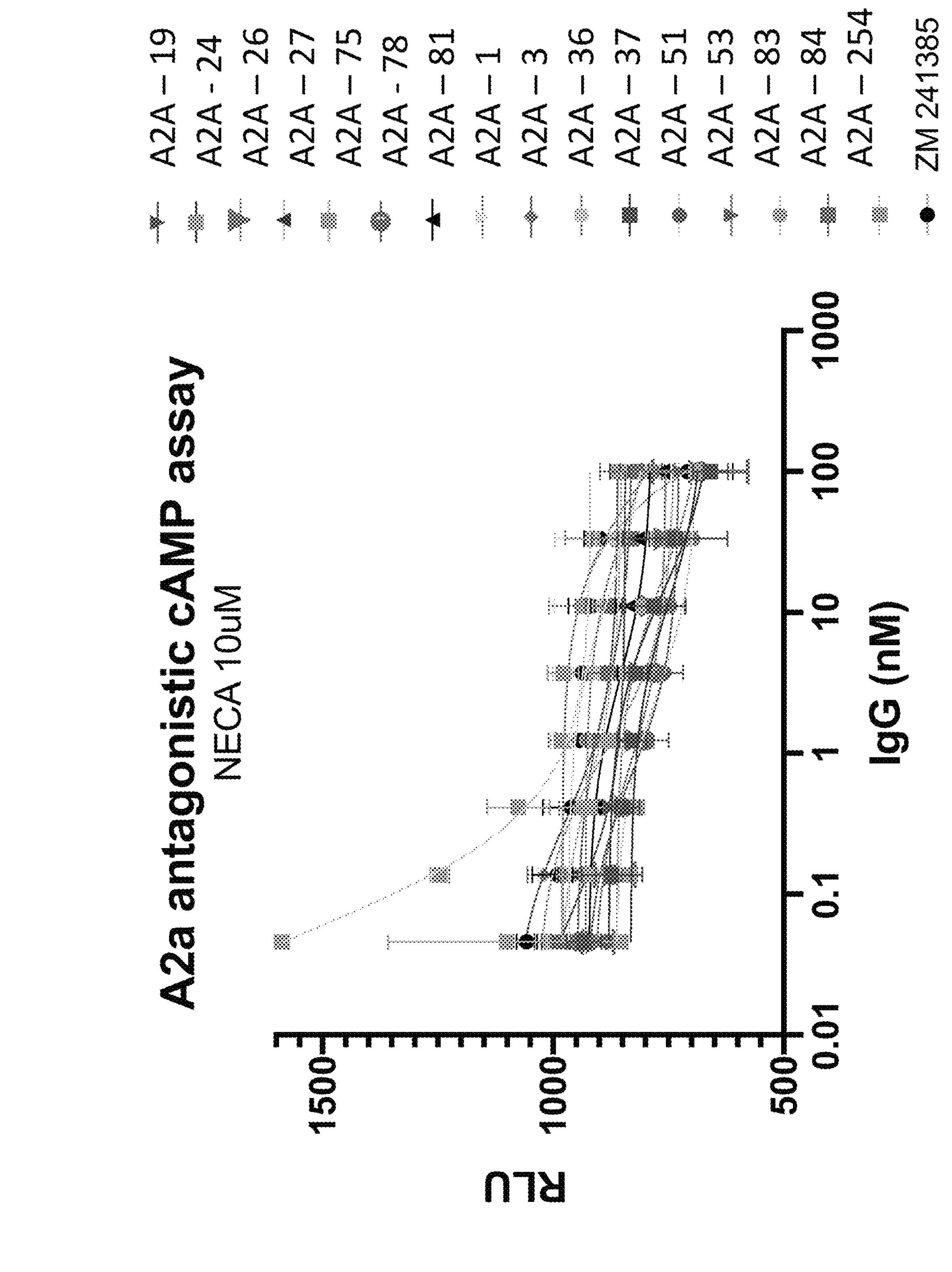
Figure 30C:
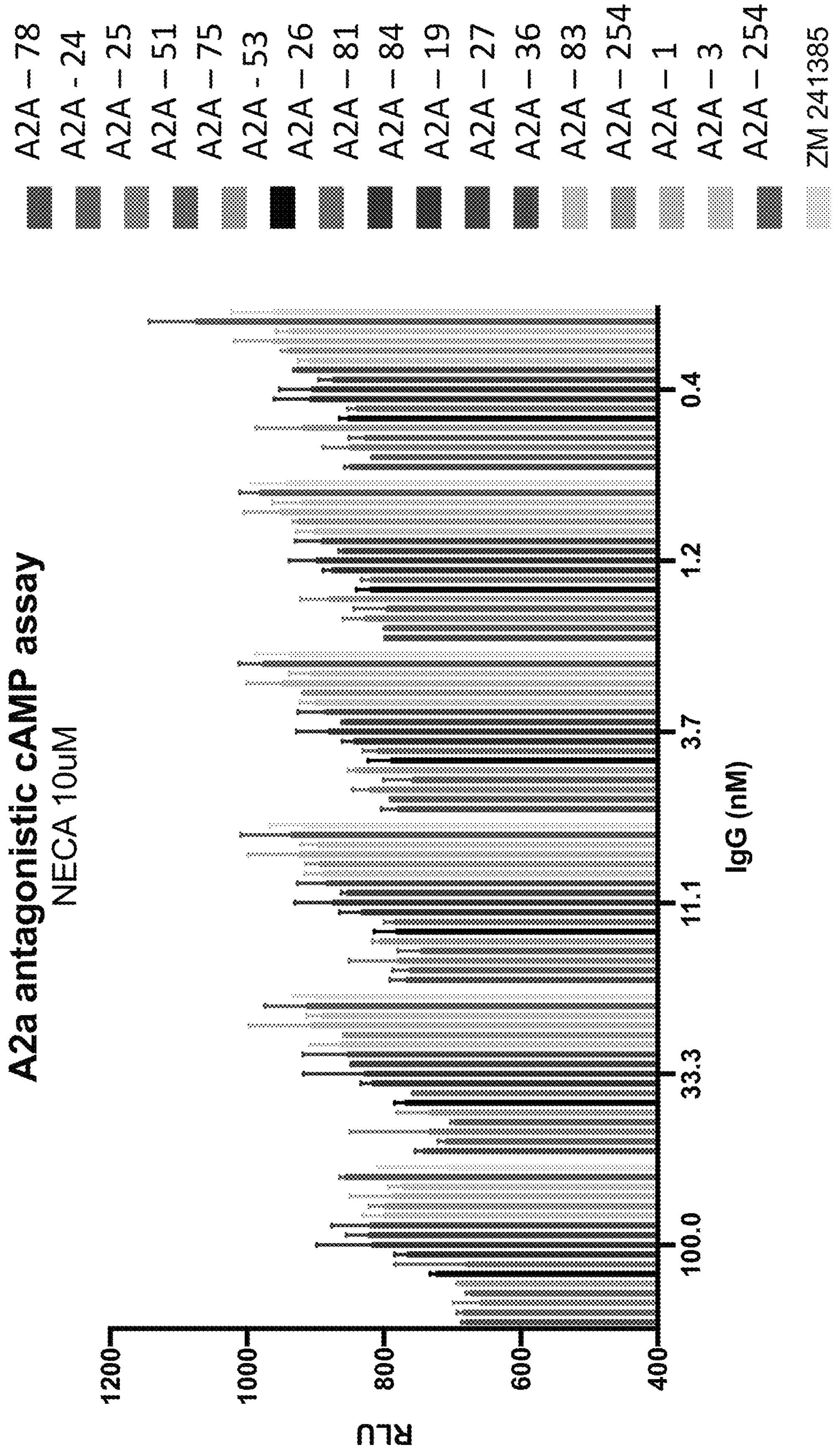

For a functional antagonistic cAMP assays, cells were pre-incubated with anti-A2AR antibody 3× titration from 100 nM followed by NECA stimulation at 0.5 uM. Data is seen in FIGS. 29A-29C. Cells were also pre-incubated with anti-A2AR antibody 3× titration from 100 nM followed by NECA stimulation at 10 uM. Data is seen in FIGS. 30A-30C.

Based on the data, for NECA titration, IgG titration (NECA 0.5 uM), and IgG titration (NECA 10 uM), A2AR variant A2A-17, A2A-19, A2A-24, A2A-26, and A2A-27 exhibited improved function in cAMP assays.

Example 21. Exemplary Sequences

TABLE 15

| Variable Heavy Chain CDRs | | | | | | |
|---|---|---|---|---|---|---|
| A2AR Variant | SEQ ID NO | CDR1 Sequence | SEQ ID NO | CDR2 Sequence | SEQ ID NO | CDR3 Sequence |
| A2A-1 | 6 | GGSISSSN | 95 | YPSGN | 184 | DEGY |
| A2A-2 | 7 | GYTFTGY | 96 | NPNSGG | 185 | GGPFDY |
| A2A-3 | 8 | GYTFTGY | 97 | NPNSGG | 186 | VYSYGFDY |
| A2A-4 | 9 | GFTFSDY | 98 | SSSGST | 187 | DNWAFDL |
| A2A-5 | 10 | GFTFSSY | 99 | SSSSSY | 188 | TWYSSSPFDY |
| A2A-6 | 11 | GFTFSNY | 100 | SSSSSY | 189 | DSGSYYDWFDP |
| A2A-7 | 12 | GFTFSSY | 101 | SGSGGS | 190 | YSNYFDY |
| A2A-8 | 13 | GYSITSGY | 102 | SYDGS | 191 | VHHYYGSSYFDY |
| A2A-9 | 14 | GYSITSGY | 103 | RYDGS | 192 | VHHYYGSSYFDY |
| A2A-10 | 15 | GYSITSGY | 104 | SYDGS | 193 | DPYYYGSSYFDY |

TABLE 15 -continued

| Variable Heavy Chain CDRs | | | | | | |
|---|---|---|---|---|---|---|
| A2AR Variant | SEQ ID NO | CDR1 Sequence | SEQ ID NO | CDR2 Sequence | SEQ ID NO | CDR3 Sequence |
| A2A-11 | 16 | GFTFSDY | 105 | NYDGSS | 194 | EYYYGSSSFAY |
| A2A-12 | 17 | GFTFNDY | 106 | NYDGSS | 195 | EYYYGSSSFAY |
| A2A-13 | 18 | GFTFSDF | 107 | SSGSST | 196 | REFAY |
| A2A-14 | 19 | GFTFSDY | 108 | SSGSGT | 197 | PNYHGSSPFAY |
| A2A-15 | 20 | GFTFSTY | 109 | SGSGGS | 198 | ARGKWRWRLGRRYDY |
| A2A-16 | 21 | GFTFNNY | 110 | SGSGGD | 199 | ARGYWRWRLLRRYDY |
| A2A-17 | 22 | GFNIGNT | 111 | NPNYGT | 200 | DYGSSSFDY |
| A2A-18 | 23 | GFSFSGY | 112 | SGSGGS | 201 | ARGYPRWRLGRRYDY |
| A2A-19 | 24 | GFTFSGY | 113 | SGSGAS | 202 | ARGYKRWRLGRRYDY |
| A2A-20 | 25 | GFAFSNY | 114 | YPKSGS | 203 | LYGYDLHWYFDV |
| A2A-21 | 26 | GGSISSGGY | 115 | NPNSGN | 204 | DEVAAAGLFDY |
| A2A-22 | 27 | GYTFTEY | 116 | HPSSGS | 205 | HEVEYYGPSSSWFAY |
| A2A-23 | 28 | GFTFSTY | 117 | SGSGGS | 206 | ARGKWRWRLGRRYDY |
| A2A-24 | 29 | GFNIGNT | 118 | NPNYGT | 207 | DYGSSSFDY |
| A2A-25 | 30 | GFTFGNY | 119 | DPANGD | 208 | EGDNSNYYAMDY |
| A2A-26 | 31 | GFTFSTY | 120 | SGSAGS | 209 | ARGHWRWRLGRRYDY |
| A2A-27 | 32 | GFTFSSY | 121 | SGSGGS | 210 | ARGYWRWRLWRRYDY |
| A2A-28 | 33 | GFTFSSQ | 122 | SGSGVS | 211 | ARGRWRWRLGRRYDY |
| A2A-29 | 34 | GYSFTGY | 123 | YPGSGN | 212 | EDDYGWYFGV |
| A2A-30 | 35 | GYRLTGY | 124 | DPASGD | 213 | HEDPIYYGNYVFAY |
| A2A-31 | 36 | GYLFTDY | 125 | YPGTG | 214 | LYYGSSWERYFDV |
| A2A-32 | 37 | GFTFIDY | 126 | NPNYGT | 215 | QGSNYGGYFDV |
| A2A-33 | 38 | GFPFSSY | 127 | SGSGGR | 216 | ARGYWRWRLGRRADY |
| A2A-34 | 39 | GFNFNTY | 128 | YPGNSD | 217 | VIYYYGSSDYTLDY |
| A2A-35 | 40 | GFTFSTY | 129 | SGSGGS | 218 | ARGKWRWRLGRRYDY |
| A2A-36 | 41 | GFNIGNT | 130 | NPNYGT | 219 | DYGSSSFDY |
| A2A-37 | 42 | GYTFTSY | 131 | NHDGSN | 220 | SMITRFAY |
| A2A-38 | 43 | GFSLTSY | 132 | DPETDD | 221 | YYYGSSAFAY |
| A2A-39 | 44 | GFTFSNY | 133 | NPNNGG | 222 | AYYSNYGVMYF |
| A2A-40 | 45 | GFNFRSY | 134 | SGGGGS | 223 | ARGGWRWRLGRRYDY |
| A2A-41 | 46 | GFSLSIY | 135 | SPGSGS | 224 | PYYYGSSRYYAMDY |
| A2A-42 | 47 | GYTFTSY | 136 | SSGGDS | 225 | DYYGSSWHFDV |
| A2A-43 | 48 | GFTFSSY | 137 | SDGGSY | 226 | YIWYYGSSWSWYFDA |
| A2A-44 | 49 | GFTFSAY | 138 | GTAGD | 227 | GYNWIFDL |
| A2A-45 | 50 | GYSFTGY | 139 | LPGSGG | 228 | GNYDAMDY |
| A2A-46 | 51 | GGYISSSN | 140 | EQDGSE | 229 | GEYSRLWYFDL |
| A2A-47 | 52 | GTFTDY | 141 | LPGSGG | 230 | PYDYDFDY |

TABLE 15 -continued

| Variable Heavy Chain CDRs | | | | | | |
|---|---|---|---|---|---|---|
| A2AR Variant | SEQ ID NO | CDR1 Sequence | SEQ ID NO | CDR2 Sequence | SEQ ID NO | CDR3 Sequence |
| A2A-48 | 53 | GYTFTSS | 142 | YPRDGS | 231 | TVVADWYFDV |
| A2A-49 | 54 | GYTFNDD | 143 | NPNNGA | 232 | KGDGGSYAAMDY |
| A2A-50 | 55 | GYSFTGY | 144 | YPKDGS | 233 | TVVADWYFDV |
| A2A-51 | 56 | GYTFNDY | 145 | NPNNGA | 234 | NYGSSYYALDY |
| A2A-52 | 57 | GYTFNDY | 146 | NPNNGG | 235 | QGSNYGGYFDV |
| A2A-53 | 58 | GFNIIDD | 147 | TDTGEP | 236 | DYIYAMDY |
| A2A-54 | 59 | GYTFTDY | 148 | DPANGD | 237 | GDYGSSYAMDY |
| A2A-55 | 60 | GYEFSSS | 149 | YPGTGN | 238 | YYYGSSAFAY |
| A2A-56 | 61 | GFTFSSY | 150 | DPGTGG | 239 | IYYDYSAMDY |
| A2A-57 | 62 | GFIFSDF | 151 | DPEDG | 240 | DYYGSSYLDY |
| A2A-58 | 63 | GFNIKDY | 152 | NPNNGG | 241 | DYYGSFHRRWYFDV |
| A2A-59 | 64 | GYTFTDY | 153 | NINNGG | 242 | DYHGSSFYWYFDV |
| A2A-60 | 65 | GYTFTEY | 154 | NFDGSS | 243 | YYDSSYYAMDY |
| A2A-61 | 66 | GFTFSTY | 155 | YPGDTD | 244 | GIAVAGTFDY |
| A2A-62 | 67 | GYTFTNY | 156 | NPNNGG | 245 | HALLWYYYAMDY |
| A2A-63 | 68 | GFTFSDH | 157 | NPNSGI | 246 | VSYSGSLHY |
| A2A-64 | 69 | GFTFDDY | 158 | NTNTGN | 247 | SNWNYFDY |
| A2A-65 | 70 | GSAFSAS | 159 | DPDNGD | 248 | PRDSGPSFAS |
| A2A-66 | 71 | GFTFSSY | 160 | YPKDGS | 249 | SRGYYYGSSYGYYDV |
| A2A-67 | 72 | GHTITSY | 161 | LPGSGT | 250 | NWGFAY |
| A2A-68 | 73 | GYTFSGY | 162 | DPSDSF | 251 | DYGSSYEFTY |
| A2A-69 | 74 | GGYISSSN | 163 | KTKTDGGT | 252 | GYSGSVDY |
| A2A-70 | 75 | GSNIKDY | 164 | SDGGS | 253 | DATGTFAY |
| A2A-71 | 76 | GGSISSSN | 165 | YHSGS | 254 | EVVSGMIGTVFDY |
| A2A-72 | 77 | GFTISTY | 166 | GTAGD | 255 | GYNWIFDY |
| A2A-73 | 78 | GFTVSTY | 167 | GTAGD | 256 | GYNWIFDF |
| A2A-74 | 79 | GFTFTTY | 168 | GTAGD | 257 | GYNWIFDF |
| A2A-75 | 80 | GGSISSSN | 169 | YHSGN | 258 | EVVSGMIGTIFDY |
| A2A-76 | 81 | GFTFSSY | 170 | GTAGD | 259 | GYNWIFDF |
| A2A-77 | 82 | GGSISSSN | 171 | YHSGN | 260 | EVVSGMIGTIFDY |
| A2A-78 | 83 | GFTFSAY | 172 | GTAGD | 261 | GYNWVFDL |
| A2A-79 | 84 | GFTFDDY | 173 | TWNGDR | 262 | DGLTGIFDY |
| A2A-80 | 85 | GFTISTY | 174 | GTAGD | 263 | GYNWIFDY |
| A2A-81 | 86 | GGSISSSN | 175 | YHSGS | 264 | EVVSGLYGTIFDY |
| A2A-82 | 87 | GYSITSGY | 176 | SYGGS | 265 | DYDYFDY |
| A2A-83 | 88 | GYAFSSY | 177 | YPGDGD | 266 | GAY |
| A2A-84 | 89 | GYTFTEY | 178 | SGGGSY | 267 | PNYSGSSPFAY |

TABLE 15 -continued

| Variable Heavy Chain CDRs | | | | | | |
|---|---|---|---|---|---|---|
| A2AR Variant | SEQ ID NO | CDR1 Sequence | SEQ ID NO | CDR2 Sequence | SEQ ID NO | CDR3 Sequence |
| A2A-85 | 90 | GFSLTAY | 179 | WTGGG | 268 | SRGYYYGSSYGYFDV |
| A2A-86 | 91 | GYSITSD | 180 | NYSGS | 269 | KLDWDGYFDV |
| A2A-87 | 92 | GFNIKNT | 181 | DPANGN | 270 | GSPYGYDGHYVMDY |
| A2A-88 | 93 | GFTFRTY | 182 | SAEGSN | 271 | DGRGSLPRPKGGFIGALSF HWPFGRWLGGSYGTYDSS EDSGGAFDI |
| A2A-89 | 94 | GFTFNNY | 183 | SYGGSD | 272 | DGRGSLPRPKGGFIGDLSF HWPFGRWLGKSYGTYDSS EDSGGAFDI |

TABLE 16

| Variable Light Chain CDRs | | | | | | |
|---|---|---|---|---|---|---|
| A2AR Variant | SEQ ID NO | CDR1 Sequence | SEQ ID NO | CDR2 Sequence | SEQ ID NO | CDR3 Sequence |
| A2A-1 | 273 | RSSQSLVYSD GNTYLN | 362 | KVSNRDS | 451 | MQGTHWPRT |
| A2A-2 | 274 | KASQDIDDDMN | 363 | EATTLVP | 452 | LQHDNFPMYT |
| A2A-3 | 275 | KSSQSVLYSSNNKNYLA | 364 | WASTRES | 453 | QQYYSTPYT |
| A2A-4 | 276 | RASQSVSSNLA | 365 | GASTRAT | 454 | QQYYSTPLT |
| A2A-5 | 277 | KASQDIDDDMN | 366 | EATTLVP | 455 | LQHDNFPWT |
| A2A-6 | 278 | RASQGISSWLA | 367 | AASSLQS | 456 | QQTNSFPRT |
| A2A-7 | 279 | KASQDVDDDMN | 368 | EATTLVP | 457 | LQHDNFPWT |
| A2A-8 | 280 | KASQNVGTNVA | 369 | SASYRYS | 458 | QRFNNYPLT |
| A2A-9 | 281 | KASQNVGSSVA | 370 | STSYRYS | 459 | QQYNSYPLT |
| A2A-10 | 282 | RASQSISDYLH | 371 | YASQSIS | 460 | QNGHSFPLT |
| A2A-11 | 283 | KASRNVGTNVA | 372 | SASYRYS | 461 | QQYNSYPLT |
| A2A-12 | 284 | RASQSISDYLH | 373 | YASQSIS | 462 | QNGHSFPHT |
| A2A-13 | 285 | KASQNVGTNVA | 374 | SASYRYS | 463 | QQYNIYPLT |
| A2A-14 | 286 | RASQSISNYLH | 375 | YASQSIS | 464 | QNGHSFPLT |
| A2A-15 | 287 | RASQSIGRYLN | 376 | AASSLHS | 465 | QQSYVTPWT |
| A2A-16 | 288 | RASQSIGTYLN | 377 | GASTLHS | 466 | QQSYSAPWT |
| A2A-17 | 289 | KASQSVRNDVV | 378 | RGNTLRP | 467 | QQYYGIPLT |
| A2A-18 | 290 | RASQSVTTYLN | 379 | SASSLQS | 468 | QQTYATPWT |
| A2A-19 | 291 | RASQSISDYLN | 380 | TASTLQS | 469 | EQSYSTPWT |
| A2A-20 | 292 | KASHSVDYDGDNYMN | 381 | WASTRLT | 470 | LQHIEYPFT |
| A2A-21 | 293 | KSSQSVLYSSNNKNYFA | 382 | DAPNRAT | 471 | QQGYTTPYT |
| A2A-22 | 294 | RASQDIGRSLS | 383 | DASRFIS | 472 | QWSNSWPYT |
| A2A-23 | 295 | RASQSIGRYLN | 384 | AASSLHS | 473 | QQSYVTPWT |
| A2A-24 | 296 | KASQSVRNDVV | 385 | RGNTLRP | 474 | QQYYGIPLT |

TABLE 16 -continued

Variable Light Chain CDRs

| A2AR Variant | SEQ ID NO | CDR1 Sequence | SEQ ID NO | CDR2 Sequence | SEQ ID NO | CDR3 Sequence |
|---|---|---|---|---|---|---|
| A2A-25 | 297 | KASQSVDYDGDSYMN | 386 | RANRLVD | 475 | QNGHSFPLT |
| A2A-26 | 298 | RASQTISRYLN | 387 | SASTLQS | 476 | QQSYSTPHT |
| A2A-27 | 299 | RASQSIGSYLN | 388 | GASNLQS | 477 | QQGYSAPRT |
| A2A-28 | 300 | RASRSISSYLN | 389 | AASSLPS | 478 | QQSYSTPRT |
| A2A-29 | 301 | KVSQDVRTAVA | 390 | DTSYLAS | 479 | QQSYSWSLT |
| A2A-30 | 302 | GGGNDIGSSMY | 391 | WMSNLAS | 480 | QQYSTYPFA |
| A2A-31 | 303 | RASQSISDYLN | 392 | GASPRES | 481 | QQDNIWPYT |
| A2A-32 | 304 | GGGNDIGSSMY | 393 | DASRFIS | 482 | QQSNEDPPFT |
| A2A-33 | 305 | RASESVDSFGNNFMN | 394 | HTSRLNS | 483 | QQNNEVPRT |
| A2A-34 | 306 | RASSSVTYIH | 395 | AVSRLDS | 484 | HQSNEDPYT |
| A2A-35 | 307 | RASQSIGRYLN | 396 | AASSLHS | 485 | QQSYVTPWT |
| A2A-36 | 308 | KASQSVRNDVV | 397 | RGNTLRP | 486 | QQYYGIPLT |
| A2A-37 | 309 | KASHSVDYDGDNYMN | 398 | DASRFIS | 487 | LRYASYRT |
| A2A-38 | 310 | RASESVNSYGNSFMH | 399 | DASRFIS | 488 | LQYGESPLT |
| A2A-39 | 311 | RSSKSLLHSSGNAYVY | 400 | YTSKPNS | 489 | QHHYGIPLT |
| A2A-40 | 312 | RASQSIGTYLN | 401 | AASSLES | 490 | QQTYNTPWT |
| A2A-41 | 313 | RASSRVSSSYLY | 402 | ATYSLDY | 491 | LQHGERPLT |
| A2A-42 | 314 | GASQSIGTIIH | 403 | DTSYLAS | 492 | QQGNTRPWT |
| A2A-43 | 315 | RASENIYVPLN | 404 | DASRFIS | 493 | QQYNSFPLYT |
| A2A-44 | 316 | RASQSVSSSYLA | 405 | GASSRAT | 494 | QQYGSSPIT |
| A2A-45 | 317 | KSSQSLLYSGEKTYPY | 406 | WASTRLT | 495 | QQSNEDSWT |
| A2A-46 | 318 | QSSQDIFNYLE | 407 | TASNLDT | 496 | QQGYSTPPEIT |
| A2A-47 | 319 | RSTRNILSNMP | 408 | NANTLAE | 497 | LQHWNYPYM |
| A2A-48 | 320 | RASQDISNNLH | 409 | EISGWLS | 498 | QQSNSWSLLT |
| A2A-49 | 321 | SASQSMSNNLH | 410 | LASNLGY | 499 | RQNGHSFPLT |
| A2A-50 | 322 | RASQDISNNLH | 411 | WASTRLT | 500 | QQWSDYPFT |
| A2A-51 | 323 | SASSSLSYMH | 412 | GASPRES | 501 | RQMSSYPPT |
| A2A-52 | 324 | SASSSVSYMN | 413 | EISGWLS | 502 | LRYASYRT |
| A2A-53 | 325 | KASQNMGSNVA | 414 | SASHRSS | 503 | QQWNYPRIT |
| A2A-54 | 326 | KASQNGGTNVD | 415 | EISGWLS | 504 | QHYYSWPPT |
| A2A-55 | 327 | RASENIYVPLN | 416 | LASYRFT | 505 | QQINGWPYT |
| A2A-56 | 328 | KASQNMGSNVA | 417 | AATRLAD | 506 | RQHYSSPPT |
| A2A-57 | 329 | KASQNGGTNVD | 418 | VASNQGT | 507 | QQYYTYPLT |
| A2A-58 | 330 | KASQGVDTNVA | 419 | SSSIS | 508 | AQNRELPFT |
| A2A-59 | 331 | KASQDVGTAIT | 420 | SASKRNT | 509 | LHHYGTPYT |
| A2A-60 | 332 | KASQDVGTSVA | 421 | PASYRSS | 510 | QQGSSNPLT |
| A2A-61 | 333 | RASQVIDDDIN | 422 | LGSNRAP | 511 | HQSYTTPHT |

TABLE 16 -continued

| Variable Light Chain CDRs | | | | | | |
|---|---|---|---|---|---|---|
| A2AR Variant | SEQ ID NO | CDR1 Sequence | SEQ ID NO | CDR2 Sequence | SEQ ID NO | CDR3 Sequence |
| A2A-62 | 334 | RASQEISGYLT | 423 | SASHRSS | 512 | QQWDNNPYT |
| A2A-63 | 335 | RASQSISRYLN | 424 | KASSLER | 513 | LQPNSYPWT |
| A2A-64 | 336 | RASQGISSWLD | 425 | TPFSLQS | 514 | QHYDDLPLT |
| A2A-65 | 337 | KASQNMGSNVA | 426 | EASTRFS | 515 | QQYSSYPLR |
| A2A-66 | 338 | RASQGILGYLN | 427 | STSNLLL | 516 | RQLSSNPLT |
| A2A-67 | 339 | RASESVDNYGISFMS | 428 | DASRFIS | 517 | QQINSWPLT |
| A2A-68 | 340 | KSSQSLLYSGEKTYPY | 429 | EASNRYT | 518 | QQWSSYPPIA |
| A2A-69 | 341 | RASQGLRHDLG | 430 | WASNRES | 519 | QKYSSTPYT |
| A2A-70 | 342 | HASESVSVAGTSLLH | 431 | AASNRES | 520 | QHWSSFPLT |
| A2A-71 | 343 | RVSQGISNYLN | 432 | AASSLQS | 521 | QQSYSTPLT |
| A2A-72 | 344 | RASQSVSSNLA | 433 | GASSRAT | 522 | QQYGSSPPT |
| A2A-73 | 345 | RASQSVSSNLA | 434 | GASSRAT | 523 | QQYGSSPLT |
| A2A-74 | 346 | RASQSVSSSYLA | 435 | GASSRAT | 524 | QQYYSTPLT |
| A2A-75 | 347 | RASQSISSYLN | 436 | AASSLQS | 525 | QQANSFPIT |
| A2A-76 | 348 | RASQSVSSNLA | 437 | DASNRAT | 526 | QQYGSSPLT |
| A2A-77 | 349 | RASQRISSYLN | 438 | AASSLQS | 527 | QQSYSTPLT |
| A2A-78 | 350 | RAIQSVSSSYLA | 439 | GASSRAT | 528 | QQYGSSPLT |
| A2A-79 | 351 | RASQSVSSYLA | 440 | GASSRAT | 529 | QQYGNSYT |
| A2A-80 | 352 | RASQSVSSNLA | 441 | GASTRAT | 530 | QQYGSSPPT |
| A2A-81 | 353 | RASQSISSYLN | 442 | AASSLQS | 531 | QQSYSTPIT |
| A2A-82 | 354 | KASQSVSNDVA | 443 | YASNRYT | 532 | QQDYRSPLT |
| A2A-83 | 355 | KASQNVGTNVA | 444 | SASYRYS | 533 | QQYNSYPLT |
| A2A-84 | 356 | SASSSVSYMY | 445 | DTSNLAS | 534 | QQWNSNPLT |
| A2A-85 | 357 | RASQSISDYLH | 446 | YASQSIS | 535 | QNGHSFPLT |
| A2A-86 | 358 | HASQNINVWLN | 447 | KASNLHT | 536 | QQGQSYPLT |
| A2A-87 | 359 | KASQNVGSNVA | 448 | SASYRYS | 537 | QQYNSYPLT |
| A2A-88 | 360 | SGISSNIGNNYVS | 449 | DNNKRASG | 538 | GTWDTSLSAGV |
| A2A-89 | 361 | SGSSSNIGNHYVS | 450 | DNTKRPSG | 539 | GTWDASLSTWV |

TABLE 17

| Variable Heavy Chain Sequences | | |
|---|---|---|
| A2AR Variant | SEQ ID NO | Sequence |
| A2A-1 | 540 | QVQLQESGPGLVKPSGTLSLTCAVSGGSISSSNWWSWVRQPPG KGLEWIGEIYPSGNTYYNPSLKSRVTISVDKSKNQFSLKLNSVT AADTAVYYCARDEGYWGQGTLVTVSS |
| A2A-2 | 541 | EVQLLESGAEVKKPGASVKVSCKASGYTFTGYYMHWVRQAP GQGLEWMGWINPNSGGTNYAQKFQGRVTMTRDTSISTAYME LSSLRSEDTAVYYCARGGPFDYWGQGTMVTVSS |

TABLE 17 -continued

| Variable Heavy Chain Sequences | | |
|---|---|---|
| A2AR Variant | SEQ ID NO | Sequence |
| A2A-3 | 542 | EVQLLESGAEVKKPGASVKASCKASGYTFTGYYMHWVRQAPGQGLEWMGWINPNSGGTNYAQKFQGRVTMTRDTSISTAYMELSRLRSDDTAVYYCARVYSYGFDYWGQGTLVTVSS |
| A2A-4 | 543 | AGQLQESGGGLVKPGGSLRPSCAASGFTFSDYYMSWIRQAPGKGLEWVSYISSSGSTIYYADSVKGRFTISRDNAKNSLYLQMNSLRAEDTAVYYCARDNWAFDLWGQGTLVTVSS |
| A2A-5 | 544 | GGALVQSGGGLVQPGGSLRLSCAASGFTFSSYSMNWVRQATGKGLEWVSSISSSSSYIYYADSVKGRFTISRDNAKNSLHLQMNSLRDEDTAVYYCARTWYSSSPFDYWGQGTLVTVSS |
| A2A-6 | 545 | EVQLLESGGGLVKPGGSPRLSCAASGFTFSNYSMNWVRQAPGKGLEWVSSISSSSSYIYYADSVNGRFTISRDYAKNSLYLQMNSLRAEDTAVCYCARDSGSYYDWFDPWGQGTLVTVSS |
| A2A-7 | 546 | QVQLVQSGGGLVQPGGSLRLSCAASGFTFSSYAMSWVRRAPGKGLEWVSAISGSGGSTYYADSVKGRFTISRDNSKNTLYLQMNSLRAEDTAVYYCAKYSNYFDYWGQGTLVTVSS |
| A2A-8 | 547 | EVQLQQPGPGLVKPSLSLSHTCSVTGYSITSGYYWNWIRQFPGKKLEWMGYISYDGSNNYNPSLKNRTSITRDTSKNQFFLKLSSVTTDDTATYYCARVHHYYGSSYFDYWGQGTTLTVSS |
| A2A-9 | 548 | EVQLQQSGPGLVKPSQSLSLTCSVTGYSITSGYYWNWIRQFPGKKLEWMGYIRYDGSNNYNPSLKNRISITRDTSKNQFFLKLNSVTTDDTATYYCARVHHYYGSSYFDYWGQGTTLTVSS |
| A2A-10 | 549 | EVQLQQSGPGLVKPSQSLSLTCSVTGYSITSGYYWNWIRQFPGNKLEWMGYISYDGSNNYNPSLKNRISITRDTSKNQFFLKLNSVTTEDTATYYCARDPYYYGSSYFDYWGQGTTLTVSS |
| A2A-11 | 550 | EVKLVESEGGLVQPGSSMKLSCTASGFTFSDYYMAWVRQVPEKGLEWVANINYDGSSTYYLDSLKSRFTISRDNAKNILYLQMSSLKSEDIATYYCAREYYYGSSSFAYWGQGTTLTVSS |
| A2A-12 | 551 | EVNPVESEGGLVQPGSSMKLSCTASGFTFNDYYMAWVRQVPEKGLEWVANINYDGSSTYYLDSLKSRFIISRDNAKNILYLQMSSLKSEDTATYYCAREYYYGSSSFAYWGQGTLVTVSA |
| A2A-13 | 552 | GGEVVESGGGLVKPGGSLKLSCAASGFTFSDFGMHWVRQAPEKGLEWVAYISSGSSTIYYADTVKGRFTISRDNAKNTLFLQMTSLRSEDTAMYYCARREFAYWGQGTLVTVSA |
| A2A-14 | 553 | EVKLEESGGGLVKPGGSLKLSCAVSGFTFSDYGMHWVRQAPEKGLEWVAYISSGSGTIYYEDTVKGRFTISRDNAKNTLFLQMTSLRSEGTAIYYCARPNYHGSSPFAYWGQGTLVTVSA |
| A2A-15 | 554 | EVQLVESGGGLVKPGGSLRLSCAASGFTFSTYGMSWVRQAPGKGLEWVSGISGSGGSTNYADSVKGRFTISRDNSKNTLYLQMNSLRAEDTAVYYCAAARGKWRWRLGRRYDYWGQGTLVTVSS |
| A2A-16 | 555 | EVQLVESGGGLVKPGGSLRLSCAASGFTFNNYAMNWVRQAPGKGLEWVSSISGSGGDTYYADSVKGRFTISRDNSKNTLYLQMNSLRAEDTAVYYCAAARGYWRWRLLRRYDYWGQGTLVTVSS |
| A2A-17 | 556 | EVQLVESGGGLVKPGGSLRLSCAASGFNIGNTYMHWFRQAPGKGLEWVGVINPNYGTTRYNDSVKGRFTISRDNSKNTLYLQMNSLRAEDTAVYYCARDYGSSSFDYWGQGTLVTVSS |
| A2A-18 | 557 | EVQLVESGGGLVKPGGSLRLSCAASGFSFSGYAMSWVRQAPGKGLEWVSVISGSGGSTNYADSVKGRFTISRDNSKNTLYLQMNSLRAEDTAVYYCAAARGYPRWRLGRRYDYWGQGTLVTVSS |
| A2A-19 | 558 | EVQLVESGGGLVKPGGSLRLSCAASGFTFSGYAMNWVRQAPGKGLEWVSTISGSGASTYYADSVKGRFTISRDNSKNTLYLQMNSLRAEDTAVYYCAAARGYKRWRLGRRYDYWGQGTLVTVSS |
| A2A-20 | 559 | EVQLVESGGGLVKPGGSLRLSCAASGFAFSNYWMNWVRQAPGKGLEWVGWFYPKSGSIKYNDSVKGRFTISRDNSKNTLYLQMNSLRAEDTAVYYCTGLYGYDLHWYFDVWGQGTLVTVSS |
| A2A-21 | 560 | QVQLVQSGAEVKKPGASVKVSCKASGGSISSGGYYWNWVRQATGQGLEWMGWMNPNSGNRGSAQKFQGRVTMTRDTSTSTVYMELSSLRSEDTAVYYCARDEVAAAGLFDYWGQGTLVTVSS |

TABLE 17 -continued

Variable Heavy Chain Sequences

| A2AR Variant | SEQ ID NO | Sequence |
|---|---|---|
| A2A-22 | 561 | EVQLVESGGGLVKPGGSLRLSCAASGYTFTEYITHWVRQAPGK<br>GLEWVGMIHPSSGSISYNDSVKGRFTISRDNSKNTLYLQMNSL<br>RAEDTAVYYCARHEVEYYGPSSSWFAYWGQGTLVTVSS |
| A2A-23 | 562 | EVQLVESGGGLVKPGGSLRLSCAASGFTFSTYGMSWVRQAPG<br>KGLEWVSGISGSGGSTNYADSVKGRFTISRDNSKNTLYLQMNS<br>LRAEDTAVYYCAAARGKWRWRLGRRYDYWGQGTLVTVSS |
| A2A-24 | 563 | EVQLVESGGGLVKPGGSLRLSCAASGFNIGNTYMHWFRQAPG<br>KGLEWVGVINPNYGTTRYNDSVKGRFTISRDNSKNTLYLQMN<br>SLRAEDTAVYYCARDYGSSSFDYWGQGTLVTVSS |
| A2A-25 | 564 | EVQLVESGGGLVKPGGSLRLSCAASGFTFGNYWMNWVRQAP<br>GKGLEWVGRIDPANGDTKYADSVKGRFTISRDNSKNTLYLQM<br>NSLRAEDTAVYYCAREGDNSNYYAMDYWGQGTLVTVSS |
| A2A-26 | 565 | EVQLLESGGGLVQPGGSLRLSCAASGFTFSTYAMGWVRQAPG<br>KGLEWVSGISGSAGSTYYADSVKGRFTISRDNSKNTLYLQMNS<br>LRAEDTAVYYCAAARGHWRWRLGRRYDYWGQGTLVTVSS |
| A2A-27 | 566 | EVQLVESGGGLVKPGGSLRLSCAASGFTFSSYAMAWVRQAPG<br>KGLEWVSAISGSGGSTYFADSVKGRFTISRDNSKNTLYLQMNS<br>LRAEDTAVYYCAAARGYWRWRLWRRYDYWGQGTLVTVSS |
| A2A-28 | 567 | EVQLVESGGGLVKPGGSLRLSCAASGFTFSSQAMSWVRQAPG<br>KGLEWVSSISGSGVSTYYADSVKGRFTISRDNSKNTLYLQMNS<br>LRAEDTAVYYCAAARGRWRWRLGRRYDYWGQGTLVTVSS |
| A2A-29 | 568 | EVQLVESGGGLVKPGGSLRLSCAASGYSFTGYDISWVRQAPGK<br>GLEWVARIYPGSGNTYYDDSVKGRFTISRDNSKNTLYLQMNSL<br>RAEDTAVYYCAREDDYGWYFGVWGQGTLVTVSS |
| A2A-30 | 569 | EVQLVESGGGLVKPGGSLRLSCAASGYRLTGYWIEWVRQAPG<br>KGLEWVGRIDPASGDTTYADSVKGRFTISRDNSKNTLYLQMNS<br>LRAEDTAVYYCARHEDPIYYGNYVFAYWGQGTLVTVSS |
| A2A-31 | 570 | EVQLVESGGGLVKPGGSLRLSCAASGYLFTDYNMNWVRQAP<br>GKGLEWVGWIYPGTGNTYNDSVKGRFTISRDNSKNTLYLQMN<br>SLRAEDTAVYYCTALYYGSSWERYFDVWGQGTLVTVSS |
| A2A-32 | 571 | EVQLVESGGGLVKPGGSLRLSCAASGFTFIDYGMHWVRQAPG<br>KGLEWVGVINPNYGTTRYNDSVKGRFTISRDNSKNTLYLQMN<br>SLRAEDTAVYYCARQGSNYGGYFDVWGQGTLVTVSS |
| A2A-33 | 572 | EVQLVESGGGLVKPGGSLRLSCAASGFPFSSYAMTWVRQAPG<br>KGLEWVSGISGSGGRTYYADSVKGRFTISRDNSKNTLYLQMNS<br>LRAEDTAVYYCAAARGYWRWRLGRRADYWGQGTLVTVSS |
| A2A-34 | 573 | EVQLVESGGGLVKPGGSLRLSCAASGFNFNTYAMNWVRQAPG<br>KGLEWVGVIYPGNSDTTYNDSVKGRFTISRDNSKNTLYLQMN<br>SLRAEDTAVYYCTGVIYYYGSSDYTLDYWGQGTLVTVSS |
| A2A-35 | 574 | EVQLVESGGGLVKPGGSLRLSCAASGFTFSTYGMSWVRQAPG<br>KGLEWVSGISGSGGSTNYADSVKGRFTISRDNSKNTLYLQMNS<br>LRAEDTAVYYCAAARGKWRWRLGRRYDYWGQGTLVTVSS |
| A2A-36 | 575 | EVQLVESGGGLVKPGGSLRLSCAASGFNIGNTYMHWFRQAPG<br>KGLEWVGVINPNYGTTRYNDSVKGRFTISRDNSKNTLYLQMN<br>SLRAEDTAVYYCARDYGSSSFDYWGQGTLVTVSS |
| A2A-37 | 576 | EVQLVESGGGLVKPGGSLRLSCAASGYTFTSYWVHWVRQAPG<br>KGLEWVANINHDGSNTYYLDSVKGRFTISRDNSKNTLYLQMN<br>SLRAEDTAVYYCASSMITRFAYWGQGTLVTVSS |
| A2A-38 | 577 | EVQLVESGGGLVKPGGSLRLSCAASGFSLTSYNIDWVRQAPGK<br>GLEWVGGVDPETDDTAYNDSVKGRFTISRDNSKNTLYLQMNS<br>LRAEDTAVYYCANYYYGSSAFAYWGQGTLVTVSS |
| A2A-39 | 578 | EVQLVESGGGLVKPGGSLRLSCAASGFTFSNYYMSWVRQAPG<br>KGLEWVGDINPNNGGTTYNDSVKGRFTISRDNSKNTLYLQMN<br>SLRAEDTAVYYCTKAYYSNYGVMYFWGQGTLVTVSS |
| A2A-40 | 579 | EVQLVESGGGLVKPGGSLRLSCAASGFNFRSYAMSWVRQAPG<br>KGLEWVSVISGGGGSTYYADSVKGRFTISRDNSKNTLYLQMNS<br>LRAEDTAVYYCAAARGGWRWRLGRRYDYWGQGTLVTVSS |

TABLE 17 -continued

| Variable Heavy Chain Sequences | | |
|---|---|---|
| A2AR Variant | SEQ ID NO | Sequence |
| A2A-41 | 580 | EVQLVESGGGLVKPGGSLRLSCAASGFSLSIYGISWVRQAPGK GLEWVGDISPGSGSTNYNDSVKGRFTISRDNSKNTLYLQMNSL RAEDTAVYYCAGPYYYGSSRYYAMDYWGQGTLVTVSS |
| A2A-42 | 581 | EVQLVESGGGLVKPGGSLRLSCAASGYTFTSYNINWVRQAPG KGLEWVATISSGGDSIYYADSVKGRFTISRDNSKNTLYLQMNS LRAEDTAVYYCERDYYGSSWHFDVWGQGTLVTVSS |
| A2A-43 | 582 | EVQLVESGGGLVKPGGSLRLSCAASGFTFSSYDMYWVRQAPG KGLEWVASISDGGSYTYYVDSVKGRFTISRDNSKNTLYLQMNS LRAEDTAVYYCARYIWYYGSSWSWYFDAWGQGTLVTVSS |
| A2A-44 | 583 | EVQLVESGGGVVQPGRSLRLSCAASGFTFSAYDIYWVRQPTGK GLEWVSAIGTAGDTYYPGSVKGRFIISRESAKNSVYLQMNSLR AGDTAVYYCAVGYNWIFDLWGQGTLVTVSS |
| A2A-45 | 584 | EVQLVESGGGLVKPGGSLRLSCAASGYSFTGYDISWFRQAPGK GLEWVGEILPGSGGTNYNDSVKGRFTISRDNSKNTLYLQMNSL RAEDTAVYYCTSGNYDAMDYWGQGTLVTVSS |
| A2A-46 | 585 | QVQLVQSGAEVKKPGASVKVSCKASGGYISSSNWWSWVRQA TGQGLEWMANIEQDGSEKNYVQKFQGRVTMTRDTSTSTVYM ELSSLRSEDTAVYYCARGEYSRLWYFDLWGQGTLVTVSS |
| A2A-47 | 586 | EVQLVESGGGLVKPGGSLRLSCAASGTFTDYYMKWVRQAPG KGLEWVGEILPGSGGTNYNDSVKGRFTISRDNSKNTLYLQMNS LRAEDTAVYYCARPYDYDFDYWGQGTLVTVSS |
| A2A-48 | 587 | EVQLVESGGGLVKPGGSLRLSCAASGYTFTSSWMHWARQAPG KGLEWVGWLYPRDGSTEYNDSVKGRFTISRDNSKNTLYLQMN SLRAEDTAVYYCITTVVADWYFDVWGQGTLVTVSS |
| A2A-49 | 588 | EVQLVESGGGLVKPGGSLRLSCAASGYTFNDDYTNWVRQAPG KGLEWVGNINPNNGAMIYNDSVKGRFTISRDNSKNTLYLQMN SLRAEDTAVYYCARKGDGGSYAAMDYWGQGTLVTVSS |
| A2A-50 | 589 | EVQLVESGGGLVKPGGSLRLSCAASGYSFTGYDISWVRQAPGK GLEWVGWIYPKDGSTKYNDSVKGRFTISRDNSKNTLYLQMNS LRAEDTAVYYCITTVVADWYFDVWGQGTLVTVSS |
| A2A-51 | 590 | EVQLVESGGGLVKPGGSLRLSCAASGYTFNDYYINWVRQAPG KGLEWVGDINPNNGANIYNDSVKGRFTISRDNSKNTLYLQMN SLRAEDTAVYYCARNYGSSYYALDYWGQGTLVTVSS |
| A2A-52 | 591 | EVQLVESGGGLVKPGGSLRLSCAASGYTFNDYYINWVRQAPG KGLEWVGDINPNNGGTTYNDSVKGRFTISRDNSKNTLYLQMN SLRAEDTAVYYCARQGSNYGGYFDVWGQGTLVTVSS |
| A2A-53 | 592 | EVQLVESGGGLVKPGGSLRLSCAASGFNIIDDYMHWVRQAPG KGLEWVGMITDTGEPTDADSVKGRFTISRDNSKNTLYLQMNS LRAEDTAVYYCVYDYIYAMDYWGQGTLVTVSS |
| A2A-54 | 593 | EVQLVESGGGLVKPGGSLRLSCAASGYTFTDYDMYWVRQAP GKGLEWVGRIDPANGDTKYADSVKGRFTISRDNSKNTLYLQM NSLRAEDTAVYYCARGDYGSSYAMDYWGQGTLVTVSS |
| A2A-55 | 594 | EVQLVESGGGLVKPGGSLRLSCAASGYEFSSSWMNWVRQAPG KGLEWVGWIYPGTGNTNYNDSVKGRFTISRDNSKNTLYLQMN SLRAEDTAVYYCANYYYGSSAFAYWGQGTLVTVSS |
| A2A-56 | 595 | EVQLVESGGGLVKPGGSLRLSCAASGFTFSSYGLPWVRQAPGK GLEWVGAIDPGTGGTASNDSVKGRFTISRDNSKNTLYLQMNSL RAEDTAVYYCARIYYDYSAMDYWGQGTLVTVSS |
| A2A-57 | 596 | EVQLVESGGGLVKPGGSLRLSCAASGFIFSDFYMAWVRQAPG KGLEWVGRIDPEDGDEHADSVKGRFTISRDNSKNTLYLQMNS LRAEDTAVYYCARDYYGSSYLDYWGQGTLVTVSS |
| A2A-58 | 597 | EVQLVESGGGLVKPGGSLRLSCAASGFNIKDYYMHWVRQAPG KGLEWVGDINPNNGGTTYNDSVKGRFTISRDNSKNTLYLQMN SLRAEDTAVYYCARDYYGSFHRRWYFDVWGQGTLVTVSS |
| A2A-59 | 598 | EVQLVESGGGLVKPGGSLRLSCAASGYTFTDYNIDWVRQAPG KGLEWVGDININNGGTTYNDSVKGRFTISRDNSKNTLYLQMNS LRAEDTAVYYCARDYHGSSFYWYFDVWGQGTLVTVSS |

TABLE 17 -continued

| Variable Heavy Chain Sequences | | |
|---|---|---|
| A2AR Variant | SEQ ID NO | Sequence |
| A2A-60 | 599 | EVQLVESGGGLVKPGGSLRLSCAASGYTFTEYITHWVRQAPGKGLEWVANINFDGSSTYYLDSVKGRFTISRDNSKNTLYLQMNSLRAEDTAVYYCARYYDSSYYAMDYWGQGTLVTVSS |
| A2A-61 | 600 | QVQLVQSGAEVKKPGASVKVSCKASGFTFSTYIMSWVRQATGQGLEWMGIIYPGDTDTRYSQKFQGRVTMTRDTSTSTVYMELSSLRSEDTAVYYCARGIAVAGTFDYWGQGTLVTVSS |
| A2A-62 | 601 | EVQLVESGGGLVKPGGSLRLSCAASGYTFTNYLIEWVRQAPGKGLEWVGDINPNNGGTYYNDSVKGRFTISRDNSKNTLYLQMNSLRAEDTAVYYCVRHALLWYYYAMDYWGQGTLVTVSS |
| A2A-63 | 602 | QVQLVQSGAEVKKPGASVKVSCKASGFTFSDHYMTWVRQATGQGLEWMGWMNPNSGITGYAQKFQGRVTMTRDTSTSTVYMELSSLRSEDTAVYYCARVSYSGSLHYWGQGTLVTVSS |
| A2A-64 | 603 | QVQLVQSGAEVKKPGASVKVSCKASGFTFDDYAMHWVRQATGQGLEWMGVINTNTGNPTYAQKFQGRVTMTRDTSTSTVYMELSSLRSEDTAVYYCARSNWNYFDYWGQGTLVTVSS |
| A2A-65 | 604 | EVQLVESGGGLVKPGGSLRLSCAASGSAFSASWMNLVRQAPGKGLEWVGWVDPDNGDTEYADSVKGRFTISRDNSKNTLYLQMNSLRAEDTAVYYCSKPRDSGPSFASWGQGTLVTVSS |
| A2A-66 | 605 | EVQLVESGGGLVKPGGSLRLSCAASGFTFSSYDMYWVRQAPGKGLEWVGWIYPKDGSTKYNDSVKGRFTISRDNSKNTLYLQMNSLRAEDTAVYYCARSRGYYYGSSYGYYDVWGQGTLVTVSS |
| A2A-67 | 606 | EVQLVESGGGLVKPGGSLRLSCAASGHTITSYGINWVRQAPGKGLEWVGEILPGSGTSDYNDSVKGRFTISRDNSKNTLYLQMNSLRAEDTAVYYCATNWGFAYWGQGTLVTVSS |
| A2A-68 | 607 | EVQLVESGGGLVKPGGSLRLSCAASGYTFSGYTMHWVRQAPGKGLEWVGEIDPSDSFANYNDSVKGRFTISRDNSKNTLYLQMNSLRAEDTAVYYCARDYGSSYEFTYWGQGTLVTVSS |
| A2A-69 | 608 | QVQLVQSGAEVKKPGASVKVSCKASGGYISSSNWWSWVRQATGQGLEWMGRIKTKTDGGTIDYAQKFQGRVTMTRDTSTSTVYMELSSLRSEDTAVYYCAKGYSGSVDYWGQGTLVTVSS |
| A2A-70 | 609 | EVQLVESGGGLVKPGGSLRLSCAASGSNIKDYYIHWVRQAPGKGLEWVATISDGGSYIFDDSVKGRFTISRDNSKNTLYLQMNSLRAEDTAVYYCARDATGTFAYWGQGTLVTVSS |
| A2A-71 | 610 | QVQLQESGPGLVKPSGTLSLTCAVSGGSISSSNWWSWVRQPPGRGLEWIGEIYHSGSTNYNPSLKSRVTISVDKPKNQFSLKLSSVTAADTAVYYCAREVVSGMIGTVFDYWGQGTLVTVSS |
| A2A-72 | 611 | QVQLVQSGGGLVQPGGSLRLSCAVSGFTISTYDIYWVRQATGKGLEWVSAIGTAGDTYYPDSVRGRFTISREDARNSLYLQMNSLRTGDTAVYYCATGYNWIFDYWGQGTLVTVSS |
| A2A-73 | 612 | QVQLVQSGGGLVQPGGSLRLSCAASGFTVSTYDIYWVRQTTGKGLELVSAIGTAGDTYYPDSVKGRFTISRENARNSLYLQMNSLRAGDTAVYYCAVGYNWIFDFWGQGTLVTVSS |
| A2A-74 | 613 | EVQLVESGGGLVQPGGSLRLSCAASGFTFTTYDMYWVRQTTGKGLEWVSAIGTAGDTYYPDSVKGRFTISRESAKNSLYLQMNSLRAGDTAVYYCTVGYNWIFDFWGHGTLVTVSS |
| A2A-75 | 614 | QVQLQESGPGLVKPSGTLSLTCAVSGGSISSSNWWSWVRQPPGKGLEWIGEIYHSGNTNYNPSLKSRVTMSVDKSKNQFSLNLHSVTAADTAVYYCAREVVSGMIGTIFDYWGQGTLVTVSS |
| A2A-76 | 615 | EVQLVESGGGLVQPGGSLRLSCAASGFTFSSYDMYWVRQPTGKGLEWVSAIGTAGDTYYSGSVKGRFTISRESAKNSLYLQMNSLRAGDTAVYYCAVGYNWIFDFWGQGTLVTVSS |
| A2A-77 | 616 | QVQLQESGPGLVKPSGTLSLTCAVSGGSISSSNWWSWVRQPPGKGLEWIGEIYHSGNTNYNPSLKSRVTMSVDKSKNQFSLNLHSVTAADTAVYYCAREVVSGMIGTIFDYWGQGTLVTVSS |
| A2A-78 | 617 | EVQLLESGGGLVQPGGSLRLSCAASGFTFSAYDIYWVRQPTGKGLEWVSAIGTAGDTYYPGSVKGRFIISRESAKNSVYLQMNSLRAGDTAVYYCAVGYNWVFDLWGQGTLVTVSS |

TABLE 17 -continued

| Variable Heavy Chain Sequences | | |
|---|---|---|
| A2AR Variant | SEQ ID NO | Sequence |
| A2A-79 | 618 | QVQLQESGGGVVRPGGSLRLSCAASGFTFDDYGMSWVRQVPG KGLEWVSGITWNGDRSGYADSVKGRFTISRDNAKNSLYLQMN SLRAEDTALYYCVRDGLTGIFDYWGQGTLVTVSS |
| A2A-80 | 619 | QVQLVQSGGGLVKPGGSLRLSCAASGFTISTYDIYWVRQATGK GLEWVSAIGTAGDTYYPGSVKGRFTISRENAKNSLYLQMNSLR AGDTAVYYCASGYNWIFDYWGQGTLVTVSS |
| A2A-81 | 620 | QVQLQESGPGLVKPSGTLSLTCAVSGGSISSSNWWSWVRQPPG KGLEWIGEIYHSGSTNYNPSLKSRVTISVDKSKNQFSLKLGSVT AADTAVYYCAREVVSGLYGTIFDYWGQGTLVTVSS |
| A2A-82 | 621 | EVQLQQSGPGLVKPSQSLSLTCSVTGYSITSGYYWNWIRQFPG NKLEWMGYISYGGSNDYNPSLKNRISITRDSSKNQFFLKLNSVT TEDTATYYCARDYDYFDYWGQGTTLTVSS |
| A2A-83 | 622 | EVQRVQSGAELVKPGASVKISCKASGYAFSSYWMNWVKQRP GKGLEWIGQIYPGDGDTNYNGKFEGKATLTADKSSSTAYMQL TSLTSDDSAVYYCARGAYWGQGTTLTVSS |
| A2A-84 | 623 | EVQLVESGGGLVKPGGSLRLSCAASGYTFTEYITHWVRQAPGK GLEWVATISGGGSYTNFPDSVKGRFTISRDNAKNTLFLQMTSL RSEDTAMYYCARPNYSGSSPFAYWGQGTLVTVSA |
| A2A-85 | 624 | EVQLQQSGPGLVAPSQSLSITCTVSGFSLTAYAISWVRQPPGKG LEWLGVIWTGGGTNYNSALKSRLSISKDNSKSQVFLKMNSLQT DDTARYYCARSRGYYYGSSYGYFDVWGTGTTVTVSS |
| A2A-86 | 625 | EVQLQESGPGLAKPSQTLPLTCSVIGYSITSDYWNWIRKFPGNK LEYMGYINYSGSTYYNPSLKSRISITRDTSKNQYYLQLNSVTTE DTATYYCTRKLDWDGYFDVWGTGTTVTVSS |
| A2A-87 | 626 | EVQLQQSEAELVRPGAPVKLSCTASGFNIKNTYMHWVKQRPE QGLEWIGRIDPANGNTKYAPKFQGKATITADTSSNTAYLQLSS LASEDSAVYFCARGSPYGYDGHYVMDYWGQGTSVTVSS |
| A2A-88 | 627 | EVQLVESGGGLVKPGGSLRLSCAASGFTFRTYGMHWVRQAPG KGLEWVAVISAEGSNKYYADSVKGRFTISRDNSKNTLYLQMN SLRAEDTAVYYCARDGRGSLPRPKGGFIGALSFHWPFGRWLG GSYGTYDSSEDSGGAFDIWGQGTLVTVSS |
| A2A-89 | 628 | QVQLVESGGGVVQPGRSLRLSCAASGFTFNNYGMHWVRQAP GKGLEWVAVISYGGSDKYYADSVKGRFTISRDNSKNTLYLQM NSLRAEDTAVYYCARDGRGSLPRPKGGFIGDLSFHWPFGRWL GKSYGTYDSSEDSGGAFDIWGQGTLVTVSS |

TABLE 18

| Variable Light Chain | | |
|---|---|---|
| Variant | SEQ ID NO | Sequence |
| A2A-1 | 629 | ELVMTQSPLSLPVTLGQPASISCRSSQSLVYSDGNTYLNWFQ QRPGQSPRRLIYKVSNRDSGVPDRFSGSGSGTDFTLKISRVEA EDVGVYYCMQGTHWPRTFGQGTKVDIK |
| A2A-2 | 630 | ELTLTQSPAFMSATPGDKVNISCKASQDIDDDMNWYQQKPG EAAIFIIQEATTLVPGIPPRFSGSGYGTDFTLTINNIESEDAAYY FCLQHDNFPMYTFGQGTKLEIK |
| A2A-3 | 631 | ELVLTQSPDSLAVSLGERATFNCKSSQSVLYSSNNKNYLAW YQQKPGQPPKLLIYWASTRESGVPDRFSGSGSGTDFTLTISSL QAEDVAVYYCQQYYSTPYTFGQGTKVDIK |
| A2A-4 | 632 | ELTLTQSPATLSVSPGERATLSCRASQSVSSNLAWYQQKPGQ APRLLIYGASTRATGIPARFSGSGSGTEFTLTISSLQAEDVAV YYCQQYYSTPLTFGGGTKVEIK |
| A2A-5 | 633 | ELTLTQSPAFMSATPGDKVNISCKASQDIDDDMNWYQQKPG EAAIFIIQEATTLVPGIPPRFSGSGYGTDFTLTINNIESEDAAYY FCLQHDNFPWTFGQGTKVDTK |

TABLE 18 -continued

| Variable Light Chain | | |
|---|---|---|
| Variant | SEQ ID NO | Sequence |
| A2A-6 | 634 | ELQMTQSPSSVSASVGDKVTITCRASQGISSWLAWYQQKPG KGPKLLIYAASSLQSGVPSRFSGSGSGTDFTPTISSLQPEDFAT YYCQQTNSFPRTLGQGTKLEIK |
| A2A-7 | 635 | ELTLTQSPAFMSATPGDKVNISCKASQDVDDDMNWYQQKP GEAAIFIIQEATTLVPGIPPRFSGSGYGTDFTLTINNIESEDAAY YFCLQHDNFPWTFGQGTRLEIK |
| A2A-8 | 636 | DIVMTQAQKFMSTSVGDRVSVTCKASQNVGTNVAWYQQKP GQSPKALIYSASYRYSGVPDRFTGSGSGTDFTLTVTNVQSED LAEYFCQRFNNYPLTFGAGTKLEIK |
| A2A-9 | 637 | DIVMTQSQKFMSTSVGDRVSATCKASQNVGSSVAWFQQKP GQSPKALIYSTSYRYSGVPDRFTGSGSGTDFTLTISNVQSEDL AEYFCQQYNSYPLTFGAGTKLEIK |
| A2A-10 | 638 | DIVMTQAPATLSVTPGDRVSLSCRASQSISDYLHWYQQKSHE SPRLLIKYASQSISGIPSRFSGSGSGSDFTLSINSVEPEDVGVYY CQNGHSFPLTFGAGTKLEIK |
| A2A-11 | 639 | DIVMTQSQKFMSTSVGDRVSVTCKASRNVGTNVAWYQQKL GQSPKTLIYSASYRYSGVPDRFTGSGSGTDFTLTISNVQSEDL AEYFCQQYNSYPLTFGAGTKLEIK |
| A2A-12 | 640 | DIQMTQTPATLSVTPGDRVSLSCRASQSISDYLHWYQQKSHE SPRLLIKYASQSISGIPSRFSGSGSGSDFTLSINSVEPEDVGVYY CQNGHSFPHTLGSGTKLEIK |
| A2A-13 | 641 | DIQMIQSQKFMSTSVGDRVSVTCKASQNVGTNVAWYQQKP GQSPKALIYSASYRYSGVPDRFTGSGSGTDFTLTIGNVQSEDL VEYFCQQYNIYPLTFGAGTKLELK |
| A2A-14 | 642 | DIVMTQSPATLSVTPGDSVSLSCRASQSISNYLHWYQQKSHE SPRLLIKYASQSISGIPSRFSGSGSGSDFTLSINSVEPEDVGVYY CQNGHSFPLTFGGGTKLELK |
| A2A-15 | 643 | DIQMTQSPSSLSASVGDRVTITCRASQSIGRYLNWYQQKPGK APKLLIYAASSLHSGVPSRFSGSGSGTDFTLTISSLQPEDFATY YCQQSYVTPWTFGGGTKLEIK |
| A2A-16 | 644 | DIQMTQSPSSLSASVGDRVTITCRASQSIGTYLNWYQQKPGK APKLLIYGASTLHSGVPSRFSGSGSGTDFTLTISSLQPEDFATY YCQQSYSAPWTFGGGTKVEIK |
| A2A-17 | 645 | DIQMTQSPSSLSASVGDRVTITCKASQSVRNDVVWYQQKPG KAPKLLIYRGNTLRPGVPSRFSGSGSGTDFTLTISSLQPEDFAT YYCQQYYGIPLTFGQGTKLEIK |
| A2A-18 | 646 | DIQMTQSPSSLSASVGDRVTITCRASQSVTTYLNWYQQKPGK APKLLIYSASSLQSGVPSRFSGSGSGTDFTLTISSLQPEDFATY YCQQTYATPWTFGGGTKVEIK |
| A2A-19 | 647 | DIQMTQSPSSLSASVGDRVTITCRASQSISDYLNWYQQKPGK APKLLIYTASTLQSGVPSRFSGSGSGTDFTLTISSLQPEDFATY YCEQSYSTPWTFGGGTKLEIK |
| A2A-20 | 648 | DIQMTQSPSSLSASVGDRVTITCKASHSVDYDGDNYMNWYQ QKPGKAPKLLIYWASTRLTGVPSRFSGSGSGTDFTLTISSLQP EDFATYYCLQHIEYPFTFGQGTKLEIK |
| A2A-21 | 649 | DIQMTQSPSSLSASVGDRVTITCKSSQSVLYSSNNKNYFAWY QQKPGKAPKLLIYDAPNRATGVPSRFSGSGSGTDFTLTISSLQ PEDFATYYCQQGYTTPYTFGGGTKVEIK |
| A2A-22 | 650 | DIQMTQSPSSLSASVGDRVTITCRASQDIGRSLSWYQQKPGK APKLLIYDASRFISGVPSRFSGSGSGTDFTLTISSLQPEDFATY YCQWSNSWPYTFGQGTKLEIK |
| A2A-23 | 651 | DIQMTQSPSSLSASVGDRVTITCRASQSIGRYLNWYQQKPGK APKLLIYAASSLHSGVPSRFSGSGSGTDFTLTISSLQPEDFATY YCQQSYVTPWTFGGGTKLEIK |
| A2A-24 | 652 | DIQMTQSPSSLSASVGDRVTITCKASQSVRNDVVWYQQKPG KAPKLLIYRGNTLRPGVPSRFSGSGSGTDFTLTISSLQPEDFAT YYCQQYYGIPLTFGQGTKLEIK |

TABLE 18 -continued

| Variable Light Chain | | |
|---|---|---|
| Variant | SEQ ID NO | Sequence |
| A2A-25 | 653 | DIQMTQSPSSLSASVGDRVTITCKASQSVDYDGDSYMNWYQQKPGKAPKLLIYRANRLVDGVPSRFSGSGSGTDFTLTISSLQPEDFATYYCQNGHSFPLTFGQGTKLEIK |
| A2A-26 | 654 | DIQMTQSPSSLSASVGDRVTITCRASQTISRYLNWYQQKPGKAPKLLIYSASTLQSGVPSRFSGSGSGTDFTLTISSLQPEDFATYYCQQSYSTPHTFGGGTKVEIK |
| A2A-27 | 655 | DIQMTQSPSSLSASVGDRVTITCRASQSIGSYLNWYQQKPGKAPKLLIYGASNLQSGVPSRFSGSGSGTDFTLTISSLQPEDFATYYCQQGYSAPRTFGGGTKLEIK |
| A2A-28 | 656 | DIQMTQSPSSLSASVGDRVTITCRASRSISSYLNWYQQKPGKAPKLLIYAASSLPSGVPSRFSGSGSGTDFTLTISSLQPEDFATYYCQQSYSTPRTFGGGTKLEIK |
| A2A-29 | 657 | DIQMTQSPSSLSASVGDRVTITCKVSQDVRTAVAWYQQKPGKAPKLLIYDTSYLASGVPSRFSGSGSGTDFTLTISSLQPEDFATYYCQQSYSWSLTFGQGTKLEIK |
| A2A-30 | 658 | DIQMTQSPSSLSASVGDRVTITCGGGNDIGSSMYWYQQKPGKAPKLLIYWMSNLASGVPSRFSGSGSGTDFTLTISSLQPEDFATYYCQQYSTYPFALGQGTKLEIK |
| A2A-31 | 659 | DIQMTQSPSSLSASVGDRVTITCRASQSISDYLNWYQQKPGKAPKLLIYGASPRESGVPSRFSGSGSGTDFTLTISSLQPEDFATYYCQQDNIWPYTFGQGTKLEIK |
| A2A-32 | 660 | DIQMTQSPSSLSASVGDRVTITCGGGNDIGSSMYWYQQKPGKAPKLLIYDASRFISGVPSRFSGSGSGTDFTLTISSLQPEDFATYYCQQSNEDPPFTFGQGTKLEIK |
| A2A-33 | 661 | DIQMTQSPSSLSASVGDRVTITCRASESVDSFGNNFMNWYQQKPGKAPKLLIYHTSRLNSGVPSRFSGSGSGTDFTLTISSLQPEDFATYYCQQNNEVPRTFGQGTKLEIK |
| A2A-34 | 662 | DIQMTQSPSSLSASVGDRVTITCRASSSVTYIHWYQQKPGKAPKLLIYAVSRLDSGVPSRFSGSGSGTDFTLTISSLQPEDFATYYCHQSNEDPYTFGQGTKLEIK |
| A2A-35 | 663 | DIQMTQSPSSLSASVGDRVTITCRASQSIGRYLNWYQQKPGKAPKLLIYAASSLHSGVPSRFSGSGSGTDFTLTISSLQPEDFATYYCQQSYVTPWTFGGGTKVEIK |
| A2A-36 | 664 | DIQMTQSPSSLSASVGDRVTITCKASQSVRNDVVWYQQKPGKAPKLLIYRGNTLRPGVPSRFSGSGSGTDFTLTISSLQPEDFATYYCQQYYGIPLTFGQGTKLEIK |
| A2A-37 | 665 | DIQMTQSPSSLSASVGDRVTITCKASHSVDYDGDNYMNWYQQKPGKAPKLLIYDASRFISGVPSRFSGSGSGTDFTLTISSLQPEDFATYYCLRYASYRTFGQGTKLEIK |
| A2A-38 | 666 | DIQMTQSPSSLSASVGDRVTITCRASESVNSYGNSFMHWYQQKPGKAPKLLIYDASRFISGVPSRFSGSGSGTDFTLTISSLQPEDFATYYCLQYGESPLTFGQGTKLEIK |
| A2A-39 | 667 | DIQMTQSPSSLSASVGDRVTITCRSSKSLLHSSGNAYVYWYQQKPGKAPKLLIYYTSKPNSGVPSRFSGSGSGTDFTLTISSLQPEDFATYYCQHHYGIPLTFGQGTKLEIK |
| A2A-40 | 668 | DIQMTQSPSSLSASVGDRVTITCRASQSIGTYLNWYQQKPGKAPKLLIYAASSLESGVPSRFSGSGSGTDFTLTISSLQPEDFATYYCQQTYNTPWTFGGGTKVEIK |
| A2A-41 | 669 | DIQMTQSPSSLSASVGDRVTITCRASSRVSSSYLYWYQQKPGKAPKLLIYATYSLDYGVPSRFSGSGSGTDFTLTISSLQPEDFATYYCLQHGERPLTFGQGTKLEIK |
| A2A-42 | 670 | DIQMTQSPSSLSASVGDRVTITCGASQSIGTIIHWYQQKPGKAPKLLIYDTSYLASGVPSRFSGSGSGTDFTLTISSLQPEDFATYYCQQGNTRPWTFGQGTKLEIK |
| A2A-43 | 671 | DIQMTQSPSSLSASVGDRVTITCRASENIYVPLNWYQQKPGKAPKLLIYDASRFISGVPSRFSGSGSGTDFTLTISSLQPEDFATYYCQQYNSFPLYTFGQGTKLEIK |

TABLE 18 -continued

| Variable Light Chain | | |
|---|---|---|
| Variant | SEQ ID NO | Sequence |
| A2A-44 | 672 | ELVLTQSPGTLSLSPGERATLSCRASQSVSSSYLAWYQQKPG QAPRLLIYGASSRATGIPDRFSGSGSGTDFTLTISRLEPEDFAV YYCQQYGSSPITFGQGTKVDIK |
| A2A-45 | 673 | DIQMTQSPSSLSASVGDRVTITCKSSQSLLYSGEKTYPYWYQ QKPGKAPKLLIYWASTRLTGVPSRFSGSGSGTDFTLTISSLQP EDFATYYCQQSNEDSWTFGQGTKLEIK |
| A2A-46 | 674 | DIQMTQSPSSLSASVGDRVTITCQSSQDIFNYLEWYQQKPGK APKLLIYTASNLDTGVPSRFSGSGSGTDFTLTISSLQPEDFATY YCQQGYSTPPEITFGGGTKVEIK |
| A2A-47 | 675 | DIQMTQSPSSLSASVGDRVTITCRSTRNILSNMPWYQQKPGK APKLLIYNANTLAEGVPSRFSGSGSGTDFTLTISSLQPEDFAT YYCLQHWNYPYMFGQGTKLEIK |
| A2A-48 | 676 | DIQMTQSPSSLSASVGDRVTITCRASQDISNNLHWYQQKPGK APKLLIYEISGWLSGVPSRFSGSGSGTDFTLTISSLQPEDFATY YCQQSNSWSLLTFGQGTKLEIK |
| A2A-49 | 677 | DIQMTQSPSSLSASVGDRVTITCSASQSMSNNLHWYQQKPG KAPKLLIYLASNLGYGVPSRFSGSGSGTDFTLTISSLQPEDFA TYYCRQNGHSFPLTFGQGTKLEIK |
| A2A-50 | 678 | DIQMTQSPSSLSASVGDRVTITCRASQDISNNLHWYQQKPGK APKLLIYWASTRLTGVPSRFSGSGSGTDFTLTISSLQPEDFAT YYCQQWSDYPFTFGQGTKLEIK |
| A2A-51 | 679 | DIQMTQSPSSLSASVGDRVTITCSASSSLSYMHWYQQKPGKA PKLLIYGASPRESGVPSRFSGSGSGTDFTLTISSLQPEDFATYY CRQMSSYPPTFGQGTKLEIK |
| A2A-52 | 680 | DIQMTQSPSSLSASVGDRVTITCSASSSVSYMNWYQQKPGK APKLLIYEISGWLSGVPSRFSGSGSGTDFTLTISSLQPEDFATY YCLRYASYRTFGQGTKLEIK |
| A2A-53 | 681 | DIQMTQSPSSLSASVGDRVTITCKASQNMGSNVAWYQQKPG KAPKLLIYSASHRSSGVPSRFSGSGSGTDFTLTISSLQPEDFAT YYCQQWNYPRITFGQGTKLEIK |
| A2A-54 | 682 | DIQMTQSPSSLSASVGDRVTITCKASQNGGTNVDWYQQKPG KAPKLLIYEISGWLSGVPSRFSGSGSGTDFTLTISSLQPEDFAT YYCQHYYSWPPTFGQGTKLEIK |
| A2A-55 | 683 | DIQMTQSPSSLSASVGDRVTITCRASENIYVPLNWYQQKPGK APKLLIYLASYRFTGVPSRFSGSGSGTDFTLTISSLQPEDFATY YCQQINGWPYTFGQGTKLEIK |
| A2A-56 | 684 | DIQMTQSPSSLSASVGDRVTITCKASQNMGSNVAWYQQKPG KAPKLLIYAATRLADGVPSRFSGSGSGTDFTLTISSLQPEDFA TYYCRQHYSSPPTFGQGTKLEIK |
| A2A-57 | 685 | DIQMTQSPSSLSASVGDRVTITCKASQNGGTNVDWYQQKPG KAPKLLIYVASNQGTGVPSRFSGSGSGTDFTLTISSLQPEDFA TYYCQQYYTYPLTFGQGTKLEIK |
| A2A-58 | 686 | DIQMTQSPSSLSASVGDRVTITCKASQGVDTNVAWYQQKPG KAPKLLIYSSSISGVPSRFSGSGSGTDFTLTISSLQPEDFATYY CAQNRELPFTFGQGTKLEIK |
| A2A-59 | 687 | DIQMTQSPSSLSASVGDRVTITCKASQDVGTAITWYQQKPGK APKLLIYSASKRNTGVPSRFSGSGSGTDFTLTISSLQPEDFATY YCLHHYGTPYTFGQGTKLEIK |
| A2A-60 | 688 | DIQMTQSPSSLSTSVGDRVTITCKASQDVGTSVAWYQQKPG KAPKLLIYPASYRSSGVPSRFSGSGSGTDFTLTISSLQPEDFAT YYCQQGSSNPLTFGQGTKLEIK |
| A2A-61 | 689 | DIQMTQSPSSLSASVGDRVTITCRASQVIDDDINWYQQKPGK APKLLIYLGSNRAPGVPSRFSGSGSGTDFTLTISSLQPEDFATY YCHQSYTTPHTFGGGTKVEIK |
| A2A-62 | 690 | DIQMTQSPSSLSASVGDRVTITCRASQEISGYLTWYQQKPGK APKLLIYSASHRSSGVPSRFSGSGSGTDFTLTISSLQPEDFATY YCQQWDNNPYTFGQGTKLEIK |

TABLE 18 -continued

| Variable Light Chain | | |
|---|---|---|
| Variant | SEQ ID NO | Sequence |
| A2A-63 | 691 | DIQMTQSPSSLSASVGDRVTITCRASQSISRYLNWYQQKPGK APKLLIYKASSLERGVPSRFSGSGSGTDFTLTISSLQPEDFATY YCLQPNSYPWTFGGGTKVEIK |
| A2A-64 | 692 | DIQMTQSPSSLSASVGDRVTITCRASQGISSWLDWYQQKPGK APKLLIYTPFSLQSGVPSRFSGSGSGTDFTLTISSLQPEDFATY YCQHYDDLPLTFGGGTKVEIK |
| A2A-65 | 693 | DIQMTQSPSSLSASVGDRVTITCKASQNMGSNVAWYQQKPG KAPKLLIYEASTRFSGVPSRFSGSGSGTDFTLTISSLQPEDFAT YYCQQYSSYPLRFGQGTKLEIK |
| A2A-66 | 694 | DIQMTQSPSSLSASVGDRVTITCRASQGILGYLNWYQQKPGK APKLLIYSTSNLLLGVPSRFSGSGSGTDFTLTISSLQPEDFATY YCRQLSSNPLTFGQGTKLEIK |
| A2A-67 | 695 | DIQMTQSPSSLSASVGDRVTITCRASESVDNYGISFMSWYQQ KPGKAPKLLIYDASRFISGVPSRFSGSGSGTDFTLTISSLQPED FATYYCQQINSWPLTFGQGTKLEIK |
| A2A-68 | 696 | DIQMTQSPSSLSASVGDRVTITCKSSQSLLYSGEKTYPYWYQ QKPGKAPKLLIYEASNRYTGVPSRFSGSGSGTDFTLTISSLQP EDFATYYCQQWSSYPPIAFGQGTKLEIK |
| A2A-69 | 697 | DIQMTQSPSSLSASVGDRVTITCRASQGLRHDLGWYQQKPG KAPKLLIYWASNRESGVPSRFSGSGSGTDFTLTISSLQPEDFA TYYCQKYSSTPYTFGGGTKVEIK |
| A2A-70 | 698 | DIQMTQSPSSLSASVGDRVTITCHASESVSVAGTSLLHWYQQ KPGKAPKLLIYAASNRESGVPSRFSGSGSGTDFTLTISSLQPE DFATYYCQHWSSFPLTFGQGTKLEIK |
| A2A-71 | 699 | ELQMTQSPSSLSASVGDRVTITCRVSQGISNYLNWYQQKPGK APKLLIYAASSLQSGVPSRFSGSGSGTDFTLTISSLQPEDFATY YCQQSYSTPLTFGGGTKVEIK |
| A2A-72 | 700 | ELTLTQSPATLSVSPGERATLSCRASQSVSSNLAWYQQKPGQ APRLLIYGASSRATGIPDRFSGSGSGTDFTLTISRLEPEDFAVY YCQQYGSSPPTFGQGTRLEIK |
| A2A-73 | 701 | ELTLTQSPATLSVSPGERATLSCRASQSVSSNLAWYQQKPGQ APRLLIYGASSRATGIPDRFSGSGSGTDFTLTISRLEPEDFAVY YCQQYGSSPLTFGPGTKVDIK |
| A2A-74 | 702 | ELVMTQSPGTLSLSPGERATLSCRASQSVSSSYLAWYQQKPG QAPRLLIYGASSRATGIPDRFSGSGSGTDFTLTISSLQAEDVA VYYCQQYYSTPLTFGGGTKVEIK |
| A2A-75 | 703 | ELVMTQFPSSLSASVGDRVTITCRASQSISSYLNWYQQKPGK APKLLIYAASSLQSGVPSRFSGSGSGTDFTLTISSLQPEDFATY YCQQANSFPITFGQGTRLEIK |
| A2A-76 | 704 | ELVMTQSPATLSVSLGERATLSCRASQSVSSNLAWYQQKPG QAPRLLIYDASNRATGIPARFSGSGSGTDFTLTISRLGPEDFA VYYCQQYGSSPLTFGGGTKVEIK |
| A2A-77 | 705 | ELVMTQSPSSLSASVGDRVTITCRASQRISSYLNWYQQKPGK APKLLIYAASSLQSRVPSRFSGSGSGTDFTLTISSLQPEDFATY YCQQSYSTPLTFGGGTKLETK |
| A2A-78 | 706 | ELTLTQSPATLSLSPGERATLSCRAIQSVSSSYLAWYQQKPG QAPRLLIYGASSRATGIPDRFSGSGSGTDFTLTISRLEPEDFAV YYCQQYGSSPLTFGGGTRLEIK |
| A2A-79 | 707 | ELTLTQSPATLSVSPGERATLSCRASQSVSSYLAWYQQKPGQ APRLLIYGASSRATGIPDRFSGSGSGTDFTLTISRLEPEDFAVY YCQQYGNSYTFGQGTKVDIK |
| A2A-80 | 708 | ELTLTQSPGTLSLSPGERATLSCRASQSVSSNLAWYQQKPGQ APRLLIYGASTRATGTPARFSGSGSGTEFTLTISSLQSEDFAVY YCQQYGSSPPTFGQGTRLEIK |
| A2A-81 | 709 | ELVMTQSPSSLSASVGDRVTITCRASQSISSYLNWYQQKPGK APKLLIYAASSLQSGVPSRFSGSGSGTDFTLTISSLQPEDFATY YCQQSYSTPITFGGGTKLEIK |

TABLE 18 -continued

| Variable Light Chain | | |
|---|---|---|
| Variant | SEQ ID NO | Sequence |
| A2A-82 | 710 | DIVITQAPKFLLVSAGDRVTITCKASQSVSNDVAWYQQKPG QSPKLLIYYASNRYTGVPDRFSGSGYGTDFTFTISTVQAEDLA VYFCQQDYRSPLTFGAGTKLELK |
| A2A-83 | 711 | DIQMKQSQKFMSTSVGDRVSVTCKASQNVGTNVAWYQQKP GQSPKALIYSASYRYSGVPDRFTGSGSGTDFTLTISNVQSGDL AEYFCQQYNSYPLTFGAGTKLEIK |
| A2A-84 | 712 | DIVMTQAPAIMSASPGEKVTMTCSASSSVSYMYWYQQKPGS SPRFLIYDTSNLASGVPVRFSGSGSGTSYSLTISSMEAEDAAT YYCQQWNSNPLTFSAGTKLEIK |
| A2A-85 | 713 | DIVMTQSPATLSVTPGDRVSLSCRASQSISDYLHWYQQKSHE SPRLLIKYASQSISGIPSRFSGSGSGTDFTLSINSVEPEDVGVY YCQNGHSFPLTFGAGTKLELK |
| A2A-86 | 714 | DIKITQSPSSLSASLGDTITITCHASQNINVWLNRYQQKPGNIP KLLIYKASNLHTGVPSRFSGSGSGTGFTLTISSLQPEDIATYYC QQGQSYPLTFGAGTKLEIK |
| A2A-87 | 715 | DIQMNQSQKFMSTSVGDRVSVTCKASQNVGSNVAWYQQKP GQSPKALIYSASYRYSGVPDRFTGSGSGTDFTPTISNVQSEDL AEYFCQQYNSYPLTFGAGTKLELK |
| A2A-88 | 716 | QSVLTQPPSVSAAPGQKVTISCSGISSNIGNNYVSWYQQLPGT APKWYDNNKRASGIPDRFSGSKSGTSATLGITGLQTGDEAD YYCGTWDTSLSAGVFGGGTKLTVL |
| A2A-89 | 717 | QSVLTQPPSVSAAPGQKVTISCSGSSSNIGNHYVSWYQQLPG TAPKWYDNTKRPSGIPDRFSGSKSGTSATLGITGLQTGDEA DYYCGTWDASLSTWVFGGGTKLTVL |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An antibody or antibody fragment that binds adenosine A2A receptor, comprising an immunoglobulin heavy chain and an immunoglobulin light chain:

a) wherein the immunoglobulin heavy chain comprises a heavy chain CDR1 comprising the amino acid sequence of SEQ: 6, a heavy chain CDR2 comprising the amino acid sequence of SEQ: 95, a heavy chain CDR3 comprising the amino acid sequence of SEQ: 184; and wherein the immunoglobulin light chain comprises a light chain CDR1 comprising the amino acid sequence of SEQ: 273, a light chain CDR2 comprising the amino acid sequence of SEQ: 362, and a light chain CDR3 comprising the amino acid sequence of SEQ: 451;

b) wherein the immunoglobulin heavy chain comprises a heavy chain CDR1 comprising the amino acid sequence of SEQ: 7, a heavy chain CDR2 comprising the amino acid sequence of SEQ: 96, a heavy chain CDR3 comprising the amino acid sequence of SEQ: 185; and wherein the immunoglobulin light chain comprises a light chain CDR1 comprising the amino acid sequence of SEQ: 274, a light chain CDR2 comprising the amino acid sequence of SEQ: 363, and a light chain CDR3 comprising the amino acid sequence of SEQ: 452;

c) wherein the immunoglobulin heavy chain comprises a heavy chain CDR1 comprising the amino acid sequence of SEQ: 8, a heavy chain CDR2 comprising the amino acid sequence of SEQ: 97, a heavy chain CDR3 comprising the amino acid sequence of SEQ: 186; and wherein the immunoglobulin light chain comprises a light chain CDR1 comprising the amino acid sequence of SEQ: 275, a light chain CDR2 comprising the amino acid sequence of SEQ: 364, and a light chain CDR3 comprising the amino acid sequence of SEQ: 453;

d) wherein the immunoglobulin heavy chain comprises a heavy chain CDR1 comprising the amino acid sequence of SEQ: 9, a heavy chain CDR2 comprising the amino acid sequence of SEQ: 98, a heavy chain CDR3 comprising the amino acid sequence of SEQ: 187; and wherein the immunoglobulin light chain comprises a light chain CDR1 comprising the amino acid sequence of SEQ: 276, a light chain CDR2 comprising the amino acid sequence of SEQ: 365, and a light chain CDR3 comprising the amino acid sequence of SEQ: 454;

e) wherein the immunoglobulin heavy chain comprises a heavy chain CDR1 comprising the amino acid sequence of SEQ: 10, a heavy chain CDR2 comprising the amino acid sequence of SEQ: 99, a heavy chain CDR3 comprising the amino acid sequence of SEQ: 188; and wherein the immunoglobulin light chain comprises a light chain CDR1 comprising the amino acid sequence of SEQ: 277, a light chain CDR2 comprising the amino acid sequence of SEQ: 366, and a light chain CDR3 comprising the amino acid sequence of SEQ: 455;

f) wherein the immunoglobulin heavy chain comprises a heavy chain CDR1 comprising the amino acid sequence of SEQ: 11, a heavy chain CDR2 comprising the amino acid sequence of SEQ: 100, a heavy chain CDR3 comprising the amino acid sequence of SEQ: 189; and wherein the immunoglobulin light chain comprises a light chain CDR1 comprising the amino acid sequence of SEQ: 278, a light chain CDR2 comprising the amino acid sequence of SEQ: 367, and a light chain CDR3 comprising the amino acid sequence of SEQ: 456;

g) wherein the immunoglobulin heavy chain comprises a heavy chain CDR1 comprising the amino acid sequence of SEQ: 12, a heavy chain CDR2 comprising the amino acid sequence of SEQ: 101, a heavy chain CDR3 comprising the amino acid sequence of SEQ: 190; and wherein the immunoglobulin light chain comprises a light chain CDR1 comprising the amino acid sequence of SEQ: 279, a light chain CDR2 comprising the amino acid sequence of SEQ: 368, and a light chain CDR3 comprising the amino acid sequence of SEQ: 457;

h) wherein the immunoglobulin heavy chain comprises a heavy chain CDR1 comprising the amino acid sequence of SEQ: 13, a heavy chain CDR2 comprising the amino acid sequence of SEQ: 102, a heavy chain CDR3 comprising the amino acid sequence of SEQ: 191; and wherein the immunoglobulin light chain comprises a light chain CDR1 comprising the amino acid sequence of SEQ: 280, a light chain CDR2 comprising the amino acid sequence of SEQ: 369, and a light chain CDR3 comprising the amino acid sequence of SEQ: 458;

i) wherein the immunoglobulin heavy chain comprises a heavy chain CDR1 comprising the amino acid sequence of SEQ: 14, a heavy chain CDR2 comprising the amino acid sequence of SEQ: 103, a heavy chain CDR3 comprising the amino acid sequence of SEQ: 192; and wherein the immunoglobulin light chain comprises a light chain CDR1 comprising the amino acid sequence of SEQ: 281, a light chain CDR2 comprising the amino acid sequence of SEQ: 370, and a light chain CDR3 comprising the amino acid sequence of SEQ: 459;

j) wherein the immunoglobulin heavy chain comprises a heavy chain CDR1 comprising the amino acid sequence of SEQ: 15, a heavy chain CDR2 comprising the amino acid sequence of SEQ: 104, a heavy chain CDR3 comprising the amino acid sequence of SEQ: 193; and wherein the immunoglobulin light chain comprises a light chain CDR1 comprising the amino acid sequence of SEQ: 282, a light chain CDR2 comprising the amino acid sequence of SEQ: 371, and a light chain CDR3 comprising the amino acid sequence of SEQ: 460;

k) wherein the immunoglobulin heavy chain comprises a heavy chain CDR1 comprising the amino acid sequence of SEQ: 16, a heavy chain CDR2 comprising the amino acid sequence of SEQ: 105, a heavy chain CDR3 comprising the amino acid sequence of SEQ: 194; and wherein the immunoglobulin light chain comprises a light chain CDR1 comprising the amino acid sequence of SEQ: 283, a light chain CDR2 comprising the amino acid sequence of SEQ: 372, and a light chain CDR3 comprising the amino acid sequence of SEQ: 461;

l) wherein the immunoglobulin heavy chain comprises a heavy chain CDR1 comprising the amino acid sequence of SEQ: 17, a heavy chain CDR2 comprising the amino acid sequence of SEQ: 106, a heavy chain CDR3 comprising the amino acid sequence of SEQ: 195; and wherein the immunoglobulin light chain comprises a light chain CDR1 comprising the amino acid sequence of SEQ: 284, a light chain CDR2 comprising the amino acid sequence of SEQ: 373, and a light chain CDR3 comprising the amino acid sequence of SEQ: 462;

m) wherein the immunoglobulin heavy chain comprises a heavy chain CDR1 comprising the amino acid sequence of SEQ: 18, a heavy chain CDR2 comprising the amino acid sequence of SEQ: 107, a heavy chain CDR3 comprising the amino acid sequence of SEQ: 196; and wherein the immunoglobulin light chain comprises a light chain CDR1 comprising the amino acid sequence of SEQ: 285, a light chain CDR2 comprising the amino acid sequence of SEQ: 374, and a light chain CDR3 comprising the amino acid sequence of SEQ: 463;

n) wherein the immunoglobulin heavy chain comprises a heavy chain CDR1 comprising the amino acid sequence of SEQ: 19, a heavy chain CDR2 comprising the amino acid sequence of SEQ: 108, a heavy chain CDR3 comprising the amino acid sequence of SEQ: 197; and wherein the immunoglobulin light chain comprises a light chain CDR1 comprising the amino acid sequence of SEQ: 286, a light chain CDR2 comprising the amino acid sequence of SEQ: 375, and a light chain CDR3 comprising the amino acid sequence of SEQ: 464;

o) wherein the immunoglobulin heavy chain comprises a heavy chain CDR1 comprising the amino acid sequence of SEQ: 20, a heavy chain CDR2 comprising the amino acid sequence of SEQ: 109, a heavy chain CDR3 comprising the amino acid sequence of SEQ: 198; and wherein the immunoglobulin light chain comprises a light chain CDR1 comprising the amino acid sequence of SEQ: 287, a light chain CDR2 comprising the amino acid sequence of SEQ: 376, and a light chain CDR3 comprising the amino acid sequence of SEQ: 465;

p) wherein the immunoglobulin heavy chain comprises a heavy chain CDR1 comprising the amino acid sequence of SEQ: 21, a heavy chain CDR2 comprising the amino acid sequence of SEQ: 110, a heavy chain CDR3 comprising the amino acid sequence of SEQ: 199; and wherein the immunoglobulin light chain comprises a light chain CDR1 comprising the amino acid sequence of SEQ: 288, a light chain CDR2 comprising the amino acid sequence of SEQ: 377, and a light chain CDR3 comprising the amino acid sequence of SEQ: 466;

q) wherein the immunoglobulin heavy chain comprises a heavy chain CDR1 comprising the amino acid sequence of SEQ: 22, a heavy chain CDR2 comprising the amino acid sequence of SEQ: 111, a heavy chain CDR3 comprising the amino acid sequence of SEQ: 200; and wherein the immunoglobulin light chain comprises a light chain CDR1 comprising the amino acid sequence of SEQ: 289, a light chain CDR2 comprising the amino acid sequence of SEQ: 378, and a light chain CDR3 comprising the amino acid sequence of SEQ: 467;

r) wherein the immunoglobulin heavy chain comprises a heavy chain CDR1 comprising the amino acid sequence of SEQ: 23, a heavy chain CDR2 comprising the amino acid sequence of SEQ: 112, a heavy chain CDR3 comprising the amino acid sequence of SEQ: 201; and wherein the immunoglobulin light chain comprises a light chain CDR1 comprising the amino acid sequence of SEQ: 290, a light chain CDR2 comprising the amino acid sequence of SEQ: 379, and a light chain CDR3 comprising the amino acid sequence of SEQ: 468;

s) wherein the immunoglobulin heavy chain comprises a heavy chain CDR1 comprising the amino acid sequence of SEQ: 24, a heavy chain CDR2 comprising the amino acid sequence of SEQ: 113, a heavy chain CDR3 comprising the amino acid sequence of SEQ: 202; and wherein the immunoglobulin light chain comprises a light chain CDR1 comprising the amino acid sequence of SEQ: 291, a light chain CDR2 comprising the amino acid sequence of SEQ: 380, and a light chain CDR3 comprising the amino acid sequence of SEQ: 469;

t) wherein the immunoglobulin heavy chain comprises a heavy chain CDR1 comprising the amino acid sequence of SEQ: 25, a heavy chain CDR2 comprising the amino acid sequence of SEQ: 114, a heavy chain CDR3 comprising the amino acid sequence of SEQ: 203; and wherein the immunoglobulin light chain comprises a light chain CDR1 comprising the amino acid sequence of SEQ: 292, a light chain CDR2 comprising the amino acid sequence of SEQ: 381, and a light chain CDR3 comprising the amino acid sequence of SEQ: 470;

u) wherein the immunoglobulin heavy chain comprises a heavy chain CDR1 comprising the amino acid sequence of SEQ: 26, a heavy chain CDR2 comprising the amino acid sequence of SEQ: 115, a heavy chain CDR3 comprising the amino acid sequence of SEQ: 204; and wherein the immunoglobulin light chain comprises a light chain CDR1 comprising the amino acid sequence of SEQ: 293, a light chain CDR2 comprising the amino acid sequence of SEQ: 382, and a light chain CDR3 comprising the amino acid sequence of SEQ: 471;

v) wherein the immunoglobulin heavy chain comprises a heavy chain CDR1 comprising the amino acid sequence of SEQ: 27, a heavy chain CDR2 comprising the amino acid sequence of SEQ: 116, a heavy chain CDR3 comprising the amino acid sequence of SEQ: 205; and wherein the immunoglobulin light chain comprises a light chain CDR1 comprising the amino acid sequence of SEQ: 294, a light chain CDR2 comprising the amino acid sequence of SEQ: 383, and a light chain CDR3 comprising the amino acid sequence of SEQ: 472;

w) wherein the immunoglobulin heavy chain comprises a heavy chain CDR1 comprising the amino acid sequence of SEQ: 28, a heavy chain CDR2 comprising the amino acid sequence of SEQ: 117, a heavy chain CDR3 comprising the amino acid sequence of SEQ: 206; and wherein the immunoglobulin light chain comprises a light chain CDR1 comprising the amino acid sequence of SEQ: 295, a light chain CDR2 comprising the amino acid sequence of SEQ: 384, and a light chain CDR3 comprising the amino acid sequence of SEQ: 473;

x) wherein the immunoglobulin heavy chain comprises a heavy chain CDR1 comprising the amino acid sequence of SEQ: 29, a heavy chain CDR2 comprising the amino acid sequence of SEQ: 118, a heavy chain CDR3 comprising the amino acid sequence of SEQ: 207; and wherein the immunoglobulin light chain comprises a light chain CDR1 comprising the amino acid sequence of SEQ: 296, a light chain CDR2 comprising the amino acid sequence of SEQ: 385, and a light chain CDR3 comprising the amino acid sequence of SEQ: 474;

y) wherein the immunoglobulin heavy chain comprises a heavy chain CDR1 comprising the amino acid sequence of SEQ: 30, a heavy chain CDR2 comprising the amino acid sequence of SEQ: 119, a heavy chain CDR3 comprising the amino acid sequence of SEQ: 208; and wherein the immunoglobulin light chain comprises a light chain CDR1 comprising the amino acid sequence of SEQ: 297, a light chain CDR2 comprising the amino acid sequence of SEQ: 386, and a light chain CDR3 comprising the amino acid sequence of SEQ: 475;

z) wherein the immunoglobulin heavy chain comprises a heavy chain CDR1 comprising the amino acid sequence of SEQ: 31, a heavy chain CDR2 comprising the amino acid sequence of SEQ: 120, a heavy chain CDR3 comprising the amino acid sequence of SEQ: 209; and wherein the immunoglobulin light chain comprises a light chain CDR1 comprising the amino acid sequence of SEQ: 298, a light chain CDR2 comprising the amino acid sequence of SEQ: 387, and a light chain CDR3 comprising the amino acid sequence of SEQ: 476;

aa) wherein the immunoglobulin heavy chain comprises a heavy chain CDR1 comprising the amino acid sequence of SEQ: 32, a heavy chain CDR2 comprising the amino acid sequence of SEQ: 121, a heavy chain CDR3 comprising the amino acid sequence of SEQ: 210; and wherein the immunoglobulin light chain comprises a light chain CDR1 comprising the amino acid sequence of SEQ: 299, a light chain CDR2 comprising the amino acid sequence of SEQ: 388, and a light chain CDR3 comprising the amino acid sequence of SEQ: 477;

bb) wherein the immunoglobulin heavy chain comprises a heavy chain CDR1 comprising the amino acid sequence of SEQ: 33, a heavy chain CDR2 comprising the amino acid sequence of SEQ: 122, a heavy chain CDR3 comprising the amino acid sequence of SEQ: 211; and wherein the immunoglobulin light chain comprises a light chain CDR1 comprising the amino acid sequence of SEQ: 300, a light chain CDR2 comprising the amino acid sequence of SEQ: 389, and a light chain CDR3 comprising the amino acid sequence of SEQ: 478;

cc) wherein the immunoglobulin heavy chain comprises a heavy chain CDR1 comprising the amino acid sequence of SEQ: 34, a heavy chain CDR2 comprising the amino acid sequence of SEQ: 123, a heavy chain CDR3 comprising the amino acid sequence of SEQ: 212; and wherein the immunoglobulin light chain comprises a light chain CDR1 comprising the amino acid sequence of SEQ: 301, a light chain CDR2 comprising the amino acid sequence of SEQ: 390, and a light chain CDR3 comprising the amino acid sequence of SEQ: 479;

dd) wherein the immunoglobulin heavy chain comprises a heavy chain CDR1 comprising the amino acid sequence of SEQ: 35, a heavy chain CDR2 comprising the amino acid sequence of SEQ: 124, a heavy chain CDR3 comprising the amino acid sequence of SEQ: 213; and wherein the immunoglobulin light chain comprises a light chain CDR1 comprising the amino acid sequence of SEQ: 302, a light chain CDR2 comprising the amino acid sequence of SEQ: 391, and a light chain CDR3 comprising the amino acid sequence of SEQ: 480;

ee) wherein the immunoglobulin heavy chain comprises a heavy chain CDR1 comprising the amino acid sequence of SEQ: 36, a heavy chain CDR2 comprising the amino acid sequence of SEQ: 125, a heavy chain CDR3 comprising the amino acid sequence of SEQ: 214; and wherein the immunoglobulin light chain comprises a light chain CDR1 comprising the amino acid sequence of SEQ: 303, a light chain CDR2 comprising the amino acid sequence of SEQ: 392, and a light chain CDR3 comprising the amino acid sequence of SEQ: 481;

ff) wherein the immunoglobulin heavy chain comprises a heavy chain CDR1 comprising the amino acid sequence of SEQ: 37, a heavy chain CDR2 comprising the amino acid sequence of SEQ: 126, a heavy chain CDR3 comprising the amino acid sequence of SEQ: 215; and wherein the immunoglobulin light chain comprises a light chain CDR1 comprising the amino acid sequence of SEQ: 304, a light chain CDR2 comprising the amino acid sequence of SEQ: 393, and a light chain CDR3 comprising the amino acid sequence of SEQ: 482;

gg) wherein the immunoglobulin heavy chain comprises a heavy chain CDR1 comprising the amino acid sequence of SEQ: 38, a heavy chain CDR2 comprising the amino acid sequence of SEQ: 127, a heavy chain CDR3 comprising the amino acid sequence of SEQ: 216; and wherein the immunoglobulin light chain comprises a light chain CDR1 comprising the amino acid sequence of SEQ: 305, a light chain CDR2 comprising the amino acid sequence of SEQ: 394, and a light chain CDR3 comprising the amino acid sequence of SEQ: 483;

hh) wherein the immunoglobulin heavy chain comprises a heavy chain CDR1 comprising the amino acid sequence of SEQ: 39, a heavy chain CDR2 comprising the amino acid sequence of SEQ: 128, a heavy chain CDR3 comprising the amino acid sequence of SEQ: 217; and wherein the immunoglobulin light chain comprises a light chain CDR1 comprising the amino acid sequence of SEQ: 306, a light chain CDR2 comprising the amino acid sequence of SEQ: 395, and a light chain CDR3 comprising the amino acid sequence of SEQ: 484;

ii) wherein the immunoglobulin heavy chain comprises a heavy chain CDR1 comprising the amino acid sequence of SEQ: 40, a heavy chain CDR2 comprising the amino acid sequence of SEQ: 129, a heavy chain CDR3 comprising the amino acid sequence of SEQ: 218; and wherein the immunoglobulin light chain comprises a light chain CDR1 comprising the amino acid sequence of SEQ: 307, a light chain CDR2 comprising the amino acid sequence of SEQ: 396, and a light chain CDR3 comprising the amino acid sequence of SEQ: 485;

jj) wherein the immunoglobulin heavy chain comprises a heavy chain CDR1 comprising the amino acid sequence of SEQ: 41, a heavy chain CDR2 comprising the amino acid sequence of SEQ: 130, a heavy chain CDR3 comprising the amino acid sequence of SEQ: 219; and wherein the immunoglobulin light chain comprises a light chain CDR1 comprising the amino acid sequence of SEQ: 308, a light chain CDR2 comprising the amino acid sequence of SEQ: 397, and a light chain CDR3 comprising the amino acid sequence of SEQ: 486;

kk) wherein the immunoglobulin heavy chain comprises a heavy chain CDR1 comprising the amino acid sequence of SEQ: 42, a heavy chain CDR2 comprising the amino acid sequence of SEQ: 131, a heavy chain CDR3 comprising the amino acid sequence of SEQ: 220; and wherein the immunoglobulin light chain comprises a light chain CDR1 comprising the amino acid sequence of SEQ: 309, a light chain CDR2 comprising the amino acid sequence of SEQ: 398, and a light chain CDR3 comprising the amino acid sequence of SEQ: 487;

ll) wherein the immunoglobulin heavy chain comprises a heavy chain CDR1 comprising the amino acid sequence of SEQ: 43, a heavy chain CDR2 comprising the amino acid sequence of SEQ: 132, a heavy chain CDR3 comprising the amino acid sequence of SEQ: 221; and wherein the immunoglobulin light chain comprises a light chain CDR1 comprising the amino acid sequence of SEQ: 310, a light chain CDR2 comprising the amino acid sequence of SEQ: 399, and a light chain CDR3 comprising the amino acid sequence of SEQ: 488;

mm) wherein the immunoglobulin heavy chain comprises a heavy chain CDR1 comprising the amino acid sequence of SEQ: 44, a heavy chain CDR2 comprising the amino acid sequence of SEQ: 133, a heavy chain CDR3 comprising the amino acid sequence of SEQ: 222; and wherein the immunoglobulin light chain comprises a light chain CDR1 comprising the amino acid sequence of SEQ: 311, a light chain CDR2 comprising the amino acid sequence of SEQ: 400, and a light chain CDR3 comprising the amino acid sequence of SEQ: 489;

nn) wherein the immunoglobulin heavy chain comprises a heavy chain CDR1 comprising the amino acid sequence of SEQ: 45, a heavy chain CDR2 comprising the amino acid sequence of SEQ: 134, a heavy chain CDR3 comprising the amino acid sequence of SEQ: 223; and wherein the immunoglobulin light chain comprises a light chain CDR1 comprising the amino acid sequence of SEQ: 312, a light chain CDR2 comprising the amino acid sequence of SEQ: 401, and a light chain CDR3 comprising the amino acid sequence of SEQ: 490;

oo) wherein the immunoglobulin heavy chain comprises a heavy chain CDR1 comprising the amino acid sequence of SEQ: 46, a heavy chain CDR2 comprising the amino acid sequence of SEQ: 135, a heavy chain CDR3 comprising the amino acid sequence of SEQ: 224; and wherein the immunoglobulin light chain comprises a light chain CDR1 comprising the amino acid sequence of SEQ: 313, a light chain CDR2 comprising the amino acid sequence of SEQ: 402, and a light chain CDR3 comprising the amino acid sequence of SEQ: 491;

pp) wherein the immunoglobulin heavy chain comprises a heavy chain CDR1 comprising the amino acid sequence of SEQ: 47, a heavy chain CDR2 comprising the amino acid sequence of SEQ: 136, a heavy chain CDR3 comprising the amino acid sequence of SEQ: 225; and wherein the immunoglobulin light chain comprises a light chain CDR1 comprising the amino acid sequence of SEQ: 314, a light chain CDR2 comprising the amino acid sequence of SEQ: 403, and a light chain CDR3 comprising the amino acid sequence of SEQ: 492;

qq) wherein the immunoglobulin heavy chain comprises a heavy chain CDR1 comprising the amino acid sequence of SEQ: 48, a heavy chain CDR2 comprising the amino acid sequence of SEQ: 137, a heavy chain CDR3 comprising the amino acid sequence of SEQ: 226; and wherein the immunoglobulin light chain comprises a light chain CDR1 comprising the amino acid sequence of SEQ: 315, a light chain CDR2 comprising the amino acid sequence of SEQ: 404, and a light chain CDR3 comprising the amino acid sequence of SEQ: 493;

rr) wherein the immunoglobulin heavy chain comprises a heavy chain CDR1 comprising the amino acid sequence of SEQ: 49, a heavy chain CDR2 comprising the amino acid sequence of SEQ: 138, a heavy chain CDR3 comprising the amino acid sequence of SEQ: 227; and wherein the immunoglobulin light chain comprises a light chain CDR1 comprising the amino acid sequence of SEQ: 316, a light chain CDR2 comprising the amino acid sequence of SEQ: 405, and a light chain CDR3 comprising the amino acid sequence of SEQ: 494;

ss) wherein the immunoglobulin heavy chain comprises a heavy chain CDR1 comprising the amino acid sequence of SEQ: 50, a heavy chain CDR2 comprising the amino acid sequence of SEQ: 139, a heavy chain CDR3 comprising the amino acid sequence of SEQ: 228; and wherein the immunoglobulin light chain comprises a light chain CDR1 comprising the amino acid sequence of SEQ: 317, a light chain CDR2 comprising the amino acid sequence of SEQ: 406, and a light chain CDR3 comprising the amino acid sequence of SEQ: 495;

tt) wherein the immunoglobulin heavy chain comprises a heavy chain CDR1 comprising the amino acid sequence of SEQ: 51, a heavy chain CDR2 comprising the amino acid sequence of SEQ: 140, a heavy chain CDR3 comprising the amino acid sequence of SEQ: 229; and wherein the immunoglobulin light chain comprises a light chain CDR1 comprising the amino acid sequence of SEQ: 318, a light chain CDR2 comprising the amino acid sequence of SEQ: 407, and a light chain CDR3 comprising the amino acid sequence of SEQ: 496;

uu) wherein the immunoglobulin heavy chain comprises a heavy chain CDR1 comprising the amino acid sequence of SEQ: 52, a heavy chain CDR2 comprising the amino acid sequence of SEQ: 141, a heavy chain CDR3 comprising the amino acid sequence of SEQ: 230; and wherein the immunoglobulin light chain comprises a light chain CDR1 comprising the amino acid sequence of SEQ: 319, a light chain CDR2 comprising the amino acid sequence of SEQ: 408, and a light chain CDR3 comprising the amino acid sequence of SEQ: 497;

vv) wherein the immunoglobulin heavy chain comprises a heavy chain CDR1 comprising the amino acid sequence of SEQ: 53, a heavy chain CDR2 comprising the amino acid sequence of SEQ: 142, a heavy chain CDR3 comprising the amino acid sequence of SEQ: 231; and wherein the immunoglobulin light chain comprises a light chain CDR1 comprising the amino acid sequence of SEQ: 320, a light chain CDR2 comprising the amino acid sequence of SEQ: 409, and a light chain CDR3 comprising the amino acid sequence of SEQ: 498;

ww) wherein the immunoglobulin heavy chain comprises a heavy chain CDR1 comprising the amino acid sequence of SEQ: 54, a heavy chain CDR2 comprising the amino acid sequence of SEQ: 143, a heavy chain CDR3 comprising the amino acid sequence of SEQ: 232; and wherein the immunoglobulin light chain comprises a light chain CDR1 comprising the amino acid sequence of SEQ: 321, a light chain CDR2 comprising the amino acid sequence of SEQ: 410, and a light chain CDR3 comprising the amino acid sequence of SEQ: 499;

xx) wherein the immunoglobulin heavy chain comprises a heavy chain CDR1 comprising the amino acid sequence of SEQ: 55, a heavy chain CDR2 comprising the amino acid sequence of SEQ: 144, a heavy chain CDR3 comprising the amino acid sequence of SEQ: 233; and wherein the immunoglobulin light chain comprises a light chain CDR1 comprising the amino acid sequence of SEQ: 322, a light chain CDR2 comprising the amino acid sequence of SEQ: 411, and a light chain CDR3 comprising the amino acid sequence of SEQ: 500;

yy) wherein the immunoglobulin heavy chain comprises a heavy chain CDR1 comprising the amino acid sequence of SEQ: 56, a heavy chain CDR2 comprising the amino acid sequence of SEQ: 145, a heavy chain CDR3 comprising the amino acid sequence of SEQ: 234; and wherein the immunoglobulin light chain comprises a light chain CDR1 comprising the amino acid sequence of SEQ: 323, a light chain CDR2 comprising the amino acid sequence of SEQ: 412, and a light chain CDR3 comprising the amino acid sequence of SEQ: 501;

yy) wherein the immunoglobulin heavy chain comprises a heavy chain CDR1 comprising the amino acid sequence of SEQ: 57, a heavy chain CDR2 comprising the amino acid sequence of SEQ: 146, a heavy chain CDR3 comprising the amino acid sequence of SEQ: 235; and wherein the immunoglobulin light chain comprises a light chain CDR1 comprising the amino acid sequence of SEQ: 324, a light chain CDR2 comprising the amino acid sequence of SEQ: 413, and a light chain CDR3 comprising the amino acid sequence of SEQ: 502;

zz) wherein the immunoglobulin heavy chain comprises a heavy chain CDR1 comprising the amino acid sequence of SEQ: 58, a heavy chain CDR2 comprising the amino acid sequence of SEQ: 147, a heavy chain CDR3 comprising the amino acid sequence of SEQ: 236; and wherein the immunoglobulin light chain comprises a light chain CDR1 comprising the amino acid sequence of SEQ: 325, a light chain CDR2 comprising the amino acid sequence of SEQ: 414, and a light chain CDR3 comprising the amino acid sequence of SEQ: 503;

aaa) wherein the immunoglobulin heavy chain comprises a heavy chain CDR1 comprising the amino acid sequence of SEQ: 59, a heavy chain CDR2 comprising the amino acid sequence of SEQ: 148, a heavy chain CDR3 comprising the amino acid sequence of SEQ: 237; and wherein the immunoglobulin light chain comprises a light chain CDR1 comprising the amino acid sequence of SEQ: 326, a light chain CDR2 comprising the amino acid sequence of SEQ: 415, and a light chain CDR3 comprising the amino acid sequence of SEQ: 504;

bbb) wherein the immunoglobulin heavy chain comprises a heavy chain CDR1 comprising the amino acid sequence of SEQ: 60, a heavy chain CDR2 comprising the amino acid sequence of SEQ: 149, a heavy chain CDR3 comprising the amino acid sequence of SEQ: 238; and wherein the immunoglobulin light chain comprises a light chain CDR1 comprising the amino acid sequence of SEQ: 327, a light chain CDR2 comprising the amino acid sequence of SEQ: 416, and a light chain CDR3 comprising the amino acid sequence of SEQ: 505;

ccc) wherein the immunoglobulin heavy chain comprises a heavy chain CDR1 comprising the amino acid sequence of SEQ: 61, a heavy chain CDR2 comprising the amino acid sequence of SEQ: 150, a heavy chain CDR3 comprising the amino acid sequence of SEQ: 239; and wherein the immunoglobulin light chain comprises a light chain CDR1 comprising the amino acid sequence of SEQ: 328, a light chain CDR2 comprising the amino acid sequence of SEQ: 417, and a light chain CDR3 comprising the amino acid sequence of SEQ: 506;

ddd) wherein the immunoglobulin heavy chain comprises a heavy chain CDR1 comprising the amino acid sequence of SEQ: 62, a heavy chain CDR2 comprising the amino acid sequence of SEQ: 151, a heavy chain CDR3 comprising the amino acid sequence of SEQ: 240; and wherein the immunoglobulin light chain comprises a light chain CDR1 comprising the amino acid sequence of SEQ: 329, a light chain CDR2 comprising the amino acid sequence of SEQ: 418, and a light chain CDR3 comprising the amino acid sequence of SEQ: 507;

eee) wherein the immunoglobulin heavy chain comprises a heavy chain CDR1 comprising the amino acid sequence of SEQ: 63, a heavy chain CDR2 comprising the amino acid sequence of SEQ: 152, a heavy chain CDR3 comprising the amino acid sequence of SEQ: 241; and wherein the immunoglobulin light chain comprises a light chain CDR1 comprising the amino acid sequence of SEQ: 330, a light chain CDR2 comprising the amino acid sequence of SEQ: 419, and a light chain CDR3 comprising the amino acid sequence of SEQ: 508;

fff) wherein the immunoglobulin heavy chain comprises a heavy chain CDR1 comprising the amino acid sequence of SEQ: 64, a heavy chain CDR2 comprising the amino acid sequence of SEQ: 153, a heavy chain CDR3 comprising the amino acid sequence of SEQ: 242; and wherein the immunoglobulin light chain comprises a light chain CDR1 comprising the amino acid sequence of SEQ: 331, a light chain CDR2 comprising the amino acid sequence of SEQ: 420, and a light chain CDR3 comprising the amino acid sequence of SEQ: 509;

ggg) wherein the immunoglobulin heavy chain comprises a heavy chain CDR1 comprising the amino acid sequence of SEQ: 65, a heavy chain CDR2 comprising the amino acid sequence of SEQ: 154, a heavy chain CDR3 comprising the amino acid sequence of SEQ: 243; and wherein the immunoglobulin light chain comprises a light chain CDR1 comprising the amino acid sequence of SEQ: 332, a light chain CDR2 comprising the amino acid sequence of SEQ: 421, and a light chain CDR3 comprising the amino acid sequence of SEQ: 510;

hhh) wherein the immunoglobulin heavy chain comprises a heavy chain CDR1 comprising the amino acid sequence of SEQ: 66, a heavy chain CDR2 comprising the amino acid sequence of SEQ: 155, a heavy chain CDR3 comprising the amino acid sequence of SEQ: 244; and wherein the immunoglobulin light chain comprises a light chain CDR1 comprising the amino acid sequence of SEQ: 333, a light chain CDR2 comprising the amino acid sequence of SEQ: 422, and a light chain CDR3 comprising the amino acid sequence of SEQ: 511;

iii) wherein the immunoglobulin heavy chain comprises a heavy chain CDR1 comprising the amino acid sequence of SEQ: 67, a heavy chain CDR2 comprising the amino acid sequence of SEQ: 156, a heavy chain CDR3 comprising the amino acid sequence of SEQ: 245; and wherein the immunoglobulin light chain comprises a light chain CDR1 comprising the amino acid sequence of SEQ: 334, a light chain CDR2 comprising the amino acid sequence of SEQ: 423, and a light chain CDR3 comprising the amino acid sequence of SEQ: 512;

jjj) wherein the immunoglobulin heavy chain comprises a heavy chain CDR1 comprising the amino acid sequence of SEQ: 68, a heavy chain CDR2 comprising the amino acid sequence of SEQ: 157, a heavy chain CDR3 comprising the amino acid sequence of SEQ: 246; and wherein the immunoglobulin light chain comprises a light chain CDR1 comprising the amino acid sequence of SEQ: 335, a light chain CDR2 comprising the amino acid sequence of SEQ: 424, and a light chain CDR3 comprising the amino acid sequence of SEQ: 513;

kkk) wherein the immunoglobulin heavy chain comprises a heavy chain CDR1 comprising the amino acid sequence of SEQ: 69, a heavy chain CDR2 comprising the amino acid sequence of SEQ: 158, a heavy chain CDR3 comprising the amino acid sequence of SEQ: 247; and wherein the immunoglobulin light chain comprises a light chain CDR1 comprising the amino acid sequence of SEQ: 336, a light chain CDR2 comprising the amino acid sequence of SEQ: 425, and a light chain CDR3 comprising the amino acid sequence of SEQ: 514;

lll) wherein the immunoglobulin heavy chain comprises a heavy chain CDR1 comprising the amino acid sequence of SEQ: 70, a heavy chain CDR2 comprising the amino acid sequence of SEQ: 159, a heavy chain CDR3 comprising the amino acid sequence of SEQ: 248; and wherein the immunoglobulin light chain comprises a light chain CDR1 comprising the amino acid sequence of SEQ: 337, a light chain CDR2 comprising the amino acid sequence of SEQ: 426, and a light chain CDR3 comprising the amino acid sequence of SEQ: 515;

mmm) wherein the immunoglobulin heavy chain comprises a heavy chain CDR1 comprising the amino acid sequence of SEQ: 71, a heavy chain CDR2 comprising the amino acid sequence of SEQ: 160, a heavy chain CDR3 comprising the amino acid sequence of SEQ: 249; and wherein the immunoglobulin light chain comprises a light chain CDR1 comprising the amino acid sequence of SEQ: 338, a light chain CDR2 comprising the amino acid sequence of SEQ: 427, and a light chain CDR3 comprising the amino acid sequence of SEQ: 516;

nnnn) wherein the immunoglobulin heavy chain comprises a heavy chain CDR1 comprising the amino acid sequence of SEQ: 72, a heavy chain CDR2 comprising the amino acid sequence of SEQ: 161, a heavy chain CDR3 comprising the amino acid sequence of SEQ: 250; and wherein the immunoglobulin light chain comprises a light chain CDR1 comprising the amino acid sequence of SEQ: 339, a light chain CDR2 comprising the amino acid sequence of SEQ: 428, and a light chain CDR3 comprising the amino acid sequence of SEQ: 517;

ooo) wherein the immunoglobulin heavy chain comprises a heavy chain CDR1 comprising the amino acid sequence of SEQ: 73, a heavy chain CDR2 comprising the amino acid sequence of SEQ: 162, a heavy chain CDR3 comprising the amino acid sequence of SEQ: 251; and wherein the immunoglobulin light chain comprises a light chain CDR1 comprising the amino acid sequence of SEQ: 340, a light chain CDR2 comprising the amino acid sequence of SEQ: 429, and a light chain CDR3 comprising the amino acid sequence of SEQ: 518;

ppp) wherein the immunoglobulin heavy chain comprises a heavy chain CDR1 comprising the amino acid sequence of SEQ: 74, a heavy chain CDR2 comprising the amino acid sequence of SEQ: 163, a heavy chain CDR3 comprising the amino acid sequence of SEQ: 252; and wherein the immunoglobulin light chain comprises a light chain CDR1 comprising the amino acid sequence of SEQ: 341, a light chain CDR2 comprising the amino acid sequence of SEQ: 430, and a light chain CDR3 comprising the amino acid sequence of SEQ: 519;

qqq) wherein the immunoglobulin heavy chain comprises a heavy chain CDR1 comprising the amino acid sequence of SEQ: 75, a heavy chain CDR2 comprising the amino acid sequence of SEQ: 164, a heavy chain CDR3 comprising the amino acid sequence of SEQ: 253; and wherein the immunoglobulin light chain comprises a light chain CDR1 comprising the amino acid sequence of SEQ: 342, a light chain CDR2 comprising the amino acid sequence of SEQ: 431, and a light chain CDR3 comprising the amino acid sequence of SEQ: 520;

rrr) wherein the immunoglobulin heavy chain comprises a heavy chain CDR1 comprising the amino acid sequence of SEQ: 76, a heavy chain CDR2 comprising the amino acid sequence of SEQ: 165, a heavy chain CDR3 comprising the amino acid sequence of SEQ: 254; and wherein the immunoglobulin light chain comprises a light chain CDR1 comprising the amino acid sequence of SEQ: 343, a light chain CDR2 comprising the amino acid sequence of SEQ: 432, and a light chain CDR3 comprising the amino acid sequence of SEQ: 521;

sss) wherein the immunoglobulin heavy chain comprises a heavy chain CDR1 comprising the amino acid sequence of SEQ: 77, a heavy chain CDR2 comprising the amino acid sequence of SEQ: 166, a heavy chain CDR3 comprising the amino acid sequence of SEQ: 255; and wherein the immunoglobulin light chain comprises a light chain CDR1 comprising the amino acid sequence of SEQ: 344, a light chain CDR2 comprising the amino acid sequence of SEQ: 433, and a light chain CDR3 comprising the amino acid sequence of SEQ: 522;

ttt) wherein the immunoglobulin heavy chain comprises a heavy chain CDR1 comprising the amino acid sequence of SEQ: 78, a heavy chain CDR2 comprising the amino acid sequence of SEQ: 167, a heavy chain CDR3 comprising the amino acid sequence of SEQ: 256; and wherein the immunoglobulin light chain comprises a light chain CDR1 comprising the amino acid sequence of SEQ: 345, a light chain CDR2 comprising the amino acid sequence of SEQ: 434, and a light chain CDR3 comprising the amino acid sequence of SEQ: 523;

uuu) wherein the immunoglobulin heavy chain comprises a heavy chain CDR1 comprising the amino acid sequence of SEQ: 79, a heavy chain CDR2 comprising the amino acid sequence of SEQ: 168, a heavy chain CDR3 comprising the amino acid sequence of SEQ: 257; and wherein the immunoglobulin light chain comprises a light chain CDR1 comprising the amino acid sequence of SEQ: 346, a light chain CDR2 comprising the amino acid sequence of SEQ: 435, and a light chain CDR3 comprising the amino acid sequence of SEQ: 524;

vvv) wherein the immunoglobulin heavy chain comprises a heavy chain CDR1 comprising the amino acid sequence of SEQ: 80, a heavy chain CDR2 comprising the amino acid sequence of SEQ: 169, a heavy chain CDR3 comprising the amino acid sequence of SEQ: 258; and wherein the immunoglobulin light chain comprises a light chain CDR1 comprising the amino acid sequence of SEQ: 347, a light chain CDR2 comprising the amino acid sequence of SEQ: 436, and a light chain CDR3 comprising the amino acid sequence of SEQ: 525;

www) wherein the immunoglobulin heavy chain comprises a heavy chain CDR1 comprising the amino acid sequence of SEQ: 81, a heavy chain CDR2 comprising the amino acid sequence of SEQ: 170, a heavy chain CDR3 comprising the amino acid sequence of SEQ: 259; and wherein the immunoglobulin light chain comprises a light chain CDR1 comprising the amino acid sequence of SEQ: 348, a light chain CDR2 comprising the amino acid sequence of SEQ: 437, and a light chain CDR3 comprising the amino acid sequence of SEQ: 526;

xxx) wherein the immunoglobulin heavy chain comprises a heavy chain CDR1 comprising the amino acid sequence of SEQ: 83, a heavy chain CDR2 comprising the amino acid sequence of SEQ: 172, a heavy chain CDR3 comprising the amino acid sequence of SEQ: 261; and wherein the immunoglobulin light chain comprises a light chain CDR1 comprising the amino acid sequence of SEQ: 350, a light chain CDR2 comprising the amino acid sequence of SEQ: 439, and a light chain CDR3 comprising the amino acid sequence of SEQ: 528;

yyy) wherein the immunoglobulin heavy chain comprises a heavy chain CDR1 comprising the amino acid sequence of SEQ: 84, a heavy chain CDR2 comprising the amino acid sequence of SEQ: 173, a heavy chain CDR3 comprising the amino acid sequence of SEQ: 262; and wherein the immunoglobulin light chain comprises a light chain CDR1 comprising the amino acid sequence of SEQ: 351, a light chain CDR2 comprising the amino acid sequence of SEQ: 440, and a light chain CDR3 comprising the amino acid sequence of SEQ: 529;

zzz) wherein the immunoglobulin heavy chain comprises a heavy chain CDR1 comprising the amino acid sequence of SEQ: 85, a heavy chain CDR2 comprising the amino acid sequence of SEQ: 174, a heavy chain CDR3 comprising the amino acid sequence of SEQ: 263; and wherein the immunoglobulin light chain comprises a light chain CDR1 comprising the amino acid sequence of SEQ: 352, a light chain CDR2 comprising the amino acid sequence of SEQ: 441, and a light chain CDR3 comprising the amino acid sequence of SEQ: 530;

aaaa) wherein the immunoglobulin heavy chain comprises a heavy chain CDR1 comprising the amino acid sequence of SEQ: 87, a heavy chain CDR2 comprising the amino acid sequence of SEQ: 176, a heavy chain CDR3 comprising the amino acid sequence of SEQ: 265; and wherein the immunoglobulin light chain comprises a light chain CDR1 comprising the amino acid sequence of SEQ: 354, a light chain CDR2 comprising the amino acid sequence of SEQ: 443, and a light chain CDR3 comprising the amino acid sequence of SEQ: 532;

bbbb) wherein the immunoglobulin heavy chain comprises a heavy chain CDR1 comprising the amino acid sequence of SEQ: 88, a heavy chain CDR2 comprising the amino acid sequence of SEQ: 177, a heavy chain CDR3 comprising the amino acid sequence of SEQ: 266; and wherein the immunoglobulin light chain comprises a light chain CDR1 comprising the amino acid sequence of SEQ: 355, a light chain CDR2 comprising the amino acid sequence of SEQ: 444, and a light chain CDR3 comprising the amino acid sequence of SEQ: 533;

cccc) wherein the immunoglobulin heavy chain comprises a heavy chain CDR1 comprising the amino acid sequence of SEQ: 89, a heavy chain CDR2 comprising the amino acid sequence of SEQ: 178, a heavy chain CDR3 comprising the amino acid sequence of SEQ: 267; and wherein the immunoglobulin light chain comprises a light chain CDR1 comprising the amino acid sequence of SEQ: 356, a light chain CDR2 comprising the amino acid sequence of SEQ: 445, and a light chain CDR3 comprising the amino acid sequence of SEQ: 534;

dddd) wherein the immunoglobulin heavy chain comprises a heavy chain CDR1 comprising the amino acid sequence of SEQ: 90, a heavy chain CDR2 comprising the amino acid sequence of SEQ: 179, a heavy chain CDR3 comprising the amino acid sequence of SEQ: 268; and wherein the immunoglobulin light chain comprises a light chain CDR1 comprising the amino acid sequence of SEQ: 357, a light chain CDR2 comprising the amino acid sequence of SEQ: 446, and a light chain CDR3 comprising the amino acid sequence of SEQ: 535;

eeee) wherein the immunoglobulin heavy chain comprises a heavy chain CDR1 comprising the amino acid sequence of SEQ: 91, a heavy chain CDR2 comprising the amino acid sequence of SEQ: 180, a heavy chain CDR3 comprising the amino acid sequence of SEQ: 269; and wherein the immunoglobulin light chain comprises a light chain CDR1 comprising the amino acid sequence of SEQ: 358, a light chain CDR2 comprising the amino acid sequence of SEQ: 447, and a light chain CDR3 comprising the amino acid sequence of SEQ: 536;

ffff) wherein the immunoglobulin heavy chain comprises a heavy chain CDR1 comprising the amino acid sequence of SEQ: 92, a heavy chain CDR2 comprising the amino acid sequence of SEQ: 181, a heavy chain CDR3 comprising the amino acid sequence of SEQ: 270; and wherein the immunoglobulin light chain comprises a light chain CDR1 comprising the amino acid sequence of SEQ: 359, a light chain CDR2 comprising the amino acid sequence of SEQ: 448, and a light chain CDR3 comprising the amino acid sequence of SEQ: 537;

gggg) wherein the immunoglobulin heavy chain comprises a heavy chain CDR1 comprising the amino acid sequence of SEQ: 93, a heavy chain CDR2 comprising the amino acid sequence of SEQ: 182, a heavy chain CDR3 comprising the amino acid sequence of SEQ: 271; and wherein the immunoglobulin light chain comprises a light chain CDR1 comprising the amino acid sequence of SEQ: 360, a light chain CDR2 comprising the amino acid sequence of SEQ: 449, and a light chain CDR3 comprising the amino acid sequence of SEQ: 538; or hhhh) wherein the immunoglobulin heavy chain comprises a heavy chain CDR1 comprising the amino acid sequence of SEQ: 94, a heavy chain CDR2 comprising the amino acid sequence of SEQ: 183, a heavy chain CDR3 comprising the amino acid sequence of SEQ: 272; and wherein the immunoglobulin light chain comprises a light chain CDR1 comprising the amino acid sequence of SEQ: 361, a light chain CDR2 comprising the amino acid sequence of SEQ: 450, and a light chain CDR3 comprising the amino acid sequence of SEQ: 539.

2. The antibody or antibody fragment of claim 1, wherein the antibody is a monoclonal antibody, a bi-specific antibody, a multispecific antibody, a grafted antibody, a humanized antibody, a synthetic antibody, a chimeric antibody, a Fab fragment, a F(ab')2 fragment, a FIT fragment, a diabody, disulfide-linked Fvs (sdFv), an intrabody, or an antigen-binding fragment thereof.

3. The antibody or antibody fragment of claim 1, wherein the antibody or antibody fragment thereof is chimeric or humanized.

4. The antibody or antibody fragment of claim 1, wherein the antibody has an EC50 less than about 10 nanomolar in a cAMP assay.

5. The antibody or antibody fragment of claim 1, wherein the antibody or antibody fragment comprises a variable heavy chain comprising an amino acid sequence at least about 90% identical to that set forth in any one of SEQ ID NOs: 540-589, 591-615, 617-619, and 621-628.

6. The antibody or antibody fragment of claim 1, wherein the antibody or antibody fragment comprises a variable light chain comprising an amino acid sequence at least about 90% identical to that set forth in any one of SEQ ID NOs: 629-678, 680-704, 706-708, and 710-717.

7. The antibody or antibody fragment thereof of claim 1, wherein the antibody or antibody fragment comprises a variable heavy chain comprising the amino acid sequence of any one of SEQ ID NOs: 540-589, 591-615, 617-619, and 621-628.

8. The antibody or antibody fragment thereof of claim 1, wherein the antibody or antibody fragment comprises a variable light chain comprising the amino acid sequence of any one of SEQ ID NOs: 629-678, 680-704, 706-708, and 710-717.

9. The antibody or antibody fragment thereof of claim 7, wherein the antibody or antibody fragment comprises a variable light chain comprising the amino acid sequence of any one of SEQ ID NOs: 629-678, 680-704, 706-708, and 710-717.

10. A method of treating cancer, comprising administering the antibody or antibody fragment of claim 1 to a subject.

11. A method of treating a neurological disease or disorder, comprising administering the antibody or antibody fragment of claim 1 to a subject.

* * * * *